United States Patent
Ameriks et al.

(10) Patent No.: US 10,087,185 B2
(45) Date of Patent: Oct. 2, 2018

(54) FUSED BICYLIC PYRIDINE COMPOUNDS AND THEIR USE AS AMPA RECEPTOR MODULATORS

(71) Applicant: Janssen Pharmaceutica NV, Beerse (BE)

(72) Inventors: Michael K. Ameriks, San Diego, CA (US); Márió Gyuris, Budapest (HU); Brian Ngo Laforteza, San Diego, CA (US); Terry Patrick Lebold, San Diego, CA (US); Stephen Todd Meyer, San Diego, CA (US); Suchitra Ravula, San Diego, CA (US); Brad M. Savall, San Diego, CA (US); Brock T. Shireman, Poway, CA (US); Warren Stanfield Wade, San Diego, CA (US); János Gerencsér, Budapest (HU)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 15/790,849

(22) Filed: Oct. 23, 2017

(65) Prior Publication Data
US 2018/0111933 A1    Apr. 26, 2018

Related U.S. Application Data

(60) Provisional application No. 62/412,868, filed on Oct. 26, 2016.

(51) Int. Cl.
| | | |
|---|---|---|
| C07D 401/14 | (2006.01) |
| C07D 401/10 | (2006.01) |
| A61K 31/437 | (2006.01) |
| A61K 31/4353 | (2006.01) |
| C07D 471/04 | (2006.01) |
| C07D 417/14 | (2006.01) |
| C07D 487/04 | (2006.01) |

(52) U.S. Cl.
CPC ......... C07D 471/04 (2013.01); C07D 401/14 (2013.01); C07D 417/14 (2013.01); C07D 487/04 (2013.01)

(58) Field of Classification Search
CPC .............. A61K 31/437; A61K 31/4353; C07D 401/10; C07D 401/14
USPC .......................... 514/300, 303; 546/119, 121
See application file for complete search history.

(56) References Cited

U.S. PATENT DOCUMENTS 8,299,056 B2 * 10/2012 Bahmanyar .......... C07D 519/00 514/210.21
2015/0344468 A1    12/2015 Gardinier et al.

FOREIGN PATENT DOCUMENTS

WO    WO 2000/001376    1/2000
WO    WO 2008/113795    9/2008

OTHER PUBLICATIONS

International Search Report for PCT/US2017/057566 dated Feb. 22, 2018.
Bagshawe, Drug Dev Res. 1995, 34, 220-230.
Bertolini, et al., J Med Chem. 1997, 40, 2011-2016.
Bodor, Adv Drug Res. 1984, 13, 224-331.
Chen et al., Bipolar Disord., 13:1-15, 2011.
Cho et al. (2007). "Two families of TARP isoforms that have distinct effects on the kinetic properties of AMPA receptors and synaptic currents." Neuron 55(6): 890-904.
Du et al., J Neurosci 24: 6578-6589, 2004.
Du et al., J Neurosci 28: 68-79, 2008.
Engin and Treit, Behav Pharmacol 18:365-374, 2007.
Fleisher et al., Adv. Drug Delivery Rev. 1996, 19, 115-130.
G.D. Considine, ed., Van Nostrand's Encyclopedia of Chemistry, p. 261, 5th ed. (2005).
G.S. Paulekuhn, et al., "Trends in Active Pharmaceutical Ingredient Salt Selection based on Analysis of the Orange Book Database", J. Med. Chem., 2007, 50:6665-72.
Gill and Bredt., Neuropsychopharmacology 36(1): 362-363 (2011).
Grove et al, "Positive modulators of the AMPA receptor", Expert Opinion on Therapeutic Patents., vol. 10, No. 10, Oct. 1, 2000, pp. 1539-1548.
Harrison, Brain 125:1428-1449, 2002.
Heckers and Konradi, Curr Top Behav Neurosci. 4:529-553, 2010.
Lazzaro et al. (2002). "Functional characterization of CP-465,022, a selective, noncompetitive AMPA receptor antagonist." Neuropharmacology 42(2): 143-153.
McNaughton et al., Behav Pharmacol 18: 329-346, 2007.

(Continued)

Primary Examiner — Niloofar Rahmani
(74) Attorney, Agent, or Firm — Thomas J. Dodd

(57) ABSTRACT

Provided herein are compounds of Formula (I), and pharmaceutically acceptable salts, N-oxides, or solvates thereof,

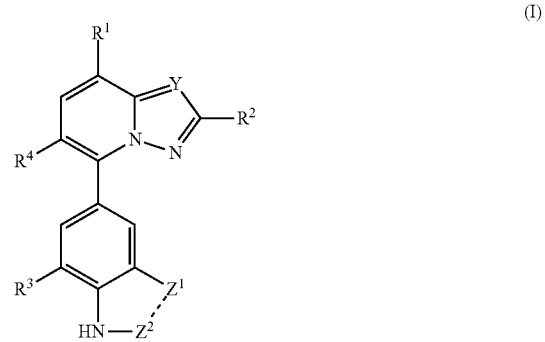

(I)

Also provided herein are pharmaceutical compositions comprising compounds of Formula (I) and methods of using compounds of Formula (I).

26 Claims, No Drawings

(56) References Cited

OTHER PUBLICATIONS

Nolen and Bloemkolk, *Neuropsychobiology,* 42 Suppl 1:11-7, 2000.
Pirotte Bi et al, "AMPA receptor positive allosteric modulators: a patent review", Expert Opinion on Therapeutic Patents, Informa Healthcare, GB, vol. 23, No. 5, May 1, 2013 (May 1, 2013), pp. 615-628.
Robinson et al., *J Med Chem.* 1996, 39 (1), 10-18.
Rogawski, Michael A., "Revisiting AMPA Receptors as an AntiEpileptic Drug Target" Epilepsy *Currents* 11.2 (2011).
S.M. Berge, et al., "Pharmaceutical Salts", *J Pharm Sci.,* 1977, 66:1-19.
Schobel et al., *Arch Gen Psych,* 66:938-946, 2009.
Shan, et al., *J Pharm Sci.* 1997, 86 (7), 765-767.
Shi et al (2009) "The stoichiometry of AMPA receptors and TARPs varies by neuronal cell type." *Neuron* 62(5): 633-640.
Small et al, *Nat. Rev. Neurosci.* 12:585-601, 2011.
Strange et al. (2006). "Functional characterisation of homomeric ionotropic glutamate receptors GluR1-GluR6 in a fluorescence-based high throughput screening assay." *Comb Chem High Throughput Screen* 9(2): 147-158.
Tregellas et al., *Am J Psychiatry* 171: 549-556, 2014.
Yeung et al., *Hippocampus* 23:278-286, 2013.
Yeung et al., *Neuropharmacology* 62: 155-160, 2012.

\* cited by examiner

FUSED BICYLIC PYRIDINE COMPOUNDS AND THEIR USE AS AMPA RECEPTOR MODULATORS

CROSS-REFERENCED TO RELATED APPLICATIONS

This application claims priority from U.S. Application No. 62/412,868, filed on Oct. 26, 2016, which is incorporated herein by reference.

FIELD OF THE INVENTION

The present invention is related to compounds having AMPA receptor modulating properties, pharmaceutical compositions comprising these compounds, chemical processes for preparing these compounds and their use in the treatment of diseases associated with AMPA receptor activity in animals, in particular humans.

BACKGROUND OF THE INVENTION

Glutamate is the primary excitatory neurotransmitter in mammalian brain. Glutamatergic signaling participates in a wide range of neural functions including learning and memory, long-term potentiation and synaptic plasticity.

Glutamate receptors can be divided into two families. The ionotropic glutamate receptors form ion channels that activate upon binding agonist, opening a pore through the plasma membrane through which cations can flow. The metabotropic glutamate receptors are G-protein-coupled receptors, activating intracellular signal transduction cascades. The ionotropic glutamate receptors can be further subdivided into four sub-families, based upon sequence homology and selectivity to exogenous agonists. These sub-families are the AMPA (α-amino-3-hydroxyl-5-methyl-4-isoxazole-propionic acid), NMDA (N-methyl-D-aspartate), kainate, and delta receptors.

The AMPA subtype of glutamate receptors are glutamate-gated ion channels expressed primarily on postsynaptic membranes of excitatory synapses in the central nervous system. AMPA receptors assemble as tetramers of subunits. Mammals express four AMPA-receptor subunits, called GluA1-GluA4. Each GluA subunit can be expressed in multiple splice variants; the two most prominent splice variants are called flop and flip. GluA subunits freely form functional homo- and hetero-tetramers. The majority of RNA encoding GluA2 subunits is edited post-transcriptionally, altering a genetically-encoded glutamine to arginine. This RNA editing causes AMPA receptors to preferentially form with two GluA2 units, and also prevents calcium entry through the activated receptor.

In their native environment, the pore-forming GluA tetramers directly or indirectly associate with numerous auxiliary proteins which modify the trafficking, localization, gating characteristics, and pharmacology of the AMPA receptor (AMPAR). These auxiliary subunits include cytoskeletal and anchoring proteins, other signaling proteins, and several intracellular and transmembrane proteins with unknown function. The wide variety of proteins which can participate in AMPA receptor complexes vastly increases the ability of a neuron to tune the response characteristics of its synapses.

Transmembrane AMPA Receptor Regulatory Proteins (TARPs) are a fairly recently discovered family of proteins that have been found to associate with and modulate the activity of AMPA receptors. (Gill and Bredt., *Neuropsychopharmacology* 36(1): 362-363 (2011). Several TARPs exhibit regiospecific expression in the brain, leading to physiological differentiation of the AMPA receptor activity. For example, TARP γ2-dependent AMPA receptors are primarily localized in the cerebellum and cerebral cortex while TARP γ8-dependent AMPA receptors are localized primarily in the hippocampus.

AMPA receptors mediate the majority of fast neurotransmission across synaptic gaps. Thus, inhibition or negative modulation of AMPA receptors is an attractive strategy for therapeutic intervention in CNS disorders characterized by excessive neuronal activity. However, since AMPA receptor activity is so ubiquitous within CNS, general antagonism affects most areas of the CNS resulting in undesired effects, such as ataxia, sedation, and/or dizziness, which are shared by all known general AMPA receptor antagonists.

Epilepsy affects over 50 million people world-wide, with 30-40% of treated patients being resistant to current pharmacotherapies and only about 8% of treated patients being maintained seizure free. Epilepsy is often defined as when a person has two or more unprovoked epileptic seizures. The International League Against Epilepsy (ILAE) defines an epileptic seizure as "a transient occurrence of signs and/or symptoms due to abnormal excessive or synchronous neuronal activity in the brain." Seizures are thought to have a number of underlying causalities which adds to the difficulty in treating epilepsy. Seizures have been divided according to their clinical presentation including generalized seizures (absence, atonic, tonic-clonic (grand mal), and myoclonic), simple and complex partial onset seizures, gelastic seizures, dacrystic seizures, and status epilepticus. Current therapies target a variety of mechanisms including GABA γ-aminobutyric acid) receptor agonism, T-type calcium channel blockers, sodium channel modulators, synaptic vesicle protein SV2A modulation, and inhibition of GABA transaminase. More recently, AMPA receptor antagonists have been investigated for treatment of seizures as well.

AMPA receptor antagonists are known anticonvulsant agents. Typically, AMPA receptor antagonists have very narrow therapeutic dosing windows; the doses needed to obtain anti-convulsant activity are close to or overlap with doses at which undesired effects are observed. (Michael A. Rogawski. "Revisiting AMPA Receptors as an AntiEpileptic Drug Target" Epilepsy *Currents* 11.2 (2011).) However, certain anticonvulsant agents such as Talampanel ((8R)-7-Acetyl-5-(4-aminophenyl)-8,9-dihydro-8-methyl-7H-1,3-dioxolo[4,5-h][2,3]benzodiazepine), selurampanel (BGG492) (N-[7-isopropyl-6-(2-methyl-2H-pyrazol-3-yl)-2,4-dioxo-1,4-dihydro-2H-qui-nazolin-3-yl]methanesulfonamide), and perampanel (5'-(2-cyanophenyl)-1'-phenyl-2,3'-bipyridinyl-6'(1'H)-one) are general (non-TARP dependent/non-selective) AMPA receptor antagonists. However, such general antagonism affects most areas of the CNS resulting in undesired effects.

Glutamate as an excitatory neurotransmitter has been known to induce neurotoxicity by, for example, abnormal excitation of central nerves. Neurotoxicity is an adverse structural or functional change in the nervous system, and can take the form of subtle or gross biochemical changes, axonal degeneration, dendritic pruning or sprouting, loss or rearrangement of synapses, or cell death. Numerous nervous diseases involve a neurotoxic component, including and not limited to cerebral ischemia, head injury, spinal cord injury, Alzheimer's disease, Parkinson's disease, amyotrophic lateral sclerosis (ALS), Huntington's chorea, AIDS nervous disturbance, epilepsy, mental disorder, mobility disturbance, pain, spasticity, nervous disturbance by toxin in food, various neurodegenerative diseases, various mental diseases, chronic pain, migraine, cancer pain and diabetic neuropathy.

Substances showing an antagonistic action to excitatory neurotransmitter receptors are potentially useful for the treatment of the above-mentioned conditions. For example, WO2000001376 suggests that inhibitors of the interaction of glutamate with the AMPA and/or kainate receptor complex could be useful in treating demyelinating disorders such as encephalitis, acute disseminated encephalomyelitis, acute demyelinating polyneuropathy (Guillain Barre syndrome), chronic inflammatory demyelinating polyneuropathy, multiple sclerosis, Marchifava-Bignami disease, central pontine myelinolysis, Devic syndrome, Balo disease, HIV- or HTLV-myelopathy, progressive multifocal leucoencephalopathy, a secondary demyelinating disorder; for example, CNS lupus erythematodes, polyarteritis nodosa, Sjogren syndrome, sarcoidosis, isolated cerebral vasculitis, etc.

Hippocampus links the limbic system to frontal cortex, thereby linking emotion to cognition (Small et al, *Nat. Rev. Neurosci.* 12:585-601, 2011). A meta-analysis of post-mortem neuro-pathology studies suggests that hippocampal volume is reduced in volume in patients with mood disorders (Harrison, *Brain* 125:1428-1449, 2002). Hippocampal neurons are particularly susceptible to stress-related atrophy. Pathological states characterized by excessive activity within hippocampus may be improved by a therapeutic intervention that selectively reduces hippocampal excitability. Modulation of neuronal excitability within hippocampus may provide a therapeutic benefit in mood disorders.

Excess activity in hippocampus has been observed in response to emotionally-charged stimuli in bipolar patients compared to controls (reviewed by Chen et al., *Bipolar Disord.*, 13:1-15, 2011). Chronic treatment with mood stabilizers such as lithium or valproate reduced AMPA receptor surface expression in hippocampus (Du et al., *J Neurosci* 28: 68-79, 2008). Tricyclic antidepressants can trigger mania in bipolar patients (Nolen and Bloemkolk, *Neuropsychobiology*, 42 Suppl 1:11-7, 2000); these treatments can increase AMPA receptor surface expression in hippocampus (Du et al., *J Neurosci* 24: 6578-6589, 2004.)

In Gray's Neuropsychological Theory of Anxiety (2003), septum and hippocampus form a 'behavioral inhibition system' activated during anxiety-provoking conflict situations. A corollary of this theory is that anxiolytic drugs act by suppressing this 'behavioral inhibition system'. Indeed, intrahippocampal micro-infusion of GABAA agonists is sufficient to replicate their anxiolytic effects (Engin and Treit, *Behav Pharmacol* 18:365-374, 2007). Traditional anxiolytics with a variety of mechanisms-of-action, including GABAA-receptor antagonists, 5-HT$_{1A}$ receptor antagonists, and SSRIs, suppress brainstem-stimulated theta rhythm within hippocampus (McNaughton et al., *Behav Pharmacol* 18: 329-346, 2007). Direct injection of inhibitors of neuronal excitability into rodent hippocampus was shown to reduce the hippocampal theta rhythm, and to produce an anxiolytic phenotype. Intrahippocampal administration of ZD7288, an HCN channel inhibitor, slowed brainstem-stimulated theta rhythm in anesthetized rat and also increased the amount of time that rats spent in the open arms of an elevated plus maze (Yeung et al., *Hippocampus* 23:278-286, 2013). Intrahippocampal administration of phenytoin, a voltage-gated sodium channel inhibitor and anticonvulsant, showed similar effects on brainstem-stimulated theta rhythm frequency in anesthetized rat and was anxiolytic in conscious rat (Yeung et al., *Neuropharmacology* 62: 155-160, 2012).

Hippocampal overactivity has been observed in patients suffering from schizophrenia (Heckers and Konradi, *Curr Top Behav Neurosci.* 4:529-553, 2010). The degree of hyperactivity was be positively correlated to the severity of the symptoms (Tregellas et al., *Am J Psychiatry* 171: 549-556, 2014). Hypermetabolism in hippocampus (esp. CA1 region) correlates with disease progression in at-risk individuals, and with disease severity in patients diagnosed with schizophrenia (Schobel et al., *Arch Gen Psych,* 66:938-946, 2009). This over-activity, combined with the sensitivity of hippocampal neurons to excitotoxic damage, may lead to the observed decrease in hippocampal volume in schizophrenic patients. Neuroprotection in prodromal and early stages may prevent progressive damage (Kaur and Cadenhead, *Curr Top Behav Neurosci,* 2010).

In view of the clinical importance of AMPA receptors, the identification of compounds that modulate AMPA receptor function represents an attractive avenue into the development of new therapeutic agents. Such compounds are provided herein.

SUMMARY OF THE INVENTION

Provided herein are compounds which are AMPA receptor modulators. In another aspect, provided herein are compounds which modulate certain TARP dependent AMPA receptors. The compounds described herein are suitable for treatment of conditions involving AMPA receptor activity, and for treatment of conditions involving selective modulation of TARP dependent AMPA receptor activity, thereby allowing for treatment of conditions such as, inter alfa, abnormal neurotransmission across synaptic gaps, excessive neuronal activity, abnormal excessive or synchronous neuronal activity in the brain, neurotoxicity (e.g., adverse structural or functional changes in the nervous system, subtle or gross biochemical changes, axonal degeneration, dendritic pruning or sprouting, loss or rearrangement of synapses, or cell death), neuronal excitability within hippocampus, neuronal excitotoxicity, hippocampal overactivity, and the like.

The invention is directed to the general and preferred embodiments defined, respectively, by the independent and dependent claims appended hereto, which are incorporated by reference herein. One aspect of this invention concerns compounds of Formula (I):

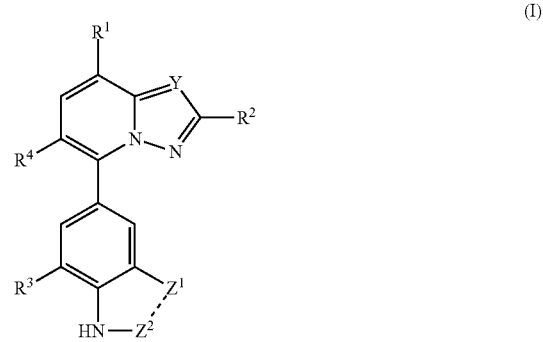

wherein
Y is N or CH;
R$^1$ is selected from the group consisting of: H, halo, and C$_{1-6}$alkyl;
R$^2$ is selected from the group consisting of: C$_{1-6}$alkyl, C$_{1-6}$haloalkyl, C$_{1-6}$alkoxy, and C$_{3-8}$cycloalkyl;

$R^3$ is selected from the group consisting of: H, halo, $C_{1-6}$alkyl, $C_{1-6}$alkoxy, CN, and $CF_3$;

$R^4$ is selected from the group consisting of: $C_{1-6}$alkyl, $C_{1-6}$haloalkyl, $C_{1-6}$alkoxy, phenyl substituted with F, and pyridyl; and

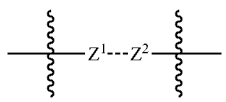

is selected from the group consisting of: —CH=N—, —CH$_2$—C(=O)—, and —S—C(=O)—; and pharmaceutically acceptable salts, N-oxides, or solvates of compounds of Formula (I).

Further embodiments are provided by pharmaceutically acceptable prodrugs of compounds of Formula (I), and pharmaceutically active metabolites of compounds of Formula (I).

In certain embodiments, the compounds of Formula (I) are compounds selected from those species described or exemplified in the detailed description below.

In a further aspect, the invention relates to enantiomers and diastereomers of the compounds of Formula (I), as well as their pharmaceutically acceptable salts.

In a further aspect, the invention relates to pharmaceutical compositions, comprising an effective amount of at least one compound selected from compounds of Formula (I), pharmaceutically acceptable salts, N-oxides or solvates of compounds of Formula (I), pharmaceutically acceptable prodrugs of compounds of Formula (I), and pharmaceutically active metabolites of Formula (I).

Pharmaceutical compositions according to the invention may further comprise one or more pharmaceutically acceptable excipients.

In another aspect, the chemical embodiments of the present invention are useful as AMPA receptor modulators. Thus, the invention is directed to a method for modulating AMPA receptor activity, including when such receptor is in a subject, comprising exposing AMPA receptor to an effective amount of at least one compound selected from compounds of Formula (I), pharmaceutically acceptable salts, N-oxides or solvates of compounds of Formula (I), pharmaceutically acceptable prodrugs of compounds of Formula (I), and pharmaceutically active metabolites of compounds of Formula (I).

In another aspect, the invention is directed to a method of treating a subject suffering from, or diagnosed with a disease, disorder, or medical condition mediated by AMPA receptor activity, comprising administering to the subject in need of such treatment an effective amount of at least one compound selected from compounds of Formula (I), pharmaceutically acceptable salts, N-oxides or solvates of compounds of Formula (I), pharmaceutically acceptable prodrugs of compounds of Formula (I), and pharmaceutically active metabolites of compounds of Formula (I). Additional embodiments of methods of treatment are set forth in the detailed description.

In another aspect, the method of studying isotopically labeled compounds in metabolic studies (preferably with $^{14}$C), reaction kinetic studies (with, for example $^2$H or $^3$H), detection or imaging techniques [such as positron emission tomography (PET) or single-photon emission computed tomography (SPECT)] including drug or substrate tissue distribution assays, or in radioactive treatment of patients. For example, an $^{18}$F or $^{11}$C labeled compound may be particularly preferred for PET or SPECT studies.

Additional embodiments of this invention include methods of making compounds of Formula (I), pharmaceutically acceptable salts, N-oxides or solvates of compounds of Formula (I), pharmaceutically acceptable prodrugs of compounds of Formula (I), and pharmaceutically active metabolites of Formula (I).

In another aspect provided herein are compounds of Formula (IA), and Formula (IB), as well as pharmaceutically acceptable salts, N-oxides or solvates of compounds of Formula (IA), and Formula (IB), pharmaceutically acceptable prodrugs of compounds of Formula (IA), and Formula (IB), and pharmaceutically active metabolites of Formula (IA), and Formula (IB).

In a further aspect, provided herein are pharmaceutical compositions, comprising an effective amount of a compound of Formula (IA), and Formula (IB), as well as pharmaceutically acceptable salts, N-oxides or solvates of compounds of Formula (IA), and Formula (IB), pharmaceutically acceptable prodrugs of compounds of Formula (IA), and Formula (IB), and pharmaceutically active metabolites of Formula (IA), and Formula (IB).

In a further aspect, provided herein are compounds of Formula (IA), and Formula (IB), as well as pharmaceutically acceptable salts, N-oxides or solvates of compounds of Formula (IA), and Formula (IB), pharmaceutically acceptable prodrugs of compounds of Formula (IA), and Formula (IB), and pharmaceutically active metabolites of Formula (IA), and Formula (IB), for the treatment of any condition described herein.

An object of the present invention is to overcome or ameliorate at least one of the disadvantages of the conventional methodologies and/or prior art, or to provide a useful alternative thereto.

Additional embodiments, features, and advantages of the invention will be apparent from the following detailed description and through practice of the invention.

DETAILED DESCRIPTION

In one aspect, provided herein are compounds of Formula (I),

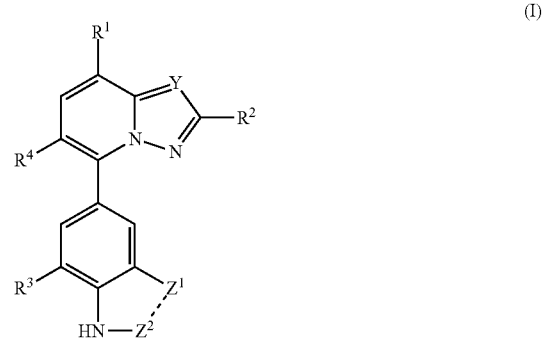

wherein
Y is N or CH;
$R^1$ is selected from the group consisting of: H, halo, and $C_{1-6}$alkyl;
$R^2$ is selected from the group consisting of: $C_{1-6}$alkyl, $C_{1-6}$haloalkyl, $C_{1-6}$alkoxy, and $C_{3-8}$cycloalkyl;

R³ is selected from the group consisting of: H, halo, C₁₋₆alkyl, C₁₋₆alkoxy, CN, and CF₃;

R⁴ is selected from the group consisting of: C₁₋₆alkyl, C₁₋₆haloalkyl, C₁₋₆alkoxy, phenyl substituted with F, and pyridyl; and

—⁂—Z¹---Z²—⁂— is selected from the group consisting of: —CH=N—, —CH₂—C(=O)—, and —S—C(=O)—; and pharmaceutically acceptable salts, N-oxides, or solvates thereof.

An additional embodiment of the invention is a compound of Formula (I) wherein Y is N.

An additional embodiment of the invention is a compound of Formula (I) wherein Y is CH.

An additional embodiment of the invention is a compound of Formula (I) wherein R¹ is H.

An additional embodiment of the invention is a compound of Formula (I) wherein R¹ is Cl or F.

An additional embodiment of the invention is a compound of Formula (I) wherein R¹ is CH₃ or CH₂CH₃.

An additional embodiment of the invention is a compound of Formula (I) wherein R² is CF₃, CHF₂, or CF₂(CH₃).

An additional embodiment of the invention is a compound of Formula (I) wherein R² is CH₃, CH₂CH₃, CH₂CH₂CH₃, or CH(CH₃)₂.

An additional embodiment of the invention is a compound of Formula (I) wherein R² is cyclopropyl.

An additional embodiment of the invention is a compound of Formula (I) wherein R² is OCH₃ or OCH₂CH₃.

An additional embodiment of the invention is a compound of Formula (I) wherein R³ is H, Cl, CH₃, or CH₂CH₃.

An additional embodiment of the invention is a compound of Formula (I) wherein R³ is OCH₃ or CN.

An additional embodiment of the invention is a compound of Formula (I) wherein R³ is CF₃.

An additional embodiment of the invention is a compound of Formula (I) wherein R⁴ is CF₃, CF₂(CH₃), or CHF₂.

An additional embodiment of the invention is a compound of Formula (I) wherein R⁴ is OCH₃.

An additional embodiment of the invention is a compound of Formula (I) wherein R⁴ is CH₂CH₃.

An additional embodiment of the invention is a compound of Formula (I) wherein R⁴ is 4-fluorophenyl, pyridin-3-yl, or pyridin-4-yl.

An additional embodiment of the invention is a compound of Formula (I) wherein

—⁂—Z¹---Z²—⁂— is —CH=N—.

An additional embodiment of the invention is a compound of Formula (I) wherein

—⁂—Z¹---Z²—⁂— is —CH₂—C(=O)—.

An additional embodiment of the invention is a compound of Formula (I) wherein

—⁂—Z¹---Z²—⁂— is —S—C(=O)—.

An additional embodiment of the invention is a compound of Formula (I) having the Formula (IA):

(IA)

wherein

R¹ is selected from the group consisting of: H, halo, CH₃, and CH₂CH₃;

R² is selected from the group consisting of: C₁₋₆alkyl, C₁₋₆haloalkyl, C₁₋₆alkoxy, and C₃₋₈cycloalkyl;

R⁴ is selected from the group consisting of: C₁₋₆alkyl, C₁₋₆haloalkyl, C₁₋₆alkoxy, phenyl substituted with F, and pyridyl; and R⁵ is selected from the group consisting of:

-continued

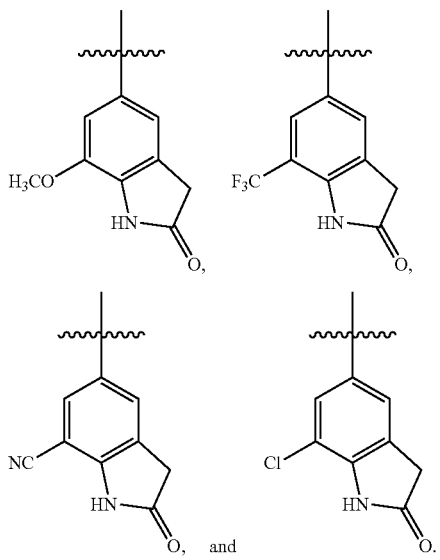

and pharmaceutically acceptable salts, N-oxides, or solvates thereof.

An additional embodiment of the invention is a compound of Formula (I) having the Formula (IA) wherein $R^1$ is H.

An additional embodiment of the invention is a compound of Formula (I) having the Formula (IA) wherein $R^2$ is $CF_3$.

An additional embodiment of the invention is a compound of Formula (I) having the Formula (IA) wherein $R^5$ is

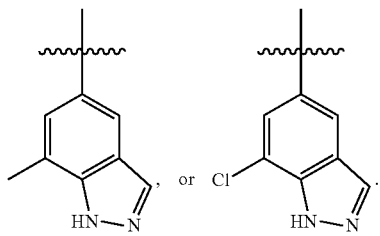 [SMILES: *c1cc(C)c2[nH]ncc2c1 ; *c1cc(Cl)c2[nH]ncc2c1]

An additional embodiment of the invention is a compound of Formula (I) having the Formula (IA) wherein $R^5$ is

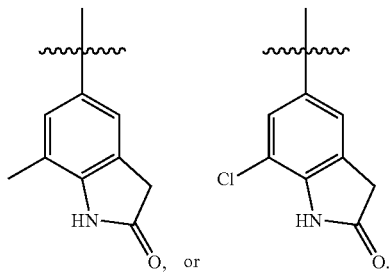 [SMILES: *c1cc(C)c2c(c1)CC(=O)N2 ; *c1cc(Cl)c2c(c1)CC(=O)N2]

An additional embodiment of the invention is a compound of Formula (I) having the Formula (IB):

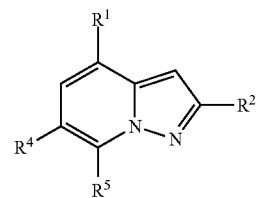

(IB)

wherein
$R^1$ is H, or $C_{1-6}$alkyl;
$R^2$ is selected from the group consisting of: $C_{1-6}$alkyl, $C_{1-6}$haloalkyl, and $C_{3-8}$cycloalkyl;
$R^4$ is $CF_2H$ or $CF_3$; and
$R^5$ is selected from the group consisting of:

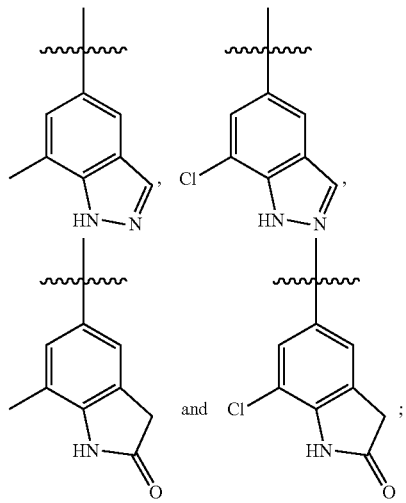

and pharmaceutically acceptable salts, N-oxides, or solvates thereof.

An additional embodiment of the invention is a compound of Formula (I) having the Formula (IB) wherein $R^2$ is $CF_3$, cyclopropyl, or $C_{1-6}$alkyl.

A further embodiment of the current invention is a compound as shown below in Table 1.

| Ex # | Compound Name |
|---|---|
| 1 | 5-(7-Chloro-1H-indazol-5-yl)-2,6-bis(trifluoromethyl)-[1,2,4]triazolo[1,5-a]pyridine; |
| 2 | 5-(7-Methyl-1H-indazol-5-yl)-2,6-bis(trifluoromethyl)-[1,2,4]triazolo[1,5-a]pyridine; |
| 3 | 5-(2,6-Bis(trifluoromethyl)-[1,2,4]triazolo[1,5-a]pyridin-5-yl)-7-chloroindolin-2-one; |
| 4 | 5-(2,6-Bis(trifluoromethyl)-[1,2,4]triazolo[1,5-a]pyridin-5-yl)-7-methylindolin-2-one; |
| 5 | 8-Chloro-5-(7-chloro-1H-indazol-5-yl)-2,6-bis(trifluoromethyl)-[1,2,4]triazolo[1,5-a]pyridine; |
| 6 | 5-(7-Chloro-1H-indazol-5-yl)-8-methyl-2,6-bis(trifluoromethyl)-[1,2,4]triazolo[1,5-a]pyridine; |
| 7 | 5-(7-Chloro-1H-indazol-5-yl)-2-(difluoromethyl)-6-(trifluoromethyl)-[1,2,4]triazolo[1,5-a]pyridine; |
| 8 | 5-(7-Methyl-1H-indazol-5-yl)-2-(difluoromethyl)-6-(trifluoromethyl)-[1,2,4]triazolo[1,5-a]pyridine; |
| 9 | 7-Chloro-5-(2-(difluoromethyl)-6-(trifluoromethyl)-[1,2,4]triazolo[1,5-a]pyridin-5-yl)indolin-2-one; |

| Ex # | Compound Name |
|---|---|
| 10 | 7-Methyl-5-(2-(difluoromethyl)-6-(trifluoromethyl)-[1,2,4]triazolo[1,5-a]pyridin-5-yl)indolin-2-one; |
| 11 | 2-(Difluoromethyl)-6-(trifluoromethyl)-5-(7-(trifluoromethyl)-1H-indazol-5-yl)-[1,2,4]triazolo[1,5-a]pyridine; |
| 12 | 5-(2-(Difluoromethyl)-6-(trifluoromethyl)-[1,2,4]triazolo[1,5-a]pyridin-5-yl)-7-methoxyindolin-2-one; |
| 13 | 5-(7-Chloro-1H-indazol-5-yl)-2-(difluoromethyl)-6-methoxy-[1,2,4]triazolo[1,5-a]pyridine; |
| 14 | 2-(Difluoromethyl)-6-methoxy-5-(7-methyl-1H-indazol-5-yl)-[1,2,4]triazolo[1,5-a]pyridine; |
| 15 | 2-(Difluoromethyl)-6-methoxy-5-(7-(trifluoromethyl)-1H-indazol-5-yl)-[1,2,4]triazolo[1,5-a]pyridine; |
| 16 | 5-(7-Chloro-1H-indazol-5-yl)-6-(difluoromethyl)-2-(trifluoromethyl)-[1,2,4]triazolo[1,5-a]pyridine; |
| 17 | 6-(Difluoromethyl)-5-(7-methyl-1H-indazol-5-yl)-2-(trifluoromethyl)-[1,2,4]triazolo[1,5-a]pyridine; |
| 18 | 7-Chloro-5-(6-(difluoromethyl)-2-(trifluoromethyl)-[1,2,4]triazolo[1,5-a]pyridin-5-yl)indolin-2-one; |
| 19 | 5-[6-(Difluoromethyl)-2-(trifluoromethyl)-[1,2,4]triazolo[1,5-a]pyridin-5-yl]-7-methyl-indolin-2-one; |
| 20 | 5-[6-(Difluoromethyl)-2-(trifluoromethyl)-[1,2,4]triazolo[1,5-a]pyridin-5-yl]-7-methoxy-indolin-2-one; |
| 21 | 5-(7-Chloro-1H-indazol-5-yl)-2-methyl-6-(trifluoromethyl)-[1,2,4]triazolo[1,5-a]pyridine; |
| 22 | 2-Methyl-5-(7-methyl-1H-indazol-5-yl)-6-(trifluoromethyl)-[1,2,4]triazolo[1,5-a]pyridine; |
| 23 | 7-Chloro-5-(2-methyl-6-(trifluoromethyl)-[1,2,4]triazolo[1,5-a]pyridin-5-yl)indolin-2-one; |
| 24 | 7-Methyl-5-(2-methyl-6-(trifluoromethyl)-[1,2,4]triazolo[1,5-a]pyridin-5-yl)indolin-2-one; |
| 25 | 5-(7-Chloro-1H-indazol-5-yl)-2-ethyl-6-(trifluoromethyl)-[1,2,4]triazolo[1,5-a]pyridine; |
| 26 | 2-Ethyl-5-(7-methyl-1H-indazol-5-yl)-6-(trifluoromethyl)-[1,2,4]triazolo[1,5-a]pyridine; |
| 27 | 7-Chloro-5-(2-ethyl-6-(trifluoromethyl)-[1,2,4]triazolo[1,5-a]pyridin-5-yl)indolin-2-one; |
| 28 | 5-(2-Ethyl-6-(trifluoromethyl)-[1,2,4]triazolo[1,5-a]pyridin-5-yl)-7-methylindolin-2-one; |
| 29 | 8-Chloro-5-(7-chloro-1H-indazol-5-yl)-2-ethyl-6-(trifluoromethyl)-[1,2,4]triazolo[1,5-a]pyridine; |
| 30 | 8-Chloro-2-ethyl-5-(7-methyl-1H-indazol-5-yl)-6-(trifluoromethyl)-[1,2,4]triazolo[1,5-a]pyridine; |
| 31 | 5-(7-Chloro-1H-indazol-5-yl)-2-ethyl-8-fluoro-6-(trifluoromethyl)-[1,2,4]triazolo[1,5-a]pyridine; |
| 32 | 7-Chloro-5-[2-ethyl-8-fluoro-6-(trifluoromethyl)-[1,2,4]triazolo[1,5-a]pyridin-5-yl]indolin-2-one; |
| 33 | 2-Cyclopropyl-8-fluoro-5-(7-methyl-1H-indazol-5-yl)-6-(trifluoromethyl)-[1,2,4]triazolo[1,5-a]pyridine; |
| 34 | 5-(7-Chloro-1H-indazol-5-yl)-8-fluoro-2-isopropyl-6-(trifluoromethyl)-[1,2,4]triazolo[1,5-a]pyridine; |
| 35 | 5-(7-Chloro-1H-indazol-5-yl)-2-ethyl-8-methyl-6-(trifluoromethyl)-[1,2,4]triazolo[1,5-]pyridine; |
| 36 | 5-(7-Chloro-1H-indazol-5-yl)-2-isopropyl-6-(trifluoromethyl)-[1,2,4]triazolo[1,5-a]pyridine; |
| 37 | 2-Isopropyl-5-(7-methyl-1H-indazol-5-yl)-6-(trifluoromethyl)-[1,2,4]triazolo[1,5-a]pyridine; |
| 38 | 5-(7-Chloro-1H-indazol-5-yl)-2-cyclopropyl-6-(trifluoromethyl)-[1,2,4]triazolo[1,5-a]pyridine; |
| 39 | 2-Cyclopropyl-5-(7-methyl-1H-indazol-5-yl)-6-(trifluoromethyl)-[1,2,4]triazolo[1,5-a]pyridine; |
| 40 | 7-Chloro-5-(2-cyclopropyl-6-(trifluoromethyl)-[1,2,4]triazolo[1,5-a]pyridin-5-yl)indolin-2-one; |
| 41 | 5-(2-Cyclopropyl-6-(trifluoromethyl)-[1,2,4]triazolo[1,5-a]pyridin-5-yl)-7-methylindolin-2-one; |
| 42 | 5-(7-Chloro-1H-indazol-5-yl)-2-(1,1-difluoroethyl)-6-(trifluoromethyl)-[1,2,4]triazolo[1,5-a]pyridine; |
| 43 | 5-(7-Chloro-1H-indazol-5-yl)-2-methoxy-6-(trifluoromethyl)-[1,2,4]triazolo[1,5-a]pyridine; |
| 44 | 5-(7-Chloro-1H-indazol-5-yl)-6-(difluoromethyl)-2-ethyl-[1,2,4]triazolo[1,5-a]pyridine; |
| 45 | 6-(Difluoromethyl)-2-ethyl-5-(7-methyl-1H-indazol-5-yl)-[1,2,4]triazolo[1,5-a]pyridine; |
| 46 | 7-Chloro-5-(6-(difluoromethyl)-2-ethyl-[1,2,4]triazolo[1,5-a]pyridin-5-yl)indolin-2-one; |
| 47 | 5-(6-(Difluoromethyl)-2-ethyl-[1,2,4]triazolo[1,5-a]pyridin-5-yl)-7-methylindolin-2-one; |
| 48 | 5-(7-Chloro-1H-indazol-5-yl)-2-cyclopropyl-6-(difluoromethyl)-[1,2,4]triazolo[1,5-a]pyridine; |
| 49 | 2-Cyclopropyl-6-(difluoromethyl)-5-(7-methyl-1H-indazol-5-yl)-[1,2,4]triazolo[1,5-a]pyridine; |
| 50 | 5-(7-Chloro-1H-indazol-5-yl)-6-methoxy-2-(trifluoromethyl)-[1,2,4]triazolo[1,5-a]pyridine; |
| 51 | 6-Methoxy-5-(7-methyl-1H-indazol-5-yl)-2-(trifluoromethyl)-[1,2,4]triazolo[1,5-a]pyridine; |
| 52 | 6-Ethyl-5-(7-methyl-1H-indazol-5-yl)-2-(trifluoromethyl)-[1,2,4]triazolo[1,5-a]pyridine; |
| 53 | 5-(7-Chloro-1H-indazol-5-yl)-6-(1,1-difluoroethyl)-2-(trifluoromethyl)-[1,2,4]triazolo[1,5-a]pyridine; |
| 54 | 6-(2-(Difluoromethyl)-6-(trifluoromethyl)-[1,2,4]triazolo[1,5-a]pyridin-5-yl)benzo[d]thiazol-2(3H)-one; |
| 55 | 6-(4-Fluorophenyl)-5-(7-methyl-1H-indazol-5-yl)-2-(trifluoromethyl)-[1,2,4]triazolo[1,5-a]pyridine; |
| 56 | 6-(4-Fluorophenyl)-5-(1H-indazol-5-yl)-2-(trifluoromethyl)-[1,2,4]triazolo[1,5-a]pyridine; |
| 57 | 5-(6-(4-Fluorophenyl)-2-(trifluoromethyl)-[1,2,4]triazolo[1,5-a]pyridin-5-yl)-7-methylindolin-2-one; |
| 58 | 5-(7-Methyl-1H-indazol-5-yl)-6-(pyridin-3-yl)-2-(trifluoromethyl)-[1,2,4]triazolo[1,5-a]pyridine; |
| 59 | 5-(7-Methyl-1H-indazol-5-yl)-6-(pyridin-4-yl)-2-(trifluoromethyl)-[1,2,4]triazolo[1,5-a]pyridine; |
| 60 | 6-(4-Fluorophenyl)-2-methyl-5-(7-methyl-1H-indazol-5-yl)-[1,2,4]triazolo[1,5-a]pyridine; |
| 61 | 2-Ethyl-6-(4-fluorophenyl)-5-(7-methyl-1H-indazol-5-yl)-[1,2,4]triazolo[1,5-a]pyridine; |
| 62 | 2-Cyclopropyl-6-(4-fluorophenyl)-5-(7-methyl-1H-indazol-5-yl)-[1,2,4]triazolo[1,5-a]pyridine; |
| 63 | 5-(2,6-Bis(trifluoromethyl)pyrazolo[1,5-a]pyridin-7-yl)-7-chloro-1H-indazole; |
| 64 | 5-(2,6-Bis(trifluoromethyl)pyrazolo[1,5-a]pyridin-7-yl)-7-methyl-1H-indazole; |
| 65 | 5-(2,6-Bis(trifluoromethyl)pyrazolo[1,5-a]pyridin-7-yl)-7-methylindolin-2-one; |
| 66 | 5-(2,6-Bis(trifluoromethyl)pyrazolo[1,5-a]pyridin-7-yl)-7-chloroindolin-2-one; |
| 67 | 5-(2-Cyclopropyl-6-(trifluoromethyl)pyrazolo[1,5-a]pyridin-7-yl)-7-methylindolin-2-one; |
| 68 | 5-(2-Cyclopropyl-6-(trifluoromethyl)pyrazolo[1,5-a]pyridin-7-yl)-7-chloroindolin-2-one; |
| 69 | 5-(2-Cyclopropyl-6-(trifluoromethyl)pyrazolo[1,5-a]pyridin-7-yl)-7-methyl-1H-indazole; |
| 70 | 7-Chloro-5-(2-cyclopropyl-6-(trifluoromethyl)pyrazolo[1,5-a]pyridin-7-yl)-1H-indazole; |
| 71 | 5-(2-Isopropyl-6-(trifluoromethyl)pyrazolo[1,5-a]pyridin-7-yl)-7-methylindolin-2-one; |
| 72 | 5-(2-Isopropyl-6-(trifluoromethyl)pyrazolo[1,5-a]pyridin-7-yl)-7-chloroindolin-2-one; |
| 73 | 7-Chloro-5-(2-isopropyl-6-(trifluoromethyl)pyrazolo[1,5-a]pyridin-7-yl)-1H-indazole; and |
| 74 | 5-(2-Isopropyl-6-(trifluoromethyl)pyrazolo[1,5-a]pyridin-7-yl)-7-methyl-1H-indazole; and | pharmaceutically acceptable salts, N-oxides, or solvates thereof.

A further embodiment of the current invention is a compound as shown below in Table 2.

TABLE 2

| Ex # | Compound Name |
|---|---|
| 75 | 7-Chloro-5-(2-cyclopropyl-8-methyl-6-(trifluoromethyl)-[1,2,4]triazolo[1,5-a]pyridin-5-yl)indolin-2-one; |
| 76 | 2-Cyclopropyl-8-methyl-5-(7-methyl-1H-indazol-5-yl)-6-(trifluoromethyl)-[1,2,4]triazolo[1,5-a]pyridine; |
| 77 | 5-(7-Chloro-1H-indazol-5-yl)-6-(difluoromethyl)-8-methyl-2-(trifluoromethyl)-[1,2,4]triazolo[1,5-a]pyridine; |
| 78 | 5-(7-Chloro-1H-indazol-5-yl)-2-(difluoromethyl)-8-methyl-6-(trifluoromethyl)-[1,2,4]triazolo[1,5-a]pyridine; |
| 79 | 2-(Difluoromethyl)-8-methyl-5-(7-methyl-1H-indazol-5-yl)-6-(trifluoromethyl)-[1,2,4]triazolo[1,5-a]pyridine; |

TABLE 2-continued

| Ex # | Compound Name |
|---|---|
| 80 | 5-(7-Chloro-1H-indazol-5-yl)-2-cyclopropyl-8-ethyl-6-(trifluoromethyl)-[1,2,4]triazolo[1,5-a]pyridine; |
| 81 | 2-Cyclopropyl-8-ethyl-5-(7-methyl-1H-indazol-5-yl)-6-(trifluoromethyl)-[1,2,4]triazolo[1,5-a]pyridine; |
| 82 | 5-(2-Cyclopropyl-8-ethyl-6-(trifluoromethyl)-[1,2,4]triazolo[1,5-a]pyridin-5-yl)-7-methylindolin-2-one; |
| 83 | 5-(7-Chloro-1H-indazol-5-yl)-8-methyl-2-propyl-6-(trifluoromethyl)-[1,2,4]triazolo[1,5-a]pyridine; |
| 84 | 8-Methyl-5-(7-methyl-1H-indazol-5-yl)-2-propyl-6-(trifluoromethyl)-[1,2,4]triazolo[1,5-a]pyridine; |
| 85 | 7-Methyl-5-(8-methyl-2-propyl-6-(trifluoromethyl)-[1,2,4]triazolo[1,5-a]pyridin-5-yl)indolin-2-one; |
| 86 | 2-(Difluoromethyl)-8-methyl-5-(7-methyl-1H-indazol-5-yl)-6-(trifluoromethyl)-[1,2,4]triazolo[1,5-a]pyridine; |
| 87 | 5-(7-Chloro-1H-indazol-5-yl)-2-(difluoromethyl)-8-ethyl--6-(trifluoromethyl)[1,2,4]triazolo[1,5-a]pyridine; |
| 88 | 2-(Difluoromethyl)-8-ethyl-5-(7-methyl-1H-indazol-5-yl)-6-(trifluoromethyl)-[1,2,4]triazolo[1,5-a]pyridine; |
| 89 | 5-(7-Chloro-1H-indazol-5-yl)-2,8-diethyl-6-(trifluoromethyl)-[1,2,4]triazolo[1,5-a]pyridine; |
| 90 | 2,8-Diethyl-5-(7-methyl-1H-indazol-5-yl)-6-(trifluoromethyl)-[1,2,4]triazolo[1,5-a]pyridine; |
| 91 | 5-(7-Chloro-1H-indazol-5-yl)-6-(difluoromethyl)-8-ethyl-2-(trifluoromethyl)-[1,2,4]triazolo[1,5-a]pyridine; |
| 92 | 6-(Difluoromethyl)-8-ethyl-5-(7-methyl-1H-indazol-5-yl)-2-(trifluoromethyl)-[1,2,4]triazolo[1,5-a]pyridine; |
| 93 | 5-(7-Chloro-1H-indazol-5-yl)-2-cyclopropyl-6-(difluoromethyl)-8-ethyl-[1,2,4]triazolo[1,5-a]pyridine; |
| 94 | 2-Cyclopropyl-6-(difluoromethyl)-8-ethyl-5-(7-methyl-1H-indazol-5-yl)-[1,2,4]triazolo[1,5-a]pyridine; |
| 95 | 6-(Difluoromethyl)-8-methyl-5-(7-methyl-1H-indazol-5-yl)-2-propyl-[1,2,4]triazolo[1,5-a]pyridine; |
| 96 | 8-Chloro-5-(7-chloro-1H-indazol-5-yl)-2-propyl-6-(trifluoromethyl)-[1,2,4]triazolo[1,5-a]pyridine; |
| 97 | 7-Chloro-5-(8-chloro-2-propyl-6-(trifluoromethyl)-[1,2,4]triazolo[1,5-a]pyridin-5-yl)indolin-2-one; |
| 98 | 5-(8-Chloro-2-propyl-6-(trifluoromethyl)-[1,2,4]triazolo[1,5-a]pyridin-5-yl)-7-methylindolin-2-one; |
| 99 | 5-(2-Cyclopropyl-8-methyl-6-(trifluoromethyl)-[1,2,4]triazolo[1,5-a]pyridin-5-yl)-7-methylindolin-2-one; |
| 100 | 7-Chloro-5-(2-ethyl-8-methyl-6-(trifluoromethyl)-[1,2,4]triazolo[1,5-a]pyridin-5-yl)indolin-2-one; |
| 101 | 2-Ethyl-8-methyl-6-(trifluoromethyl)-5-(7-(trifluoromethyl)-1H-indazol-5-yl)-[1,2,4]triazolo[1,5-a]pyridine; |
| 102 | 5-(2-Ethyl-8-methyl-6-(trifluoromethyl)-[1,2,4]triazolo[1,5-a]pyridin-5-yl)-7-(trifluoromethyl)indolin-2-one; |
| 103 | 7-Chloro-5-(2-ethyl-8-methyl-6-(trifluoromethyl)-[1,2,4]triazolo[1,5-a]pyridin-5-yl)indolin-2-one; |
| 104 | 7-Ethyl-5-(8-methyl-2,6-bis(trifluoromethyl)-[1,2,4]triazolo[1,5-a]pyridin-5-yl)indolin-2-one; |
| 105 | 7-Methyl-5-(8-methyl-2,6-bis(trifluoromethyl)-[1,2,4]triazolo[1,5-a]pyridin-5-yl)indolin-2-one; |
| 106 | 7-Methoxy-5-(8-methyl-2,6-bis(trifluoromethyl)-[1,2,4]triazolo[1,5-a]pyridin-5-yl)indolin-2-one; |
| 107 | 8-Methyl-5-(7-methyl-1H-indazol-5-yl)-2,6-bis(trifluoromethyl)-[1,2,4]triazolo[1,5-a]pyridine; |
| 108 | 5-(8-Methyl-2,6-bis(trifluoromethyl)-[1,2,4]triazolo[1,5-a]pyridin-5-yl)-2-oxoindoline-7-carbonitrile; |
| 109 | 5-(7-Chloro-1H-indazol-5-yl)-6-(difluoromethyl)-8-methyl-2-(trifluoromethyl)-[1,2,4]triazolo[1,5-a]pyridine; |
| 110 | 7-Chloro-5-(6-(difluoromethyl)-8-methyl-2-(trifluoromethyl)-[1,2,4]triazolo[1,5-a]pyridin-5-yl)indolin-2-one; |
| 111 | 6-(Difluoromethyl)-8-methyl-5-(7-methyl-1H-indazol-5-yl)-2-(trifluoromethyl)-[1,2,4]triazolo[1,5-a]pyridine; |
| 112 | 5-(7-Chloro-1H-indazol-5-yl)-2-cyclopropyl-6-(difluoromethyl)-8-methyl-[1,2,4]triazolo[1,5-a]pyridine; |
| 113 | 7-Chloro-5-(2-cyclopropyl-6-(difluoromethyl)-8-methyl-[1,2,4]triazolo[1,5-a]pyridin-5-yl)indolin-2-one; |
| 114 | 2-Cyclopropyl-6-(difluoromethyl)-8-methyl-5-(7-methyl-1H-indazol-5-yl)-[1,2,4]triazolo[1,5-a]pyridine; |
| 115 | 5-(7-Chloro-1H-indazol-5-yl)-6-(difluoromethyl)-2-ethyl-8-methyl-[1,2,4]triazolo[1,5-a]pyridine; |
| 116 | 5-(7-Chloro-1H-indazol-5-yl)-2,8-dimethyl-6-(trifluoromethyl)-[1,2,4]triazolo[1,5-a]pyridine; |
| 117 | 5-(7-Chloro-1H-indazol-5-yl)-2-ethoxy-8-methyl-6-(trifluoromethyl)-[1,2,4]triazolo[1,5-a]pyridine; |
| 118 | 7-Chloro-5-(2-cyclopropyl-6-(trifluoromethyl)pyrazolo[1,5-a]pyridin-7-yl)-1H-indazole; |
| 119 | 5-[6-(Difluoromethyl)-2-(trifluoromethyl)pyrazolo[1,5-a]pyridin-7-yl]-7-methyl-indolin-2-one; |
| 120 | 7-(7-Chloro-1H-indazol-5-yl)-6-(difluoromethyl)-2-(trifluoromethyl)pyrazolo[1,5-a]pyridine; |
| 121 | 6-(Difluoromethyl)-7-(7-methyl-1H-indazol-5-yl)-2-(trifluoromethyl)pyrazolo[1,5-a]pyridine; |
| 122 | 5-[6-(Difluoromethyl)-4-methyl-2-(trifluoromethyl)pyrazolo[1,5-a]pyridin-7-yl]-7-methyl-indolin-2-one; |
| 123 | 6-(Difluoromethyl)-4-methyl-7-(7-methyl-1H-indazol-5-yl)-2-(trifluoromethyl)pyrazolo[1,5-a]pyridine; |
| 124 | 7-Chloro-5-[6-(difluoromethyl)-4-methyl-2-(trifluoromethyl)pyrazolo[1,5-a]pyridin-7-yl]indolin-2-one; and |
| 125 | 7-(7-Chloro-1H-indazol-5-yl)-6-(difluoromethyl)-4-methyl-2-(trifluoromethyl)pyrazolo[1,5-a]pyridine; and | pharmaceutically acceptable salts, N-oxides, or solvates thereof.

An additional embodiment of the invention is a pharmaceutical composition comprising:

(A) an effective amount of at least one compound of Formula (I):

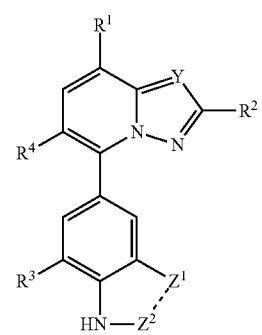

(I)

wherein
Y is N or CH;
R$^1$ is selected from the group consisting of: H, halo, and C$_{1-6}$alkyl;
R$^2$ is selected from the group consisting of: C$_{1-6}$alkyl, C$_{1-6}$haloalkyl, C$_{1-6}$alkoxy, and C$_{3-8}$cycloalkyl;
R$^3$ is selected from the group consisting of: H, halo, C$_{1-6}$alkyl, C$_{1-6}$alkoxy, CN, and CF$_3$;
R$^4$ is selected from the group consisting of: C$_{1-6}$alkyl, C$_{1-6}$haloalkyl, C$_{1-6}$alkoxy, phenyl substituted with F, and pyridyl; and

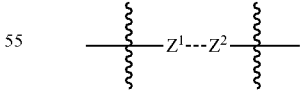

is selected from the group consisting of: —CH=N—, —CH$_2$—C(=O)—, and —S—C(=O)—; and
pharmaceutically acceptable salts, N-oxides or solvates of compounds of Formula (I); and
(B) at least one pharmaceutically acceptable excipient.

An additional embodiment of the invention is a pharmaceutical composition comprising and effective amount of at least one compound of Formula (IA) and Formula (IB), as well as pharmaceutically acceptable salts, N-oxides or solvates of compounds of Formula (IA) and Formula (IB), pharmaceutically acceptable prodrugs of compounds of Formula (IA) and Formula (IB), and pharmaceutically active metabolites of Formula (IA) and Formula (IB); and at least one pharmaceutically acceptable excipient.

An additional embodiment of the invention is a pharmaceutical composition comprising and effective amount of at least one compound in Table 1, as well as pharmaceutically acceptable salts, N-oxides or solvates of compounds of Table 1, pharmaceutically acceptable prodrugs of compounds of Table 1, and pharmaceutically active metabolites of Table 1; and at least one pharmaceutically acceptable excipient.

An additional embodiment of the invention is a pharmaceutical composition comprising and effective amount of at least one compound in Table 2, as well as pharmaceutically acceptable salts, N-oxides or solvates of compounds of Table 2, pharmaceutically acceptable prodrugs of compounds of Table 2, and pharmaceutically active metabolites of Table 2; and at least one pharmaceutically acceptable excipient.

Also within the scope of the invention are isotopic variations of compounds of Formula (I) as well as Formula (IA) and Formula (IB), such as, e.g., deuterated compounds of Formula (I) as well as Formula (IA) and Formula (IB). Also within the scope of the invention are the pharmaceutically acceptable salts, N-oxides or solvates of the isotopic variations of the compounds of Formula (I) as well as Formula (IA) and Formula (IB). Also within the scope of the invention are the pharmaceutically acceptable prodrugs of the isotopic variations of the compounds of Formula (I) as well as Formula (IA) and Formula (IB), and pharmaceutically active metabolites of the isotopic variations of the compounds of Formula (I) as well as Formula (IA) and Formula (IB).

An additional embodiment of the invention is a method of treating a subject suffering from or diagnosed with a disease, disorder, or medical condition mediated by AMPA receptor activity, comprising administering to a subject in need of such treatment an effective amount of at least one compound selected from compounds of Formula (I):

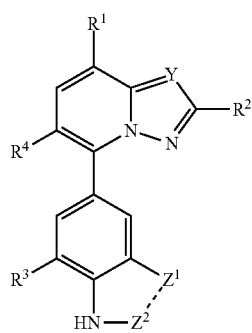

wherein
Y is N or CH;
$R^1$ is selected from the group consisting of: H, halo, and $C_{1-6}$alkyl;
$R^2$ is selected from the group consisting of: $C_{1-6}$alkyl, $C_{1-6}$haloalkyl, $C_{1-6}$alkoxy, and $C_{3-8}$cycloalkyl;
$R^3$ is selected from the group consisting of: H, halo, $C_{1-6}$alkyl, $C_{1-6}$alkoxy, CN, and $CF_3$;

$R^4$ is selected from the group consisting of: $C_{1-6}$alkyl, $C_{1-6}$haloalkyl, $C_{1-6}$alkoxy, phenyl substituted with E and pyridyl; and

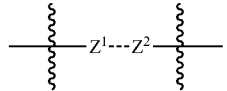

is selected from the group consisting of: —CH═N—, —$CH_2$—C(═O)—, and —S—C(═O)—; and
pharmaceutically acceptable salts, N-oxides, or solvates thereof, to a subject in need thereof.

An additional embodiment of the invention is a method of treating a subject suffering from or diagnosed with a disease, disorder, or medical condition mediated by AMPA receptor activity, comprising administering to a subject in need of such treatment an effective amount of at least one compound selected from compounds of Formula (IA) and Formula (IB), as well as pharmaceutically acceptable salts, N-oxides or solvates of compounds of Formula (IA) and Formula (IB), pharmaceutically acceptable prodrugs of compounds of Formula (IA) and Formula (IB), and pharmaceutically active metabolites of Formula (IA) and Formula (IB).

The AMPA subtype of glutamate receptors are glutamate-gated ion channels expressed primarily on postsynaptic membranes of excitatory synapses in the central nervous system. AMPA receptors assemble as tetramers of subunits. Mammals express four AMPA-receptor subunits, called GluA1-GluA4. In their native environment, the pore-forming GluA tetramers directly or indirectly associate with numerous auxiliary proteins. The wide variety of proteins which can participate in AMPA receptor complexes vastly increases the ability of a neuron to tune the response characteristics of its synapses.

AMPA receptors mediate the majority of fast neurotransmission across synaptic gaps. However, since AMPA receptor activity is so ubiquitous within CNS, general antagonism affects most areas of the CNS resulting in undesired effects, such as ataxia, sedation, and/or dizziness, which are shared by all known general AMPA receptor antagonists.

In order to circumvent the problems with side-effects noted above, it is hereby proposed that selective modulation of TARP γ8-associated AMPA receptor complexes provides effective therapeutic agents which also avoid or reduce the side-effects associated with the administration of non-selective AMPA receptor modulators. TARP γ8 is primarily expressed in the hippocampus and the cortex, while TARP γ2 is primarily expressed in the cerebellum. In one aspect, selective modulation of TARP γ8 potentially avoids modulation of TARP γ2-associated AMPA receptor complexes, which are more prevalent in the cerebellum, thereby reducing side effects associated with general (non-TARP dependent/non-selective) AMPA antagonism.

For instance, selective modulation of TARP γ8-associated AMPA receptor complexes is contemplated as an effective anti-seizure/anti-epileptic therapeutic with reduced the side effects (e.g. sedation, ataxis, and/or dizziness) associated with general (non-TARP dependent/non-selective) AMPA antagonists. Similarly, reduction of hippocampal over-excitability, using selective modulation of TARP γ8-associated AMPA receptor complexes may lead to normalization of the symptoms of schizophrenia, and it may protect against the subsequent decline in hippocampal volume. In a further instance, selectively attenuating hippocampal excitability, via selective modulation of TARP γ8-associated AMPA receptor complexes, could provide therapeutic benefit to patients with bipolar disorder. Likewise, selective modulation of TARP γ8-associated AMPA receptor complexes within the hippocampus may provide an effective anxiolytic.

Accordingly, provided herein are compounds which are selective modulators of TARP γ8-associated AMPA receptor complexes. Compounds which are selective modulators of TARP γ8-associated AMPA receptor complexes ameliorate and/or eliminate the side effects (e.g. sedation, ataxis, and/or dizziness) of general (non-TARP dependent/non-selective) AMPA receptor modulators.

In some embodiments, provided herein are compounds which selectively modulate the activity of complexes comprising GluA1 receptors associated with the protein TARP γ8.

In one embodiment, selective modulation of TARP γ8-associated AMPA receptor complexes refers to selective antagonism of TARP γ8-associated AMPA receptor complexes. In another embodiment, selective modulation of TARP γ8-associated AMPA receptor complexes refers to selective partial inhibition of TARP γ8-associated AMPA receptor complexes. In a further embodiment, selective antagonism of TARP γ8-associated AMPA receptor complexes refers to negative allosteric modulation of TARP γ8-associated AMPA receptor complexes. The invention relates to methods of using the compounds described herein to treat subjects diagnosed with or suffering from a disease, disorder, or condition mediated by AMPA receptor activity. These methods are accomplished by administering to the subject a compound of the invention. In some embodiments, the compounds described herein are selective for modulation of TARP γ8 associated AMPA receptor complexes.

An AMPA receptor mediated disease, disorder or condition includes and is not limited to cerebral ischemia, head injury, spinal cord injury, Alzheimer's disease, Parkinson's disease, amyotrophic lateral sclerosis (ALS), Huntington's chorea, AIDS nervous disturbance, epilepsy, mental disorder, mobility disturbance, pain, spasticity, nervous disturbance by toxin in food, various neurodegenerative diseases, various mental diseases, chronic pain, migraine, cancer pain, diabetic neuropathy, encephalitis, acute disseminated encephalomyelitis, acute demyelinating polyneuropathy (Guillain Barre syndrome), chronic inflammatory demyelinating polyneuropathy, multiple sclerosis, Marchifava-Bignami disease, central pontine myelinolysis, Devic syndrome, Balo disease, HIV- or HTLV-myelopathy, progressive multifocal leucoencephalopathy, a secondary demyelinating disorder (for example, CNS lupus erythematodes, polyarteritis nodosa, Sjogren syndrome, sarcoidosis, isolated cerebral vasculitis, etc.), schizophrenia, depression, and bipolar disorder. In some embodiments, the AMPA mediated disease, disorder or condition is depression, anxiety disorders, anxious depression, post traumatic stress disorder, epilepsy, schizophrenia, prodromal schizophrenia, or a cognitive disorder.

In one group of embodiments, an AMPA receptor mediated disease, disorder or condition is a condition related to hippocampal hyperexcitability. In one embodiment, provided herein are methods to selectively dampen hippocampal activity in the brain comprising administration of compounds described herein to a subject in need thereof. In one embodiment, provided herein are methods for the treatment of an AMPA receptor mediated disease, disorder or condition which is depression comprising administration of compounds described herein to a subject in need thereof. As used herein, depression includes and is not limited to major depression, psychotic depression, persistent depressive disorder, post-partum depression, seasonal affective disorder, depression which is resistant to other anti-depressants, manic-depression associated with bipolar disorder, post traumatic stress disorder, and the like. In another embodiment, provided herein are methods for the treatment of an AMPA receptor mediated disease, disorder or condition which is post traumatic stress disorder (PTSD) comprising administration of compounds described herein to a subject in need thereof. In another embodiment, provided herein are methods for the treatment of an AMPA receptor mediated disease, disorder or condition which is epilepsy, schizophrenia, or prodromal schizophrenia comprising administration of compounds described herein to a subject in need thereof. In yet another embodiment, provided herein are methods for the treatment of an AMPA receptor mediated disease, disorder or condition which is a cognitive disorder comprising administration of compounds described herein to a subject in need thereof. As used herein, cognitive disorder includes and is not limited to mild cognitive impairment, amnesia, dementia, delirium, cognitive impairment associated with anxiety disorders, mood disorders, psychotic disorders and the like.

In some embodiments, administration of a compound of the invention, or pharmaceutically acceptable salt thereof, is effective in preventing the disease; for example, preventing a disease, condition or disorder in an individual who may be predisposed to the disease, condition or disorder but does not yet experience or display the pathology or symptomatology of the disease.

Additional embodiments, features, and advantages of the invention will be apparent from the following detailed description and through practice of the invention.

The invention may be more fully appreciated by reference to the following description, including the following glossary of terms and the concluding examples. For the sake of brevity, the disclosures of the publications, including patents, cited in this specification are herein incorporated by reference.

Certain Definitions

As used herein, the terms "including", "containing" and "comprising" are used herein in their open, non-limiting sense.

The term "alkyl" refers to a straight- or branched-chain alkyl group having from 1 to 12 carbon atoms in the chain. In some embodiments, an alkyl group is a $C_1$-$C_6$alkyl group. In some embodiments, an alkyl group is a $C_1$-$C_4$alkyl group. Examples of alkyl groups include methyl (Me) ethyl (Et), n-propyl, isopropyl, butyl, isobutyl, sec-butyl, tert-butyl (tBu), pentyl, isopentyl, tert-pentyl, hexyl, isohexyl, and groups that in light of the ordinary skill in the art and the teachings provided herein would be considered equivalent to any one of the foregoing examples.

The term "haloalkyl" refers to a straight- or branched-chain alkyl group having from 1 to 12 carbon atoms in the chain and having at least one of the hydrogens replaced with a halogen. In some embodiments, a haloalkyl group is a $C_1$-$C_6$haloalkyl group. In some embodiments, a haloalkyl group is a $C_1$-$C_4$haloalkyl group. One exemplary substitutent is fluoro. Preferred substituted alkyl groups of the invention include trihalogenated alkyl groups such as trifluoromethyl groups. Haloalkyl includes and is not limited to —$CF_3$, —$CH_2F$, —$CHF_2$, —$CH_2C_1$, —$CH_2$—$CF_3$, and the like.

The term "cycloalkyl" refers to monocyclic, non-aromatic hydrocarbon groups having from 3 to 8 carbon atoms.

Examples of cycloalkyl groups include, for example, cyclopropyl, cyclobutyl, cyclopentyl, cyclohexyl, and the like.

The term "halogen" represents chlorine, fluorine, bromine, or iodine. The term "halo" represents chloro, fluoro, bromo, or iodo.

The term "substituted" means that the specified group or moiety bears one or more substituents. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system. In cases where a specified moiety or group is not expressly noted as being optionally substituted or substituted with any specified substituent, it is understood that such a moiety or group is intended to be unsubstituted.

The terms "para", "meta", and "ortho" have the meanings as understood in the art. Thus, for example, a fully substituted phenyl group has substituents at both "ortho"(o) positions adjacent to the point of attachment of the phenyl ring, both "meta" (m) positions, and the one "para" (p) position across from the point of attachment. To further clarify the position of substituents on the phenyl ring, the 2 different ortho positions will be designated as ortho and ortho' and the 2 different meta positions as meta and meta' as illustrated below.

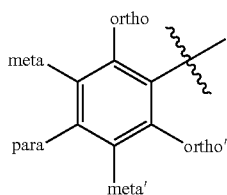

When referring to substituents on a pyridyl group, the terms "para", "meta", and "ortho" refer to the placement of a substituent relative to the point of attachment of the pyridyl ring. For example the structure below is described as 3-pyridyl with the $X^1$ substituent in the ortho position, the $X^2$ substituent in the meta position, and $X^3$ substituent in the para position:

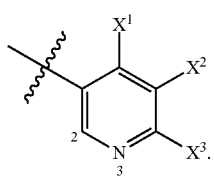

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently.

The terms "buffered" solution or "buffer" solution are used herein interchangeably according to their standard meaning. Buffered solutions are used to control the pH of a medium, and their choice, use, and function is known to those of ordinary skill in the art. See, for example, G. D. Considine, ed., Van Nostrand's Encyclopedia of Chemistry, p. 261, $5^{th}$ ed. (2005), describing, inter alia, buffer solutions and how the concentrations of the buffer constituents relate to the pH of the buffer. For example, a buffered solution is obtained by adding $MgSO_4$ and $NaHCO_3$ to a solution in a 10:1 w/w ratio to maintain the pH of the solution at about 7.5.

Any formula given herein is intended to represent compounds having structures depicted by the structural formula as well as certain variations or forms. In particular, compounds of any formula given herein may have asymmetric centers and therefore exist in different enantiomeric forms. All optical isomers of the compounds of the general formula, and mixtures thereof, are considered within the scope of the formula. Thus, any formula given herein is intended to represent a racemate, one or more enantiomeric forms, one or more diastereomeric forms, one or more atropisomeric forms, and mixtures thereof. Furthermore, certain structures may exist as geometric isomers (i.e., cis and trans isomers), as tautomers, or as atropisomers.

It is also to be understood that compounds that have the same molecular formula but differ in the nature or sequence of bonding of their atoms or the arrangement of their atoms in space are termed "isomers."

Stereoisomers that are not mirror images of one another are termed "diastereomers" and those that are non-superimposable mirror images of each other are termed "enantiomers." When a compound has an asymmetric center, for example, it is bonded to four different groups, and a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+)- or (−)-isomers respectively). A chiral compound can exist as either an individual enantiomer or as a mixture thereof. A mixture containing equal proportions of the enantiomers is called a "racemic mixture."

"Tautomers" refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenyl nitromethane, that are likewise formed by treatment with acid or base.

Tautomeric forms may be relevant to the attainment of the optimal chemical reactivity and biological activity of a compound of interest.

Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

A wavy line " ~~~ " indicates the point of attachment to the rest of the molecule.

Additionally, any formula given herein is intended to refer also to hydrates, solvates, and polymorphs of such compounds, and mixtures thereof, even if such forms are not listed explicitly.

Certain compounds of Formula (I) (as well as Formulas (IA), and (IB)), or pharmaceutically acceptable salts of Formula (I) (as well as Formulas (IA), and (IB)) may be obtained as solvates. Solvates include those formed from the interaction or complexation of compounds of the invention with one or more solvents, either in solution or as a solid or crystalline form. In some embodiments, the solvent is water and the solvates are hydrates. In addition, certain crystalline forms of compounds of Formula (I) (as well as Formulas (IA), and (IB)) or pharmaceutically acceptable salts of compounds of Formula (I) (as well as Formulas (IA), and (IB)) may be obtained as co-crystals. In certain embodiments of the invention, compounds of Formula (I) (as well as Formulas (IA), and (IB)) were obtained in a crystalline form. In other embodiments, crystalline forms of compounds of Formula (I) (as well as Formulas (IA), and (IB)) were cubic in nature. In other embodiments, pharmaceutically acceptable salts of compounds of Formula (I) (as well as Formulas (IA), and (IB)) were obtained in a crystalline form. In still other embodiments, compounds of Formula (I) (as well as Formulas (IA), and (IB)) were obtained in one of several polymorphic forms, as a mixture of crystalline forms, as a polymorphic form, or as an amorphous form. In other embodiments, compounds of Formula (I) (as well as Formulas (IA), and (IB)) convert in solution between one or more crystalline forms and/or polymorphic forms.

Reference to a compound herein stands for a reference to any one of: (a) the actually recited form of such compound, and (b) any of the forms of such compound in the medium in which the compound is being considered when named. For example, reference herein to a compound such as R—COOH, encompasses reference to any one of, for example, R—COOH$_{(s)}$, R—COOH$_{(sol)}$, and R—COO$^-$$_{(sol)}$. In this example, R—COOH$_{(s)}$ refers to the solid compound, as it could be for example in a tablet or some other solid pharmaceutical composition or preparation; R—COOH$_{(sol)}$ refers to the undissociated form of the compound in a solvent; and R—COO$^-$$_{(sol)}$ refers to the dissociated form of the compound in a solvent, such as the dissociated form of the compound in an aqueous environment, whether such dissociated form derives from R—COOH, from a salt thereof, or from any other entity that yields R—COO$^-$ upon dissociation in the medium being considered. In another example, an expression such as "exposing an entity to compound of formula R—COOH" refers to the exposure of such entity to the form, or forms, of the compound R—COOH that exists, or exist, in the medium in which such exposure takes place. In still another example, an expression such as "reacting an entity with a compound of formula R—COOH" refers to the reacting of (a) such entity in the chemically relevant form, or forms, of such entity that exists, or exist, in the medium in which such reacting takes place, with (b) the chemically relevant form, or forms, of the compound R—COOH that exists, or exist, in the medium in which such reacting takes place. In this regard, if such entity is for example in an aqueous environment, it is understood that the compound R—COOH is in such same medium, and therefore the entity is being exposed to species such as R—COOH$_{(aq)}$ and/or R—COO$^-$$_{(aq)}$, where the subscript "(aq)" stands for "aqueous" according to its conventional meaning in chemistry and biochemistry. A carboxylic acid functional group has been chosen in these nomenclature examples; this choice is not intended, however, as a limitation but it is merely an illustration. It is understood that analogous examples can be provided in terms of other functional groups, including but not limited to hydroxyl, basic nitrogen members, such as those in amines, and any other group that interacts or transforms according to known manners in the medium that contains the compound. Such interactions and transformations include, but are not limited to, dissociation, association, tautomerism, solvolysis, including hydrolysis, solvation, including hydration, protonation, and deprotonation. No further examples in this regard are provided herein because these interactions and transformations in a given medium are known by any one of ordinary skill in the art.

In another example, a zwitterionic compound is encompassed herein by referring to a compound that is known to form a zwitterion, even if it is not explicitly named in its zwitterionic form. Terms such as zwitterion, zwitterions, and their synonyms zwitterionic compound(s) are standard IUPAC-endorsed names that are well known and part of standard sets of defined scientific names. In this regard, the name zwitterion is assigned the name identification CHEBI27369 by the Chemical Entities of Biological Interest (ChEBI) dictionary of molecular entities. As generally well known, a zwitterion or zwitterionic compound is a neutral compound that has formal unit charges of opposite sign. Sometimes these compounds are referred to by the term "inner salts". Other sources refer to these compounds as "dipolar ions", although the latter term is regarded by still other sources as a misnomer. As a specific example, aminoethanoic acid (the amino acid glycine) has the formula $H_2NCH_2COOH$, and it exists in some media (in this case in neutral media) in the form of the zwitterion $^+H_3NCH_2COO^-$. Zwitterions, zwitterionic compounds, inner salts and dipolar ions in the known and well established meanings of these terms are within the scope of this invention, as would in any case be so appreciated by those of ordinary skill in the art. Because there is no need to name each and every embodiment that would be recognized by those of ordinary skill in the art, no structures of the zwitterionic compounds that are associated with the compounds of this invention are given explicitly herein. They are, however, part of the embodiments of this invention. No further examples in this regard are provided herein because the interactions and transformations in a given medium that lead to the various forms of a given compound are known by any one of ordinary skill in the art.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorus, sulfur, fluorine, chlorine, and iodine such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$, $^{125}I$, respectively. Such isotopically labeled compounds are useful in metabolic studies (preferably with $^{14}C$), reaction kinetic studies (with, for example $^2H$ or $^3H$), detection or imaging techniques [such as positron emission tomography (PET) or single-photon emission computed tomography (SPECT)] including drug or substrate tissue distribution assays, or in radioactive treatment of patients. In particular, an $^{18}F$ or $^{11}C$ labeled compound may be particularly preferred for PET or SPECT studies. Further, substitution with heavier isotopes such as deuterium or tritium (i.e., $^2H$, $^3H$) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

When referring to any formula given herein, the selection of a particular moiety from a list of possible species for a specified variable is not intended to define the same choice of the species for the variable appearing elsewhere. In other words, where a variable appears more than once, the choice of the species from a specified list is independent of the choice of the species for the same variable elsewhere in the formula, unless stated otherwise.

According to the foregoing interpretive considerations on assignments and nomenclature, it is understood that explicit reference herein to a set implies, where chemically meaningful and unless indicated otherwise, independent reference to embodiments of such set, and reference to each and every one of the possible embodiments of subsets of the set referred to explicitly.

By way of a first example on substituent terminology, if substituent $S^1_{example}$ is one of $S_1$ and $S_2$, and substituent $S^2_{example}$ is one of $S_3$ and $S_4$, then these assignments refer to embodiments of this invention given according to the choices $S^1_{example}$ is $S_1$ and $S^2_{example}$ is $S_3$; $S^1_{example}$ is $S_1$ and $S^2_{example}$ is $S_4$; $S^1_{example}$ is $S_2$ and $S^2_{example}$ is $S_3$; $S^1_{example}$ is $S_2$ and $S^2_{example}$ is $S_4$; and equivalents of each one of such choices. The shorter terminology "$S^1_{example}$ is one of $S_1$ and $S_2$, and $S^2_{example}$ is one of $S_3$ and $S_4$" is accordingly used herein for the sake of brevity, but not by way of limitation. The foregoing first example on substituent terminology, which is stated in generic terms, is meant to illustrate the various substituent assignments described herein. The foregoing convention given herein for substituents extends, when applicable, to members such as $R^1$, $R^2$, $R^3$, $R^4$, $R^{4a}$, $R^{4b}$, $R^{4c}$, $R^{4d}$, $R^5$, $R^{5a}$, Hal, PG, $Z^1$, and $Z^2$, and any other generic substituent symbol used herein.

Furthermore, when more than one assignment is given for any member or substituent, embodiments of this invention comprise the various groupings that can be made from the listed assignments, taken independently, and equivalents thereof. By way of a second example on substituent terminology, if it is herein described that substituent $S_{example}$ is one of $S_1$, $S_2$, and $S_3$, this listing refers to embodiments of this invention for which $S_{example}$ is $S_1$; $S_{example}$ is $S_2$; $S_{example}$ is $S_3$; $S_{example}$ is one of $S_1$ and $S_2$; $S_{example}$ is one of $S_1$ and $S_3$; $S_{example}$ is one of $S_2$ and $S_3$; $S_{example}$ is one of $S_1$, $S_2$ and $S_3$; and $S_{example}$ is any equivalent of each one of these choices. The shorter terminology "$S_{example}$ is one of $S_1$, $S_2$, and $S_3$" is accordingly used herein for the sake of brevity, but not by way of limitation. The foregoing second example on substituent terminology, which is stated in generic terms, is meant to illustrate the various substituent assignments described herein. The foregoing convention given herein for substituents extends, when applicable, to members such $R^1$, $R^2$, $R^3$, $R^4$, $R^{4a}$, $R^{4b}$, $R^{4c}$, $R^{4d}$, $R^5$, $R^{5a}$, Hal, PG, $Z^1$, and $Z^2$, and any other generic substituent symbol used herein.

The nomenclature "$C_{i-j}$" with j>i, when applied herein to a class of substituents, is meant to refer to embodiments of this invention for which each and every one of the number of carbon members, from i to j including i and j, is independently realized. By way of example, the term $C_{1-3}$ refers independently to embodiments that have one carbon member ($C_1$), embodiments that have two carbon members ($C_2$), and embodiments that have three carbon members ($C_3$).

The term $C_{n-m}$alkyl refers to an aliphatic chain, whether straight or branched, with a total number N of carbon members in the chain that satisfies n≤N≤m, with m>n. Any disubstituent referred to herein is meant to encompass the various attachment possibilities when more than one of such possibilities are allowed. For example, reference to disubstituent -A-B-, where A≠B, refers herein to such disubstituent with A attached to a first substituted member and B attached to a second substituted member, and it also refers to such disubstituent with A attached to the second substituted member and B attached to the first substituted member.

The invention includes also pharmaceutically acceptable salts of the compounds of Formula (I) (as well as Formulas (IA), and (IB)), preferably of those described above and of the specific compounds exemplified herein, and methods of treatment using such salts.

The term "pharmaceutically acceptable" means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

A "pharmaceutically acceptable salt" is intended to mean a salt of a free acid or base of compounds represented by Formula (I) (as well as Formulas (IA), and (IB)) that are non-toxic, biologically tolerable, or otherwise biologically suitable for administration to the subject. It should possess the desired pharmacological activity of the parent compound. See, generally, G. S. Paulekuhn, et al., "Trends in Active Pharmaceutical Ingredient Salt Selection based on Analysis of the Orange Book Database", *J. Med. Chem.*, 2007, 50:6665-72, S. M. Berge, et al., "Pharmaceutical Salts", *J Pharm Sci.*, 1977, 66:1-19, and *Handbook of Pharmaceutical Salts, Properties, Selection, and Use*, Stahl and Wermuth, Eds., Wiley-VCH and VHCA, Zurich, 2002. Examples of pharmaceutically acceptable salts are those that are pharmacologically effective and suitable for contact with the tissues of patients without undue toxicity, irritation, or allergic response. A compound of Formula (I) (as well as Formulas (IA), and (IB)) may possess a sufficiently acidic group, a sufficiently basic group, or both types of functional groups, and accordingly react with a number of inorganic or organic bases, and inorganic and organic acids, to form a pharmaceutically acceptable salt.

Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, y-hydroxybutyrates, glycolates, tartrates, methane-sulfonates, propanesulfonates, naphthalene-1-sulfonates, naphthalene-2-sulfonates, and mandelates.

When the compounds of Formula (I) (as well as Formulas (IA), and (IB)) contain a basic nitrogen, the desired pharmaceutically acceptable salt may be prepared by any suitable method available in the art. For example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid, glutaric acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, ethanesulfonic acid, any compatible mixture of acids such as those given as examples herein, and any other acid and mixture thereof that are regarded as equivalents or acceptable substitutes in light of the ordinary level of skill in this technology.

When the compound of Formula (I) (as well as Formulas (IA), and (IB)) is an acid, such as a carboxylic acid or sulfonic acid, the desired pharmaceutically acceptable salt may be prepared by any suitable method, for example, treatment of the free acid with an inorganic or organic base, such as an amine (primary, secondary or tertiary), an alkali metal hydroxide, alkaline earth metal hydroxide, any compatible mixture of bases such as those given as examples herein, and any other base and mixture thereof that are regarded as equivalents or acceptable substitutes in light of the ordinary level of skill in this technology. Illustrative examples of suitable salts include organic salts derived from amino acids, such as N-methyl-D-glucamine, lysine, choline, glycine and arginine, ammonia, carbonates, bicarbonates, primary, secondary, and tertiary amines, and cyclic amines, such as tromethamine, benzylamines, pyrrolidines, piperidine, morpholine, and piperazine, and inorganic salts derived from sodium, calcium, potassium, magnesium, manganese, iron, copper, zinc, aluminum, and lithium.

The invention also relates to pharmaceutically acceptable prodrugs of Formula (I) (as well as Formulas (IA), and (IB)), and treatment methods employing such pharmaceutically acceptable prodrugs. The term "prodrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the compound of Formula (I) (as well as Formulas (IA), and (IB)). A "pharmaceutically acceptable prodrug" is a prodrug that is non-toxic, biologically tolerable, and otherwise biologically suitable for administration to the subject. Illustrative procedures for the selection and preparation of suitable prodrug derivatives are described, for example, in "Design of Prodrugs", ed. H. Bundgaard, Elsevier, 1985.

Exemplary prodrugs include compounds having an amino acid residue, or a polypeptide chain of two or more (e.g., two, three or four) amino acid residues, covalently joined through an amide or ester bond to a free amino, hydroxyl, or carboxylic acid group of a compound of Formula (I) (as well as Formulas (IA), and (IB)). Examples of amino acid residues include the twenty naturally occurring amino acids, commonly designated by three letter symbols, as well as 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone.

Additional types of prodrugs may be produced, for instance, by derivatizing free carboxyl groups of structures of Formula (I) (as well as Formulas (IA), and (IB)) as amides or alkyl esters. Examples of amides include those derived from ammonia, primary $C_{1-6}$alkyl amines and secondary di($C_{1-6}$alkyl) amines. Secondary amines include 5- or 6-membered heterocycloalkyl or heteroaryl ring moieties. Examples of amides include those that are derived from ammonia, $C_{1-3}$alkyl primary amines, and di($C_{1-2}$alkyl) amines. Examples of esters of the invention include $C_{1-7}$alkyl, $C_{5-7}$cycloalkyl, phenyl, and phenyl($C_{1-6}$alkyl) esters. Preferred esters include methyl esters. Prodrugs may also be prepared by derivatizing free hydroxy groups using groups including hemisuccinates, phosphate esters, dimethylaminoacetates, and phosphoryloxymethyloxycarbonyls, following procedures such as those outlined in Fleisher et al., *Adv. Drug Delivery Rev.* 1996, 19, 115-130. Carbamate derivatives of hydroxy and amino groups may also yield prodrugs. Carbonate derivatives, sulfonate esters, and sulfate esters of hydroxy groups may also provide prodrugs. Derivatization of hydroxy groups as (acyloxy)methyl and (acyloxy)ethyl ethers, wherein the acyl group may be an alkyl ester, optionally substituted with one or more ether, amine, or carboxylic acid functionalities, or where the acyl group is an amino acid ester as described above, is also useful to yield prodrugs. Prodrugs of this type may be prepared as described in Robinson et al., *J Med Chem.* 1996, 39 (1), 10-18. Free amines can also be derivatized as amides, sulfonamides or phosphonamides. All of these prodrug moieties may incorporate groups including ether, amine, and carboxylic acid functionalities.

The present invention also relates to pharmaceutically active metabolites of the compounds of Formula (I) (as well as Formulas (IA), and (IB)), which may also be used in the methods of the invention. A "pharmaceutically active metabolite" means a pharmacologically active product of metabolism in the body of a compound of Formula (I) or salt thereof. Prodrugs and active metabolites of a compound may be determined using routine techniques known or available in the art. See, e.g., Bertolini, et al., *J Med Chem.* 1997, 40, 2011-2016; Shan, et al., *J Pharm Sci.* 1997, 86 (7), 765-767; Bagshawe, *Drug Dev Res.* 1995, 34, 220-230; Bodor, *Adv Drug Res.* 1984, 13, 224-331; Bundgaard, *Design of Prodrugs* (Elsevier Press, 1985); and Larsen, *Design and Application of Prodrugs, Drug Design and Development* (Krogsgaard-Larsen, et al., eds., Harwood Academic Publishers, 1991).

The compounds of Formula (I) (as well as Formulas (IA), and (IB)) and their pharmaceutically acceptable salts, pharmaceutically acceptable prodrugs, and pharmaceutically active metabolites of the present invention are useful as modulators of the AMPA receptor in the methods of the invention. As such modulators, the compounds may act as antagonists, agonists, or inverse agonists. The term "modulators" include both inhibitors and activators, where "inhibitors" refer to compounds that decrease, prevent, inactivate, desensitize, or down-regulate the AMPA receptor expression or activity, and "activators" are compounds that increase, activate, facilitate, sensitize, or up-regulate AMPA receptor expression or activity.

The term "pharmaceutically acceptable vehicle" refers to a diluent, adjuvant, excipient or carrier with which a compound of the invention is administered. A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of a agent and that is compatible therewith. Examples of excipients include calcium carbonate, calcium phosphate, various sugars and types of starch, cellulose derivatives, gelatin, vegetable oils, and polyethylene glycols.

The term "subject" includes humans. The terms "human," "patient," and "subject" are used interchangeably herein.

The term "treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder.

In treatment methods according to the invention, a therapeutically effective amount of a pharmaceutical agent according to the invention is administered to a subject suffering from or diagnosed as having such a disease, disorder, or condition. A "therapeutically effective amount" means an amount or dose sufficient to generally bring about the desired therapeutic or prophylactic benefit in patients in need of such treatment for the designated disease, disorder, or condition. Effective amounts or doses of the compounds of the present invention may be ascertained by routine methods such as modeling, dose escalation studies or clinical trials, and by taking into consideration routine factors, e.g., the mode or route of administration or drug delivery, the pharmacokinetics of the compound, the severity and course of the disease, disorder, or condition, the subject's previous or ongoing therapy, the subject's health status and response to drugs, and the judgment of the treating physician. An example of a dose is in the range of from about 0.001 to about 200 mg of compound per kg of subject's body weight per day, preferably about 0.05 to 100 mg/kg/day, or about 1 to 35 mg/kg/day, in single or divided dosage units (e.g., BID, TID, QID). For a 70-kg human, an illustrative range for a suitable dosage amount is from about 0.05 to about 7 g/day, or about 10 mg to about 2.5 g/day.

"Compounds of the present invention," and equivalent expressions, are meant to embrace compounds of the Formula (I) (as well as Formulas (IA), and (IB) as described herein, which expression includes the pharmaceutically acceptable salts, and the solvates, e.g., hydrates, where the context so permits. Similarly, reference to intermediates, whether or not they themselves are claimed, is meant to embrace their salts, and solvates, where the context so permits.

Once improvement of the patient's disease, disorder, or condition has occurred, the dose may be adjusted for preventative or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms.

In addition, the compounds of the invention may be used in combination with additional active ingredients in the treatment of the above conditions. The additional active ingredients may be coadministered separately with a compound of the invention or included with such an agent in a pharmaceutical composition according to the invention. In an exemplary embodiment, additional active ingredients are those that are known or discovered to be effective in the treatment of conditions, disorders, or diseases mediated by orexin activity, such as another orexin modulator or a compound active against another target associated with the particular condition, disorder, or disease. The combination may serve to increase efficacy (e.g., by including in the combination a compound potentiating the potency or effectiveness of an active agent according to the invention), decrease one or more side effects, or decrease the required dose of the active agent according to the invention.

The compounds of the invention are used, alone or in combination with one or more additional active ingredients, to formulate pharmaceutical compositions of the invention. A pharmaceutical composition of the invention comprises: (a) an effective amount of at least one compound in accordance with the invention; and (b) a pharmaceutically acceptable excipient.

Delivery forms of the pharmaceutical compositions containing one or more dosage units of the active agents may be prepared using suitable pharmaceutical excipients and compounding techniques known or that become available to those skilled in the art. The compositions may be administered in the inventive methods by a suitable route of delivery, e.g., oral, parenteral, rectal, topical, or ocular routes, or by inhalation.

The preparation may be in the form of tablets, capsules, sachets, dragees, powders, granules, lozenges, powders for reconstitution, liquid preparations, or suppositories. Preferably, the compositions are formulated for intravenous infusion, topical administration, or oral administration.

For oral administration, the compounds of the invention can be provided in the form of tablets or capsules, or as a solution, emulsion, or suspension. To prepare the oral compositions, the compounds may be formulated to yield a dosage of, e.g., from about 0.05 to about 100 mg/kg daily, or from about 0.05 to about 35 mg/kg daily, or from about 0.1 to about 10 mg/kg daily. For example, a total daily dosage of about 5 mg to 5 g daily may be accomplished by dosing once, twice, three, or four times per day.

Oral tablets may include a compound according to the invention mixed with pharmaceutically acceptable excipients such as inert diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are suitable disintegrating agents. Binding agents may include starch and gelatin. The lubricating agent, if present, may be magnesium stearate, stearic acid or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, compounds of the invention may be mixed with a solid, semi-solid, or liquid diluent. Soft gelatin capsules may be prepared by mixing the compound of the invention with water, an oil such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions or syrups or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The active agents of this invention may also be administered by non-oral routes. For example, the compositions may be formulated for rectal administration as a suppository. For parenteral use, including intravenous, intramuscular, intraperitoneal, or subcutaneous routes, the compounds of the invention may be provided in sterile aqueous solutions or suspensions, buffered to an appropriate pH and isotonicity or in parenterally acceptable oil. Suitable aqueous vehicles include Ringer's solution and isotonic sodium chloride. Such forms will be presented in unit-dose form such as ampules or disposable injection devices, in multi-dose forms such as vials from which the appropriate dose may be withdrawn, or in a solid form or pre-concentrate that can be used to prepare an injectable formulation. Illustrative infusion doses may range from about 1 to 1000 .mu·g/kg/minute of compound, admixed with a pharmaceutical carrier over a period ranging from several minutes to several days.

For topical administration, the compounds may be mixed with a pharmaceutical carrier at a concentration of about 0.1% to about 10% of drug to vehicle. Another mode of administering the compounds of the invention may utilize a patch formulation to affect transdermal delivery. Compounds of the invention may alternatively be administered in methods of this invention by inhalation, via the nasal or oral routes, e.g., in a spray formulation also containing a suitable carrier.

Exemplary compounds useful in methods of the invention will now be described by reference to the illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Unless otherwise specified, the variables are as defined above in reference to Formula (I), (as well as Formulas (IA), and (IB)). Reactions may be performed between the melting point and the reflux temperature of the solvent, and preferably between 0° C. and the reflux temperature of the solvent. Reactions may be heated employing conventional heating or microwave heating. Reactions may also be conducted in sealed pressure vessels above the normal reflux temperature of the solvent.

Abbreviations

Table 3. Abbreviations and acronyms used herein include the following.

TABLE 3

| Term | Acronym/Abbreviation |
|---|---|
| Acetonitrile | ACN |
| Acetic Acid | AcOH |
| Chloroform | $CHCl_3$ |
| Diatomaceous Earth | Celite ® |
| Cesium carbonate | $Cs_2C_2O_3$ |
| Cesium fluoride | CsF |
| Copper (II) acetate | $Cu(OAc)_2$ |
| Copper (II) sulfate | $Cu_2SO_4$ |
| Diethylaminosulfur trifluoride | DAST |
| 1,2-Dichloroethane | DCE |
| Dichloromethane | DCM |
| N,N-Dimethylformamide | DMF |
| 2,3-Dichloro-5,6-dicyano-1,4-benzoquinone | DDQ |
| 1,3-Dimethyl-3,4,5,6-tetrahydro-2-pyrimidinone | DMPU |
| Dimethylsulfoxide | DMSO |
| Diethyl ether | $Et_2O$ |
| Ethyl acetate | EtOAc |
| Ethanol | EtOH |
| Hydrochloric acid | HCl |
| High-Pressure Liquid Chromatography | HPLC |
| Potassium carbonate | $K_2CO_3$ |
| Potassium acetate | KOAc |
| Magnesium sulfate | MgSO4 |
| Methyl tert-butylether | MTBE |
| Sodium fluoride | NaF |
| Sodium hydroxide | NaOH |
| Sodium sulfate | $Na_2SO_4$ |
| Ammonia | $NH_3$ |
| Nitrogen gas | $N_2$ |
| para-Toluene sulfonate | OTs |
| Tris(dibenzylideneacetone)dipalladium(0) | $Pd_2(dba)_3$ |
| [1,1'-Bis(diphenylphosphino)ferrocene]dichloropalladium(II) | $Pd(dppf)Cl_2$ |
| [1,1'-Bis(diphenylphosphino)ferrocene]dichloropalladium(II) dichloromethane complex | $Pd(dppf)Cl_2$—$CH_2Cl_2$ |
| Tetrakis(triphenylphosphine) palladium(0) | $Pd(PPh_3)_4$ |
| Room temperature | rt |
| Trifluoroacetic acid | TFA |
| Tetrahydrofuran | THF |
| Chloro(2-dicyclohexylphosphino-2',4',6'-triisopropyl-1,1'-biphenyl)[2-(2'-amino-1,1'-biphenyl)]palladium(II) | XPhos-Pd-G2 |

PREPARATIVE EXAMPLES

Exemplary compounds useful in methods of the invention will now be described by reference to the illustrative synthetic schemes for their general preparation below and the specific examples to follow.

SCHEME 1

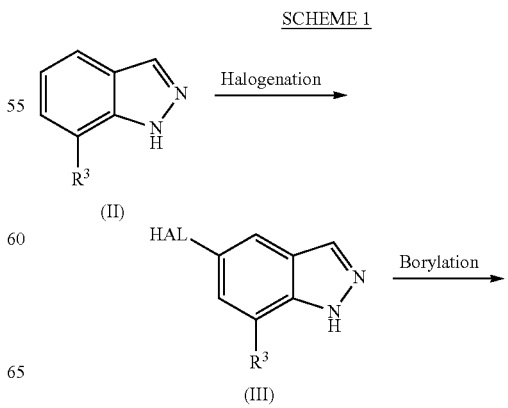

-continued

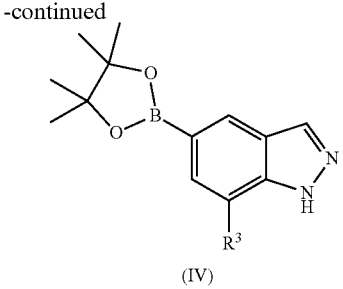

(IV)

According to SCHEME 1, a compound of formula (IV), where $R^3$ is H, halo, $CH_3$ or $CF_3$, is commercially available or synthetically accessible from a compound of formula (II), where $R^3$ is defined as above. An indazole compound of formula (II) is treated with an electrophilic halogen source such as bromine, in a suitable solvent such as TFA, to provide a compound of formula (III). A compound of formula (III) is treated with a borylating agent such as bis(pinacolato)diboron, in the presence of a palladium catalyst such as Pd(dppf)Cl$_2$, and the like, and a suitable base, such as potassium acetate, and the like, employing conventional heating, at a temperature such as 100° C., in a solvent such as 1,4-dioxane, and the like, to provide a compound of formula (IV), where $R^3$ is H, halo, $CH_3$, or $CF_3$.

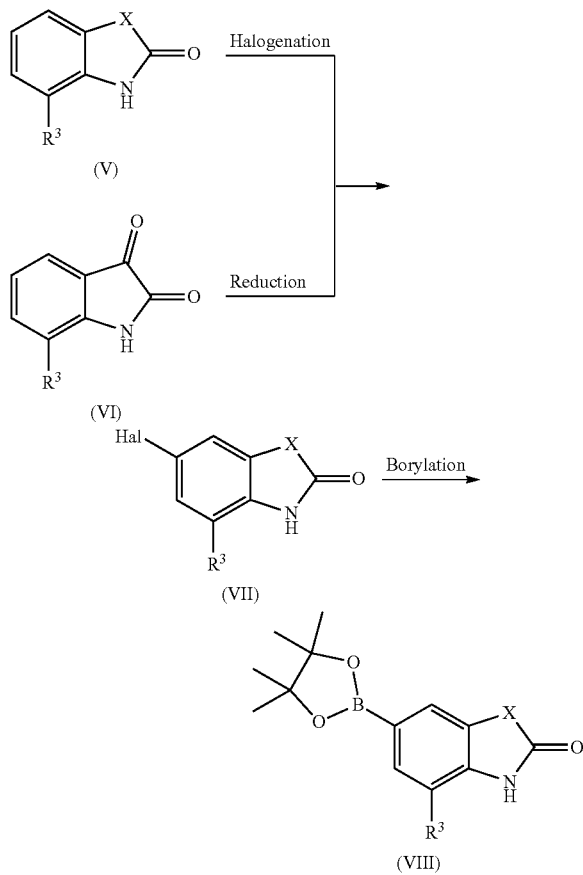

According to SCHEME 2, a compound of formula (VIII), where X is $CH_2$ or S, and $R^3$ is H, halo, $CH_3$, or $OCH_3$, is commercially available or synthetically accessible from a compound of formula (V), formula (VI), or formula (VII), where $R^3$ is defined as above. A compound of formula (V) is treated with an electrophilic halogen source such as bromine, in a suitable solvent such as TFA or AcOH, to provide a compound of formula (VII), where X is $CH_2$ and $R^3$ is H, halo, or $CH_3$. Alternatively, an isatin compound of formula (VI), where $R^3$ is $OCH_3$, is treated with hydrazine hydrate at a temperature such as 80° C., in a suitable solvent such as butanol, followed by treatment with a suitable base, such as trieythlamine and heating at a temperature such as 100° C. to provide a compound of formula (VII), where X is $CH_2$ and $R^3$ is $OCH_3$.

A compound of formula (VII) is treated with a borylating agent such as bis(pinacolato)diboron, in the presence of a palladium catalyst such as Pd(dppf)Cl$_2$, and the like, and a suitable base, such as potassium acetate, employing conventional heating, at a temperature such as 100° C., in a solvent such as 1,4-dioxane, and the like, to provide a compound of formula (VIII), where X and $R^3$ are defined as above.

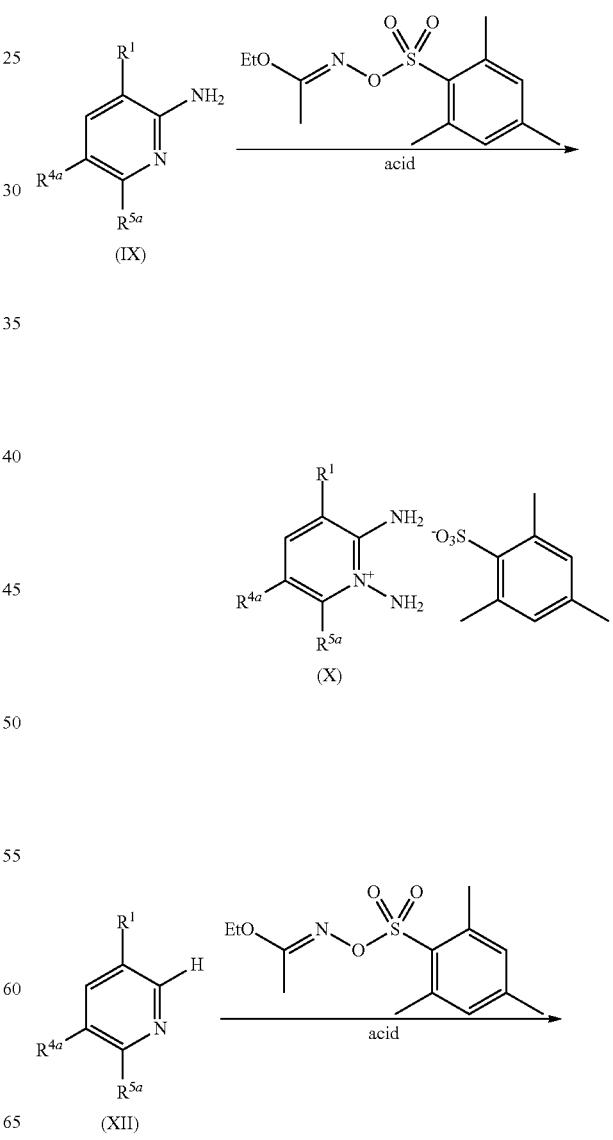

-continued

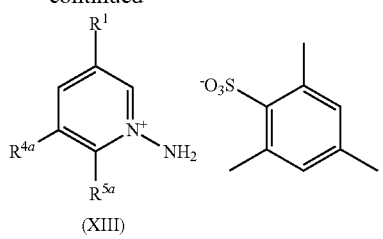

(XIII)

According to SCHEME 3, an amino pyridinium salt compound of formula (X) is prepared from a commercially available or synthetically accessible compound of formula (IX), where $R^1$ is H, halo, $C_{1-6}$alkyl; $R^{4a}$ is halo, $C_{1-6}$haloalkyl, or $C_{1-6}$alkoxy; and $R^{5a}$ is H or halo. For example, a commercially available or synthetically accessible compound of formula (IX) is dissolved in a solvent such as DCM and reacted with an aminating reagent (formed by treatment of (E)-N-((mesitylsulfonyl)oxy)acetimidate with an acid such as perchloric acid, TFA, and the like), in a solvent such as dioxane and water, at a temperature ranging from 0° C. to provide a compound of formula (X), where $R^1$ is H, halo, $C_{1-6}$alkyl; $R^{4a}$ is halo, $C_{1-6}$haloalkyl, or $C_{1-6}$alkoxy; and $R^{5a}$ is H or halo.

In a similar fashion, a compound of formula (XII) where $R^1$ is H or $CH_3$; $R^4$ is $C_{1-6}$haloalkyl; and $R^{5a}$ is Cl, is reacted with an aminating reagent (formed by treatment of (E)-N-((mesitylsulfonyl)oxy)acetimidate with an acid such as perchloric acid, TFA, and the like) to provide an amino pyridinium salt compound of formula (XIII).

SCHEME 4

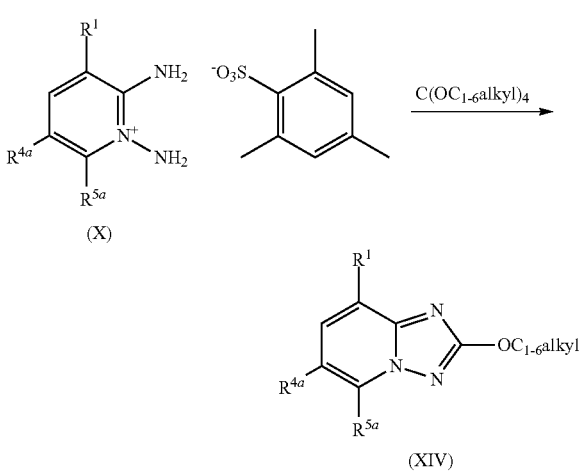

(XIV)

According to SCHEME 4, an amino pyridinium salt compound of formula (X) is treated with tetramethoxymethane, tetraethoxymethane, and the like, in a suitable solvent such as AcOH, employing conventional heating, at a temperature ranging from rt to 70° C., to provide a compound of formula (XIV), where $R^1$ is H or $CH_3$, $R^{4a}$ is $C_{1-6}$haloalkyl, and $R^{5a}$ is Cl.

SCHEME 5

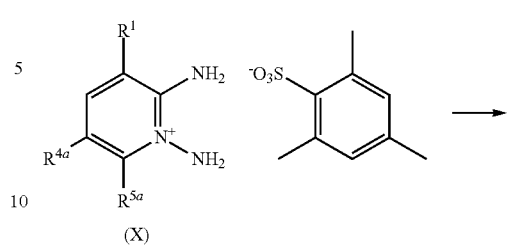

(X)

(XV)

An amino pyridinium salt compound of formula (X), where $R^1$ is H, halo, or $C_{1-6}$alkyl; $R^{4a}$ is halo or $C_{1-6}$haloalkyl; and $R^{5a}$ is H; is condensed with a suitably substituted anhydride such as isobutyric anhydride, propionic anhydride, and the like, in an acid solvent such as isobutyric acid, propionic acid, and the like, employing microwave heating, at a temperature such as 150° C. to provide a compound of formula (XV), where $R^1$ is H, halo, or $C_{1-6}$alkyl; $R^{4a}$ is halo or $C_{1-6}$haloalkyl; $R^{5a}$ is H; and $R^2$ is $C_{1-6}$alkyl.

In an alternate method, an amino pyridinium salt compound of formula (X), where $R^1$ is H, halo or $C_{1-6}$alkyl; $R^{4a}$ is halo, $C_{1-6}$alkoxy, or $C_{1-6}$haloalkyl; and $R^{5a}$ is H or halo; is condensed with a suitably substituted anhydride such as trifluoroacetic anhydride, and the like, or a suitably substituted ester such as methyl difluoroacetate, methyl 2,2-difluoropropionate, and the like, in the presence of a base such as triethylamine in a suitable solvent such as methanol, toluene, and the like, at a temperature ranging from rt to 45° C., to provide a compound of formula (XV), where $R^1$ is H, halo or $C_{1-6}$alkyl; $R^2$ is $C_{1-6}$haloalkyl; $R^{4a}$ is halo, $C_{1-6}$alkoxy, or $C_{1-6}$haloalkyl; and $R^{5a}$ is H or halo.

In an alternate method, a compound of formula (X), where $R^1$ is H, $C_{1-6}$alkyl, or halo, $R^{4a}$ is halo, $C_{1-6}$haloalkyl; and $R^{5a}$ is H or halo; is treated with an aliphatic or carbocyclic aldehyde of formula $R^6(C=O)H$, where $R^6$ is $C_{1-6}$alkyl or $C_{3-8}$cycloalkyl, in the presence of an additive such as $Cu(OAc)_2$ or $Na_2S_2O_5$, in a suitable solvent such as AcOH, MeOH, DMF, or a mixture thereof, at temperatures such as 70° C. to 90° C. to provide a compound of formula (XV), where $R^1$ is H, $C_{1-6}$alkyl or halo; $R^2$ is $C_{1-6}$alkyl or $C_{3-8}$cycloalkyl; $R^{4a}$ is halo, $C_{1-6}$haloalkyl; and $R^{5a}$ is H or halo.

SCHEME 6

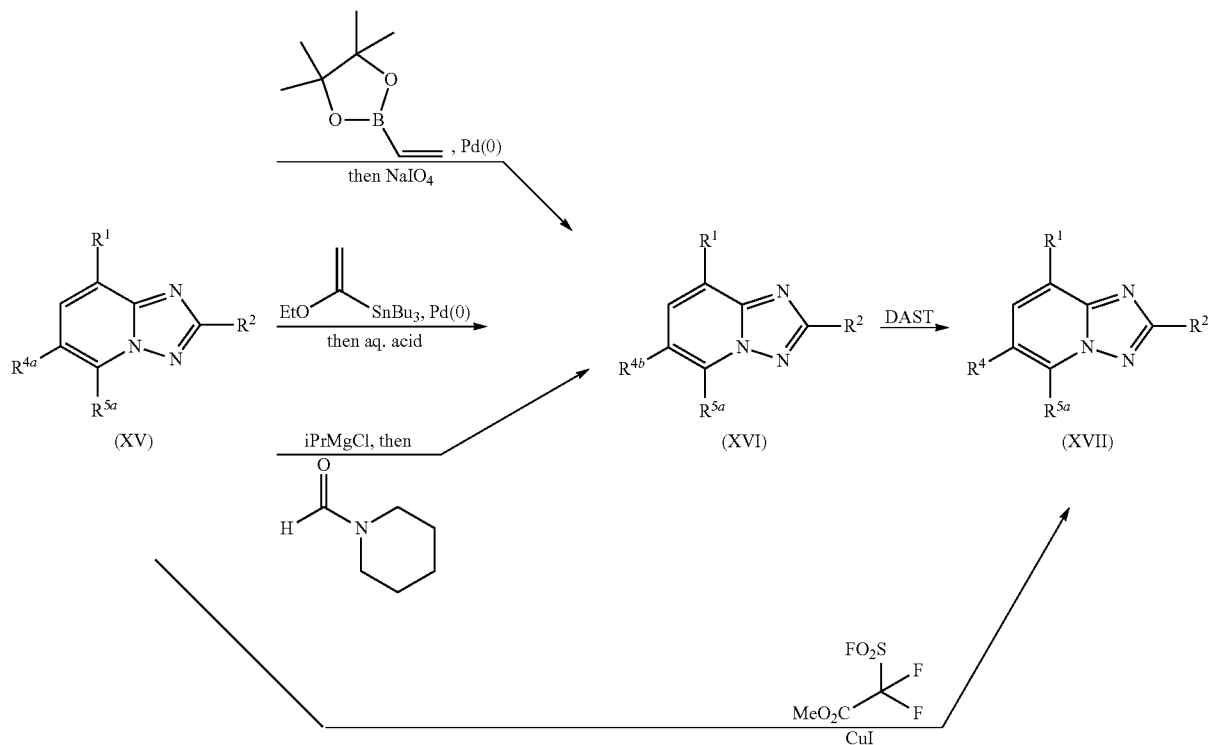

According to SCHEME 6, a compound of formula (XVII), where $R^1$ is $C_{1-6}$alkyl; $R^2$ is $C_{1-6}$alkyl, $C_{3-8}$cycloalkyl, or $C_{1-6}$haloalkyl; $R^4$ is $CF_2H$; and $R^{5a}$ is H; is prepared from a compound of formula (XV), where $R^1$ is $C_{1-6}$alkyl; $R^2$ is $C_{1-6}$alkyl, $C_{3-8}$cycloalkyl, or $C_{1-6}$haloalkyl; $R^4$ is iodo; and $R^{5a}$ is H. For example, a compound of formula (XV) is treated with vinylboronic acid pinacolester in the presence of a palladium catalyst such as $Pd(PPh_3)_4$, a suitable base such as sodium carbonate, in a solvent such as dioxane and water, employing microwave heating, at a temperature such as 110° C., to give a vinyl product that is oxidatively cleaved by treatment with sodium periodate to provide a compound of formula (XVI), where $R^{4b}$ is (C=O)H. A compound of formula (XVI), where $R^{4b}$ is (C=O)H, is treated with a nucleophilic fluorinating reagent such as DAST, in a suitable solvent such as DCM, employing conventional heating, at a temperature such as 35° C., to provide a compound of formula (XVII).

In another embodiment, a compound of formula (XV), where $R^1$ is H; $R^2$ is $C_{1-6}$alkyl, $C_{3-8}$cycloalkyl, or $C_{1-6}$haloalkyl; $R^4$ is halo; and $R^{5a}$ is H, is treated with tributyl(1-ethoxyvinyl)stannane in the presence of a palladium catalyst such as $Pd_2(dba)_3$, a phosphine ligand such as tri-o-tolyl-phosphine, a suitable base such as triethylamine, in a solvent such as DMF, employing microwave heating, at a temperature such as 110° C., to give an enol ether product that is immediately hydrolyzed with an aqueous acid such as HCl to provide a compound of formula (XVI), where $R^{4b}$ is (C=O)CH_3$. A compound of formula (XVI), where $R^{4b}$ is (C=O)CH_3$, is treated with a nucleophilic fluorinating reagent such as DAST, in a suitable solvent such as DCM, employing conventional heating, at a temperature such as 35° C., to provide a compound of formula (XVII), where $R^1$ is H; $R^2$ is $C_{1-6}$haloalkyl; $R^4$ is $C_{1-6}$haloalkyl; and $R^{5a}$ is H.

In another embodiment, a compound of formula (XV), where $R^1$ is H or $C_{1-6}$alkyl; $R^2$ is $C_{1-6}$alkyl, $C_{3-8}$cycloalkyl, or $C_{1-6}$haloalkyl; $R^4$ is $C_{1-6}$haloalkyl; and $R^{5a}$ is Cl; is prepared from a compound of formula (XV), where $R^1$ is H or $C_{1-6}$alkyl; $R^2$ is $C_{1-6}$alkyl, $C_{3-8}$cycloalkyl, or $C_{1-6}$haloalkyl; $R^{4a}$ is I; and $R^5$ is Cl. For example, a compound of formula (XV) undergoes a metal-halogen exchange reaction in the presence of a strong base such as isopropylmagnesium chloride, in a suitable solvent such as THF, and the like, at a temperature such as 0° C., followed by treatment with a formylating reagent such as N-formylpiperidine, to provide an aldehyde compound of formula (XVI), $R^{4b}$ is (C=O)H. A compound of formula (XVI) is treated with a nucleophilic fluorinating as previously described, to provide a compound of formula (XVII), where $R^4$ is $C_{1-6}$haloalkyl.

In an alternate method, a compound of formula (XVII), where $R^1$ is H or $C_{1-6}$alkyl; $R^2$ is $C_{1-6}$ alkyl or $C_{1-6}$haloalkyl; $R^4$ is $C_{1-6}$haloalkyl; and $R^{5a}$ is H; is prepared from a compound of formula (XV), where $R^1$ is $CH_3$; $R^2$ is $C_{1-6}$ alkyl or $C_{1-6}$haloalkyl; $R^{4a}$ is I; and $R^{5a}$ is H. A compound of formula (XV) is treated with a trifluoromethylating reagent such as methyl 2,2-difluoro-2-(fluorosulfonyl)acetate, in the presence of an additive such as CuI, in a suitable solvent system such as DMF/DMPU, employing microwave heating, at a temperature such as 130° C. to provide a compound of formula (XVII), where $R^4$ is $C_{1-6}$haloalkyl.

SCHEME 7

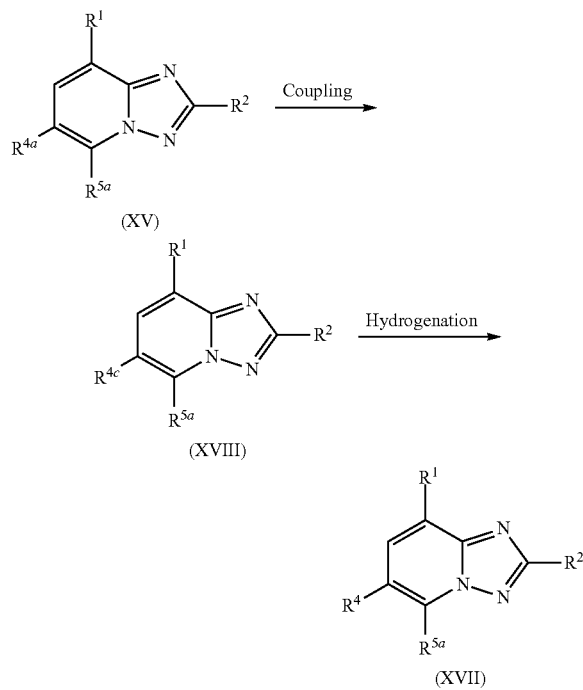

According to SCHEME 7, a compound of formula (XVIII), where $R^{4c}$ is $C_{1-6}$alkenyl, is prepared from a compound of formula (XV), $R^1$ is H; $R^2$ is $C_{1-6}$haloalkyl; $R^{4a}$ is I; and $R^{5a}$ is Cl in a metal mediated cross coupling reaction such as a Stille coupling. For example, a compound of formula (XV) is treated with an organostannane reagent such as tributyl(vinyl)tin, and the like, in a suitable solvent such as DCE, employing microwave heating, at a temperature such as 120° C., to provide a compound of formula (XVIII), where $R^{4c}$ is CH=CH$_2$. Hydrogenation of a compound of formula (XVIII), under conditions known to one skilled in the art, for example, under an atmosphere of hydrogen gas, in the presence of suitable catalyst such as Pd/C, and the like, in a suitable solvent such as MeOH, EtOAc, and the like, provides a compound of formula (XVII), where $R^4$ is $C_{1-6}$alkyl.

SCHEME 8

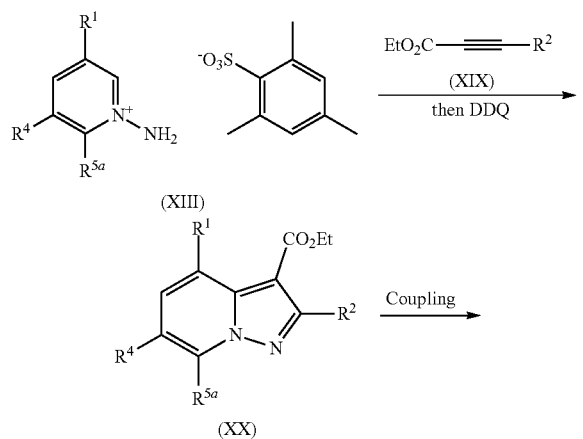

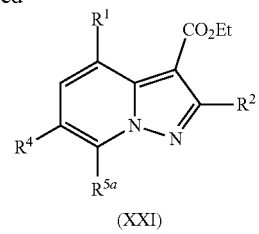

According to SCHEME 8, a compound of formula (XIII), where $R^1$ is H or CH$_3$; $R^4$ is $C_{1-6}$haloalkyl; and $R^{5a}$ is Cl; undergoes a [3+2] cycloaddition in the presence of an alkynoate of formula (XIX), where $R^2$ is CF$_3$, and a suitable base such as Et$_3$N, K$_2$CO$_3$, and the like, in a solvent such as DMF. Subsequent treatment with a suitable oxidant such as DDQ, provides a compound of formula (XX).

A compound of formula (XX) is coupled with a suitably substituted commercially available or synthetically accessible boronic ester of formula (IV), in a metal mediated cross coupling reaction such as a Suzuki reaction. For example, a compound of formula (XX), where $R^1$ is H or CH$_3$; $R^4$ is $C_{1-6}$haloalkyl; and $R^{5a}$ is Cl; is reacted with 7-chloro-5-(4,4,5,5-tetramethyl-1,3,2-dioxaborolan-2-yl)-1H-indazole, in the presence of a suitable palladium catalyst such as Pd(dppf)Cl$_2$, and the like, a suitable base such as K$_2$CO$_3$, Cs$_2$CO$_3$, Na$_2$CO$_3$, NaHCO$_3$, and the like, in a suitable solvent such as dioxane, water, or a mixture thereof, employing conventional of microwave heating at a temperature such as 110° C., to provide a compound of formula (XXI), where $R^{5a}$ is 7-chloro-1H-indazol-5-yl.

SCHEME 9

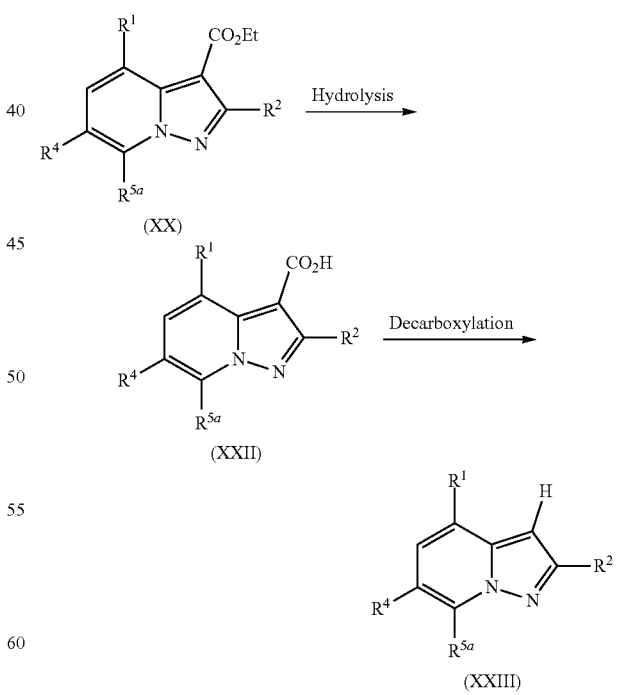

According to SCHEME 9, an ester compound of formula (XX) is hydrolyzed under conditions known to one skilled in the art, for example, treatment with a suitable base such as lithium hydroxide, in a solvent system such as dioxane/ water, at a suitable temperature such as 60° C., to provide a compound of formula (XXII). A compound of formula (XXII) is decarboxylated by treatment with catalytic amounts of silver carbonate and acetic acid, in a suitable solvent such a DMSO, employing conventional heating, at a temperature such as 120° C., to provide a compound of formula (XXIII), where $R^1$ is H or $CH_3$; $R^2$ and $R^4$ are $C_{1-6}$haloalkyl; and $R^{5a}$ is Cl.

A compound of formula (XXI), where $R^1$ is H; $R^4$ is $C_{1-6}$halkyl; and $R^{5a}$ is 7-chloro-1H-indazol-5-yl, is hydrolyzed and decarboxylated according to the methods described in SCHEME 9, to provide a compound of Formula (I).

SCHEME 10

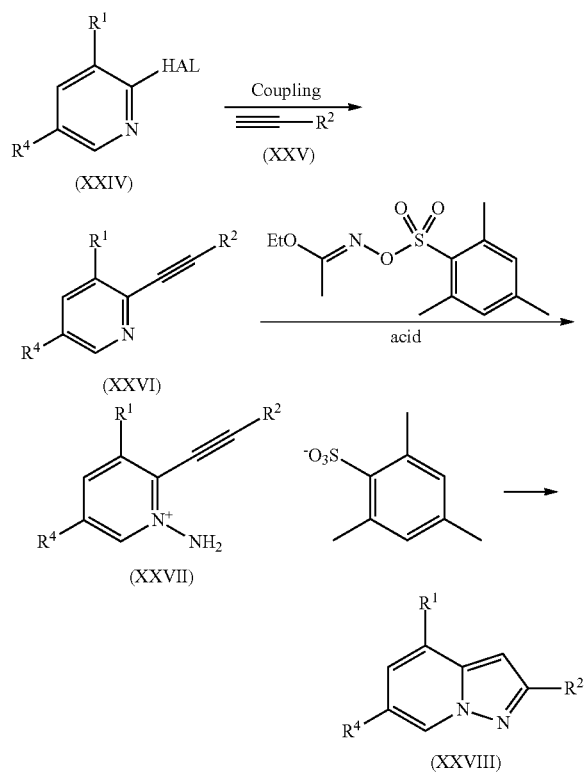

SCHEME 11

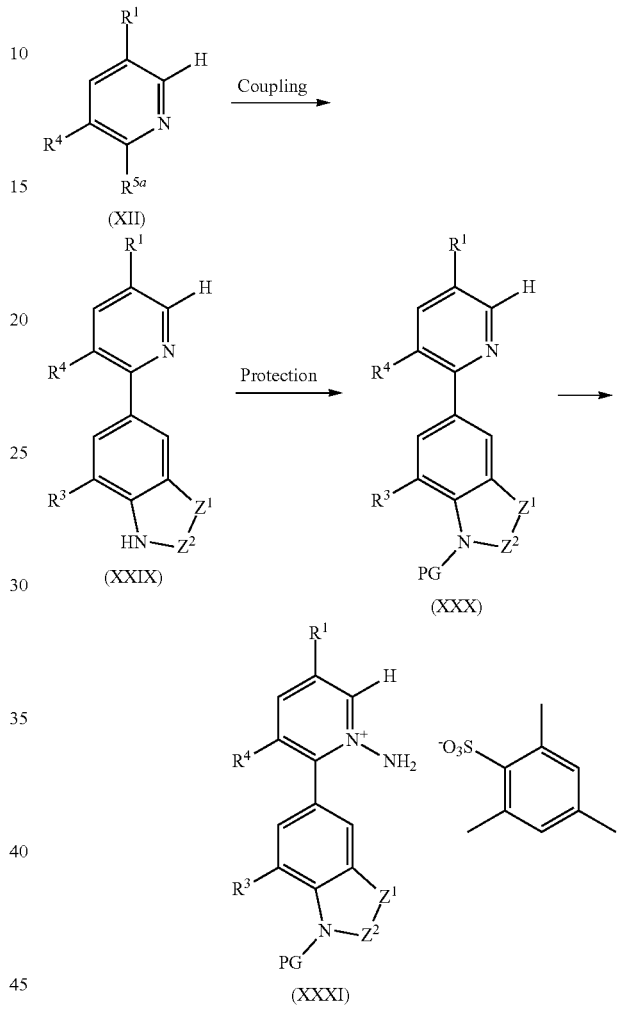

According to SCHEME 10, a compound of formula (XXVI), where $R^1$ is H, $R^2$ is $C_{1-6}$alkyl or $C_{3-8}$cycloalkyl, and $R^4$ is $C_{1-6}$haloalkyl, is prepared by a Sonogashira coupling reaction with a terminal alkyne and compound of formula (XXIV), where $R^1$ is H, $R^4$ is $C_{1-6}$haloalkyl, and HAL is Br. For example, a compound of formula (XXIV) is treated with an terminal alkyne of formula (XXV), where $R^2$ is $C_{1-6}$ alkyl or $C_{3-8}$cycloalkyl, in the presence of a copper co-catalyst such as CuI, a palladium catalyst such as $Pd(PPh_3)_4$, $PdCl_2(PPh_3)_2$, $Pd(PPh_3)_4$, and the like, a suitable amine base such as diisopropylethylamine and the like, in a suitable solvent such THF, DMF, and the like, employing conventional heating, at a temperature such as 70° C., to provide a compound of formula (XXVI), where $R^1$, $R^2$, and $R^4$ are defined as above.

A compound of formula (XXVI) is reacted with an aminating reagent (prepared by treatment of (E)-N-((mesitylsulfonyl)oxy)acetimidate with an acid such as TFA) using previously described conditions to provide a pyridinium compound of formula (XXVII). A compound of formula (XXVII) is heated in a solvent such as AcOH at a suitable temperature such as 80° C. to provide a compound of formula (XXVIII), where $R^1$ is H, $R^1$ is $C_{1-6}$alkyl or $C_{3-8}$cycloalkyl, and $R^4$ is $C_{1-6}$haloalkyl.

According to SCHEME 11, a compound of formula (XII) where $R^1$ is H; $R^4$ is $C_{1-6}$haloalkyl; and $R^{5a}$ is Br, is reacted with a suitably substituted commercially available or synthetically accessible boronic ester such as a compound of formula (IV), in a metal mediated cross coupling reaction such as a Suzuki reaction as previously described, to provide a compound of formula (XXIX). A compound of formula (XXIX) is protected with a suitable nitrogen protecting group (PG), such as tetrahydropyranyl (THP), under conditions known to one skilled in the art to provide a compound of formula (XXX). A compound of formula (XXVI) is reacted with an aminating reagent (prepared by treatment of (E)-N-((mesitylsulfonyl)oxy)acetimidate with an acid such as TFA) using previously described conditions to provide a pyridinium compound of formula (XXXI), where —$Z^1$—$Z^2$— is —CH═N—, and PG is THP.

SCHEME 12

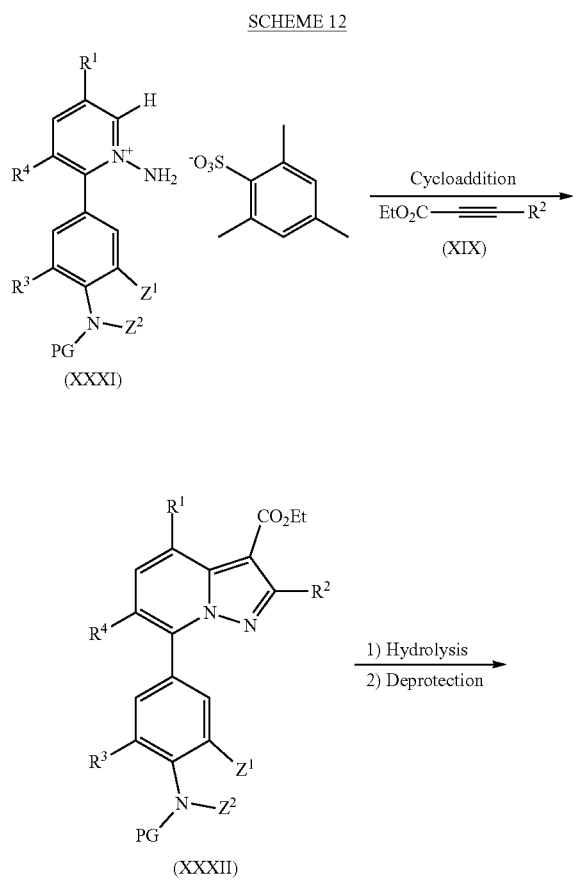

SCHEME 13

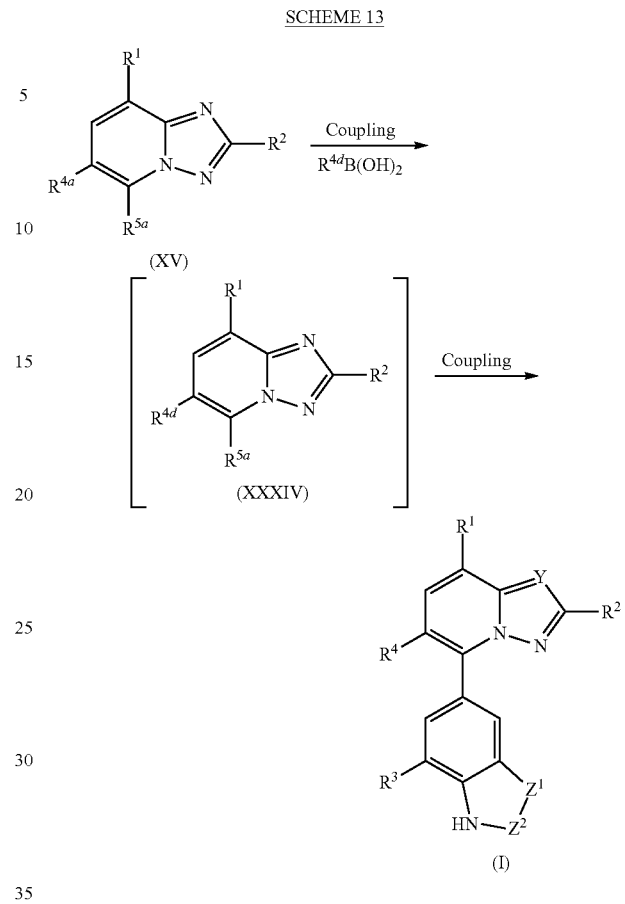

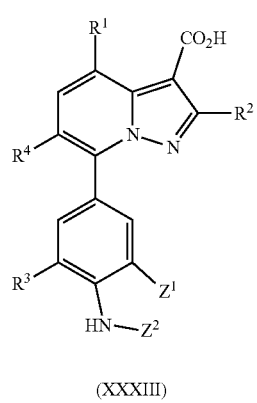

According to SCHEME 12, a compound of formula (XXXI) undergoes a [3+2] cycloaddition in the presence of an alkynoate of formula (XIX), where $R^2$ is isopropyl, under conditions previously described, to provide a compound of formula (XXXII). A compound of formula (XXXIII) is prepared in two steps from a compound of formula (XXXII). In a first step, a compound of formula (XXXII) is hydrolyzed under conditions previously described, followed by deprotection of the THP protecting group by treatment with an aqueous acid such as HCl, to provide a compound of formula (XXXIII), where $R^1$ is H; $R^4$ is $C_{1-6}$haloalkyl; and —$Z^1$—$Z^2$— is —CH=N—.

According to SCHEME 13, a compound of formula (XV) where $R^1$ is H; and $R^2$ is $C_{1-6}$alkyl, $C_{1-8}$haloalkyl, or $C_{3-8}$cycloalkyl; $R^{4a}$ is I; and $R^{5a}$ is Cl; is reacted in a Suzuki metal mediated cross coupling reaction with a suitably substituted commercially available phenyl or pyridyl boronic acid of formula $R^{4d}$—B(OH)$_2$, a suitable palladium catalyst such as Pd(PPh$_3$)$_4$, XPhos-Pd-G2, Pd(dppf)Cl$_2$, PdCl$_2$—CH$_2$Cl$_2$, and the like, a base such as Na$_2$CO$_3$, K$_2$CO$_3$, Cs$_2$CO$_3$, and the like, employing microwave heating, at a temperature such as 110° C. to 190° C., in a solvent system such as dioxane, water, or a mixture thereof, to provide a compound of formula (XXXIV), which is not isolated. The compound of formula (XXXIV), is treated immediately in the same reaction vessel with a commercially available or synthetically accessible boronic ester of formula (IV) or formula (VIII), where $R^3$ is H or CH$_3$; and —$Z^1$—$Z^2$— is —CH=N— or —CH$_2$—C(=O)—; in a Suzuki reaction using conditions previously described, to provide a compound of Formula (I), where Y is N; $R^1$ is H; $R^2$ is $C_{1-5}$alkyl, $C_{1-5}$haloalkyl, or $C_{3-8}$cycloalkyl; $R^3$ is H or CH$_3$; $R^4$ is phenyl substituted with F, or pyridyl; and —$Z^1$—$Z^2$— is —CH=N— or —CH$_2$—C(=O)—.

SCHEME 14

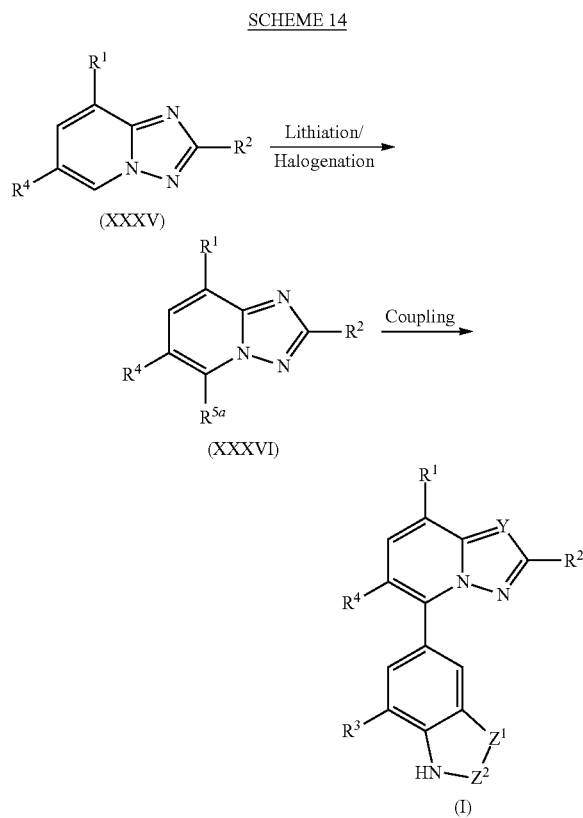

A compound of formula (XXXV), prepared by the methods previously described in the preceding schemes, where Y is N or CH; $R^1$ is H, halo or $C_{1-6}$alkyl; $R^2$ is $C_{1-6}$alkyl, $C_{1-6}$haloalkyl, $C_{1-6}$alkoxyalkyl or $C_{3-8}$cycloalkyl; and $R^4$ is $C_{1-6}$alkyl, $C_{1-6}$haloalkyl, or $C_{1-6}$alkoxy; is treated with a base such as n-butyllithium in a suitable solvent such as THF at a suitable temperature ranging from −70° C. to −78° C., followed by quenching with an electrophilic halogen source such as 1,2-diiodoethane, hexachloroethane, bromine, and the like, to provide a compound of formula (XXXVI), where $R^{5a}$ is Br, Cl or I. A compound of formula (XXXVI) is coupled with a commercially available or synthetically accessible boronic ester of formula (IV) or formula (VIII), under Suzuki conditions previously described, to provide a compound of Formula (I), where Y is N or CH; $R^1$ is H, halo, or $C_{1-6}$alkyl; $R^2$ is $C_{1-6}$alkyl, $C_{1-6}$haloalkyl, $C_{1-6}$alkoxyalkyl or $C_{3-8}$cycloalkyl; $R^3$ is H, $CH_3$, or halo; $R^4$ is $C_{1-6}$alkyl, $C_{1-6}$haloalkyl, or $C_{1-6}$alkoxy; and —$Z^1$—$Z^2$— is —CH=N—, —$CH_2$—C(=O)—, or —S—C(=O)—.

A compound of formula (XXI), where $R^1$ is H; $R^4$ is $C_{1-6}$haloalkyl; and $R^{5a}$ is 7-chloro-1H-indazol-5-yl, is hydrolyzed and decarboxylated according to the methods described in SCHEME 9, to provide a compound of Formula (I).

A compound of formula (XXXIII), where $R^1$ is H; $R^4$ is $C_{1-6}$haloalkyl; and —$Z^1$—$Z^2$— is —CH=N— is decarboxylated according to the methods described in SCHEME 9, to provide a compound of Formula (I).

Compounds of Formula (I) may be converted to their corresponding salts using methods known to one of ordinary skill in the art. For example, an amine of Formula (I) is treated with trifluoroacetic acid, HCl, or citric acid in a solvent such as $Et_2O$, $CH_2Cl_2$, THF, $CH_3OH$, chloroform, or isopropanol to provide the corresponding salt form. Alternately, trifluoroacetic acid or formic acid salts are obtained as a result of reverse phase HPLC purification conditions. Crystalline forms of pharmaceutically acceptable salts of compounds of Formula (I) may be obtained in crystalline form by recrystallization from polar solvents (including mixtures of polar solvents and aqueous mixtures of polar solvents) or from non-polar solvents (including mixtures of non-polar solvents).

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention.

Compounds prepared according to the schemes described above may be obtained as single forms, such as single enantiomers, by form-specific synthesis, or by resolution. Compounds prepared according to the schemes above may alternately be obtained as mixtures of various forms, such as racemic (1:1) or non-racemic (not 1:1) mixtures. Where racemic and non-racemic mixtures of enantiomers are obtained, single enantiomers may be isolated using conventional separation methods known to one of ordinary skill in the art, such as chiral chromatography, recrystallization, diastereomeric salt formation, derivatization into diastereomeric adducts, biotransformation, or enzymatic transformation. Where regioisomeric or diastereomeric mixtures are obtained, as applicable, single isomers may be separated using conventional methods such as chromatography or crystallization.

The following specific examples are provided to further illustrate the invention and various preferred embodiments.

EXAMPLES

In obtaining the compounds described in the examples below and the corresponding analytical data, the following experimental and analytical protocols were followed unless otherwise indicated.

Unless otherwise stated, reaction mixtures were magnetically stirred at rt (rt) under a nitrogen atmosphere. Where solutions were "dried," they were generally dried over a drying agent such as $Na_2SO_4$ or $MgSO_4$. Where mixtures, solutions, and extracts were "concentrated", they were typically concentrated on a rotary evaporator under reduced pressure. Reactions under microwave irradiation conditions were carried out in a Biotage Initiator or CEM (Microwave Reactor) Discover instrument.

For the reactions conducted under continuous flow conditions, "flowed through a LTF-VS mixer" refers to the use of a Chemyx Fusion 100 Touch Syringe Pump that is in line via ¹⁄₁₆" PTFE (PolyTetraFluoroEthylene) tubing to a LTF-VS mixer (Little Things Factory GmbH (http://www.ltf-gmbh.com), unless otherwise indicated.

Normal-phase silica gel chromatography (FCC) was performed on silica gel ($SiO_2$) using prepacked cartridges.

Preparative reverse-phase high performance liquid chromatography (RP HPLC) was performed on either:

An Agilent HPLC with an Xterra Prep RP18 column (5 μM, 30×100 or 50×150 mm) or an XBridge $^{18}$C OBD column (5 μM, 30×100 or 50×150 mm), and a mobile phase of 5% ACN in 20 mM $NH_4OH$ was held for 2 min, then a gradient of 5-99% ACN over 15 min, then held at 99% ACN for 5 min, with a flow rate of 40 or 80 mL/min.

or

A Shimadzu LC-8A Series HPLC with an Inertsil ODS-3 column (3 μm, 30×100 mm, T=45° C.), mobile phase of 5% ACN in H₂O (both with 0.05% TFA) was held for 1 min, then a gradient of 5-99% ACN over 6 min, then held at 99% ACN for 3 min, with a flow rate of 80 mL/min.

or

A Shimadzu LC-8A Series HPLC with an XBridge C18 OBD column (5 μm, 50×100 mm), mobile phase of 5% ACN in H₂O (both with 0.05% TFA) was held for 1 min, then a gradient of 5-99% ACN over 14 min, then held at 99% ACN for 10 min, with a flow rate of 80 mL/min.

or

A Gilson HPLC with an XBridge C18 column (5 μm, 100×50 mm), mobile phase of 5-99% ACN in 20 mM NH₄OH over 10 min and then hold at 99 ACN for 2 min, at a flow rate of 80 mL/min.

Preparative supercritical fluid high performance liquid chromatography (SFC) was performed either on a Jasco preparative SFC system, an APS 1010 system from Berger instruments, or a SFC-PICLAB-PREP 200 (PIC SOLUTION, Avignon, France). The separations were conducted at 100-150 bar with a flow rate ranging from 40-60 mL/min. The column was heated to 35-40° C.

Mass spectra (MS) were obtained on an Agilent series 1100 MSD using electrospray ionization (ESI) in positive mode unless otherwise indicated. Calculated (calcd.) mass corresponds to the exact mass.

Nuclear magnetic resonance (NMR) spectra were obtained on Bruker model DRX spectrometers. Definitions for multiplicity are as follows: s=singlet, d=doublet, t=triplet, q=quartet, m=multiplet, br=broad. It will be understood that for compounds comprising an exchangeable proton, said proton may or may not be visible on an NMR spectrum depending on the choice of solvent used for running the NMR spectrum and the concentration of the compound in the solution.

Chemical names were generated using ChemDraw Ultra 12.0, ChemDraw Ultra 14.0 (CambridgeSoft Corp., Cambridge, Mass.) or ACD/Name Version 10.01 (Advanced Chemistry).

Intermediate 1: 7-Chloro-5-(4,4,5,5-tetramethyl-1,3,2-dioxaborolan-2-yl)-1H-indazole

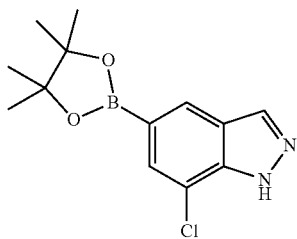 [SMILES: CC1(C)OB(c2cc(Cl)c3[nH]ncc3c2)OC1(C)C]

To a solution of 5-bromo-7-chloro-1H-indazole (1.0 g, 4.3 mmol) in dioxane (15 mL) was added KOAc (850 mg, 8.6 mmol), bis(pinacolato)diboron (1.3 g, 5.2 mmol) and PdCl₂(dppf)-CH₂Cl₂ (316 mg, 0.43 mmol). The solution was degassed with nitrogen and then heated at 85° C. for 16 h. After cooling to rt, the reaction mixture was diluted with brine and extracted with EtOAc (x 2). The combined organic extracts were dried over Na₂SO₄, concentrated, and the crude product was triturated with DCM to provide the title compound as a white solid (916 mg, 76%). MS (ESI): mass calcd. for C₁₃H₁₆BClN₂O₂, 278.5; m/z found, 279.1 [M+H]⁺. ¹H NMR (400 MHz, DMSO-d₆) δ 13.72 (s, 1H), 8.25 (s, 1H), 8.18-8.05 (m, 1H), 7.56 (s, 1H), 1.31 (s, 12H).

Intermediate 2: 7-Methyl-5-(4,4,5,5-tetramethyl-1,3,2-dioxaborolan-2-yl)-1H-indazole

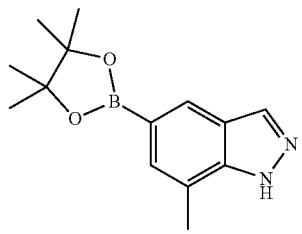 [SMILES: Cc1cc(B2OC(C)(C)C(C)(C)O2)cc2cn[nH]c12]

The title compound was prepared in a manner analogous to Intermediate 1, substituting 5-bromo-7-methyl-1H-indazole for 5-bromo-7-chloro-1H-indazole. MS (ESI): mass calcd. for C₁₄H₁₉BN₂O₂, 258.1; m/z found, 259.1 [M+H]⁺. ¹H NMR (400 MHz, DMSO-d₆) δ 13.21 (s, 1H), 8.10 (d, J=1.3 Hz, 1H), 7.98 (s, 1H), 5.76 (s, 1H), 2.52 (s, 3H), 1.30 (s, 12H).

Intermediate 3: 7-Methyl-5-(4,4,5,5-tetramethyl-1,3,2-dioxaborolan-2-yl)indolin-2-one

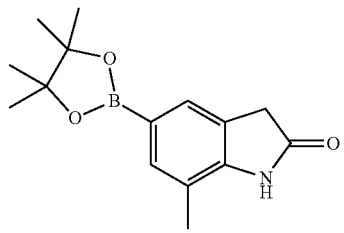 [SMILES: Cc1cc(B2OC(C)(C)C(C)(C)O2)cc2c1NC(=O)C2]

The title compound was prepared in a manner analogous to Intermediate 1, substituting 5-bromo-7-methylindolin-2-one for 5-bromo-7-chloro-1H-indazole. MS (ESI): mass calcd. for C₁₆H₁₂ClF₂NO₂, 273.1; m/z found, 274.1 [M+H]⁺. ¹H NMR (400 MHz, DMSO-d₆) δ 10.55 (s, 1H), 7.32 (s, 1H), 7.31 (s, 1H), 3.47 (s, 2H), 2.19 (s, 3H), 1.26 (s, 12H).

Intermediate 4: 5-(4,4,5,5-Tetramethyl-1,3,2-dioxaborolan-2-yl)-7-(trifluoromethyl)-1H-indazole

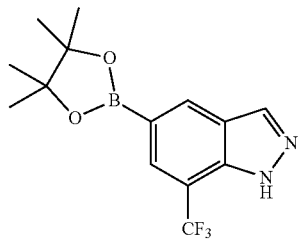 [SMILES: CC1(C)OB(c2cc(C(F)(F)F)c3[nH]ncc3c2)OC1(C)C]

The title compound is prepared in a manner analogous to Intermediate 1, substituting 5-bromo-7-(trifluoromethyl)-1H-indazole for 5-bromo-7-chloro-1H-indazole. MS (ESI): mass calcd. for $C_{14}H_{19}BN_2O_2$, 312.0; m/z found, 313.2 [M+H]+. 1H NMR (400 MHz, CDCl3) δ 10.38 (s, 1H), 8.48-8.44 (m, 1H), 8.18 (s, 1H), 8.09-8.07 (m, J=1.0 Hz, 1H), 1.38 (s, 12H).

Intermediate 5: 7-Chloro-5-(4,4,5,5-tetramethyl-1,3,2-dioxaborolan-2-yl)indolin-2-one

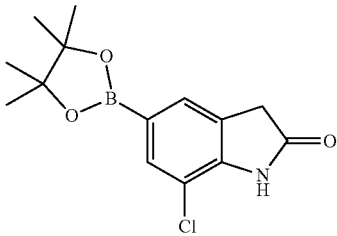 [SMILES: CC1(C)OB(c2cc(Cl)c3c(c2)CC(=O)N3)OC1(C)C]

Step A: 5-Bromo-7-chloroindolin-2-one

To a cooled (0° C.) solution of 7-chloroindolin-2-one (1.0 g, 6.0 mmol) in TFA (11 mL) was added N-bromosuccinimide (1.0 g, 6.0 mmol) portionwise, and the resulting mixture was stirred at 0° C. for 6 h. The solvent was removed in vacuo and the residue was diluted and evaporated successively with DCM (25 mL) and EtOAc (25 mL). The crude product was triturated with EtOH to provide the title compound as a white solid (861 mg, 58%). MS (ESI): mass calcd. for $C_8H_5BrClNO$, 244.9; m/z found, 246.0 [M+H]+. 1H NMR (500 MHz, DMSO-d6) δ 10.92 (s, 1H), 7.52-7.48 (m, 1H), 7.38 (d, J=1.2 Hz, 1H), 3.62 (s, 2H).

Step B: 7-Chloro-5-(4,4,5,5-tetramethyl-1,3,2-dioxaborolan-2-yl)indolin-2-one

The title compound was prepared in a manner analogous to Intermediate 1, substituting 5-bromo-7-chloroindolin-2-one for 5-bromo-7-chloro-1H-indazole. The crude product was triturated with DCM to provide the title compound as a white solid (1.6 g, 65%). MS (ESI): mass calcd. for $C_{14}H_{17}BClNO_3$, 293.1; m/z found, 294.1 [M+H]+. 1H NMR (400 MHz, DMSO-d6) δ 10.94 (s, 1H), 7.43 (d, J=1.1 Hz, 1H), 7.41 (d, J=1.2 Hz, 1H), 3.60 (t, J=1.0 Hz, 2H), 1.28 (s, 12H).

Intermediate 6: 7-Methoxy-5-(4,4,5,5-tetramethyl-1,3,2-dioxaborolan-2-yl)indolin-2-one

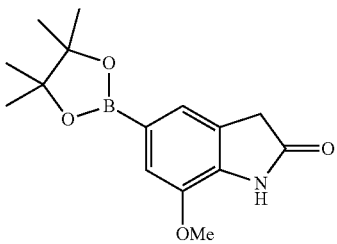 [SMILES: COc1cc(B2OC(C)(C)C(C)(C)O2)cc2c1NC(=O)C2]

Step A: 5-Bromo-7-methoxyindoline-2,3-dione

To a suspension of 7-methoxyindoline-2,3-dione (1.0 g, 5.6 mmol) in AcOH (5.6 mL) was added bromine (0.35 mL, 6.7 mmol) at 0° C. The mixture was allowed to stir at rt for 2 h and was then poured into ice and stirred for 0.5 h. The resulting mixture was filtered and the solids were washed with H2O to afford the title compound as an orange solid (1.3 g, 92%). MS (ESI): mass calcd. for $C_9H_6BrNO_3$, 256.0; m/z found, 257.6 [M+H]+. 1H NMR (400 MHz, DMSO-d6) δ 11.22 (s, 1H), 7.48 (d, J=1.7 Hz, 1H), 7.25 (dd, J=1.8, 0.7 Hz, 1H), 3.90 (s, 3H).

Step B: 5-Bromo-7-methoxyindolin-2-one

To a solution of 5-bromo-7-methoxyindoline-2,3-dione (670 mg, 2.6 mmol) in n-butanol (8 mL) was added hydrazine hydrate (153 µL, 3.1 mmol). The mixture was heated at 80° C. for 3 h. The temperature was maintained at 80° C. and triethylamine (548 µL, 3.9 mmol) was added. The temperature was then increased to 100° C. and the reaction was stirred at reflux for 24 h. The reaction was cooled to rt and the mixture was concentrated in vacuo. The crude residue was suspended in hexanes and the resulting mixture was filtered. The solids were washed with hexanes to afford the title compound (297 mg, 46%). MS (ESI): mass calcd. for $C_9H_8BrNO_2$, 242.0; m/z found, 242.9. 1H NMR (400 MHz, DMSO-d6) δ 10.52 (s, 1H), 7.09 (d, J=1.7 Hz, 1H), 7.02 (q, J=1.2 Hz, 1H), 3.82 (s, 3H), 3.50 (t, J=1.0 Hz, 2H).

Step C: 7-Methoxy-5-(4,4,5,5-tetramethyl-1,3,2-dioxaborolan-2-yl)indolin-2-one

The title compound was prepared in a manner analogous to Intermediate 1, substituting 5-bromo-7-methoxyindolin-2-one for 5-bromo-7-chloro-1H-indazole. The crude product was triturated with EtOAc to provide the title compound as yellow solid (265 mg, 75% yield). MS (ESI): mass calcd. for $C_{15}H_{20}BNO_4$, 289.1; m/z found, 290.1 [M+H]+. 1H NMR (400 MHz, DMSO-d6) δ 10.55 (s, 1H), 7.16 (d, J=1.1 Hz, 1H), 7.10 (s, 1H), 3.82 (s, 3H), 3.48 (s, 2H), 1.28 (s, 12H).

Intermediate 7: 6-(4,4,5,5-Tetramethyl-1,3,2-dioxaborolan-2-yl)-3-((2-(trimethylsilyl)ethoxy)methyl)benzo[d]thiazol-2(3H)-one

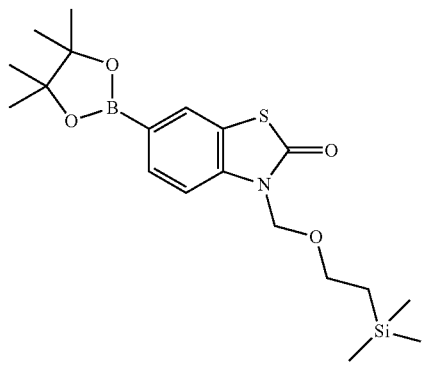

Step A: 6-Bromo-3-((2-(trimethylsilyl)ethoxy)methyl)benzo[d]thiazol-2(3H)-one

To a cooled (0° C.) solution of 6-bromobenzo[d]thiazol-2(3H)-one (1.0 g, 4.4 mmol) in THF (8.0 mL) was added 60 wt % sodium hydride in mineral oil (208 mg, 5.2 mmol) portionwise. Stirring was maintained at 0° C. for 20 minutes, and (2-(chloromethoxy)ethyl) trimethylsilane (0.77 ml, 4.4 mmol) was then added dropwise over a period of 10 minutes. The mixture was warmed to rt and stirred for 2 h. The crude mixture was diluted with water and extracted with DCM (×2). The combined organic extracts were washed with brine, dried over $Na_2SO_4$, and concentrated in vacuo. Purification (FCC, $SiO_2$; 0-50% EtOAc/hexanes) provided the title compound as a white solid (1.2 g, 76%). $^1$H NMR (400 MHz, DMSO-$d_6$) δ 8.07-8.04 (m, 1H), 7.66-7.61 (m, 1H), 7.38 (dd, J=8.3, 2.8 Hz, 1H), 5.42 (d, J=2.7 Hz, 2H), 3.63 (t, J=7.8 Hz, 2H), 0.92 (t, J=7.8 Hz, 2H), 0.00 (s, 9H).

Step B: 6-(4,4,5,5-Tetramethyl-1,3,2-dioxaborolan-2-yl)-3-((2-trimethylsilyl)ethoxy)methyl)benzo[d]thiazol-2(3H)-one The title compound was prepared in a manner analogous to Intermediate 1, substituting 6-bromo-3-((2-trimethylsilyl)ethoxy)methyl)benzo[d]thiazol-2(3H)-one for 5-bromo-7-chloro-1H-indazole. $^1$H NMR (400 MHz, DMSO-$d_6$) δ 8.02 (d, J=1.1 Hz, 1H), 7.74 (dd, J=8.1, 1.2 Hz, 1H), 7.45 (d, J=8.1 Hz, 1H), 5.43 (s, 2H), 3.64 (dd, J=8.4, 7.5 Hz, 2H), 2.59-2.58 (m, 2H), 1.38 (s, 12H), 0.00 (s, 9H).

Intermediate 8:
1,2-Diamino-5-(trifluoromethyl)pyridin-1-ium 2,4,6-trimethylbenzenesulfonate

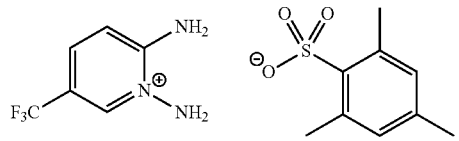

To a cooled (0° C.) solution of ethyl (1E)-N-(2,4,6-trimethylphenyl)sulfonyloxyethanimidate (5.3 g, 19 mmol) in dioxane (23 mL) was added 70% perchloric acid (20 mL, 232 mmol) dropwise. Following the addition, the temperature was maintained at 0° C. for 10 minutes and then ice-cold water (95 mL) was added at once. The resulting precipitate was collected by vacuum filtration and washed with water (caution: this compound has been reported to be potentially explosive when dry). The white solid was immediately dissolved in DCM (40 mL), dried over $Na_2SO_4$, and filtered. The filtrate was then added dropwise to a cooled (0° C.) solution of 5-(trifluoromethyl)pyridin-2-amine (1.5 g, 9.3 mmol) in DCM (79 mL). The reaction was allowed to warm to rt and stirred for 2 h. Diethyl ether was added and the resulting white solid was collected by vacuum filtration to provide the title compound (3.5 g, 100%). $^1$H NMR (600 MHz, DMSO-$d_6$) δ 9.49-8.70 (bm, 2H), 8.64 (s, 1H), 8.09 (m, 1H), 7.19 (d, J=9.4 Hz, 1H), 6.81 (s, 2H), 6.74 (br s, 2H), 2.49 (s, 3H), 2.17 (s, 3H).

Intermediate 9: 1,6-Diamino-2-chloro-3-(trifluoromethyl)pyridin-1-ium 2,4,6-trimethylbenzenesulfonate

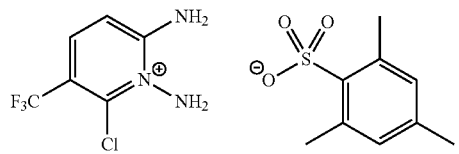

Step A:
6-Chloro-5-(trifluoromethyl)pyridin-2-amine

Nine separate sealed tubes, each containing a mixture of 2,6-dichloro-3-(trifluoromethyl)pyridine (10.0 g, 46.3 mmol) and ammonium hydroxide (91 g, 100 mL, 2600 mmol) were stirred at 100° C. for 12 h. After cooling to rt, the contents of all of the sealed tubes were combined and the solvents were concentrated in vacuo. Purification of the (FCC, $SiO_2$; 5-20% EtOAc/petroleum ether) afforded the title compound as a colorless oil (57 g, 66%), which solidified upon standing. MS (ESI): mass calcd. for $C_6H_4ClF_3N_2$, 196.0; m/z found, 196.8 [M+H]$^+$. $^1$H NMR (400 MHz, CDCl$_3$) δ 7.69 (d, J=8.0 Hz, 1H), 6.42 (d, J=8.4 Hz, 1H), 5.01 (br s, 2H).

Step B: 1,6-Siamino-2-chloro-3-(trifluoromethyl)pyridin-1-ium 2,4,6-trimethylbenzenesulfonate To a cooled (−5° C.) solution of TFA (429 mL) and water (45 mL) was added ethyl (1E)-N-(2,4,6-trimethylphenyl)sulfonyloxyethanimidate (124 g, 435 mmol), and the mixture was stirred at 0° C. for 1.5 h. Ice water (500 mL) was added, and the resulting precipitate was filtered and washed with water (2×50 mL). The solid was dissolved in DCM (500 mL), dried over $Na_2SO_4$, and filtered. The filtrate was added dropwise to a cooled (0° C.) suspension of 6-chloro-5-(trifluoromethyl)pyridin-2-amine (57 g, 290 mmol) in DCM (500 mL). After stirring at rt for 1 h, the reaction mixture was poured into MTBE (200 mL) and then filtered. The filter cake was washed with MTBE (3×50 mL) and dried under vacuum. The solid was triturated with 5:1 DCM/MeOH (300 mL) for 3 h and filtered. The filter cake was washed with DCM (2×150 mL) and dried under vacuum to afford the title compound as a gray solid (75 g, 61%). $^1$H NMR (400 MHz, DMSO-$d_6$) δ 9.63 (br s, 1H), 9.06 (br s, 1H), 8.08 (d, J=9.6 Hz, 1H), 7.13 (d, J=9.6 Hz, 1H), 6.75 (s, 1H), 6.58 (s, 1H), 2.50 (s, 6H), 2.17 (s, 3H).

Intermediate 10:
1,6-Diamino-2-chloro-3-iodopyridin-1-ium 2,4,6-trimethylbenzenesulfonate

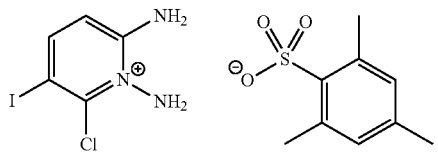

Step A: 6-Chloro-5-iodopyridin-2-amine

To a solution of 6-chloropyridin-2-amine (50.0 g, 389 mmol) in DMF (700 mL) was added N-iodosuccinimide (105 g, 467 mmol). The brown solution was stirred at rt for 12 h. The mixture was poured into water (2.1 L) and filtered. The filter cake was washed with water (2×500 mL) and then dried under vacuum. Purification (FCC, $SiO_2$; 5-20% EtOAc/petroleum ether) afforded the title compound (83 g, 75%) as a pink solid. MS (ESI): mass calcd. for $C_5H_4ClIN_2$, 253.9; m/z found, 254.7 [M+H]$^+$. $^1$H NMR (400 MHz, CDCl$_3$) δ 7.74 (d, J=8.0 Hz, 1H), 6.20 (d, J=8.0 Hz, 1H), 4.69 (br s, 2H).

Step B: 1,6-Diamino-2-chloro-3-iodopyridin-1-ium 2,4,6-trimethylbenzenesulfonate The title compound was prepared in a manner analogous to Intermediate 9, substituting 6-chloro-5-iodopyridin-2-amine for 6-chloro-5-(trifluoromethyl)pyridin-2-amine in Step B. $^1$H NMR (400 MHz, DMSO-$d_6$) δ 8.86 (br s, 2H), 8.07 (d, J=9.6 Hz, 1H), 6.84 (d, J=9.6 Hz, 1H), 6.73 (br s, 2H), 6.58 (s, 2H), 2.48 (s, 6H), 2.16 (s, 3H).

Intermediate 11: 1,6-Diamino-2-bromo-3-methoxypyridin-1-ium 2,4,6-trimethylbenzenesulfonate

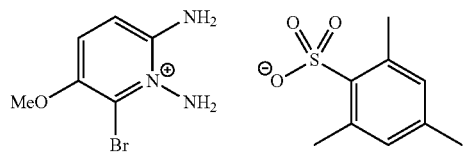

The title compound was prepared in a manner analogous to Intermediate 8, substituting 6-bromo-5-methoxypyridin-2-amine for 5-(trifluoromethyl)pyridin-2-amine. $^1$H NMR (500 MHz, DMSO-$d_6$) δ 8.34 (br s, 2H), 7.95 (d, J=9.8 Hz, 1H), 7.08 (d, J=9.8 Hz, 1H), 6.74 (br s, 2H), 6.55 (s, 2H), 3.86 (s, 3H), 2.49 (s, 3H), 2.17 (s, 3H).

Intermediate 12: 1,2-Diamino-5-iodo-3-methylpyridin-1-ium 2,4,6-trimethylbenzenesulfonate

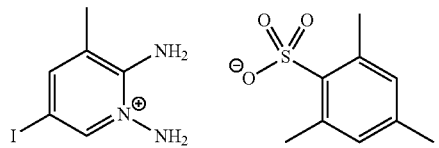

To a cooled (0° C.) solution of ethyl (1E)-N-(2,4,6-trimethylphenyl)sulfonyloxyethanimidate (0.732 g, 2.56 mmol) in dioxane (3.2 mL) was added 70% perchloric acid (2.75 mL, 32.2 mmol) dropwise. Following the addition, the temperature was maintained at 0° C. for 10 minutes and then ice-cold water (13 mL) was added at once. The resulting precipitate was collected by vacuum filtration and washed with water (caution: this compound has been reported to be potentially explosive when dry). The white solid was immediately dissolved in DCM (5.5 mL), dried over Na$_2$SO$_4$, and filtered. The filtrate was then added dropwise to a cooled (0° C.) solution of 5-iodo-3-methylpyridin-2-amine (0.3 g, 1.28 mmol) in DCM (11 mL). The reaction was warmed to room temperature and stirred for 3.5 h. Diethyl ether was added and the resulting white solid was collected by vacuum filtration to provide the title compound (517 mg, 89%). $^1$H NMR (500 MHz, DMSO-$d_6$) δ 8.28 (br s, 2H), 8.22 (d, J=2.1 Hz, 1H), 7.97 (s, 1H), 6.81 (br s, 2H), 6.73 (s, 2H), 2.49 (s, 6H), 2.19 (s, 3H), 2.17 (s, 3H).

Intermediate 13: 1,2-Diamino-3,6-dichloro-5-(trifluoromethyl)pyridin-1-ium 2,4,6-trimethylbenzenesulfonate

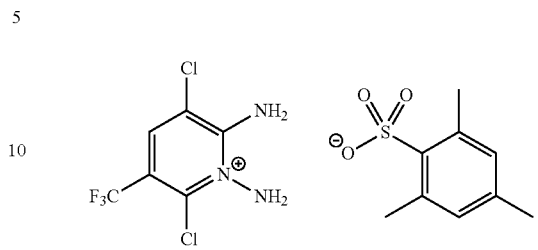

Step A: 3,6-Dichloro-5-(trifluoromethyl)pyridin-2-amine

To a solution of 6-chloro-5-(trifluoromethyl)pyridin-2-amine (1.10 g, 5.60 mmol) in DMF (2.3 mL) was added N-chlorosuccinimide (822 mg, 6.16 mmol), and the reaction was heated at 60° C. for 2 h. After cooling to rt, Et$_2$O (6 mL) was added and the mixture was neutralized with 1N NaOH. The aqueous layer was extracted with EtOAc (×2), and the combined organics were washed with brine (×3), dried over Na$_2$SO$_4$ and filtered. The filtrate was concentrated in vacuo to afford a yellow solid (1.34 g) which was used without further purification. MS (ESI): mass calcd. for C$_6$H$_3$Cl$_2$F$_3$N$_2$, 230.0; m/z found, 230.9 [M+H]$^+$.

Step B: 1,2-Diamino-3,6-dichloro-5-(trifluoromethyl)pyridin-1-ium 2,4,6-trimethylbenzenesulfonate The title compound was prepared in a manner analogous to Intermediate 8, substituting 3,6-dichloro-5-(trifluoromethyl)pyridine-2-amine for 5-(trifluoromethyl)pyridin-2-amine. MS (ESI): mass calcd. for C$_6$H$_5$Cl$_2$F$_3$N$_3$, 246.0; m/z found, 247.0 [M+H]$^+$.

Intermediate 14: 1,2-Diamino-3-fluoro-5-(trifluoromethyl)pyridin-1-ium 2,4,6-trimethylbenzenesulfonate

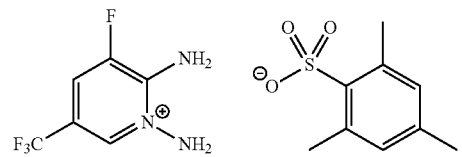

The title compound was prepared in a manner analogous to Intermediate 8, substituting 3-fluoro-5-(trifluoromethyl)pyridin-2-amine for 5-(trifluoromethyl)pyridin-2-amine. $^1$H NMR (500 MHz, DMSO-$d_6$) δ 9.42 (br s, 2H), 8.56 (m, 1H), 8.37 (m, 1H), 7.01 (s, 2H), 6.73 (s, 2H), 2.48 (s, 6H), 2.17 (s, 3H).

Intermediate 15: 1,2-Diamino-5-bromopyridin-1-ium 2,4,6-trimethylbenzenesulfonate

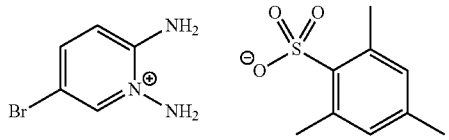

To a cooled (−5° C.) mixture of TFA (18.0 mL, 235 mmol) and water (2.5 mL) was added ethyl (1E)-N-(2,4,6-trimethylphenyl)sulfonyloxyethanimidate (12.4 g, 43.4 mmol) and the mixture was maintained at −5° C. for 1.5 h. Ice cold water (30 mL) was added and the mixture was extracted with DCM (20 mL). The organic layer was dried over $Na_2SO_4$, filtered and added to an ice-cold solution of 5-bromopyridin-2-amine (5.0 g, 29 mmol) in DCM (20 mL). The reaction mixture was stirred for 16 h at rt. To the crude reaction mixture was added diethyl ether (30 mL) and the resulting white precipitate was filtered and washed with ether to provide the title compound (4.5 g, 40%). MS (ESI): mass calcd. for $C_5H_7BrN_3$, 188.0; m/z found, 189.0 [M+H]⁺.

Intermediate 16: 5-Chloro-2,6-bis(trifluoromethyl)-[1,2,4]triazolo[1,5-a]pyridine

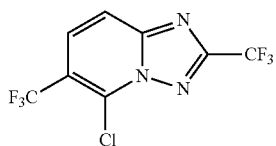 [SMILES: FC(F)(F)c1nc2ccc(C(F)(F)F)c(Cl)n2n1]

To a suspension of 1,6-diamino-2-chloro-3-(trifluoromethyl)pyridin-1-ium 2,4,6-trimethylbenzenesulfonate (Intermediate 9, 500 mg, 1.21 mmol) in MeOH (6.2 mL) at 0° C. was added $Et_3N$ (0.51 mL, 3.65 mmol), followed by trifluoroacetic anhydride (0.26 mL, 1.86 mmol) dropwise via syringe. The reaction was maintained at 0° C. for 10 min then stirred at rt for 16 h. The reaction mixture was diluted with EtOAc and sat. aq. $NaHCO_3$, and then the layers were separated. The aqueous layer was extracted with EtOAc (×2), and the combined organic extracts were washed with brine, dried over $Na_2SO_4$ and filtered. The filtrate was concentrated in vacuo. Purification (FCC, $SiO_2$; 0-50% EtOAc/hexanes) afforded the title compound as a white solid (233 mg, 66%). MS (ESI): mass calcd. for $C_8H_2ClF_6N_3$, 289.0; m/z found, 290.0 [M+H]⁺. ¹H NMR (500 MHz, $CDCl_3$) δ 7.97 (m, 1H), 7.93 (m, 1H).

Intermediate 17: 5-Chloro-6-iodo-2-(trifluoromethyl)-[1,2,4]triazolo[1,5-a]pyridine

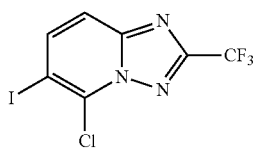 [SMILES: FC(F)(F)c1nc2ccc(I)c(Cl)n2n1]

The title compound was prepared in a manner analogous to Intermediate 16, substituting 1,6-diamino-2-chloro-3-iodopyridin-1-ium 2,4,6-trimethylbenzenesulfonate for 1,6-diamino-2-chloro-3-(trifluoromethyl)pyridin-1-ium 2,4,6-trimethylbenzenesulfonate. MS (ESI): mass calcd. for $C_7H_2ClF_3IN_3$, 346.9; m/z found, 347.8 [M+H]⁺. ¹H NMR (500 MHz, $CDCl_3$) δ 8.00 (d, J=9.3 Hz, 1H), 7.60 (d, J=9.3 Hz, 1H).

Intermediate 18: 5-Bromo-6-methoxy-2-(trifluoromethyl)-[1,2,4]triazolo[1,5-a]pyridine

The title compound was prepared in a manner analogous to Intermediate 16, substituting 1,6-diamino-2-bromo-3-methoxypyridin-1-ium 2,4,6-trimethylbenzenesulfonate for 1,6-diamino-2-chloro-3-(trifluoromethyl)pyridin-1-ium 2,4,6-trimethylbenzenesulfonate. MS (ESI): mass calcd. for $C_8H_5BrF_3N_3O$, 295.0; m/z found, 296.0 [M+H]⁺. ¹H NMR (500 MHz, $CDCl_3$) δ 7.82 (d, J=9.6 Hz, 1H), 7.59 (d, J=9.7 Hz, 1H), 4.05 (s, 3H).

Intermediate 19: 6-Iodo-8-methyl-2-(trifluoromethyl)-[1,2,4]triazolo[1,5-a]pyridine

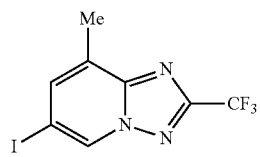 [SMILES: Cc1cc(I)cn2nc(C(F)(F)F)nc12]

The title compound was prepared in a manner analogous to Intermediate 16, substituting 1,2-diamino-5-iodo-3-methylpyridin-1-ium 2,4,6-trimethylbenzenesulfonate for 1,6-diamino-2-chloro-3-(trifluoromethyl)pyridin-1-ium 2,4,6-trimethylbenzenesulfonate. MS (ESI): mass calcd. for $C_8H_5F_3IN_3$, 326.9; m/z found, 327.9 [M+H]⁺. ¹H NMR (500 MHz, $CDCl_3$) δ 8.75 (m 1H), 7.64 (m, 1H), 2.66 (s, 3H).

Intermediate 20: 6-Bromo-2-(trifluoromethyl)-[1,2,4]triazolo[1,5-a]pyridine

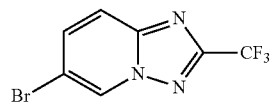 [SMILES: FC(F)(F)c1nc2ccc(Br)cn2n1]

The title compound was prepared in a manner analogous to Intermediate 16, substituting 1,2-diamino-5-bromopyridin-1-ium 2,4,6-trimethylbenzenesulfonate for 1,6-diamino-2-chloro-3-(trifluoromethyl)pyridin-1-ium 2,4,6-trimethylbenzenesulfonate. ¹H NMR (500 MHz, DMSO-$d_6$) δ 9.59 (m 1H), 8.04 (m, 1H), 8.01 (m, 1H).

Intermediate 21: 5-Chloro-2-(difluoromethyl)-6-(trifluoromethyl)-[1,2,4]triazolo[1,5-a]pyridine

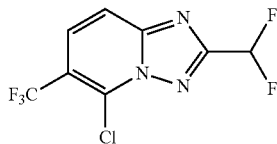 [SMILES: FC(F)c1nc2ccc(C(F)(F)F)c(Cl)n2n1]

The title compound was prepared in a manner analogous to Intermediate 16, substituting methyl difluoroacetate for trifluoroacetic anhydride and heating to 45° C. instead of stirring at rt. MS (ESI): mass calcd. for $C_8H_3ClF_5N_3$, 271.0; m/z found, 272.0 [M+H]$^+$.

Intermediate 22: 5-Bromo-2-(difluoromethyl)-6-methoxy-[1,2,4]triazolo[1,5-a]pyridine

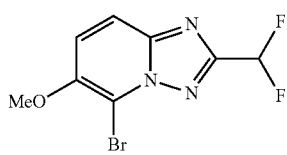 [SMILES: COc1ccc2nc(C(F)F)nn2c1Br]

The title compound was prepared in a manner analogous to Intermediate 16, substituting 1,6-diamino-2-bromo-3-methoxypyridin-1-ium 2,4,6-trimethylbenzenesulfonate for 1,6-diamino-2-chloro-3-(trifluoromethyl)pyridin-1-ium 2,4,6-trimethylbenzenesulfonate and methyl difluoroacetate for trifluoroacetic anhydride, along with heating at 45° C. instead of stirring at rt. MS (ESI): mass calcd. for $C_8H_6BrF_2N_3O$, 277.0; m/z found, 278.0 [M+H]$^+$.

Intermediate 23: 5-Chloro-2-ethyl-6-(trifluoromethyl)-[1,2,4]triazolo[1,5-a]pyridine

To a solution of 1,6-diamino-2-chloro-3-(trifluoromethyl)pyridin-1-ium 2,4,6-trimethylbenzenesulfonate (Intermediate 9) (300 mg, 0.73 mmol) in AcOH (5.8 mL) and MeOH (2.85 mL) were added Cu(OAc)$_2$ (66 mg, 0.36 mmol) and propionaldehyde (0.16 mL, 2.19 mmol). The reaction was heated at 70° C. for 5 h, then cooled to rt and diluted with EtOAc. The mixture was carefully neutralized with 4N NaOH (ca. 25 mL), and the aqueous layer then extracted EtOAc (×2). The combined organics were washed with brine, dried over Na$_2$SO$_4$ and filtered. The filtrate was concentrated in vacuo. Purification (FCC, SiO$_2$; 0-50% EtOAc/hexanes) afforded the title compound as a pale yellow solid (90 mg, 49%). MS (ESI): mass calcd. for $C_9H_7ClF_3N_3$, 249.0; m/z found, 250.1 [M+H]$^+$.

Intermediate 24: 5-Chloro-2-cyclopropyl-6-(trifluoromethyl)-[1,2,4]triazolo[1,5-a]pyridine

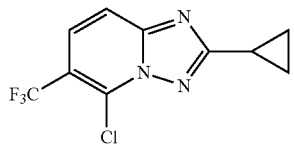 [SMILES: FC(F)(F)c1ccc2nc(C3CC3)nn2c1Cl]

The title compound was prepared in a manner analogous to Intermediate 23, substituting cyclopropanecarboxaldehyde for propionaldehyde and heating to 90° C. instead of 70° C. MS (ESI): mass calcd. for $C_{10}H_7ClF_3N_3$, 261.0; m/z found, 262.0 [M+H]$^+$. $^1$H NMR (400 MHz, CDCl$_3$) δ 7.73 (m, 1H), 7.62 (d, J=9.3 Hz, 1H), 2.32 (m, 1H), 1.18 (m, 4H).

Intermediate 25: 5-Chloro-2-ethyl-6-iodo-[1,2,4]triazolo[1,5-a]pyridine

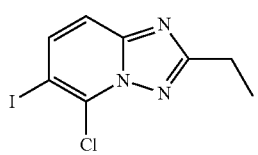

The title compound was prepared in a manner analogous to Intermediate 23, substituting 1,6-diamino-2-chloro-3-iodopyridin-1-ium 2,4,6-trimethylbenzenesulfonate for 1,6-diamino-2-chloro-3-(trifluoromethyl)pyridin-1-ium 2,4,6-trimethylbenzenesulfonate. MS (ESI): mass calcd. for $C_8H_7ClIN_3$, 306.9; m/z found, 307.9 [M+H]$^+$. $^1$H NMR (400 MHz, CDCl$_3$) δ 7.80 (d, J=9.2 Hz, 1H), 7.41 (d, J=9.2 Hz, 1H), 2.99 (q, J=7.6 Hz, 2H), 1.43 (t, J=7.6 Hz, 3H).

Intermediate 26: 5-Chloro-2-cyclopropyl-6-iodo-[1,2,4]triazolo[1,5-a]pyridine

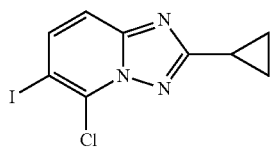 [SMILES: Clc1c(I)ccc2nc(C3CC3)nn12]

The title compound was prepared in a manner analogous to Intermediate 23, substituting 1,6-diamino-2-chloro-3-iodopyridin-1-ium 2,4,6-trimethylbenzenesulfonate for 1,6-diamino-2-chloro-3-(trifluoromethyl)pyridin-1-ium 2,4,6-trimethylbenzenesulfonate and cyclopropanecarboxaldehyde for propionaldehyde. MS (ESI): mass calcd. for $C_9H_7ClIN_3$, 318.9; m/z found, 319.9 [M+H]$^+$. $^1$H NMR (500 MHz, CDCl$_3$) δ 7.77 (d, J=9.2 Hz, 1H), 7.33 (d, J=9.2 Hz, 1H), 2.27 (m, 1H), 1.14 (m, 4H).

Intermediate 27: 2-Isopropyl-6-(trifluoromethyl)-[1,2,4]triazolo[1,5-a]pyridine

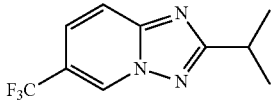

To a solution of 1,2-diamino-5-(trifluoromethyl)pyridin-1-ium 2,4,6-trimethylbenzenesulfonate (Intermediate 8, 0.5 g, 1.3 mmol) in isobutyric acid (1.9 mL) was added isobutyric anhydride (0.66 mL, 4.0 mmol). The reaction was stirred in a microwave reactor at 150° C. for 30 min, and then diluted with EtOAc and H$_2$O. The mixture was then neutralized with 4N NaOH, the aqueous layer extracted twice with EtOAc, and the combined organics washed with brine, dried over Na$_2$SO$_4$, and filtered. The filtrate was concentrated in vacuo. Purification (FCC, SiO$_2$; 0-50% EtOAc/hexanes) afforded the title compound as a white solid (192 mg, 63%). MS (ESI): mass calcd. for C$_{10}$H$_{10}$F$_3$N$_3$, 229.1; m/z found, 230.1 [M+H]$^+$. $^1$H NMR (400 MHz, CDCl$_3$) δ 8.87 (s, 1H), 7.78 (d, J=9.3 Hz, 1H), 7.63 (dd, J=9.3, 1.7 Hz, 1H), 3.36-3.23 (m, 1H), 1.45 (d, J=7.0 Hz, 6H).

Intermediate 28: 8-Fluoro-2-isopropyl-6-(trifluoromethyl)-[1,2,4]triazolo[1,5-a]pyridine

The title compound was prepared in a manner analogous to Intermediate 27, substituting 1,2-diamino-3-fluoro-5-(trifluoromethyl)pyridin-1-ium 2,4,6-trimethylbenzenesulfonate for 1,2-diamino-5-(trifluoromethyl)pyridin-1-ium 2,4,6-trimethylbenzenesulfonate. MS (ESI): mass calcd. for C$_{10}$H$_9$F$_4$N$_3$, 247.1; m/z found, 249.9 [M+H]$^+$. $^1$H NMR (400 MHz, DMSO-d$_6$) δ 9.54 (t, J=1.3 Hz, 1H), 8.04 (dd, J=10.4, 1.5 Hz, 1H), 3.24 (dt, J=13.9, 6.9 Hz, 1H), 1.38 (d, J=6.9 Hz, 6H).

Intermediate 29: 2-Ethyl-6-iodo-8-methyl[1,2,4]triazolo[1,5-a]pyridine

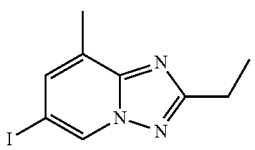

The title compound was prepared in a manner analogous to Intermediate 27, substituting 1,2-diamino-5-iodo-3-methylpyridin-1-ium 2,4,6-trimethylbenzenesulfonate for 1,2-diamino-5-(trifluoromethyl)pyridin-1-ium 2,4,6-trimethylbenzenesulfonate, propionic anhydride for isobutyric anhydride, and propionic acid for isobutyric acid. MS (ESI): mass calcd. for C$_9$H$_{10}$IN$_3$, 287.1; m/z found, 288.0 [M+H]$^+$. $^1$H NMR (500 MHz, DMSO-d$_6$) δ 9.12-9.02 (m, 1H), 7.70-7.60 (m, 1H), 2.82 (q, J=7.6 Hz, 2H), 2.48 (t, J=0.9 Hz, 3H), 1.30 (t, J=7.6 Hz, 3H).

Intermediate 30: 2-Ethyl-8-fluoro-6-(trifluoromethyl)-[1,2,4]triazolo[1,5-a]pyridine

To a solution of 2-diamino-3-fluoro-5-(trifluoromethyl)pyridin-1-ium 2,4,6-trimethylbenzenesulfonate (250 mg, 0.63 mmol) in DMF (3.0 mL) was added propionaldehyde (0.17 ml, 2.4 mmol), followed by sodium metabisulfite (255 mg, 1.3 mmol). The mixture was stirred at 90° C. for 1 h. The reaction mixture was cooled to rt, diluted with water, and extracted with EtOAc (×2). The combined organic extracts were washed with brine, dried over Na$_2$SO$_4$, and concentrated in vacuo. Purification (FCC, SiO$_2$; 0-100% EtOAc/hexanes) provided the title compound as a white solid (88 mg, 60%). MS (ESI): mass calcd. for C$_9$H$_7$F$_4$N$_3$, 233.1; m/z found, 234.0 [M+H]$^+$. $^1$H NMR (500 MHz, DMSO-d$_6$) δ 9.55-9.51 (m, 1H), 8.04 (dd, J=10.4, 1.6 Hz, 1H), 2.92 (q, J=7.6 Hz, 2H), 1.34 (t, J=7.6 Hz, 3H).

Intermediate 31: 2-Cyclopropyl-8-fluoro-6-(trifluoromethyl)-[1,2,4]triazolo[1,5-a]pyridine

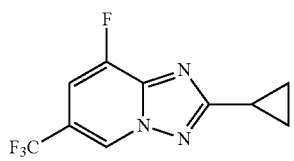 [SMILES: Fc1cc(C(F)(F)F)cn2nc(C3CC3)nc12]

The title compound was prepared in a manner analogous to Intermediate 30, substituting cyclopropanecarboxaldehyde for propionaldehyde. MS (ESI): mass calcd. for C$_{10}$H$_7$F$_4$N$_3$, 245.1; m/z found, 246.0 [M+H]$^+$. $^1$H NMR (400 MHz, DMSO-d$_6$) δ 9.47 (t, J=1.3 Hz, 1H), 8.02 (dd, J=10.4, 1.5 Hz, 1H), 2.26 (tt, J=8.2, 4.8 Hz, 1H), 1.16-1.11 (m, 2H), 1.06-1.01 (m, 2H).

Intermediate 32: 8-Methyl-2,6-bis(trifluoromethyl)-[1,2,4]triazolo[1,5-a]pyridine

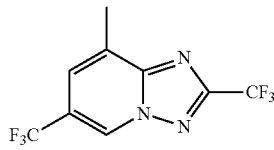 [SMILES: Cc1cc(C(F)(F)F)cn2nc(C(F)(F)F)nc12]

A microwave vial was charged with 6-iodo-8-methyl-2-(trifluoromethyl)-[1,2,4]triazolo[1,5-a]pyridine (139 mg, 0.43 mmol), methyl 2,2-difluoro-2-(fluorosulfonyl)acetate (0.14 mL, 1.1 mmol), CuI (202 mg, 1.1 mmol), DMPU (0.3 mL, 2.4 mmol), and DMF (2.7 mL). The vial was evacuated under vacuum and backfilled with Na (×3), and then capped and sealed. The reaction was then stirred in a microwave reactor at 130° C. for 30 min. The mixture was cooled to rt and filtered over a pad of Celite®, eluting with MeOH. After concentrating the filtrate in vacuo, the residue was dissolved in a mixture of EtOAc and H$_2$O. The organic layer was washed with sat. aq. NH$_4$Cl, and then the combined aqueous layers extracted with EtOAc (×2). The combined organics were washed with brine (×3), dried over Na$_2$SO$_4$ and filtered. The filtrate was concentrated in vacuo. Purification (FCC, SiO$_2$; 0-50% EtOAc/hexanes) afforded the title compound as a pale yellow oil (79 mg, 69%). $^1$H NMR (500 MHz, CDCl$_3$) δ 8.85 (s, 1H), 7.60 (s, 1H), 2.76 (s, 3H).

Intermediate 33: 2-Ethyl-8-methyl-6-(trifluoromethyl)-[1,2,4]triazolo[1,5-a]pyridine

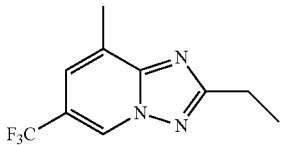

The title compound was prepared in a manner analogous to Intermediate 32, substituting 2-ethyl-6-iodo-8-methyl-[1,2,4]triazolo[1,5-a]pyridine for 6-iodo-8-methyl-2-(trifluoromethyl)-[1,2,4]triazolo[1,5-a]pyridine. MS (ESI): mass calcd. for C$_{10}$H$_{10}$F$_3$N$_3$, 229.2; m/z found, 230.1 [M+H]$^+$. $^1$H NMR (500 MHz, DMSO-d$_6$) δ 9.38 (dd, J=1.7, 0.9 Hz, 1H), 7.73 (t, J=1.5 Hz, 1H), 2.89 (q, J=7.6 Hz, 2H), 2.58 (s, 3H), 1.34 (t, J=7.6 Hz, 3H).

Intermediate 34: 5-Chloro-2-methyl-6-(trifluoromethyl)-[1,2,4]triazolo[1,5-a]pyridine

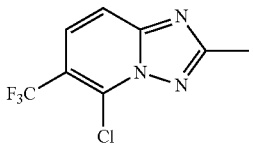

The title compound was prepared in a manner analogous to Intermediate 23, substituting acetaldehyde for propionaldehyde. MS (ESI): mass calcd. for C$_8$H$_5$ClF$_3$N$_3$, 235.0; m/z found, 236.0 [M+H]$^+$.

Intermediate 35: 5-Chloro-6-(difluoromethyl)-2-ethyl-[1,2,4]triazolo[1,5-a]pyridine

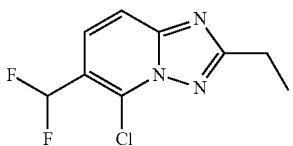

Step A: 5-Chloro-2-ethyl-[1,2,4]triazolo[1,5-a]pyridine-6-carbaldehyde

To a solution of 5-chloro-2-ethyl-6-iodo-[1,2,4]triazolo[1,5-a]pyridine (Intermediate 25, 409 mg, 1.33 mmol) in THF (4.4 mL) at 0° C. was added isopropylmagnesium chloride (2.0 M in THF; 0.8 mL, 1.60 mmol). The mixture was stirred at 0° C. for 1 h, then N-formylpiperidine (0.18 mL, 1.60 mmol) was added. The reaction was allowed to warm to rt and stirred for 2 h. The mixture was then transferred to a stirring solution of AcOH (1 mL) and diluted with EtOAc. Sat. aq. NH$_4$Cl and H$_2$O were added, and the aqueous layer was extracted with EtOAc (×2). The combined organics were washed with brine, dried over Na$_2$SO$_4$, filtered, and concentrated in vacuo. Purification (FCC, SiO$_2$; 0-50% EtOAc/hexanes) afforded the title compound as a white solid (194 mg, 70%). MS (ESI): mass calcd. for C$_9$H$_8$ClN$_3$O, 209.0; m/z found, 210.0 [M+H]$^+$.

Step B: 5-Chloro-6-(difluoromethyl)-2-ethyl-[1,2,4]triazolo[1,5-a]pyridine

To a solution of 5-chloro-2-ethyl-[1,2,4]triazolo[1,5-a]pyridine-6-carbaldehyde (217 mg, 1.04 mmol) in DCM (21 mL) at 0° C. under an Na atmosphere was added diethylaminosulfur trifluoride (0.82 mL, 6.21 mmol) dropwise via syringe. The mixture was stirred at rt for 3 h and at 35° C. for 3 h. After cooling to rt, the reaction mixture was poured over ice (ca. 25 mL), diluted with sat. aq. NaHCO$_3$ (30 mL), and extracted with DCM (×2). The combined organics were washed with brine, dried over Na$_2$SO$_4$, filtered, and concentrated under reduced pressure. Purification (FCC, SiO$_2$; 0-100% EtOAc/hexanes) afforded the title compound (193 mg, 80%). MS (ESI): mass calcd. for C$_9$H$_8$ClF$_2$N$_3$, 231.0; m/z found, 232.1 [M+H]$^+$. $^1$H NMR (400 MHz, CDCl$_3$) δ 7.79-7.69 (m, 2H), 7.03 (t, J=54.4 Hz, 1H), 3.02 (q, J=7.6 Hz, 2H), 1.45 (t, J=7.6 Hz, 3H).

Intermediate 36: 5-Chloro-2-cyclopropyl-6-(difluoromethyl)-[1,2,4]triazolo[1,5-a]pyridine

The title compound was made in an analogous manner to Intermediate 35, substituting 5-chloro-2-cyclopropyl-6-iodo-[1,2,4]triazolo[1,5-a]pyridine (Intermediate 26) for 5-chloro-2-ethyl-6-iodo-[1,2,4]triazolo[1,5-a]pyridine in Step A. MS (ESI): mass calcd. for C$_{10}$H$_8$ClF$_2$N$_3$, 243.0; m/z found, 244.1 [M+H]$^+$.

Intermediate 37: 5-Chloro-6-(difluoromethyl)-2-(trifluoromethyl)-[1,2,4]triazolo[1,5-a]pyridine

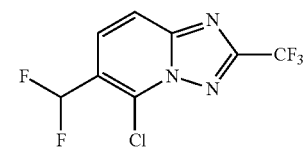 [SMILES: FC(F)c1ccc2nc(C(F)(F)F)nn2c1Cl]

The title compound was made in an analogous manner to Intermediate 35, substituting 5-chloro-6-iodo-2-(trifluoromethyl)-[1,2,4]triazolo[1,5-a]pyridine (Intermediate 17) for 5-chloro-2-ethyl-6-iodo-[1,2,4]triazolo[1,5-a]pyridine in Step A. MS (ESI): mass calcd. for C$_8$H$_3$ClF$_5$N$_3$, 271.0; m/z found, 272.0 [M+H]$^+$. $^1$H NMR (400 MHz, CDCl$_3$) δ 8.00-7.96 (m, 1H), 7.96-7.91 (m, 1H), 7.07 (t, J=56 Hz, 1H).

Intermediate 38: 5-Iodo-2-isopropyl-6-(trifluoromethyl)-[1,2,4]triazolo[1,5-a]pyridine

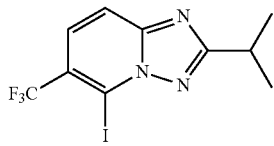 [SMILES: CC(C)c1nc2ccc(C(F)(F)F)c(I)n2n1]

To a solution of 2-isopropyl-6-(trifluoromethyl)-[1,2,4]triazolo[1,5-a]pyridine (Intermediate 27, 100 mg, 0.44 mmol) in THF (2.9 mL) at −78° C. was added n-butyllithium (1.6 M in hexanes; 0.33 mL, 0.52 mmol) dropwise via syringe. After stirring at −78° C. for 30 min, a solution of 1,2-diiodoethane (148 mg, 0.524 mmol) in THF (0.75 mL) was added, and stirring maintained for 10 min at −78° C. The reaction was then warmed to rt for an additional 30 min before being quenched with sat. aq. NH$_4$Cl. The aqueous layer was extracted with EtOAc (×2), and the combined organics were washed with brine, dried over Na$_2$SO$_4$, filtered, and concentrated in vacuo. Purification (FCC, SiO$_2$; 0-50% EtOAc/hexanes) afforded the title compound as a white solid (127 mg, 82%). MS (ESI): mass calcd. for C$_{10}$H$_9$F$_3$IN$_3$, 355.0; m/z found, 356.0 [M+H]$^+$. $^1$H NMR (400 MHz, CDCl$_3$) δ 7.71-7.63 (m, 2H), 3.42-3.29 (m, 1H), 1.46 (d, J=7.0 Hz, 6H).

Intermediate 39: 2-Ethyl-8-fluoro-5-iodo-6-(trifluoromethyl)-[1,2,4]triazolo[1,5-a]pyridine

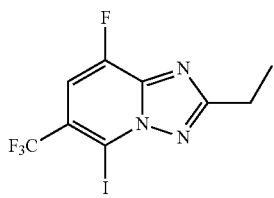 [SMILES: CCc1nc2c(F)cc(C(F)(F)F)c(I)n2n1]

The title compound was prepared in a manner analogous to Intermediate 38, substituting 2-ethyl-8-fluoro-6-(trifluoromethyl)-[1,2,4]triazolo[1,5-a]pyridine for 2-isopropyl-6-(trifluoromethyl)-[1,2,4]triazolo[1,5-a]pyridine. MS (ESI): mass calcd. for C$_9$H$_6$F$_4$IN$_3$, 359.0; m/z found, 359.9 [M+H]$^+$. $^1$H NMR (400 MHz, DMSO-d$_6$) δ 8.00 (d, J=10.9 Hz, 1H), 2.94 (q, J=7.6 Hz, 2H), 1.36 (t, J=7.6 Hz, 3H).

Intermediate 40: 5-Chloro-2-ethyl-8-fluoro-6-(trifluoromethyl)-[1,2,4]triazolo[1,5-a]pyridine

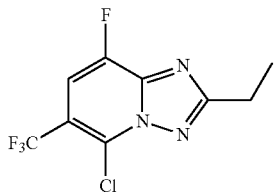 [SMILES: CCc1nc2c(F)cc(C(F)(F)F)c(Cl)n2n1]

To a cooled (−78° C.) solution of 2-ethyl-8-fluoro-6-(trifluoromethyl)-[1,2,4]triazolo[1,5-a]pyridine (55 mg, 0.24 mmol) in THF (1.5 mL) was added n-butyllithium (1.6M/hexanes, 0.17 mL, 0.28 mmol) dropwise over a period of 10 minutes. Stirring was maintained at −78° C. for 30 minutes, and then a solution of hexachloroethane (67 mg, 0.28 mmol) in THF (1.5 mL) was added dropwise over a period of 10 minutes. After the addition, the mixture was warmed to rt and stirred for another 10 minutes. The reaction was quenched with saturated aq. NH$_4$Cl and the aqueous layer was extracted with EtOAc (×2). The combined organic extracts were dried over Na$_2$SO$_4$ and concentrated in vacuo. Purification (FCC, SiO$_2$; 0-50% EtOAc/hexanes) provided the title compound as a white solid (36 mg, 56%). MS (ESI): mass calcd. for C$_9$H$_6$ClF$_4$N$_3$, 267.6; m/z found, 269.0 [M+H]$^+$. $^1$H NMR (400 MHz, DMSO-d$_6$) δ 8.15 (d, J=10.4 Hz, 1H), 2.97 (q, J=7.6 Hz, 2H), 1.36 (t, J=7.6 Hz, 3H).

Intermediate 41: Ethyl 7-chloro-2,6-bis(trifluoromethyl)pyrazolo[1,5-a]pyridine-3-carboxylate

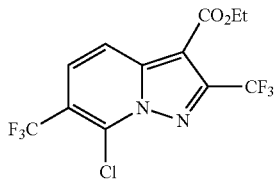 [SMILES: CCOC(=O)c1c(C(F)(F)F)nn2c(Cl)c(C(F)(F)F)ccc12]

Step A:
2-Chloro-3-(trifluoromethyl)pyridin-1-ium-1-amine 2,4,6-trimethylbenzenesulfonate To a mixture of TFA (80 mL, 104 mmol) and H$_2$O (8.2 mL) was added ethyl (1E)-N-(2,4,6-trimethylphenyl)sulfonyloxyethanimidate (15 g, 52.6 mmol) at −5° C. and the reaction mixture was stirred for 1.5 h. To the reaction mixture was added ice water (150 mL). The precipitate was collected and washed with water (20×50 mL). The white solid was dissolved in DCM (250 mL), dried over Na$_2$SO$_4$, and filtered. The filtrate was cooled to 0° C. and to this solution was added dropwise 2-chloro-3-(trifluoromethyl)pyridine (9.6 g, 52.9 mmol). The reaction mixture was allowed to warm to rt and stirred for 22 h. The reaction mixture was diluted with Et$_2$O (800 mL) and the precipitate was collected. The solid was washed with Et$_2$O (100 mL) and dried in vacuo. The crude product was triturated with Et$_2$O (100 mL) to give the title compound (6.18 g, 30%) as a white crystalline solid. $^1$H NMR (500 MHz, DMSO-d$_6$) δ 9.15 (dd, J=6.4, 1.3 Hz, 1H), 8.87 (br s, 2H), 8.70 (dd, J=8.3, 1.4 Hz, 1H), 8.14 (dd, J=8.1, 6.5 Hz, 1H), 6.74 (s, 2H), 2.53-2.47 (m, 6H), 2.17 (s, 3H).

Step B: Ethyl 7-chloro-2,6-bis(trifluoromethyl)pyrazolo[1,5-c]pyridine-3-carboxylate To a cooled solution (0° C.) of 2-chloro-3-(trifluoromethyl)pyridin-1-ium-1-amine 2,4,6-trimethylbenzenesulfonate (1.83 g, 4.61 mmol) in DMF (15 mL) were added ethyl 4,4,4-trifluorobut-2-ynoate (550 µL, 3.85 mmol) and triethylamine (640 µL, 4.59 mmol). The reaction mixture was stirred at rt for 18 h. The mixture was cooled to 0° C. and 2,3-dichloro-5,6-dicyano-p-benzoquinone (2.1 g, 9.25 mmol) was added. After stirring at rt for 1 h, the mixture was diluted with EtOAc (300 mL) and washed sequentially with water (2×100 mL), 10% aq. NaHCO$_3$ (50 mL) and water (50 mL). The organic layer was dried over MgSO$_4$, filtered and evaporated. Purification (FCC, SiO$_2$; 40-60% EtOAc/hexanes) afforded the title compound (715 mg, 51%) as a white crystalline solid. MS (ESI): mass calcd. for $C_{12}H_7ClF_6N_2O_2$, 360.0; m/z found, 361.0 [M+H]$^+$. $^1$H NMR (300 MHz, DMSO-d$_6$) δ 8.33 (d, J=9.5 Hz, 1H), 8.05 (d, J=9.5 Hz, 1H), 4.38 (q, J=7.1 Hz, 2H), 1.36 (t, J=7.1 Hz, 3H).

Intermediate 42: 7-Chloro-2,6-bis(trifluoromethyl)pyrazolo[1,5-a]pyridine

Step A: 7-Chloro-2,6-bis(trifluoromethyl)pyrazolo[1,5-c]pyridine-3-carboxylic acid To a suspension of ethyl 7-chloro-2,6-bis(trifluoromethyl)pyrazolo[1,5-c]pyridine-3-carboxylate (535 mg, 1.48 mmol) in a mixture of 1,4-dioxane and water (5:1, 22.2 mL) was added lithium hydroxide monohydrate (93 mg, 2.21 mmol). The reaction mixture was stirred at 60° C. for 1 h. Additional lithium hydroxide monohydrate (62 mg, 1.48 mmol) was added, and the stirring was continued at 60° C. for 1.5 h. After cooling to rt, the mixture was acidified to pH 3 by addition of 1 M HCl, and then the solvents were removed in vacuo. The residue was taken up in water (40 mL) and extracted with EtOAc (2×100 mL). The combined organic layers were washed with water (1×30 mL), dried over MgSO$_4$, filtered and evaporated. Purification (FCC, SiO$_2$; 5% IPA/Et$_2$O) afforded the title compound (185 mg, 37%) as a white crystalline solid. MS (ESI): mass calcd. for $C_{10}H_4ClF_6N_2O_2$, 332.0; m/z found, 331.0 [M−H]$^-$.

Step B: 7-Chloro-2,6-bis(trifluoromethyl)pyrazolo[1,5-a]pyridine

To a solution of 7-chloro-2,6-bis(trifluoromethyl)pyrazolo[1,5-c]pyridine-3-carboxylic acid (109 mg, 0.328 mmol) in DMSO (5.5 mL) was added silver carbonate (25 mg, 0.0907 mmol) and AcOH (3 µL, 0.0524 mmol). The reaction mixture was stirred at 120° C. for 2 h. After cooling to rt, the mixture was diluted with EtOAc (50 mL) and washed successively with water (3×20 mL) and brine (2×20 mL). The organic layer was dried over MgSO$_4$, filtered and evaporated. Purification (FCC, SiO$_2$; 10% EtOAc/hexanes) afforded the title compound (53 mg, 56%) as a white crystalline solid. $^1$H NMR (300 MHz, DMSO-d$_6$) δ 8.14 (d, J=9.4 Hz, 1H), 7.82 (d, J=9.4 Hz, 1H), 7.55 (s, 1H).

Intermediate 43: 7-Bromo-2-cyclopropyl-6-(trifluoromethyl)pyrazolo[1,5-a]pyridine

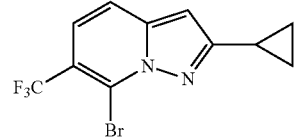 [SMILES: FC(F)(F)c1ccc2cc(C3CC3)nn2c1Br]

Step A: 2-(2-Cyclopropylethynyl)-5-(trifluoromethyl)pyridine

A mixture of 2-bromo-5-(trifluoromethyl)pyridine (5 g, 22.1 mmol), cyclopropylacetylene (2.43 mL, 28.7 mmol), CuI (1.89 g, 9.92 mmol), Pd(PPh$_3$)$_4$ (409 mg, 0.354 mmol), and diisopropylamine (5.27 mL, 37.6 mmol) in THF (60 mL) was stirred at 70° C. for 18 h. The reaction mixture was evaporated under reduced pressure. Purification (FCC, SiO$_2$; 100% Et$_2$O) afforded the title compound which was repurified (FCC, SiO$_2$; 50% DCM/hexanes) to give the title compound (3.72, 79%) as a light brown solid. MS (ESI): mass calcd. for $C_{11}H_8F_3N$, 211.1; m/z found, 211.8 [M+H]$^+$.

Step B: 2-(2-Cyclopropylethynyl)-5-(trifluoromethyl)pyridin-1-ium-1-amine;2,4,6-trimethylbenzenesulfonate To a cooled (−5° C.) mixture of TFA (12.1 mL, 158 mmol) and water (1.4 mL) was added ethyl (1E)-N-(2,4,6-trimethylphenyl)sulfonyloxyethanimidate (3.38 g, 11.8 mmol), and the reaction mixture was stirred for 1.5 h. Ice water (60 mL) was added, and the resulting precipitate was collected and washed with water (10×10 mL). The solid was dissolved in DCM (40 mL), dried over MgSO$_4$, and filtered. The filtrate was cooled to 0° C. and 2-(2-cyclopropylethynyl)-5-(trifluoromethyl)pyridine (1.67 g, 7.91 mmol) was added. The reaction mixture was allowed to warm to rt and stirred for 2 h. The mixture was cooled to 0° C. and diluted with Et$_2$O (80 mL). The precipitate was collected and washed with Et$_2$O (2×20 mL) to give the title compound (2.00 g, 59%) as a pale yellow solid.

Step C: 2-Cyclopropyl-6-(trifluoromethyl)pyrazolo[1,5-a]pyridine

A solution of 2-(2-cyclopropylethynyl)-5-(trifluoromethyl)pyridin-1-ium-1-amine 2,4,6-trimethylbenzenesulfonate (1.46 g, 3.42 mmol) in AcOH (14 mL) was stirred at 80° C. for 16 h. After cooling to rt, ice water (20 mL) was added and the pH was adjusted to ~9 by the addition of 2 M NaOH. The aqueous layer was extracted with DCM (2×70 mL). The combined organic layers were washed with water (1×50 mL), dried over MgSO$_4$, filtered and evaporated. The residue was purified by flash column chromatography (SiO$_2$; 100% diisopropyl ether) to give the title compound (727 mg, 93%) as a light brown liquid. MS (ESI): mass calcd. for CHH$_9$F$_3$N$_2$, 226.1; m/z found, 227.1 [M+H]$^+$.

Step D: 7-Bromo-2-cyclopropyl-6-(trifluoromethyl) pyrazolo[1,5-a]pyridine

To a cooled (−70° C.) solution of 2-cyclopropyl-6-(trifluoromethyl)pyrazolo[1,5-c]pyridine (101 mg, 0.447 mmol) in THF (1 mL) was added n-butyllithium (2.27 M in n-hexane, 260 μL, 0.590 mmol). The reaction mixture was allowed to warm to −40° C. and stirred for 30 min. The reaction mixture was cooled to −70° C. and bromine (30 μL, 0.583 mmol) in THF (600 μL) was added. The temperature was maintained at −70° C. for 1 h and then at rt for 21 h. The reaction was quenched with sat. aq. NH$_4$Cl (1 mL) and the solvents removed in vacuo. The residue was taken up in DCM (50 mL) and the organic layer was washed with water (30 mL), dried over MgSO$_4$, filtered and evaporated. Purification (FCC, SiO$_2$; 50% DCM/hexanes) afforded the title compound (54 mg, 39%) as a yellow solid. MS (ESI): mass calcd. for C$_{11}$H$_8$BrF$_3$N$_2$, 304.0; m/z found, 305.0 [M+H]$^+$. $^1$H NMR (500 MHz, DMSO-d$_6$) δ 7.75 (d, J=9.2 Hz, 1H), 7.42 (d, J=9.3 Hz, 1H), 6.69 (s, 1H), 2.21-2.14 (m, 1H), 1.11-1.03 (m, 2H), 0.91-0.82 (m, 2H).

Intermediate 44: 7-Bromo-2-isopropyl-6-(trifluoromethyl)pyrazolo[1,5-a]pyridine

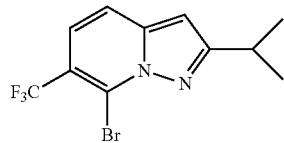

The title compound was prepared in a manner analogous to Intermediate 43, substituting 3-methylbut-1-yne for cyclopropylacetylene in Step A. MS (ESI): mass calcd. for C$_{11}$H$_{10}$BrF$_3$N$_2$, 306.0; m/z found, 306.7 [M+H]$^+$.

Intermediate 45: tert-Butyl 7-methyl-5-(4,4,5,5-tetramethyl-1,3,2-dioxaborolan-2-yl)-1H-indazole-1-carboxylate

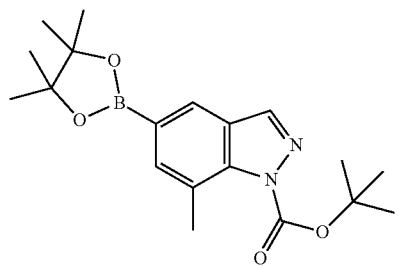 [SMILES: Cc1cc(B2OC(C)(C)C(C)(C)O2)cc2cnn(C(=O)OC(C)(C)C)c12]

Step A: tert-Butyl 5-bromo-7-methyl-1H-indazole-1-carboxylate

A mixture of 5-bromo-7-methyl-1H-indazole (5 g, 23.7 mmol), di-tert-butyl dicarbonate (7.8 g, 35.7 mmol), triethylamine (3.65 mL, 26.2 mmol), and 4-dimethylaminopyridine (300 mg, 2.46 mmol) in acetonitrile (100 mL) was stirred at room temperature for 4 h. The reaction mixture was evaporated to give the title compound (7.2 g, 97% crude yield) as a yellow solid, which was used directly in the next step. MS (ESI): mass calcd. for C$_{13}$H$_{15}$BrN$_2$O$_2$, 310.0; m/z found, 254.7 [M+H-t-Bu]$^+$ Step B: tert-Butyl 7-methyl-5-(4,4,5,5-tetramethyl-1,3,2-dioxaborolan-2-yl)-1H-indazole-1-carboxylate The title compound was prepared in a manner analogous to Intermediate 1, substituting tert-butyl 5-bromo-7-methyl-3a,7a-dihydro-1H-indazole-1-carboxylate for 5-bromo-7-chloro-1H-indazole.
$^1$H NMR (500 MHz, DMSO-d$_6$) δ 8.93 (s, 1H), 8.02-8.00 (m, 1H), 7.31-7.28 (m, 1H), 2.53-2.47 (m, 3H), 1.65 (s, 9H), 1.30 (s, 12H).

Intermediate 46: 5-Iodo-8-methyl-2,6-bis(trifluoromethyl)-[1,2,4]triazolo[1,5-a]pyridine

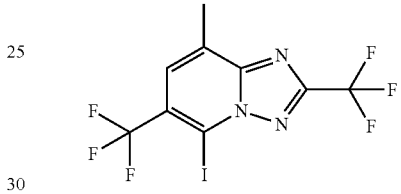

The title compound was prepared in a manner analogous to Intermediate 38, substituting 8-methyl-2,6-bis(trifluoromethyl)-[1,2,4]triazolo[1,5-a]pyridine (Intermediate 32) for 2-isopropyl-6-(trifluoromethyl)-[1,2,4]triazolo[1,5-a] pyridine. MS (ESI): mass calcd. for C$_9$H$_4$F$_6$IN$_3$, 394.9; m/z found, 396.0 [M+H]$^+$. $^1$H NMR (400 MHz, CDCl$_3$) δ 7.57 (s, 1H), 2.66 (s, 3H).

Intermediate 47: 5,8-Dichloro-2-ethyl-6-(trifluoromethyl)-[1,2,4]triazolo[1,5-a]pyridine

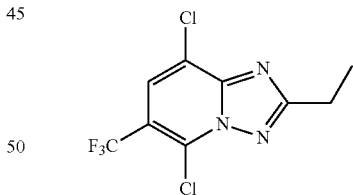

To a solution of 1,2-diamino-3,6-dichloro-5-(trifluoromethyl)pyridin-1-ium 2,4,6-trimethylbenzenesulfonate (Intermediate 13, 397 mg, 0.89 mmol) in AcOH (7 mL) and MeOH (3.5 mL) was added Cu(OAc)$_2$ (80.8 mg, 0.45 mmol) and propionaldehyde (0.19 mL, 2.67 mmol). The mixture was heated to 70° C. for 6 h. Additional Cu(OAc)$_2$ (162 mg, 0.89 mmol) was added, and the mixture heated to 80° C. for 6 h. After cooling to rt, the solvent was removed in vacuo, and the residue suspended in EtOAc. The suspension was washed with saturated aq. NH$_4$Cl, and the aqueous layer extracted with EtOAc (×2). The combined organics were washed with brine, dried over Na$_2$SO$_4$, and filtered. The filtrate was concentrated in vacuo. Purification (FCC, SiO$_2$; 0-50% EtOAc/hexanes) afforded the title compound as a white solid (90 mg, 36%). MS (ESI): mass calcd. for $C_9H_6Cl_2F_3N_3$, 283.0; m/z found, 284.0 [M+H]$^+$.

Intermediate 48: 5-Chloro-2-cyclopropyl-8-fluoro-6-(trifluoromethyl)-[1,2,4]triazolo[1,5-a]pyridine

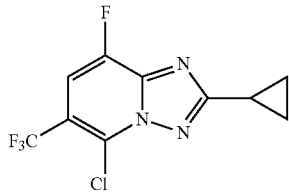 [SMILES: Fc1cc(C(F)(F)F)c(Cl)n2nc(C3CC3)nc12]

The title compound was prepared in a manner analogous to Intermediate 40, substituting 2-cyclopropyl-8-fluoro-6-(trifluoromethyl)-[1,2,4]triazolo[1,5-a]pyridine (Intermediate 31) for 2-ethyl-8-fluoro-6-(trifluoromethyl)-[1,2,4]triazolo[1,5-a]pyridine. MS (ESI): mass calcd. for $C_{10}H_6ClF_4N_3$, 279.0; m/z found, 279.9 [M+H]$^+$. $^1$H NMR (400 MHz, DMSO-d$_6$) δ 8.02 (d, J=10.5 Hz, 1H), 2.22 (tt, J=8.3, 4.9 Hz, 1H), 1.09-1.03 (m, 2H), 0.96 (dt, J=7.2, 4.0 Hz, 2H).

Intermediate 49: 5-Chloro-8-fluoro-2-isopropyl-6-(trifluoromethyl)-[1,2,4]triazolo[1,5-a]pyridine

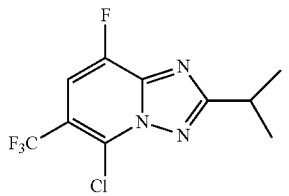 [SMILES: CC(C)c1nc2c(F)cc(C(F)(F)F)c(Cl)n2n1]

The title compound was prepared in a manner analogous to Intermediate 40, substituting 8-fluoro-2-isopropyl-6-(trifluoromethyl)-[1,2,4]triazolo[1,5-a]pyridine (Intermediate 28) for 2-ethyl-8-fluoro-6-(trifluoromethyl)-[1,2,4]triazolo[1,5-a]pyridine. MS (ESI): mass calcd. for $C_{10}H_8ClF_4N_3$, 281.6; m/z found, 283.0 [M+H]$^+$.

Intermediate 50: 5-Chloro-2-ethyl-8-methyl-6-(trifluoromethyl)-[1,2,4]triazolo[1,5-a]pyridine

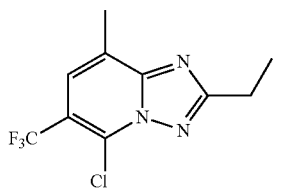 [SMILES: CCc1nc2c(C)cc(C(F)(F)F)c(Cl)n2n1]

The title compound was prepared in a manner analogous to Intermediate 40, substituting 2-ethyl-8-methyl-6-(trifluoromethyl)-[1,2,4]triazolo[1,5-a]pyridine (Intermediate 33) for 2-ethyl-8-fluoro-6-(trifluoromethyl)-[1,2,4]triazolo[1,5-a]pyridine. MS (ESI): mass calcd. for $C_{10}H_9ClF_3N_3$, 263.0; m/z found, 264.0 [M+H]$^+$.

Intermediate 51: 5-Chloro-2-(1,1-difluoroethyl)-6-(trifluoromethyl)-[1,2,4]triazolo[1,5-a]pyridine

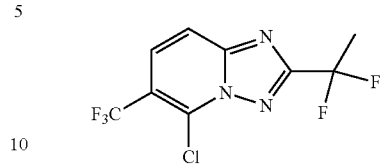

The title compound was prepared in a manner analogous to Intermediate 16, substituting methyl 2,2-difluoropropionate for trifluoroacetic anhydride and heating to 45° C. instead of stirring at rt. MS (ESI): mass calcd. for $C_9H_5ClF_5N_3$, 285.0; m/z found, 285.9 [M+H]$^+$.

Intermediate 52: 5-Chloro-2-methoxy-6-(trifluoromethyl)-[1,2,4]triazolo[1,5-a]pyridine

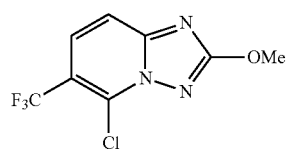

To a solution of 1,6-diamino-2-chloro-3-(trifluoromethyl)pyridin-1-ium 2,4,6-trimethylbenzenesulfonate (Intermediate 9, 100 mg, 0.24 mmol) in AcOH (0.3 mL, 5.24 mmol) was added tetramethoxymethane (0.65 mL, 4.86 mmol). The mixture was heated at 70° C. for 2 h. After cooling to rt, the solvent was removed in vacuo. The residue was dissolved in EtOAc and washed with sat. aq. NaHCO$_3$. The aqueous layer was extracted twice with EtOAc. The combined organics were washed with brine, dried over Na$_2$SO$_4$ and filtered. The filtrate was concentrated in vacuo. Purification (FCC, SiO$_2$; 0-50% EtOAc/hexanes) afforded a white solid (21 mg, 34%). MS (ESI): mass calcd. for $C_8H_5ClF_3N_3O$, 251.0; m/z found, 252.0 [M+H]$^+$.

Intermediate 53: 5-Chloro-6-ethyl-2-(trifluoromethyl)-[1,2,4]triazolo[1,5-a]pyridine

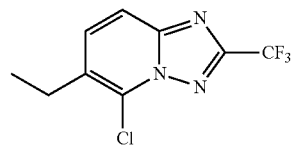 [SMILES: CCc1ccc2nc(C(F)(F)F)nn2c1Cl]

Step A: 5-Chloro-2-(trifluoromethyl)-6-vinyl-[1,2,4]triazolo[1,5-a]pyridine

A microwave vial was charged with 5-chloro-6-iodo-2-(trifluoromethyl)-[1,2,4]triazolo[1,5-a]pyridine (Intermediate 17, 200 mg, 0.58 mmol), tributyl(vinyl)tin (0.22 mL, 0.75 mmol), Pd(PPh$_3$)$_2$Cl$_2$ (40.4 mg, 0.058 mmol), and 1,2-dichloroethane (4.1 mL). The vial was evacuated under vacuum, backfilled with Na (×3), then capped and sealed. The reaction was stirred in a microwave reactor at 120° C.

for 30 min. EtOAc (12 mL) and 15% aqueous KHF₂ solution (4 mL) were added, and the mixture stirred at rt for 1 h. The aqueous layer was extracted with EtOAc (×2), and the combined organics washed with brine, dried over Na₂SO₄, filtered, and concentrated in vacuo. Purification (FCC, SiO₂; 0-30% EtOAc/hexanes) afforded the title compound (112 mg, 79%). MS (ESI): mass calcd. for $C_9H_5ClF_3N_3$, 247.0; m/z found, 248.1 [M+H]⁺. ¹H NMR (500 MHz, CDCl₃) δ 7.92 (d, J=9.3 Hz, 1H), 7.82-7.76 (m, 1H), 7.13-7.03 (m, 1H), 5.95 (d, J=17.5 Hz, 1H), 5.67 (d, J=11.1 Hz, 1H).

Step B: 5-Chloro-6-ethyl-2-(trifluoromethyl)-[1,2,4]triazolo[1,5-a]pyridine

A mixture of 5-chloro-2-(trifluoromethyl)-6-vinyl-[1,2,4]triazolo[1,5-a]pyridine (30 mg, 0.121 mmol) and 10% palladium on carbon (6 mg, 0.056 mmol) in MeOH (1.2 mL) was stirred under an atmosphere of H₂ for 3 h. After purging with nitrogen, the reaction was filtered over a pad of Celite®, eluting with EtOAc. After concentrating the filtrate in vacuo, the residue was used directly without further purification. MS (ESI): mass calcd. for $C_9H_7ClF_3N_3$, 249.0; m/z found, 250.1 [M+H]⁺.

Intermediate 54: 6-(1,1-Difluoroethyl)-5-iodo-2-(trifluoromethyl)-[1,2,4]triazolo[1,5-a]pyridine

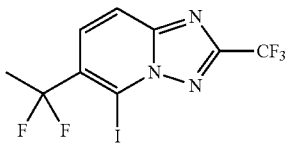 [SMILES: CC(F)(F)c1ccc2nc(C(F)(F)F)nn2c1I]

Step A: 1-(2-(Trifluoromethyl)-[1,2,4]triazolo[1,5-a]pyridin-6-yl)ethan-1-one

A solution of 6-bromo-2-(trifluoromethyl)-[1,2,4]triazolo[1,5-a]pyridine (Intermediate 20, 400 mg, 1.5 mmol), tributyl(1-ethoxyvinyl)stannane (0.61 ml, 1.8 mmol), tri-o-tolylphosphine (91.5 mg, 0.3 mmol) and Pd₂(dba)₃ (138 mg, 0.15 mmol) in anhydrous DMF (10.0 mL) was degassed with nitrogen for 10 minutes. Triethylamine (0.25 ml, 1.8 mmol) was then added and the reaction mixture was heated at 110° C. in a microwave for 50 minutes. After cooling to rt, concentrated aq. HCl (1.0 ml) was added and stirring was maintained for 2 h. The reaction was neutralized with aqueous sodium bicarbonate and the resulting suspension was extracted with DCM (×2). The combined organic extracts were dried over Na₂SO₄ and concentrated in vacuo. Purification (FCC, SiO₂; 0-50% EtOAc/hexanes) provided the title compound as a white solid (343 mg, 98%). MS (ESI): mass calcd. for $C_9H_6F_3N_3O$, 229.1; m/z found, 229.9 [M+H]⁺. ¹H NMR (400 MHz, DMSO-d₆) δ 9.91 (dd, J=1.7, 0.9 Hz, 1H), 8.22 (dd, J=9.4, 1.7 Hz, 1H), 8.08 (dd, J=9.4, 0.9 Hz, 1H), 2.70 (s, 3H).

Step B: 6-(1,1-Difluoroethyl)-2-(trifluoromethyl)-[1,2,4]triazolo[1,5-a]pyridine The title compound was prepared in a manner analogous to Intermediate 35, substituting 1-(2-(trifluoromethyl)-[1,2,4]triazolo[1,5-a]pyridin-6-yl)ethan-1-one for 5-chloro-2-ethyl-[1,2,4]triazolo[1,5-a]pyridine-6-carbaldehyde in Step B. MS (ESI): mass calcd. for $C_9H_6F_5N_3$, 251.1; m/z found, 252.0 [M+H]⁺. ¹H NMR (400 MHz, CDCl₃) δ 8.85-8.84 (m, 1H), 7.94-7.91 (m, 1H), 7.78-7.73 (m, 1H), 2.04 (t, J=18.2 Hz, 3H).

Step C: 6-(1,1-Difluoroethyl)-5-iodo-2-(trifluoromethyl)-[1,2,4]triazolo[1,5-a]pyridine The title compound was prepared in a manner analogous to Intermediate 38, substituting 6-(1,1-difluoroethyl)-2-(trifluoromethyl)-[1,2,4]triazolo[1,5-a]pyridine for 2-isopropyl-6-(trifluoromethyl)-[1,2,4]triazolo[1,5-a]pyridine. ¹H NMR (400 MHz, CDCl₃) δ 7.89-7.75 (m, 2H), 2.13 (t, J=18.1 Hz, 3H).

Intermediate 55: 5-Chloro-6-iodo-2-methyl-[1,2,4]triazolo[1,5-a]pyridine

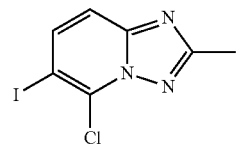

To a solution of 1,6-diamino-2-chloro-3-iodopyridin-1-ium 2,4,6-trimethylbenzenesulfonate (Intermediate 10, 500 mg, 1.06 mmol) in acetic anhydride (4.0 mL) was added aqueous HCl (37% solution; 59 µL, 0.71 mmol). The mixture was heated at 100° C. overnight. After cooling to 0° C., the reaction was carefully quenched with sat. aq. NaHCO₃. The aqueous layer was extracted twice with EtOAc, and the combined organics washed with brine, dried over Na₂SO₄ and filtered. The filtrate was concentrated in vacuo and the residue was triturated with DCM to afford the title compound as a tan solid (93 mg, 30%). MS (ESI): mass calcd. for $C_7H_5ClIN_3$, 292.9; m/z found, 293.9 [M+H]⁺. ¹H NMR (400 MHz, DMSO-d₆) δ 8.00 (d, J=9.2 Hz, 1H), 7.57 (d, J=9.1 Hz, 1H), 2.50 (s, 3H).

Intermediate 56: 5-(4,4,5,5-Tetramethyl-1,3,2-dioxaborolan-2-yl)-7-(trifluoromethyl)indolin-2-one

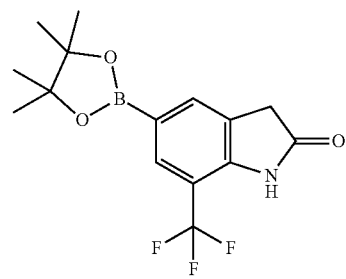 [SMILES: CC1(C)OB(c2cc3c(c(C(F)(F)F)c2)NC(=O)C3)OC1(C)C]

The title compound was prepared in a manner analogous to Intermediate 6, substituting 7-(trifluoromethyl)indoline-2,3-dione for 7-methoxyindoline-2,3-dione in Step A. ¹H NMR (400 MHz, DMSO-d₆) δ 11.03 (s, 1H), 7.72-7.61 (m, 2H), 3.59 (s, 2H), 1.29 (s, 12H).

Intermediate 57: 7-Ethyl-5-(4,4,5,5-tetramethyl-1,3,2-dioxaborolan-2-yl)indolin-2-one

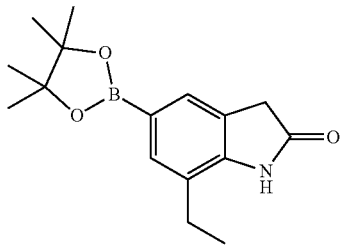 [SMILES: CCc1cc(B2OC(C)(C)C(C)(C)O2)cc2c1NC(=O)C2]

The title compound was prepared in a manner analogous to Intermediate 5, substituting 7-ethylindolin-2-one for 7-chloroindolin-2-one in Step A. MS (ESI): mass calcd. for $C_{16}H_{22}BNO_3$, 287.2; m/z found, 288.1 $[M+H]^+$. $^1$H NMR (400 MHz, DMSO-$d_6$) δ 10.57 (s, 1H), 7.34 (d, J=1.1 Hz, 1H), 7.32 (d, J=1.3 Hz, 1H), 3.47 (s, 2H), 2.56 (q, J=7.5 Hz, 2H), 1.27 (s, 12H), 1.10 (t, J=7.5 Hz, 3H).

Intermediate 58: 2-Oxo-5-(4,4,5,5-tetramethyl-1,3,2-dioxaborolan-2-yl)indoline-7-carbonitrile

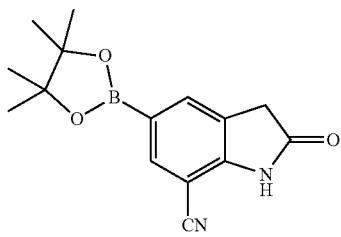 [SMILES: CC1(C)OB(c2cc(C#N)c3c(c2)CC(=O)N3)OC1(C)C]

The title compound was prepared in a manner analogous to Intermediate 5, substituting 2-oxoindoline-7-carbonitrile for 7-chloroindolin-2-one in Step A. MS (ESI): mass calcd. for $C_{15}H_{17}BN_2O_3$, 284.1; m/z found, 285.1 $[M+H]^+$. $^1$H NMR (500 MHz, DMSO-$d_6$) δ 11.50 (s, 1H), 7.73-7.68 (m, 1H), 7.70-7.65 (m, 1H), 3.58 (s, 2H), 1.29 (s, 12H).

Intermediate 59: 1,2-Diamino-3-methyl-5-(trifluoromethyl)pyridin-1-ium 2,4,6-trimethylbenzenesulfonate

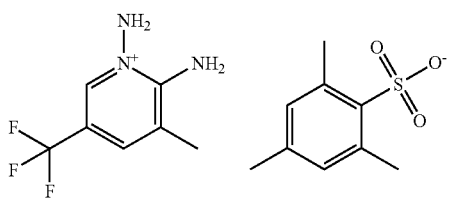

Step A: 3-Methyl-5-(trifluoromethyl)pyridin-2-amine

A microwave vial was charged with 2-amino-3-chloro-5-(trifluoromethyl)pyridine (1 g, 5.09 mmol), trimethylboroxine (1.4 mL, 10.2 mmol), $K_2CO_3$ (2.11 g, 15.3 mmol), Pd(dppf)Cl$_2$—CH$_2$Cl$_2$ (415 mg, 10 mol %), and 1,2-dimethoxyethane (12.7 mL). The headspace was purged by evacuating under vacuum and refilling with nitrogen (3∴). The reaction mixture was irradiated at 130° C. in a microwave reactor for 30 min. The process was repeated with two additional batches, and then the combined mixtures were diluted with CH$_2$Cl$_2$ and then filtered. The filtrate was concentrated in vacuo, and the residue purified by silica gel chromatography (0-15% MeOH in CH$_2$Cl$_2$) to afford the title compound as a yellow solid (1.6 g, 59% yield). MS (ESI): mass calcd. for $C_7H_7F_3N_2$, 176.1; m/z found, 177.1 $[M+H]^+$.

Step B: 1,2-Diamino-3-methyl-5-(trifluoromethyl)pyridin-1-ium 2,4,6-trimethylbenzenesulfonate The title compound was prepared in a manner analogous to Intermediate 12, substituting 3-methyl-5-(trifluoromethyl)pyridin-2-amine for 5-iodo-3-methylpyridin-2-amine. MS (ESI): mass calcd. for $C_7H_9F_3N_3$, 192.1; m/z found, 192.0.

Intermediate 60: 1,2-Diamino-5-iodo-4-methylpyridin-1-ium 2,4,6-trimethylbenzenesulfonate

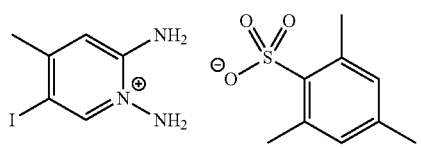

The title compound was prepared in a manner analogous to Intermediate 12, substituting 5-iodo-4-methylpyridin-2-amine for 5-iodo-3-methylpyridin-2-amine. MS (ESI): mass calcd. for $C_6H_9IN_3$, 250.1; m/z found, 249.9.

Intermediate 61: 1,2-Diamino-3-chloro-5-(trifluoromethyl)pyridin-1-ium 2,4,6-trimethylbenzenesulfonate

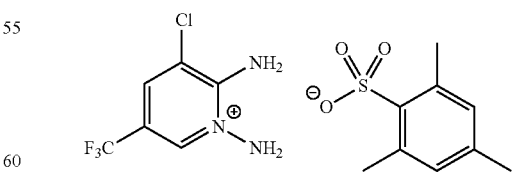

The title compound was prepared in a manner analogous to Intermediate 12, substituting 3-chloro-5-(trifluoromethyl)pyridin-2-amine for 5-iodo-3-methylpyridin-2-amine. MS (ESI): mass calcd. for $C_6H_6ClF_3N_2$, 212.0; m/z found, 212.0.

Intermediate 62: 7-Chloro-6-(difluoromethyl)-2-(trifluoromethyl)pyrazolo[1,5-a]pyridine

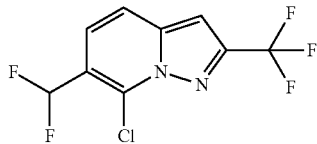 [SMILES: FC(F)c1ccc2cc(C(F)(F)F)nn2c1Cl]

Step A: 2-Chloropyridine-3-carbaldehyde

To a solution of diisopropylamine (14.8 mL, 106 mmol) in tetrahydrofuran (200 mL) was added n-butyllithium (2.27 M solution in n-hexane, 42 mL, 95.3 mmol) slowly at −78° C. under argon. The reaction mixture was stirred at −78° C. for 15 min. To the reaction mixture was added 2-chloropyridine (10 g, 88.1 mmol) as a solution in tetrahydrofuran (150 mL) dropwise at −78° C. The reaction mixture was stirred at −78° C. for 15 min. To the reaction mixture was added N,N-dimethylformamide (8.2 mL, 106 mmol) dropwise at −78° C. The reaction mixture was stirred at −78° C. for 15 min. The reaction mixture was stirred at 0° C. for 1 h. The reaction mixture was poured into a vigorously stirred mixture of ethyl acetate (1.5 L) and aqueous ammonium chloride (1 M, 500 mL). The organic layer was washed with water (1×1 L) and brine (1×1 L). The organic layer was dried over magnesium sulfate, filtered and evaporated. Purification (FCC, SiO$_2$, eluting with n-hexane:ethyl acetate (50: 1→4:1)) afforded the title compound (2.70 g, 19.1 mmol, 21%) as a yellow solid. MS (ESI): mass calcd. for C$_6$H$_4$ClNO, 141.0; m/z found, 160.0 [M+H+H$_2$O]$^+$. $^1$H NMR (500 MHz, DMSO-d$_6$) δ 10.30-10.26 (m, 1H), 8.68 (dd, J=4.7, 2.0 Hz, 1H), 8.26 (dd, J=7.6, 2.0 Hz, 1H), 7.66-7.62 (m, 1H).

Step B: 2-Chloro-3-(difluoromethyl)pyridine

To a solution of 2-chloropyridine-3-carbaldehyde (250 mg, 1.77 mmol) in dichloromethane (2.5 mL) was added diethylaminosulfur trifluoride (DAST, 350 µL, 2.65 mmol) over 30 min at 0° C. The reaction mixture was warmed to r and stirred for 2 h. The reaction was quenched with saturated sodium bicarbonate solution (4 mL) and the mixture was extracted with dichloromethane (3×10 mL). The combined organic layers were washed with brine (1×5 mL), dried over magnesium sulfate, filtered and evaporated. Purification (FCC, SiO$_2$, eluting with n-hexane:ethyl acetate (4:1)) afforded the title compound (100 mg, 0.611 mmol, 34%) as a yellow liquid. $^1$H NMR (500 MHz, CDCl$_3$) δ 8.56-8.51 (m, 1H), 8.05-8.00 (m, 1H), 7.40 (dd, J=7.7, 4.8 Hz, 1H), 6.94 (t, J=54.5 Hz, 1H).

Step C: 2-Chloro-3-(difluoromethyl)pyridin-1-ium-1-amine;2,4,6-trimethylbenzenesulfonate To a mixture of trifluoroacetic acid (13.6 mL, 178 mmol) and water (1.62 mL) was added ethyl O-mesitylsulfonylacetohydroxamate (3.8 g, 13.3 mmol) at −5° C. and the reaction mixture was stirred at −5° C. for 1.5 h. The reaction was quenched with ice water (25 mL). The precipitate was collected and washed with water (20×25 mL). The white solid was dissolved in dichloromethane (50 mL), dried over magnesium sulfate and filtered. To the filtrate was added 2-chloro-3-(difluoromethyl)pyridine (1.45 g, 8.87 mmol) at 0° C. The reaction mixture was warmed to room temperature and the mixture was stirred at room temperature for 72 h. The reaction mixture was slowly diluted with diethyl ether (100 mL). The precipitate was collected and washed with diethyl ether (2×20 mL) to afford the title compound (2.05 g, 5.41 mmol, 61%) as a white crystalline solid. MS (ESI): mass calcd. for C$_6$H$_6$ClF$_2$N$_2$, 179.0; m/z found, 179.0. $^1$H NMR (500 MHz, DMSO-d$_6$) δ 9.10-9.04 (m, 1H), 8.71 (br s, 2H), 8.55-8.50 (m, 1H), 8.13-8.07 (m, 1H), 7.38 (t, J=52.8 Hz, 1H), 6.74 (s, 2H), 2.52-2.49 (m, 6H), 2.17 (s, 3H).

Step D: Ethyl 7-chloro-6-(difluoromethyl)-2-(trifluoromethyl)pyrazolo[1,5-a]pyridine-3-carboxylate To a solution of 2-chloro-3-(difluoromethyl)pyridin-1-ium-1-amine;2,4,6-trimethylbenzenesulfonate (1.22 g, 3.22 mmol) in N,N-dimethylformamide (15 mL) was added ethyl 4,4,4-trifluoro-2-butynoate (460 µL, 3.22 mmol) and triethylamine (449 µL, 3.22 mmol) at 0° C. The reaction mixture was stirred at room temperature for 18 h. To the reaction mixture was added 2,3-dichloro-5,6-dicyano-p-benzoquinone (730 mg, 3.22 mmol) at 0° C. The reaction mixture was stirred at room temperature for 1 h. The reaction mixture was poured into water (20 mL). The precipitate was collected and washed with water (2×10 mL). Purification (FCC, SiO$_2$, eluting with n-hexane:dichloromethane (2:1)) afforded the title compound (360 mg, 1.05 mmol, 32%) as a white crystalline solid. MS (ESI): mass calcd. for C$_{12}$H$_8$ClFN$_2$O$_2$, 342.0; m/z found, 343.0 [M+H]$^-$.

Step E: 7-Chloro-6-(difluoromethyl)-2-(trifluoromethyl)pyrazolo[1,5-c]pyridine-3-carboxylic acid To a solution of ethyl 7-chloro-6-(difluoromethyl)-2-(trifluoromethyl)pyrazolo[1,5-c]pyridine-3-carboxylate (850 mg, 2.48 mmol) in a mixture of 1,4-dioxane (10 mL) and water (2 mL) was added lithium hydroxide monohydrate (156 mg, 3.72 mmol) and the reaction mixture was stirred at 60° C. for 4 h. The mixture was concentrated to 2 mL under vacuum. The residue was diluted with water (5 mL) and washed with chloroform (1×5 mL). The aqueous layer was acidified to pH 4 by addition of 1 M hydrochloric acid. The precipitate was collected and washed with water (2×10 mL) to afford the title compound (470 mg, 1.49 mmol, 60%) as a white crystalline solid. MS (ESI): mass calcd. for C$_{10}$H$_4$ClF$_5$N$_2$O$_2$, 314.0; m/z=313.1 [M−H]$^-$.

Step F: 7-Chloro-6-(difluoromethyl)-2-(trifluoromethyl)pyrazolo[1,5-c]pyridine To a solution of 7-chloro-6-(difluoromethyl)-2-(trifluoromethyl)pyrazolo[1,5-a]pyridine-3-carboxylic acid (305 mg, 0.969 mmol) in dimethyl sulfoxide (3 mL) was added silver carbonate (80 mg, 0.29 mmol) and acetic acid (8 µL, 0.14 mmol). The reaction mixture was stirred at 120° C. for 1 h. The reaction mixture was diluted with diethyl ether (20 mL) and the mixture was washed with brine (10×10 mL). The organic layer was dried over magnesium sulfate, filtered and evaporated. Purification (FCC, SiO$_2$, eluting with n-pentane:diethyl ether (4:1)) afforded the title compound (160 mg, 0.591 mmol, 60%) as a white crystalline solid.

Intermediate 63: 7-Chloro-6-(difluoromethyl)-4-methyl-2-(trifluoromethyl)pyrazolo[1,5-c]pyridine

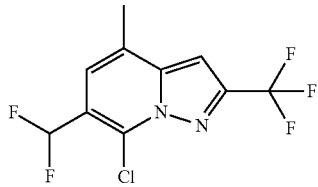

Step A:
2-Chloro-3-(difluoromethyl)-5-methylpyridine

To a solution of 2-chloro-5-methylpyridine-3-carbaldehyde (5.00 g, 32.1 mmol) in dichloromethane (50 mL) was added diethylaminosulfur trifluoride (DAST) (6.4 mL, 48.4 mmol) over 30 min at 0° C. The reaction mixture was warmed to room temperature and stirred for 2 h. The reaction was quenched with saturated sodium bicarbonate solution (40 mL). The mixture was extracted with dichloromethane (3×100 mL). The combined organic layers were washed with brine (1×25 mL). The organic layer was dried over magnesium sulfate, filtered and evaporated. Purification (FCC, SiO$_2$, n-hexane:ethyl acetate (10:1)) afforded the title compound (3.45 g, 19.4 mmol, 60%) as a yellow liquid.

Step B: 2-Chloro-3-(difluoromethyl)-5-methylpyridin-1-ium-1-amine;2,4,6-trimethylbenzenesulfonate To a mixture of trifluoroacetic acid (15 mL, 196 mmol) and water (1.8 mL) was added ethyl o-mesitylsulfonylacetohydroxamate (4.10 g, 14.4 mmol) at −5° C. The reaction mixture was stirred at −5° C. for 1.5 h. To the reaction mixture was added ice water (25 mL). The precipitate was collected and washed with water (20×25 mL). The white solid was dissolved in dichloromethane (50 mL), dried over magnesium sulfate and filtered. To the filtrate was added 2-chloro-3-(difluoromethyl)-5-methylpyridine (1.70 g, 9.57 mmol) at 0° C. The reaction mixture was warmed to room temperature and stirred at room temperature for 18 h. The reaction mixture was diluted slowly with diethyl ether (100 mL). The precipitate was collected and washed with diethyl ether (2×20 mL) to give the title compound (2.59 g, 6.50 mmol, 68%) as a white crystalline solid. MS (ESI): mass calcd. for C$_7$H$_8$ClF$_2$N$_2$, 193.0; m/z found, 194.1 [M+H]$^+$.

Step C: Ethyl 7-chloro-6-(difluoromethyl)-4-methyl-2-(trifluoromethyl)pyrazolo[1,5-a]pyridine-3-carboxylate To a solution of 2-chloro-3-(difluoromethyl)-5-methylpyridin-1-ium-1-amine; 2,4,6-trimethylbenzenesulfonate (5.1 g, 13 mmol) in N,N-dimethylformamide (70 mL) was added ethyl 4,4,4-trifluoro-2-butynoate (1.85 mL, 12.9 mmol) and triethylamine (1.81 mL, 13 mmol) at 0° C. The reaction mixture was stirred at room temperature for 18 h. To the reaction mixture was added 2,3-dichloro-5,6-dicyano-p-benzoquinone (2.9 g, 12.8 mmol) at 0° C. and the reaction mixture was stirred at room temperature for 1 h. The reaction mixture was poured into water (500 mL). The precipitate was collected and washed with water (2×50 mL). Purification (FCC, SiO$_2$, eluting with n-hexane:dichloromethane (2:1)) afforded the title compound (2.60 g, 7.29 mmol, 56%) as a white crystalline solid. MS (ESI): mass calcd. for C$_{13}$H$_{10}$ClF$_5$N$_2$O$_2$, 356.0; m/z found, 357.1 [M+H]$^+$.

Step D: 7-Chloro-6-(difluoromethyl)-4-methyl-2-(trifluoromethyl)pyrazolo[1,5-c]pyridine-3-carboxylic acid To a solution of ethyl 7-chloro-6-(difluoromethyl)-4-methyl-2-(trifluoromethyl)pyrazolo[1,5-a]pyridine-3-carboxylate (2.6 g, 7.29 mmol) in a mixture of 1,4-dioxane (30 mL) and water (6 mL) was added lithium hydroxide monohydrate (459 mg, 10.9 mmol) and the reaction mixture was stirred at 60° C. for 4 h. To the reaction mixture was added lithium hydroxide monohydrate (459 mg, 10.9 mmol) and the reaction mixture was stirred at 60° C. for 18 h. To the reaction mixture was added lithium hydroxide monohydrate (459 mg, 10.9 mmol) and the reaction mixture was stirred at 60° C. for 2 h. To the reaction mixture was added a fourth portion of lithium hydroxide monohydrate (459 mg, 10.9 mmol) and the reaction mixture was stirred at 60° C. for 2 h. The reaction mixture was concentrated to 6 mL under vacuum. The residue was diluted with water (20 mL) and the mixture was washed with chloroform (1×10 mL). The aqueous layer was acidified to pH 4 by addition of 1 M hydrochloric acid. The precipitate was collected and the solid was washed with water (2×20 mL) to give the title compound (1.80 g, 5.48 mmol, 75%) as a white crystalline solid. MS (ESI): mass calcd. for C$_{11}$H$_6$ClF$_5$N$_2$O$_2$, 328.0; m/z found, 329.0 [M+H]$^+$.

Step E: 7-Chloro-6-(difluoromethyl)-4-methyl-2-(trifluoromethyl)pyrazolo[1,5-a]pyridine To a solution of 7-chloro-6-(difluoromethyl)-4-methyl-2-(trifluoromethyl)pyrazolo[1,5-a]pyridine-3-carboxylic acid (1.80 g, 5.48 mmol) in dimethyl sulfoxide (18 mL) was added silver carbonate (453 mg, 1.64 mmol) and acetic acid (47 µL, 0.821 mmol). The reaction mixture was stirred at 120° C. for 1 h. The reaction mixture was diluted with diethyl ether (100 mL) and the mixture was washed with brine (10×50 mL). The organic layer was dried over magnesium sulfate, filtered and evaporated. Purification (FCC, SiO$_2$, n-pentane:diethyl ether (4:1)) afforded the title compound (1.30 g, 4.56 mmol, 83%) as a white crystalline solid. $^1$H NMR (300 MHz, DMSO-d$_6$) δ 7.59 (s, 1H), 7.57-7.52 (m, 1H), 7.44 (t, J=53.7 Hz, 1H), 2.62 (s, 3H).

Intermediate 64: 5-Chloro-6-(difluoromethyl)-8-ethyl-2-(trifluoromethyl)-[1,2,4]triazolo[1,5-a]pyridine

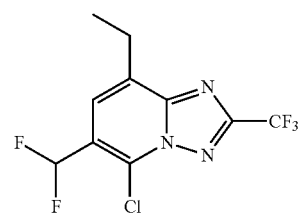 [SMILES: CCc1cc(C(F)F)c(Cl)n2nc(C(F)(F)F)nc12]

Step A: 3-Ethyl-5-iodopyridin-2-amine

To a solution of 3-ethylpyridin-2-amine (815 mg, 6.67 mmol) in DMF (5.4 mL) was added a solution of N-iodosuccinimide (1.95 g, 8.67 mmol) in DMF (5.4 mL), and the mixture stirred at 30° C. for 4 h. The reaction was diluted with EtOAc, and the organic layer washed with saturated aqueous $Na_2S_2O_3$. The aqueous layer was extracted with EtOAc (2×), and the combined organics washed with brine (4×), dried over $Na_2SO_4$, filtered, and concentrated. Purification (FCC, $SiO_2$, 0-15% MeOH in $CH_2Cl_2$) afforded the title compound as an orange solid (1.45 g, 87% yield). MS (ESI): mass calcd. for $C_7H_9IN_2$, 248.0; m/z found, 248.9 $[M+H]^+$. $^1H$ NMR (400 MHz, $CDCl_3$) δ 8.10 (d, J=2.1 Hz, 1H), 7.55-7.51 (m, 1H), 4.52 (s, 2H), 2.40 (q, J=7.5 Hz, 2H), 1.25 (t, J=7.5 Hz, 3H).

Step B: 1,2-Diamino-3-ethyl-5-iodopyridin-1-ium 2,4,6-trimethylbenzenesulfonate The title compound was prepared in a manner analogous to Intermediate 12, substituting 3-ethyl-5-iodopyridin-2-amine for 5-iodo-3-methylpyridin-2-amine. MS (ESI): mass calcd. for $C_6H_9IN_3$, 250.0; m/z found, 249.9.

Step C: 8-Ethyl-6-iodo-2-(trifluoromethyl)-[1,2,4]triazolo[1,5-a]pyridine

To a suspension of 1,2-diamino-3-ethyl-5-iodopyridin-1-ium 2,4,6-trimethylbenzenesulfonate (400 mg, 0.863 mmol) in MeOH (3.3 mL) at 0° C. was added $Et_3N$ (0.36 mL, 0.728 mmol), followed by trifluoroacetic anhydride (0.18 mL, 1.32 mmol) dropwise via syringe. The reaction was maintained at 0° C. for 10 min then stirred at room temperature for 16 h. The reaction mixture was concentrated in vacuo. Purification (FCC, $SiO_2$, 0-50% EtOAc/hexanes) afforded the title compound as a white solid (249 mg, 84%). MS (ESI): mass calcd. for $C_9H_7F_3IN_3$, 341.0; m/z found, 341.9 $[M+H]^+$.

Step D: 8-Ethyl-2-(trifluoromethyl)-6-vinyl-[1,2,4]triazolo[1,5-a]pyridine

A microwave vial was charged with 8-ethyl-6-iodo-2-(trifluoromethyl)-[1,2,4]triazolo[1,5-a]pyridine (48 mg, 0.141 mmol), vinylboronic acid pinacol ester (28.6 μL, 0.169 mmol), $Pd(PPh_3)_4$ (16.3 mg, 10 mol %), 1,4-dioxane (1.9 mL), and saturated aqueous $Na_2CO_3$ (0.48 mL). The headspace was purged by evacuating under vacuum and refilling with nitrogen (3×), and stirred in a microwave reactor at 110° C. for 30 min. After diluting the mixture with $CH_2Cl_2$ and $H_2O$, the aqueous layer was extracted with $CH_2Cl_2$ (2×), and the combined organics washed with brine, dried over $Na_2SO_4$, filtered, and concentrated in vacuo. Purification (FCC, $SiO_2$, 0-50% EtOAc in hexanes) afforded the title compound as a white solid (28.6 mg, 84% yield). MS (ESI): mass calcd. for $C_{11}H_{10}F_3N_3$, 241.1; m/z found, 242.1 $[M+H]^+$.

Step E: 8-Ethyl-2-(trifluoromethyl)-[1,2,4]triazolo[1,5-a]pyridine-6-carbaldehyde To a solution of 8-ethyl-2-(trifluoromethyl)-6-vinyl-[1,2,4]triazolo[1,5-a]pyridine (116 mg, 0.481 mmol) in 1,4-dioxane (5.6 mL) was added a suspension of $NaIO_4$ (308 mg, 1.44 mmol) in $H_2O$ (1.2 mL). The mixture was stirred at room temperature for 2.5 h and then additional $NaIO_4$ (1 equiv) added. After stirring overnight, sat. aq. $NaHCO_3$ was added, and the aqueous layer extracted with EtOAc (2×). The combined organics were washed with brine, dried over $Na_2SO_4$, filtered, and concentrated in vacuo. Purification (FCC, $SiO_2$, 0-50% EtOAc in hexanes) afforded the title compound as a white solid (72 mg, 61% yield). MS (ESI): mass calcd. for $C_{10}H_8F_3N_3O$, 243.1; m/z found, 244.1 $[M+H]^+$.

Step F: 6-(Difluoromethyl)-8-ethyl-2-(trifluoromethyl)-[1,2,4]triazolo[1,5-a]pyridine To a solution of 8-ethyl-2-(trifluoromethyl)-[1,2,4]triazolo[1,5-a]pyridine-6-carbaldehyde (72 mg, 0.296 mmol) in DCM (5.9 mL) at 0° C. under an Na atmosphere was added diethylaminosulfur trifluoride (0.23 mL, 1.78 mmol) dropwise via syringe. The mixture was stirred at room temperature for 2 h and then poured over ice (ca. 10 mL), diluted with sat. aq. $NaHCO_3$, and extracted with $CH_2Cl_2$ (2×). The combined organics were washed with brine, dried over $Na_2SO_4$, filtered, and concentrated under reduced pressure. Purification (FCC, $SiO_2$; 0-50% EtOAc/hexanes) afforded the title compound (69 mg, 88%). MS (ESI): mass calcd. for $C_{10}H_8F_5N_3$, 265.1; m/z found, 266.1 $[M+H]^+$.

Step G. 5-Chloro-6-(difluoromethyl)-8-ethyl-2-(trifluoromethyl)-[1,2,4]triazolo[1,5-a]pyridine To a cooled (−78° C.) solution of 6-(difluoromethyl)-8-ethyl-2-(trifluoromethyl)-[1,2,4]triazolo[1,5-a]pyridine (69 mg, 0.26 mmol) in THF (1.3 mL) was added n-butyllithium (1.6M/hexanes, 0.20 mL, 0.312 mmol) dropwise via syringe. Stirring was maintained at −78° C. for 30 minutes, and then a solution of hexachloroethane (92.4 mg, 0.39 mmol) in THF (0.627 mL) was added dropwise via syringe. After the addition, the mixture was warmed to room temperature and stirred for another 30 minutes. The reaction was quenched with saturated aq. $NH_4Cl$ and the aqueous layer was extracted with EtOAc (×2). The combined organic extracts were dried over $Na_2SO_4$ and concentrated in vacuo. Purification (FCC, $SiO_2$; 0-50% EtOAc/hexanes) provided the title compound as a white solid (64 mg, 83%). MS (ESI): mass calcd. for $CioH_7ClF_5N_3$, 299.0; m/z found, 301.0 $[M+H]^+$.

Intermediate 65: 5-Chloro-2-cyclopropyl-8-ethyl-6-(trifluoromethyl)-[1,2,4]triazolo[1,5-a]pyridine

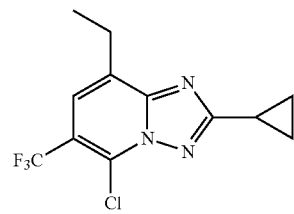 [SMILES: CCc1cc(C(F)(F)F)c(Cl)n2nc(C3CC3)nc12]

Step A: 3-Ethyl-5-(trifluoromethyl)pyridin-2-amine

A round bottom flask was charged with 3-iodo-5-(trifluoromethyl)pyridine-2-amine (3.0 g, 10.4 mmol), triethylborane (13.5 mL, 13.54 mmol, 1.0 M solution), $Cs_2CO_3$ (20.4 g, 62.5 mmol), $Pd(dppf)Cl_2$—$CH_2Cl_2$ (851 mg, 10 mol %), and DMF (60.5 mL). The headspace was purged by evacuating under vacuum and refilling with nitrogen (3×), and the mixture heated to 50° C. for 20 h. The reaction mixture was cooled to room temperature, filtered, and the filtrate poured into $H_2O$ (400 mL). The aqueous layer was extracted with EtOAc (3×), and the combined organics washed with brine (5×), dried over Na$_2$SO$_4$, filtered, and concentrated. Purification (FCC, SiO$_2$, 0-100% EtOAc in hexanes) afforded the title compound as a 95% pure orange solid (1.36 g, 65% yield). MS (ESI): mass calcd. for C$_8$H$_9$F$_3$N$_2$, 190.1; m/z found, 191.0 [M+H]$^+$. $^1$H NMR (400 MHz, CDCl$_3$) δ 8.09 (s, 1H), 7.37 (d, J=1.6 Hz, 1H), 4.77 (s, 2H), 2.37 (q, J=7.5 Hz, 2H), 1.19 (t, J=7.5 Hz, 3H).

Step B: 1,2-Diamino-3-ethyl-5-(trifluoromethyl)pyridin-1-ium 2,4,6-trimethylbenzenesulfonate To a cooled (0° C.) solution of ethyl (1E)-N-(2,4,6-trimethylphenyl)sulfonyloxyethanimidate (4.08 g, 14.3 mmol) in dioxane (17.7 mL) was added 70% perchloric acid (15.3 mL, 179.5 mmol) dropwise. Following the addition, the temperature was maintained at 0° C. for 10 minutes and then ice-cold water (73.3 mL) was added at once. The resulting precipitate was collected by vacuum filtration and washed with water (caution: this compound has been reported to be potentially explosive when dry). The white solid was immediately dissolved in DCM (66.7 mL), dried over Na$_2$SO$_4$, and filtered. The filtrate was then added dropwise to a cooled (0° C.) solution of 3-ethyl-5-(trifluoromethyl)pyridin-2-amine (1.36 g, 7.15 mmol) in DCM (61.1 mL). The reaction was warmed to room temperature and stirred for 3.5 h. Diethyl ether was added and the resulting white solid was collected by vacuum filtration to provide the title compound 2.69 g, 93%. MS (ESI): mass calcd. for C$_8$H$_{11}$F$_3$N$_3$, 206.1; m/z found, 206.1.

Step C: 2-Cyclopropyl-8-ethyl-6-(trifluoromethyl)-[1,2,4]triazolo[1,5-a]pyridine To a solution of 1,2-diamino-3-ethyl-5-(trifluoromethyl)pyridin-1-ium 2,4,6-trimethylbenzenesulfonate (400 mg, 0.98 mmol) in AcOH (11.6 mL) were added Cu(OAc)$_2$ (89.5 mg, 0.49 mmol) and cyclopropanecarbaldehyde (0.221 mL, 2.96 mmol). The reaction was heated at 70° C. for 6 h, then cooled to rt and diluted with EtOAc. The reaction was cooled to rt and filtered. The filtrate was concentrated in vacuo, and the filtrate was re-dissolved in EtOAc. The organic layer was washed with NH$_4$C$_1$, and re-extracted with EtOAc. The combined organics were washed with brine, dried over Na$_2$SO$_4$ and filtered. Purification (FCC, SiO$_2$; 0-50% EtOAc/hexanes) afforded the title compound as a pale yellow solid (168 mg, 67%).

Step D: 5-Chloro-2-cyclopropyl-8-ethyl-6-(trifluoromethyl)-[1,2,4]triazolo[1,5-a]pyridine The title compound was prepared in a manner analogous to Intermediate 40, using 2-cyclopropyl-8-ethyl-6-(trifluoromethyl)-[1,2,4]triazolo[1,5-a]pyridine. MS (ESI): mass calcd. for C$_{12}$H$_{11}$ClF$_3$N$_3$, 289.1; m/z found, 290.1 [M+H]$^+$.

Intermediate 66: 6-Iodo-8-methyl-2-propyl-[1,2,4]triazolo[1,5-a]pyridine

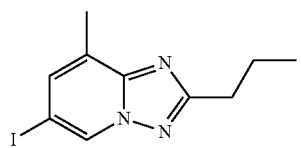

Method A

6-Iodo-8-methyl-2-propyl-[1,2,4]triazolo[1,5-a]pyridine

To a solution of 1,2-diamino-5-iodo-3-methylpyridin-1-ium 2,4,6-trimethylbenzenesulfonate (Intermediate 12) (500 mg, 1.11 mmol) in AcOH (13.1 mL) were added Cu(OAc)$_2$ (101 mg, 0.56 mmol) and butyraldehyde (0.3 mL, 3.34 mmol). The mixture was heated to 70° C. for 18 h, then cooled to room temperature. More Cu(OAc)$_2$ (0.5 equiv) was added and the reaction heated to 70° C. for an additional 4.5 h. After cooling to room temperature, the mixture was filtered and the filtrate concentrated in vacuo. The residue was dissolved in EtOAc, and washed with saturated aqueous NaHCO$_3$ solution. The aqueous layer was extracted with EtOAc (×2), and the combined organics were washed with brine, dried over Na$_2$SO$_4$ and filtered. The filtrate was concentrated in vacuo. Purification (FCC, SiO$_2$; 0-50% EtOAc/hexanes) afforded the title compound (195 mg, 58%). MS (ESI): mass calcd. for C$_{10}$H$_{12}$IN$_3$, 301.0; m/z found, 302.0 [M+H]$^+$.

Method B

6-Iodo-8-methyl-2-propyl-[1,2,4]triazolo[1,5-a]pyridine

To a solution of 1,2-diamino-5-iodo-3-methylpyridin-1-ium 2,4,6-trimethylbenzenesulfonate (Intermediate 12) (500 mg, 1.11 mmol) in butyric acid (1.6 mL) was added butyric anhydride (0.55 mL, 3.34 mmol). The reaction was stirred in a microwave reactor at 180° C. for 30 min, and then diluted with EtOAc and H$_2$O. The mixture was then neutralized with 4N NaOH, the aqueous layer extracted twice with EtOAc, and the combined organics washed with brine, dried over Na$_2$SO$_4$, and filtered. The filtrate was concentrated in vacuo. Purification (FCC, SiO$_2$; 0-50% EtOAc/hexanes) afforded the title compound as a white solid (269 mg, 80%).

Intermediate 67: 5-Chloro-8-methyl-2-propyl-6-(trifluoromethyl)-[1,2,4]triazolo[1,5-a]pyridine

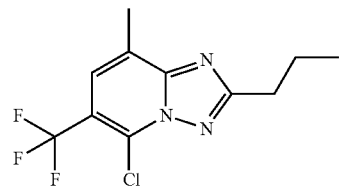 [SMILES: CCCc1nc2c(C)cc(C(F)(F)F)c(Cl)n2n1]

Step A:
3-Methyl-5-(trifluoromethyl)pyridin-2-amine

A microwave vial was charged with 2-amino-3-chloro-5-(trifluoromethyl)pyridine (1 g, 5.09 mmol), trimethylboroxine (1.4 mL, 10.2 mmol), K$_2$CO$_3$ (2.11 g, 15.3 mmol), Pd(dppf)Cl$_2$—CH$_2$Cl$_2$ (415 mg, 10 mol %), and 1,2-dimethoxyethane (12.7 mL). The headspace was purged by evacuating under vacuum and refilling with nitrogen (3×), and the mixture irradiated at 130° C. in a microwave reactor for 30 min. The process was repeated with two additional batches, and then the combined mixtures were diluted with CH$_2$Cl$_2$ and then filtered. The filtrate was concentrated in vacuo. Purification (FCC, SiO$_2$; 0-15% MeOH in CH$_2$Cl$_2$) afforded the title compound as a yellow solid (1.6 g, 59% yield). MS (ESI): mass calcd. for C$_7$H$_7$F$_3$N$_2$, 176.1; m/z found, 177.1 [M+H]$^+$.

Step B: 1,2-Diamino-3-methyl-5-(trifluoromethyl) pyridin-1-ium 2,4,6-trimethylbenzenesulfonate The title compound was prepared in a manner analogous to Intermediate 12, substituting 3-methyl-5-(trifluoromethyl)pyridin-2-amine for 5-iodo-3-methylpyridin-2-amine. MS (ESI): mass calcd. for C$_7$H$_9$F$_3$N$_3$, 192.1; m/z found, 192.0.

Step C: 8-Methyl-2-propyl-6-(trifluoromethyl)-[1,2,4]triazolo[1,5-a]pyridine

Method A

The title compound was prepared in a manner analogous to Intermediate 66, Method A, using 1,2-diamino-3-methyl-5-(trifluoromethyl)pyridin-1-ium 2,4,6-trimethylbenzenesulfonate (Intermediate 59). MS (ESI): mass calcd. for C$_{11}$H$_{12}$F$_3$N$_3$, 243.1; m/z found, 244.2 [M+H]$^+$.

Method B

A microwave vial was charged with 6-iodo-8-methyl-2-propyl-[1,2,4]triazolo[1,5-a]pyridine (Intermediate 66, 269 mg, 0.89 mmol), methyl 2,2-difluoro-2-(fluorosulfonyl)acetate (0.28 mL, 2.23 mmol), CuI (425 mg, 2.23 mmol), DMPU (0.61 mL, 5.06 mmol), and DMF (5.6 mL). The vial was evacuated under vacuum and backfilled with N$_2$ (×3), and then capped and sealed. The reaction was then stirred in a microwave reactor at 130° C. for 45 min. The mixture was cooled to room temperature and filtered over a pad of Celite®, eluting with MeOH. After concentrating the filtrate in vacuo, the residue was dissolved in EtOAc and washed with sat. aq. NH$_4$Cl. The aqueous layer was extracted with EtOAc (×2), and the combined organics washed with brine (×3), dried over Na$_2$SO$_4$ and filtered. The filtrate was concentrated in vacuo. Purification (FCC, SiO$_2$; 0-50% EtOAc/hexanes) afforded the title compound (137 mg, 63%). MS (ESI): mass calcd. for C$_{11}$H$_{11}$ClF$_3$N$_3$, 277.1; m/z found, 278.1 [M+H]$^+$.

Step D: 5-Chloro-8-methyl-2-propyl-6-(trifluoromethyl)-[1,2,4]triazolo[1,5-a]pyridine The title compound was prepared in a manner analogous to Intermediate 40, MS (ESI): mass calcd. for C$_{11}$H$_{11}$ClF$_3$N$_3$, 277.1; m/z found, 278.1 [M+H]$^+$.

Intermediate 68: 5-Chloro-2-(difluoromethyl)-8-methyl-6-(trifluoromethyl)-[1,2,4]triazolo[1,5-a]pyridine

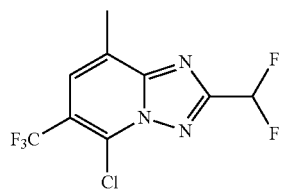 [SMILES: Cc1cc(C(F)(F)F)c(Cl)n2nc(C(F)F)nc12]

Step A: 2-(Difluoromethyl)-6-iodo-8-methyl-[1,2,4]triazolo[1,5-a]pyridine

To a suspension of 1,2-diamino-5-iodo-3-methylpyridin-1-ium 2,4,6-trimethylbenzenesulfonate (Intermediate 12) (500 mg, 1.11 mmol) in MeOH (5.7 mL) at 0° C. was added Et$_3$N (0.46 mL, 3.34 mmol), followed by methyl difluoroacetate (0.15 mL, 1.7 mmol) dropwise via syringe. The reaction was maintained at 45° C. and stirred for 16 h. The reaction mixture was concentrated in vacuo. Purification (FCC, SiO$_2$, 0-50% EtOAc/hexanes) afforded the title compound (304 mg, 88%). MS (ESI): mass calcd. for C$_8$H$_6$F$_2$IN$_3$, 309.0; m/z found, 310.2 [M+H]$^+$. $^1$H NMR (500 MHz, CDCl$_3$) δ 8.74 (dq, J=1.4, 0.7 Hz, 1H), 7.61 (p, J=1.2 Hz, 1H), 6.89 (t, J=53.6 Hz, 1H), 2.67 (t, J=0.9 Hz, 3H).

Step B: 2-(Difluoromethyl)-8-methyl-6-(trifluoromethyl)-[1,2,4]triazolo[1,5-a]pyridine The title compound was prepared in a manner analogous to Intermediate 32, substituting 2-(difluoromethyl)-6-iodo-8-methyl-[1,2,4]triazolo[1,5-a]pyridine for 6-iodo-8-methyl-2-(trifluoromethyl)-[1,2,4]triazolo[1,5-a]pyridine. MS (ESI): mass calcd. for C$_9$H$_6$F$_5$N$_3$, 251.1; m/z found, 251.9 [M+H]$^+$.

Step C: 2-(Difluoromethyl)-8-methyl-6-(trifluoromethyl)-[1,2,4]triazolo[1,5-a]pyridine To a cooled (−78° C.) solution of 2-(difluoromethyl)-6-iodo-8-methyl-[1,2,4]triazolo[1,5-a]pyridine (150 mg, 0.59 mmol) in THF (4.5 mL) was added n-butyllithium (1.6M/hexanes, 0.44 mL, 0.717 mmol) dropwise over a period of 10 minutes. Stirring was maintained at −78° C. for 30 minutes, and then a solution of hexachloroethane (169 mg, 0.717 mmol) in THF (1.8 mL) was added dropwise over a period of 10 minutes. After the addition, the mixture was warmed to rt and stirred for another 10 minutes. The reaction was quenched with saturated aq. NH$_4$Cl and the aqueous layer was extracted with EtOAc (×2). The combined organic extracts were dried over Na$_2$SO$_4$ and concentrated in vacuo. Purification (FCC, SiO$_2$; 0-50% EtOAc/hexanes) provided the title compound as a white solid (71.4 mg, 42%). MS (ESI): mass calcd. for C$_9$H$_5$ClF$_5$N$_3$, 285.0; m/z found, 285.9 [M+H]$^+$.

Intermediate 69: 5-Chloro-2-(difluoromethyl)-8-ethyl-6-(trifluoromethyl)-[1,2,4]triazolo[1,5-a]pyridine

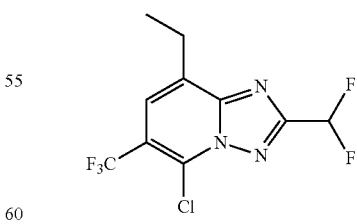

Step A: 8-Chloro-2-(difluoromethyl)-6-(trifluoromethyl)-[1,2,4]triazolo[1,5-a]pyridine To a suspension of 1,2-diamino-3-chloro-5-(trifluoromethyl)pyridin-1-ium 2,4,6-trimethylbenzenesulfonate (Intermediate 61, 600 mg, 1.45 mmol) in MeOH (7.4 mL) was added Et₃N (0.61 mL, 4.4 mmol), followed by methyl difluoroacetate (0.19 mL, 2.2 mmol) dropwise via syringe. The reaction was maintained at 45° C. and stirred for 16 h. The reaction mixture was concentrated in vacuo. Purification (FCC, SiO₂, 0-50% EtOAc/hexanes) afforded the title compound (335 mg, 85% yield). MS (ESI): mass calcd. for C₈H₃ClF₅N₃, 271.0; m/z found, 271.9 [M+H]⁺.

Step B: 2-(Difluoromethyl)-6-(trifluoromethyl)-8-vinyl-[1,2,4]triazolo[1,5-a]pyridine A microwave vial was charged with 8-chloro-2-(difluoromethyl)-6-(trifluoromethyl)-[1,2,4]triazolo[1,5-a]pyridine (110 mg, 0.405 mmol), vinylboronic acid pinacol ester (82.4 µL, 0.486 mmol), Pd(dppf)Cl₂—CH₂Cl₂ (33.1 mg, 10 mol %), 1,4-dioxane (1.2 mL), and saturated aqueous NaHCO₃ (1.2 mL). The headspace was purged by evacuating under vacuum and refilling with nitrogen (3×), and stirred in a microwave reactor at 110° C. for 30 min. After diluting the mixture with EtOAc and H₂O, the aqueous layer was extracted with EtOAc (2×), and the combined organics washed with brine, dried over Na₂SO₄, filtered, and concentrated in vacuo. The residue was purified by silica gel chromatography (0-50% EtOAc in hexanes) to afford the title compound as a pale yellow oil (81 mg, 76% yield). MS (ESI): mass calcd. for C₁₀H₆F₅N₃, 263.0; m/z found, 263.9 [M+H]⁺.

Step C: 2-(Difluoromethyl)-8-ethyl-6-(trifluoromethyl)-[1,2,4]triazolo[1,5-a]pyridine A mixture of 2-(difluoromethyl)-6-(trifluoromethyl)-8-vinyl-[1,2,4]triazolo[1,5-a]pyridine (80 mg, 0.304 mmol) and 10% palladium on carbon (16.2 mg, 0.015 mmol) in MeOH (2.96 mL) was stirred under an atmosphere of H₂ for 1 h. After purging with nitrogen, the reaction was filtered over a pad of Celite®, eluting with EtOAc. After concentrating the filtrate in vacuo, the residue was used directly without further purification. MS (ESI): mass calcd. for C₁₀H₈F₅N₃, 265.1; m/z found, 265.8 [M+H]⁺.

Step D: 5-Chloro-2-(difluoromethyl)-8-ethyl-6-(trifluoromethyl)-[1,2,4]triazolo[1,5-a]pyridine The title compound was prepared in a manner analogous to Intermediate 40, MS (ESI): mass calcd. for C₁₀H₇ClF₅N₃, 299.0; m/z found, 299.7 [M+H]⁺.

Intermediate 70: 5-Chloro-2,8-diethyl-6-(trifluoromethyl)-[1,2,4]triazolo[1,5-a]pyridine

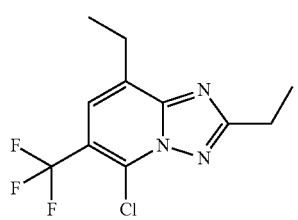 [SMILES: CCc1nc2c(CC)cc(C(F)(F)F)c(Cl)n2n1]

Step A: 2,8-Diethyl-6-(trifluoromethyl)-[1,2,4]triazolo[1,5-a]pyridine

The title compound was prepared in a manner analogous to Intermediate 66, Method B, using 1,2-diamino-3-ethyl-5-(trifluoromethyl)pyridin-1-ium 2,4,6-trimethylbenzenesulfonate (Intermediate 65, product from Step B) and substituting propionic anhydride and propionic acid for butyric anhydride and butyric acid. MS (ESI): mass calcd. for C₁₁H₁₂F₃N₃, 243.1; m/z found, 244.1 [M+H]⁺.

Step B. 5-Chloro-2,8-diethyl-6-(trifluoromethyl)-[1,2,4]triazolo[1,5-a]pyridine

To a cooled (−78° C.) solution of 2,8-diethyl-6-(trifluoromethyl)-[1,2,4]triazolo[1,5-a]pyridine (150 mg, 0.61 mmol) in THF (3.0 mL) was added n-butyllithium (1.6M/hexanes, 0.58 mL, 0.92 mmol) dropwise over a period of 10 minutes Stirring was maintained at −78° C. for 30 minutes, and then a solution of hexachloroethane (292 mg, 1.23 mmol) in THF (1.5 mL) was added dropwise over a period of 10 minutes. After the addition, the mixture was warmed to rt and stirred for another 10 minutes. The reaction was quenched with saturated aq. NH₄Cl and the aqueous layer was extracted with EtOAc (×2). The combined organic extracts were dried over Na₂SO₄ and concentrated in vacuo. Purification (FCC, SiO₂; 0-50% EtOAc/hexanes) provided the title compound as a white solid (131 mg, 77%). MS (ESI): mass calcd. for C₁₁H₁₁ClF₃N₃, 277.1; m/z found, 278.0 [M+H]⁺.

Intermediate 71: 5-Chloro-2-cyclopropyl-6-(difluoromethyl)-8-ethyl-[1,2,4]triazolo[1,5-a]pyridine

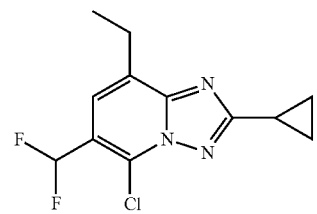 [SMILES: CCc1cc(C(F)F)c(Cl)n2nc(C3CC3)nc12]

Step A: 2-Cyclopropyl-8-ethyl-6-iodo-[1,2,4]triazolo[1,5-a]pyridine

To a solution of 1,2-diamino-3-ethyl-5-iodopyridin-1-ium 2,4,6-trimethylbenzenesulfonate (Intermediate 64, product from Step B) (400 mg, 0.86 mmol) in AcOH (10.2 mL) were added Cu(OAc)₂ (78 mg, 0.43 mmol) and cyclopropanecarboxaldehyde (0.19 mL, 2.59 mmol). The mixture was heated to 70° C. for 16 h. After cooling to room temperature, the mixture was filtered and the filtrate concentrated in vacuo. The residue was dissolved in EtOAc, and washed with saturated aqueous NaH₄Cl solution. The aqueous layer was extracted with EtOAc (×2), and the combined organics were washed with brine, dried over Na₂SO₄ and filtered. The filtrate was concentrated in vacuo. Purification (FCC, SiO₂, 0-50% EtOAc/hexanes) afforded the title compound (210 mg, 78%). MS (ESI): mass calcd. for C₁₁H₁₂IN₃, 313.0; m/z found, 314.0 [M+H]⁺.

Step B: 5-Chloro-2-cyclopropyl-6-(difluoromethyl)-8-ethyl-[1,2,4]triazolo[1,5-a]pyridine The title compound was prepared in a manner analogous to Intermediate 64, Steps D-G, using 2-cyclopropyl-8-ethyl- 6-iodo-[1,2,4]triazolo[1,5-a]pyridine in Step D. MS (ESI): mass calcd. for $C_{12}H_{12}ClF_2N_3$, 271.1; m/z found, 272.0 [M+H]$^+$.

Intermediate 72: 5-Chloro-6-(difluoromethyl)-8-methyl-2-propyl-[1,2,4]triazolo[1,5-a]pyridine

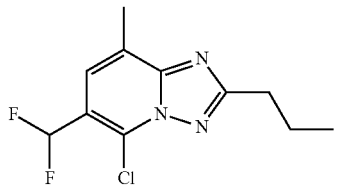 [SMILES: CCCc1nc2c(C)cc(C(F)F)c(Cl)n2n1]

The title compound was made in an analogous manner to Intermediate 64, Steps D-G using 6-iodo-8-methyl-2-propyl-[1,2,4]triazolo[1,5-a]pyridine (Intermediate 66) in Step D. MS (ESI): mass calcd. for $C_{11}H_{12}ClF_2N_3$, 259.1; m/z found, 260.1 [M+H]$^+$.

Intermediate 73: 5,8-Dichloro-2-propyl-6-(trifluoromethyl)-[1,2,4]triazolo[L5-a]pyridine

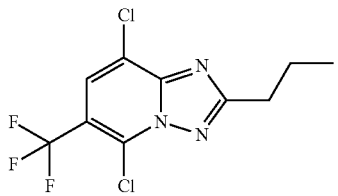 [SMILES: CCCc1nc2c(Cl)cc(C(F)(F)F)c(Cl)n2n1]

The title compound was prepared in a manner analogous to Intermediate 66, Method A, substituting 1,2-diamino-3,6-dichloro-5-(trifluoromethyl)pyridin-1-ium 2,4,6-trimethylbenzenesulfonate (Intermediate 13) for 1,2-diamino-5-iodo-3-methylpyridin-1-ium 2,4,6-trimethylbenzenesulfonate. MS (ESI): mass calcd. for $C_{10}H_8Cl_2F_3N_3$, 297.0; m/z found, 297.8 [M+H]$^+$.

Intermediate 74: 5-Chloro-2-cyclopropyl-8-methyl-6-(trifluoromethyl)-[1,2,4]triazolo[1,5-a]pyridine

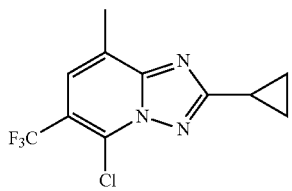 [SMILES: Cc1cc(C(F)(F)F)c(Cl)n2nc(C3CC3)nc12]

Step A: 2-Cyclopropyl-6-iodo-8-methyl-[1,2,4]triazolo[1,5-a]pyridine

To a solution of 1,2-diamino-5-iodo-3-methylpyridin-1-ium 2,4,6-trimethylbenzenesulfonate (Intermediate 12) (725 mg, 1.61 mmol) in DMF (6.0 mL) was added cyclopropanecarbaldehyde (0.48 ml, 6.4 mmol) followed by sodium metabisulfite (614 mg, 3.2 mmol). The mixture was stirred at 90° C. for 2 h. The reaction mixture was cooled to rt, diluted with water, and extracted with EtOAc (2x). The combined organic extracts were washed with brine; dried over $Na_2SO_4$ and concentrated in vacuo. Purification by flash chromatography (SiO$_2$; 0-100% EtOAc/hexanes) provided the title compound as a white solid (277.6 mg, 58% yield). MS (ESI): mass calcd. for $C_{10}H_{10}IN_3$, 299.1; m/z found, 300.0. [M+H]$^+$. $^1$H NMR (500 MHz, DMSO-d$_6$) δ 9.02-8.87 (m, 1H), 7.67-7.57 (m, 1H), 2.44 (t, J=0.9 Hz, 3H), 2.16-2.09 (m, 1H), 1.06-1.00 (m, 2H), 0.98-0.93 (m, 2H).

Step B: 2-Cyclopropyl-8-methyl-6-(trifluoromethyl)-[1,2,4]triazolo[1,5-a]pyridine The title compound was prepared in a manner analogous to Intermediate 32, using 2-cyclopropyl-6-iodo-8-methyl-[1,2,4]triazolo[1,5-a]pyridine. MS (ESI): mass calcd. for $C_{11}H_{10}F_3N_3$, 241.2; m/z found, 242.1 [M+H]$^+$. $^1$H NMR (500 MHz, DMSO-d$_6$) δ 9.32 (dt, J=2.0, 1.0 Hz, 1H), 7.80-7.62 (m, 1H), 2.54 (t, J=0.9 Hz, 3H), 2.24-2.15 (m, 1H), 1.11-1.06 (m, 2H), 1.03-0.98 (m, 2H).

Step C: 5-Chloro-2-cyclopropyl-8-methyl-6-(trifluoromethyl)-[1,2,4]triazolo[1,5-a]pyridine To a cooled (-78° C.) solution of 2-cyclopropyl-8-methyl-6-(trifluoromethyl)-[1,2,4]triazolo[1,5-a]pyridine (325 mg, 1.34 mmol) in THF (15 mL) was added n-butyllithium (1.6M/hexanes, 1.01 mL, 1.6 mmol) dropwise via syringe. Stirring was maintained at -78° C. for 30 minutes, and then a solution of hexachloroethane (383 mg, 1.61 mmol) in THF was added dropwise via syringe. After the addition, the mixture was warmed to room temperature and stirred for another 30 minutes. The reaction was quenched with saturated aq. NH$_4$Cl and the aqueous layer was extracted with EtOAc (x2). The combined organic extracts were dried over $Na_2SO_4$ and concentrated in vacuo. Purification (FCC, SiO$_2$; 0-50% EtOAc/hexanes) provided title compound as a white solid (258 mg, 69%). MS (ESI): mass calcd. for $C_{11}H_9ClF_3N_3$, 275.66; m/z found, 276.0 [M+H]$^+$. $^1$H NMR (500 MHz, DMSO-d$_6$) δ 7.83 (q, J=1.0 Hz, 1H), 2.53 (d, J=1.1 Hz, 3H), 2.27 (tt, J=8.2, 4.8 Hz, 1H), 1.16-1.10 (m, 2H), 1.06-1.01 (m, 2H).

Intermediate 75: 5-Chloro-6-(difluoromethyl)-8-methyl-2-(trifluoromethyl)-[1,2,4]triazolo[1,5-a]pyridine

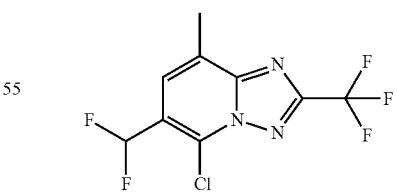

The title compound was prepared in a manner analogous to Intermediate 64, Steps D-G, using 6-iodo-8-methyl-2-(trifluoromethyl)-[1,2,4]triazolo[1,5-a]pyridine (Intermediate 19) in Step D. MS (ESI): mass calcd. for $C_9H_5ClF_5N_3$, 285.6; m/z found, 286.8 [M+H]$^+$. $^1$H NMR (500 MHz, DMSO-d$_6$) δ 7.98 (q, J=1.1 Hz, 1H), 7.43 (t, J=53.4 Hz, 1H), 2.64 (d, J=1.1 Hz, 3H).

Intermediate 76: 5-Chloro-8-methyl-2,6-bis(trifluoromethyl)-[1,2,4]triazolo[1,5-a]pyridine

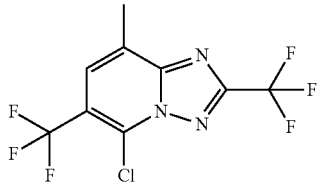

The title compound was prepared in a manner analogous to Intermediate 40, using 8-methyl-2,6-bis(trifluoromethyl)-[1,2,4]triazolo[1,5-a]pyridine (Intermediate 32). MS (ESI): mass calcd. for $C_9H_4ClF_6N_3$, 303.6; m/z found, 304.0 [M+H]$^+$. $^1$H NMR (400 MHz, DMSO-$d_6$) δ 8.12 (q, J=1.1 Hz, 1H), 2.65 (d, J=1.1 Hz, 3H).

Intermediate 77: 5-Chloro-2-cyclopropyl-6-(difluoromethyl)-8-methyl-[1,2,4]triazolo[1,5-a]pyridine

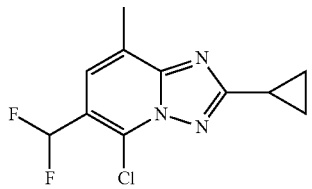 [SMILES: Cc1cc(C(F)F)c(Cl)n2nc(C3CC3)nc12]

The title compound was prepared in a manner analogous to Intermediate 64, Steps D-G, using 2-cyclopropyl-6-iodo-8-methyl-[1,2,4]triazolo[1,5-a]pyridine (Intermediate 74, product from Step A) in Step D. MS (ESI): mass calcd. for $C_{11}H_{10}ClF_2N_3$, 257.6; m/z found, 257.9 [M+H]$^+$. $^1$H NMR (500 MHz, DMSO-$d_6$) δ 7.70 (q, J=1.0 Hz, 1H), 7.33 (t, J=53.8 Hz, 1H), 2.52 (d, J=1.1 Hz, 3H), 2.32-2.17 (m, 1H), 1.16-0.96 (m, 4H).

Intermediate 78: 5-Chloro-6-(difluoromethyl)-2-ethyl-8-methyl-[1,2,4]triazolo[1,5-a]pyridine

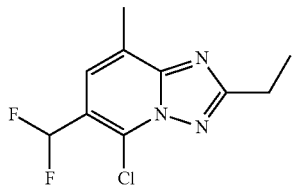 [SMILES: CCc1nc2c(C)cc(C(F)F)c(Cl)n2n1]

The title compound was prepared in a manner analogous to Intermediate 64, Steps D-G, using 2-ethyl-6-iodo-8-methyl-[1,2,4]triazolo[1,5-a]pyridine (Intermediate 29) in Step D. MS (ESI): mass calcd. for $C_{10}H_{10}ClF_2N_3$, 245.6; m/z found, 247.1 [M+H]$^+$.

Intermediate 79: 5-Chloro-2,8-dimethyl-6-(trifluoromethyl)-[1,2,4]triazolo[1,5-a]pyridine

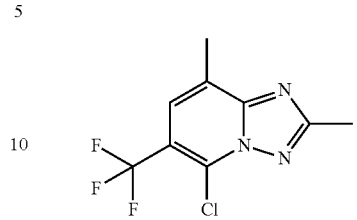

The title compound was prepared in a manner analogous to Intermediate 74, using 1,2-diamino-5-iodo-3-methylpyridin-1-ium 2,4,6-trimethylbenzenesulfonate (Intermediate 12) and acetaldehyde in Step A. MS (ESI): mass calcd. for $C_9H_7ClF_3N_3$, 249.6; m/z found, 249.8 [M+H]$^+$.

Intermediate 80: 2-Ethoxy-8-methyl-6-(trifluoromethyl)-[1,2,4]triazolo[1,5-a]pyridine

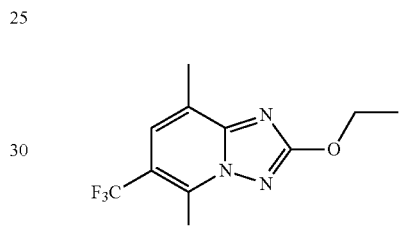

Step A: 2-ethoxy-6-iodo-8-methyl-[1,2,4]triazolo[1,5-a]pyridine

To a solution of 1,2-diamino-5-iodo-3-methylpyridin-1-ium 2,4,6-trimethylbenzenesulfonate (Intermediate 12) (250 mg, 0.56 mmol) in acetic acid (0.75 mL) was added tetraethoxymethane (4.7 ml, 22.3 mmol). The mixture was stirred at 80° C. for 18 h. The reaction mixture was cooled to rt, diluted with water, neutralized with saturated sodium bicarbonate solution and extracted with EtOAc (2×). The combined organic extracts were washed with brine; dried over $Na_2SO_4$ and concentrated in vacuo. Purification by flash chromatography (SiO$_2$; 0-100% EtOAc/hexanes) provided the title compound as a white solid (55.0 mg, 33% yield). MS (ESI): mass calcd. for $C_9H_{10}IN_3O$, 303.1; m/z found, 303.8 [M+H]$^+$. $^1$H NMR (400 MHz, DMSO-$d_6$) δ 9.08-8.92 (m, 1H), 7.76-7.52 (m, 1H), 4.39 (q, J=6.8 Hz, 2H), 2.42 (t, J=1.0 Hz, 3H), 1.37 (t, J=7.0 Hz, 3H).

Step B: 2-Ethoxy-8-methyl-6-(trifluoromethyl)-[1,2,4]triazolo[1,5-a]pyridine

The title compound was prepared in a manner analogous to Intermediate 74, using Steps B-C using 2-ethoxy-8-methyl-6-(trifluoromethyl)-[1,2,4]triazolo[1,5-a]pyridine in Step B. MS (ESI): mass calcd. for $C_{10}H_9ClF_3N_3O$, 279.6; m/z found, 279.8.

Example 1: 5-(7-Chloro-1H-indazol-5-yl)-2,6-bis(trifluoromethyl)-[1,2,4]triazolo[1,5-a]pyridine

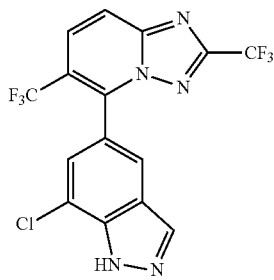 [SMILES: FC(F)(F)c1nc2ccc(C(F)(F)F)c(-c3cc(Cl)c4[nH]ncc4c3)n2n1]

A microwave vial was charged with 5-chloro-2,6-bis(trifluoromethyl)-[1,2,4]triazolo[1,5-a]pyridine (Intermediate 16, 30 mg, 0.10 mmol), 7-chloro-5-(4,4,5,5-tetramethyl-1,3,2-dioxaborolan-2-yl)-1H-indazole (Intermediate 1, 35 mg, 0.12 mmol), Pd(dppf)Cl$_2$—CH$_2$Cl$_2$ (8.5 mg, 0.01 mmol) saturated aqueous Na$_2$CO$_3$ (0.35 mL), and 1,4-dioxane (1.4 mL). The vial was evacuated under vacuum, backfilled with Na (×3), then capped and sealed. The reaction was stirred in a microwave reactor at 110° C. for 30 min. After cooling to rt, the mixture was diluted with EtOAc and washed with H$_2$O. The aqueous layer was extracted with EtOAc (×2), and the combined organics were washed with brine, dried over Na$_2$SO$_4$, and filtered. After concentrating the filtrate in vacuo, the residue was purified by flash column chromatography (SiO$_2$; 0-50% EtOAc/hex) to afford the title compound as a white solid (35 mg, 82%). MS (ESI): mass calcd. for C$_{15}$H$_6$ClF$_6$N$_5$, 405.0; m/z found, 406.0 [M+H]$^+$. $^1$H NMR (600 MHz, DMSO-d$_6$) δ 13.98 (s, 1H), 8.39 (s, 1H), 8.29-8.27 (m, 2H), 8.04 (d, J=0.7 Hz, 1H), 7.75 (s, 1H).

Example 2: 5-(7-Methyl-1H-indazol-5-yl)-2,6-bis(trifluoromethyl)-[1,2,4]triazolo[1,5-a]pyridine

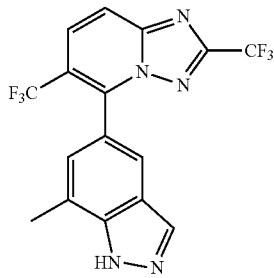 [SMILES: Cc1cc(-c2c(C(F)(F)F)ccc3nc(C(F)(F)F)nn23)cc2cn[nH]c12]

The title compound was prepared in a manner analogous to Example 1, substituting 7-methyl-5-(4,4,5,5-tetramethyl-1,3,2-dioxaborolan-2-yl)-1H-indazole (Intermediate 2) for 7-chloro-5-(4,4,5,5-tetramethyl-1,3,2-dioxaborolan-2-yl)-1H-indazole. MS (ESI): mass calcd. for C$_{16}$H$_9$F$_6$N$_5$, 385.1; m/z found, 386.1 [M+H]$^+$. $^1$H NMR (600 MHz, DMSO-d$_6$) δ 13.48 (s, 1H), 8.26-8.25 (m, 2H), 8.22 (d, J=1.3 Hz, 1H), 7.83 (s, 1H), 7.30 (s, 1H), 2.59 (s, 3H).

Example 3: 5-(2,6-Bis(trifluoromethyl)-[1,2,4]triazolo[1,5-a]pyridin-5-yl)-7-chloroindolin-2-one

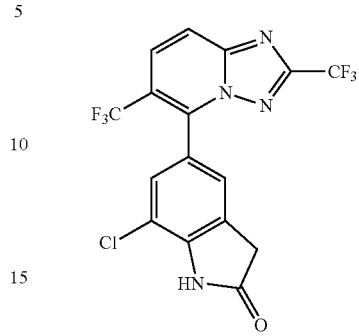

The title compound was prepared in a manner analogous to Example 1, substituting 7-chloro-5-(4,4,5,5-tetramethyl-1,3,2-dioxaborolan-2-yl)-indolin-2-one (Intermediate 5) for 7-chloro-5-(4,4,5,5-tetramethyl-1,3,2-dioxaborolan-2-yl)-1H-indazole. MS (ESI): mass calcd. for C$_{16}$H$_7$ClF$_6$N$_4$O, 420.0; m/z found, 421.0 [M+H]$^+$. $^1$H NMR (500 MHz, DMSO-d$_6$) δ 11.13 (s, 1H), 8.26-8.24 (m, 2H), 7.56 (s, 1H), 7.41 (s, 1H), 3.74 (d, J=4.9 Hz, 2H).

Example 4: 5-(2,6-Bis(trifluoromethyl)-[1,2,4]triazolo[1,5-a]pyridin-5-yl)-7-methylindolin-2-one

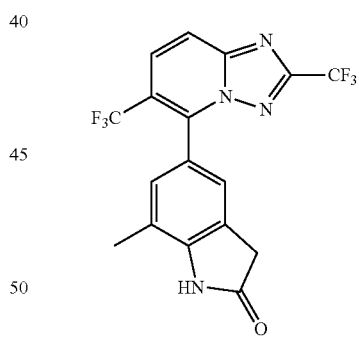

The title compound was prepared in a manner analogous to Example 1, substituting 7-methyl-5-(4,4,5,5-tetramethyl-1,3,2-dioxaborolan-2-yl)-indolin-2-one (Intermediate 3) for 7-chloro-5-(4,4,5,5-tetramethyl-1,3,2-dioxaborolan-2-yl)-1H-indazole. MS (ESI): mass calcd. for C$_{17}$H$_{10}$F$_6$N$_4$O, 400.1; m/z found, 401.1 [M+H]$^+$. $^1$H NMR (500 MHz, DMSO-d$_6$) δ 10.74 (s, 1H), 8.22 (s, 2H), 7.25 (s, 1H), 7.20 (s, 1H), 3.61 (d, J=4.9 Hz, 2H), 2.26 (s, 3H).

Example 5: 8-Chloro-5-(7-chloro-1H-indazol-5-yl)-2,6-bis(trifluoromethyl)-[1,2,4]triazolo[1,5-a]pyridine

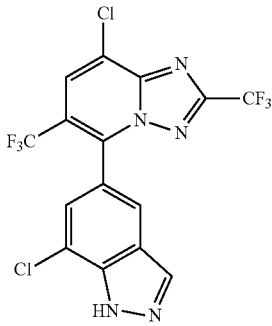 [SMILES: FC(F)(F)c1nc2c(Cl)cc(C(F)(F)F)c(-c3cc(Cl)c4[nH]ncc4c3)n2n1]

Step A. 5,8-Dichloro-2,6-bis(trifluoromethyl)-[1,2,4]triazolo[1,5-a]pyridine The title compound was prepared in a manner analogous to Intermediate 16, substituting 1,2-diamino-3,6-dichloro-5-(trifluoromethyl)pyridin-1-ium 2,4,6-trimethylbenzenesulfonate for 1,6-diamino-2-chloro-3-(trifluoromethyl)pyridin-1-ium 2,4,6-trimethylbenzenesulfonate.

Step B. 8-Chloro-5-(7-chloro-1H-indazol-5-yl)-2,6-bis(trifluoromethyl)-[1,2,4]triazolo[1,5-a]pyridine The title compound was prepared in a manner analogous to Example 1, substituting 5,8-dichloro-2,6-bis(trifluoromethyl)-[1,2,4]triazolo[1,5-a]pyridine for 5-chloro-2,6-bis(trifluoromethyl)-[1,2,4]triazolo[1,5-a]pyridine (Intermediate 16) employing conventional heating at 90° C. for 16 h. MS (ESI): mass calcd. for $C_{15}H_5Cl_2F_6N_5$, 439.0; m/z found, 440.0 [M+H]$^+$. $^1$H NMR (600 MHz, DMSO-d$_6$) δ 14.02 (s, 1H), 8.61 (s, 1H), 8.41 (s, 1H), 8.01 (s, 1H), 7.70 (s, 1H).

Example 6: 5-(7-Chloro-1H-indazol-5-yl)-8-methyl-2,6-bis(trifluoromethyl)-[1,2,4]triazolo[1,5-a]pyridine

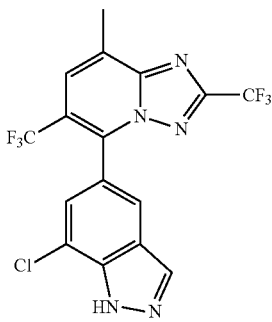 [SMILES: Cc1cc(C(F)(F)F)c(-c2cc(Cl)c3[nH]ncc3c2)n2nc(C(F)(F)F)nc12]

The title compound was prepared in a manner analogous to Example 1, substituting 5-iodo-8-methyl-2,6-bis(trifluoromethyl)-[1,2,4]triazolo[1,5-a]pyridine (Intermediate 46) for 5-chloro-2,6-bis(trifluoromethyl)-[1,2,4]triazolo[1,5-a]pyridine (Intermediate 16). MS (ESI): mass calcd. for $C_{16}H_8ClF_6N_5$, 419.0; m/z found, 420.0 [M+H]$^+$. $^1$H NMR (400 MHz, CD$_3$OD) δ 8.26 (s, 1H), 8.00-7.97 (m, 1H), 7.93 (s, 1H), 7.58 (s, 1H), 3.35 (s, 1H), 2.77 (s, 3H).

Example 7: 5-(7-Chloro-1H-indazol-5-yl)-2-(difluoromethyl)-6-(trifluoromethyl)-[1,2,4]triazolo[1,5-a]pyridine

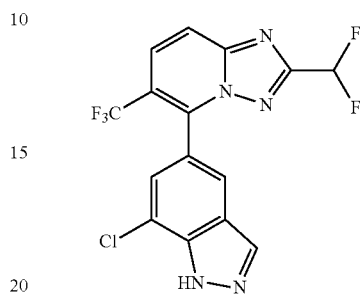

The title compound was prepared in a manner analogous to Example 1, substituting 5-chloro-2-(difluoromethyl)-6-(trifluoromethyl)-[1,2,4]triazolo[1,5-a]pyridine (Intermediate 21) for 5-chloro-2,6-bis(trifluoromethyl)-[1,2,4]triazolo[1,5-a]pyridine (Intermediate 16) employing conventional heating at 90° C. for 17 h. $^1$H NMR (600 MHz, CD$_3$OD) δ 8.27 (s, 1H), 8.16 (d, J=9.5 Hz, 1H), 8.07 (d, J=9.5 Hz, 1H), 7.95 (s, 1H), 7.61 (s, 1H), 6.92 (t, J=53.0 Hz, 1H).

Example 8: 5-(7-Methyl-1H-indazol-5-yl)-2-(difluoromethyl)-6-(trifluoromethyl)-[1,2,4]triazolo[1,5-a]pyridine

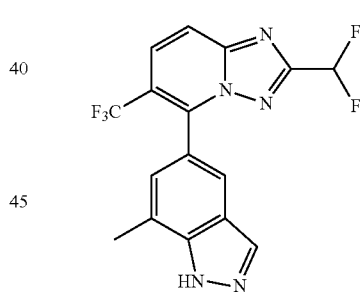

The title compound was prepared in a manner analogous to Example 1, substituting 5-chloro-2-(difluoromethyl)-6-(trifluoromethyl)-[1,2,4]triazolo[1,5-a]pyridine (Intermediate 21) for 5-chloro-2,6-bis(trifluoromethyl)-[1,2,4]triazolo[1,5-a]pyridine (Intermediate 16) and 7-methyl-5-(4,4,5,5-tetramethyl-1,3,2-dioxaborolan-2-yl)-1H-indazole (Intermediate 2) for 7-chloro-5-(4,4,5,5-tetramethyl-1,3,2-dioxaborolan-2-yl)-1H-indazole employing conventional heating at 90° C. for 17 h. MS (ESI): mass calcd. for $C_{16}H_{10}F_5N_5$, 367.1; m/z found, 368.1 [M+H]$^+$. $^1$H NMR (600 MHz, CD$_3$OD) δ 8.18-8.13 (m, 2H), 8.03 (d, J=9.6 Hz, 1H), 7.80 (s, 1H), 7.29 (s, 1H), 6.90 (t, J=53.0 Hz, 1H), 2.65 (s, 3H).

Example 9: 7-Chloro-5-(2-(difluoromethyl)-6-(trifluoromethyl)-[1,2,4]triazolo[1,5-a]pyridin-5-yl)indolin-2-one

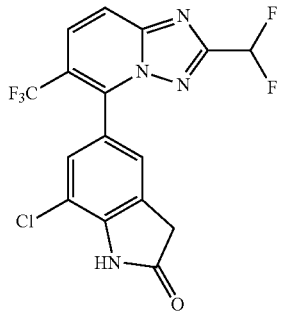 [SMILES: O=C1Cc2cc(-c3c(C(F)(F)F)ccc4nc(C(F)F)nn34)cc(Cl)c2N1]

The title compound was prepared in a manner analogous to Example 1, substituting 5-chloro-2-(difluoromethyl)-6-(trifluoromethyl)-[1,2,4]triazolo[1,5-a]pyridine (Intermediate 21) for 5-chloro-2,6-bis(trifluoromethyl)-[1,2,4]triazolo[1,5-a]pyridine (Intermediate 16) and 7-chloro-5-(4,4,5,5-tetramethyl-1,3,2-dioxaborolan-2-yl)-indolin-2-one (Intermediate 5) for 7-chloro-5-(4,4,5,5-tetramethyl-1,3,2-dioxaborolan-2-yl)-1H-indazole employing conventional heating at 90° C. for 17 h. MS (ESI): mass calcd. for $C_{16}H_8ClF_5N_4O$, 402.0; m/z found, 403.0 [M+H]$^+$. $^1$H NMR (600 MHz, CD$_3$OD) δ 8.12 (d, J=9.5 Hz, 1H), 8.04 (dd, J=9.5, 0.5 Hz, 1H), 7.45 (d, J=1.5 Hz, 1H), 7.36 (d, J=1.5 Hz, 1H), 6.93 (t, J=53.1 Hz, 1H), 4.63 (s, 2H).

Example 10: 7-Methyl-5-(2-(difluoromethyl)-6-(trifluoromethyl)-[1,2,4]triazolo[1,5-a]pyridin-5-yl)indolin-2-one

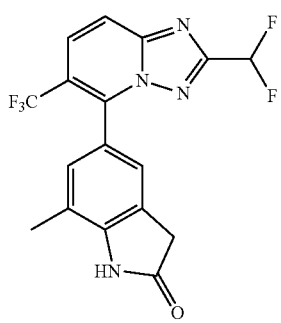 [SMILES: Cc1cc(-c2c(C(F)(F)F)ccc3nc(C(F)F)nn23)cc2c1NC(=O)C2]

The title compound was prepared in a manner analogous to Example 1, substituting 5-chloro-2-(difluoromethyl)-6-(trifluoromethyl)-[1,2,4]triazolo[1,5-a]pyridine (Intermediate 21) for 5-chloro-2,6-bis(trifluoromethyl)-[1,2,4]triazolo[1,5-a]pyridine (Intermediate 16) and 7-methyl-5-(4,4,5,5-tetramethyl-1,3,2-dioxaborolan-2-yl)-indolin-2-one (Intermediate 3) for 7-chloro-5-(4,4,5,5-tetramethyl-1,3,2-dioxaborolan-2-yl)-1H-indazole, employing conventional heating at 90° C. for 17 h. MS (ESI): mass calcd. for $C_{17}H_{11}F_5N_4O$, 382.1; m/z found, 383.1 [M+H]$^+$. $^1$H NMR (600 MHz, CD$_3$OD) δ 8.11 (d, J=9.5 Hz, 1H), 8.00 (d, J=9.5 Hz, 1H), 7.22 (d, J=24.1 Hz, 2H), 6.91 (t, J=53.1 Hz, 1H), 4.63 (s, 2H), 2.35 (s, 3H).

Example 11: 2-(Difluoromethyl)-6-(trifluoromethyl)-5-(7-(trifluoromethyl)-1H-indazol-5-yl)-[1,2,4]triazolo[1,5-a]pyridine

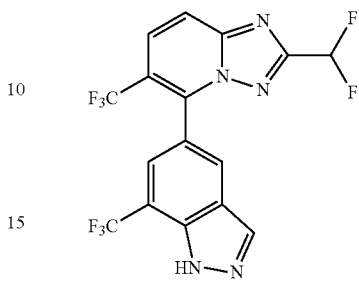

The title compound was prepared in a manner analogous to Example 1, substituting 5-chloro-2-(difluoromethyl)-6-(trifluoromethyl)-[1,2,4]triazolo[1,5-a]pyridine (Intermediate 21) for 5-chloro-2,6-bis(trifluoromethyl)-[1,2,4]triazolo[1,5-a]pyridine and 5-(4,4,5,5-tetramethyl-1,3,2-dioxaborolan-2-yl)-7-(trifluoromethyl)-1H-indazole (Intermediate 4) for 7-chloro-5-(4,4,5,5-tetramethyl-1,3,2-dioxaborolan-2-yl)-1H-indazole, employing conventional heating at 90° C. for 17 h. MS (ESI): mass calcd. for $C_{16}H_7F_8N_5$, 421.1; m/z found, 422.1 [M+H]$^+$. $^1$H NMR (500 MHz, CD$_3$OD) δ 8.36 (s, 1H), 8.30 (s, 1H), 8.18 (d, J=9.5 Hz, 1H), 8.09 (d, J=9.5 Hz, 1H), 7.93 (s, 1H), 6.93 (t, J=53.0 Hz, 1H).

Example 12: 5-(2-(Difluoromethyl)-6-(trifluoromethyl)-[1,2,4]triazolo[1,5-a]pyridin-5-yl)-7-methoxyindolin-2-one

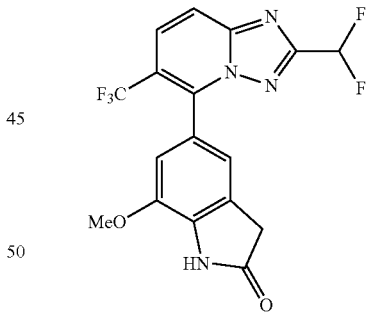

The title compound was prepared in a manner analogous to Example 1, substituting 5-chloro-2-(difluoromethyl)-6-(trifluoromethyl)-[1,2,4]triazolo[1,5-a]pyridine (Intermediate 21) for 5-chloro-2,6-bis(trifluoromethyl)-[1,2,4]triazolo[1,5-a]pyridine and 7-methoxy-5-(4,4,5,5-tetramethyl-1,3,2-dioxaborolan-2-yl)-indolin-2-one (Intermediate 6) for 7-chloro-5-(4,4,5,5-tetramethyl-1,3,2-dioxaborolan-2-yl)-1H-indazole, employing conventional heating at 90° C. for 17 h. MS (ESI): mass calcd. for $C_{17}H_{11}F_5N_4O_2$, 398.1; m/z found, 399.0 [M+H]$^+$. $^1$H NMR (500 MHz, CDCl$_3$) δ 7.96-7.94 (m, 2H), 7.00 (s, 1H), 6.95-6.71 (m, 2H), 3.89 (s, 3H), 3.67 (s, 2H).

Example 13: 5-(7-Chloro-1H-indazol-5-yl)-2-(difluoromethyl)-6-methoxy-[1,2,4]triazolo[1,5-a]pyridine

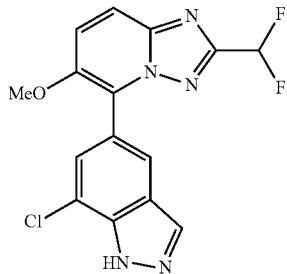 [SMILES: COc1ccc2nc(C(F)F)nn2c1-c1cc(Cl)c2[nH]ncc2c1]

The title compound was prepared in a manner analogous to Example 1, substituting 5-bromo-2-(difluoromethyl)-6-methoxy-[1,2,4]triazolo[1,5-a]pyridine (Intermediate 22) for 5-chloro-2,6-bis(trifluoromethyl)-[1,2,4]triazolo[1,5-a]pyridine. MS (ESI): mass calcd. for $C_{15}H_{10}ClF_2N_5O$, 349.1; m/z found, 350.1 $[M+H]^+$. $^1H$ NMR (600 MHz, $CD_3OD$) δ 8.24 (s, 1H), 8.10 (d, J=1.3 Hz, 1H), 7.96 (d, J=9.8 Hz, 1H), 7.87 (d, J=9.8 Hz, 1H), 7.71 (d, J=1.2 Hz, 1H), 6.91 (t, J=53.3 Hz, 1H), 3.91 (s, 3H).

Example 14: 2-(Difluoromethyl)-6-methoxy-5-(7-methyl-1H-indazol-5-yl)-[1,2,4]triazolo[1,5-a]pyridine

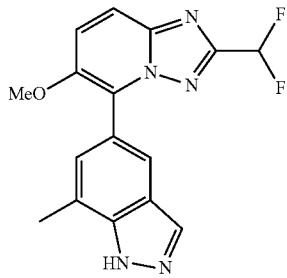 [SMILES: COc1ccc2nc(C(F)F)nn2c1-c1cc(C)c2[nH]ncc2c1]

The title compound was prepared in a manner analogous to Example 1, substituting 5-bromo-2-(difluoromethyl)-6-methoxy-[1,2,4]triazolo[1,5-a]pyridine (Intermediate 22) for 5-chloro-2,6-bis(trifluoromethyl)-[1,2,4]triazolo[1,5-a]pyridine; 7-methyl-5-(4,4,5,5-tetramethyl-1,3,2-dioxaborolan-2-yl)-1H-indazole (Intermediate 2) for 7-chloro-5-(4,4,5,5-tetramethyl-1,3,2-dioxaborolan-2-yl)-1H-indazole; and XPhos-Pd-G2 for $Pd(dppf)Cl_2$—$CH_2Cl_2$. MS (ESI): mass calcd. for $C_{16}H_{13}F_2N_5O$, 329.1; m/z found, 330.1 $[M+H]^+$. $^1H$ NMR (600 MHz, $CD_3OD$) δ 8.13 (s, 1H), 7.94-7.91 (m, 2H), 7.82 (d, J=9.8 Hz, 1H), 7.40 (s, 1H), 6.87 (t, J=53.3 Hz, 1H), 3.86 (s, 3H), 2.64 (s, 3H).

Example 15: 2-(Difluoromethyl)-6-methoxy-5-(7-(trifluoromethyl)-1H-indazol-5-yl)-[1,2,4]triazolo[1,5-a]pyridine

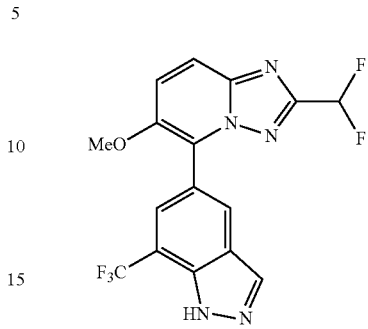

The title compound was prepared in a manner analogous to Example 1, substituting 5-bromo-2-(difluoromethyl)-6-methoxy-[1,2,4]triazolo[1,5-a]pyridine (Intermediate 22) for 5-chloro-2,6-bis(trifluoromethyl)-[1,2,4]triazolo[1,5-a]pyridine; 5-(4,4,5,5-tetramethyl-1,3,2-dioxaborolan-2-yl)-7-(trifluoromethyl)-1H-indazole (Intermediate 4) for 7-chloro-5-(4,4,5,5-tetramethyl-1,3,2-dioxaborolan-2-yl)-1H-indazole; and XPhos-Pd-G2 for $Pd(dppf)Cl_2$—$CH_2Cl_2$. MS (ESI): mass calcd. for $C_{16}H_{10}F_5N_5O$, 383.1; m/z found, 384.0 $[M+H]^+$. $^1H$ NMR (600 MHz, DMSO-$d_6$) δ 13.91 (s, 1H), 8.45-8.43 (m, 2H), 8.05-7.99 (m, 3H), 7.19 (t, J=52.9 Hz, 1H), 3.88 (s, 3H).

Example 16: 5-(7-Chloro-1H-indazol-5-yl)-6-(difluoromethyl)-2-(trifluoromethyl)-[1,2,4]triazolo[1,5-a]pyridine

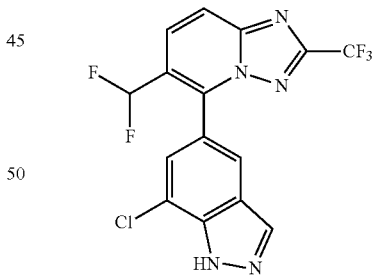

The title compound was prepared in a manner analogous to Example 1, substituting 5-chloro-6-(difluoromethyl)-2-(trifluoromethyl)-[1,2,4]triazolo[1,5-a]pyridine (Intermediate 37) for 5-chloro-2,6-bis(trifluoromethyl)-[1,2,4]triazolo[1,5-a]pyridine. MS (ESI): mass calcd. for $C_{15}H_7ClF_5N_5$, 387.0; m/z found, 388.0 $[M+H]^+$. $^1H$ NMR (600 MHz, DMSO-$d_6$) δ 14.00 (s, 1H), 8.41 (s, 1H), 8.23 (d, J=9.4 Hz, 1H), 8.18 (d, J=9.4 Hz, 1H), 8.02 (d, J=1.2 Hz, 1H), 7.78 (s, 1H), 6.86 (t, J=53.4 Hz, 1H).

Example 17: 6-(Difluoromethyl)-5-(7-methyl-1H-indazol-5-yl)-2-(trifluoromethyl)-[1,2,4]triazolo[1,5-a]pyridine

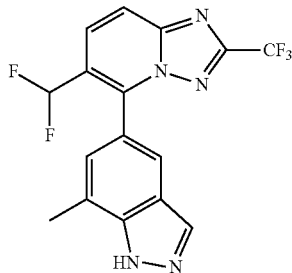 [SMILES: Cc1cc(-c2c(C(F)F)ccc3nc(C(F)(F)F)nn23)cc2cn[nH]c12]

The title compound was prepared in a manner analogous to Example 1, substituting 5-chloro-6-(difluoromethyl)-2-(trifluoromethyl)-[1,2,4]triazolo[1,5-a]pyridine (Intermediate 37) for 5-chloro-2,6-bis(trifluoromethyl)-[1,2,4]triazolo[1,5-a]pyridine and 7-methyl-5-(4,4,5,5-tetramethyl-1,3,2-dioxaborolan-2-yl)-1H-indazole (Intermediate 2) for 7-chloro-5-(4,4,5,5-tetramethyl-1,3,2-dioxaborolan-2-yl)-1H-indazole, employing conventional heating at 90° C. for 17 h. MS (ESI): mass calcd. for $C_{16}H_{10}F_5N_5$, 367.1; m/z found, 368.1 [M+H]$^+$. $^1$H NMR (600 MHz, DMSO-d$_6$) δ 13.51 (s, 1H), 8.25 (s, 1H), 8.21-8.15 (m, 2H), 7.85 (s, 1H), 7.34 (s, 1H), 6.76 (t, J=53.7 Hz, 1H), 2.60 (s, 3H).

Example 18: 7-Chloro-5-(6-(difluoromethyl)-2-(trifluoromethyl)-[1,2,4]triazolo[1,5-a]pyridin-5-yl)indolin-2-one

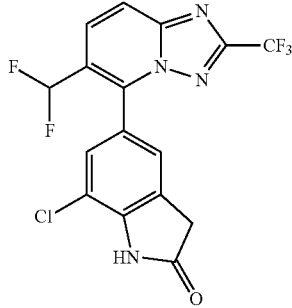 [SMILES: O=C1Cc2cc(-c3c(C(F)F)ccc4nc(C(F)(F)F)nn34)cc(Cl)c2N1]

The title compound was prepared in a manner analogous to Example 1, substituting 5-chloro-6-(difluoromethyl)-2-(trifluoromethyl)-[1,2,4]triazolo[1,5-a]pyridine (Intermediate 37) for 5-chloro-2,6-bis(trifluoromethyl)-[1,2,4]triazolo[1,5-a]pyridine and 7-chloro-5-(4,4,5,5-tetramethyl-1,3,2-dioxaborolan-2-yl)-indolin-2-one (Intermediate 5) for 7-chloro-5-(4,4,5,5-tetramethyl-1,3,2-dioxaborolan-2-yl)-1H-indazole, employing conventional heating at 90° C. for 17 h. MS (ESI): mass calcd. for $C_{16}H_8ClF_5N_4O$, 402.0; m/z found, 403.0 [M+H]$^+$. $^1$H NMR (600 MHz, DMSO-d$_6$) δ 11.13 (s, 1H), 8.19 (d, J=9.4 Hz, 1H), 8.14 (d, J=9.4 Hz, 1H), 7.56 (d, J=1.5 Hz, 1H), 7.41 (d, J=1.4 Hz, 1H), 6.84 (t, J=53.5 Hz, 1H), 3.73 (s, 2H).

Example 19: 5-[6-(Difluoromethyl)-2-(trifluoromethyl)-[1,2,4]triazolo[1,5-a]pyridin-5-yl]-7-methyl-indolin-2-one

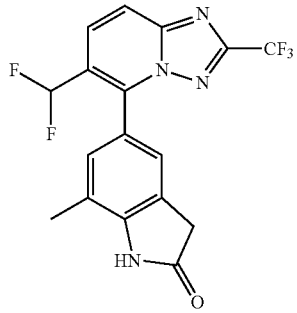 [SMILES: Cc1cc(-c2c(C(F)F)ccc3nc(C(F)(F)F)nn23)cc2c1NC(=O)C2]

The title compound was prepared in a manner analogous to Example 1, substituting 5-chloro-6-(difluoromethyl)-2-(trifluoromethyl)-[1,2,4]triazolo[1,5-a]pyridine (Intermediate 37) for 5-chloro-2,6-bis(trifluoromethyl)-[1,2,4]triazolo[1,5-a]pyridine and 7-methyl-5-(4,4,5,5-tetramethyl-1,3,2-dioxaborolan-2-yl)-indolin-2-one (Intermediate 3) for 7-chloro-5-(4,4,5,5-tetramethyl-1,3,2-dioxaborolan-2-yl)-1H-indazole, employing conventional heating at 90° C. for 16 h. MS (ESI): mass calcd. for $C_{17}H_{11}F_5N_4O$, 382.1; m/z found, 383.1 [M+H]$^+$. $^1$H NMR (500 MHz, DMSO-d$_6$) δ 10.77 (s, 1H), 8.21-8.10 (m, 2H), 7.29 (s, 1H), 7.23 (s, 1H), 6.77 (t, J=53.7 Hz, 1H), 3.62 (s, 2H), 2.28 (s, 3H).

Example 20: 5-[6-(Difluoromethyl)-2-(trifluoromethyl)-[1,2,4]triazolo[1,5-a]pyridin-5-yl]-7-methoxy-indolin-2-one

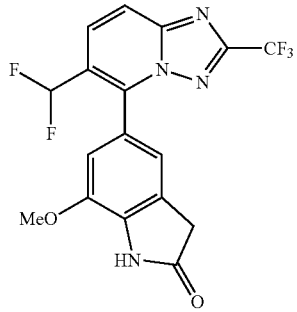 [SMILES: COc1cc(-c2c(C(F)F)ccc3nc(C(F)(F)F)nn23)cc2c1NC(=O)C2]

The title compound was prepared in a manner analogous to Example 1, substituting 5-chloro-6-(difluoromethyl)-2-(trifluoromethyl)-[1,2,4]triazolo[1,5-a]pyridine (Intermediate 37) for 5-chloro-2,6-bis(trifluoromethyl)-[1,2,4]triazolo[1,5-a]pyridine and 7-methoxy-5-(4,4,5,5-tetramethyl-1,3,2-dioxaborolan-2-yl)-indolin-2-one (Intermediate 6) for 7-chloro-5-(4,4,5,5-tetramethyl-1,3,2-dioxaborolan-2-yl)-1H-indazole, employing conventional heating at 90° C. for 16 h. MS (ESI): mass calcd. for $C_{17}H_{11}F_5N_4O_2$, 398.1; m/z found, 399.1 [M+H]$^+$. $^1$H NMR (400 MHz, CDCl$_3$) δ 8.03 (d, J=9.4 Hz, 1H), 7.96 (d, J=9.4 Hz, 1H), 7.73 (s, 1H), 7.10-7.07 (m, 1H), 7.04-7.01 (m, 1H), 6.54 (t, J=54.1 Hz, 1H), 3.91 (s, 3H), 3.68 (s, 2H).

Example 21: 5-(7-Chloro-1H-indazol-5-yl)-2-methyl-6-(trifluoromethyl)-[1,2,4]triazolo[1,5-a]pyridine

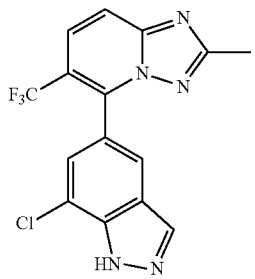 [SMILES: Cc1nc2ccc(C(F)(F)F)c(-c3cc(Cl)c4[nH]ncc4c3)n2n1]

The title compound was prepared in a manner analogous to Example 1, substituting 5-chloro-2-methyl-6-(trifluoromethyl)-[1,2,4]triazolo[1,5-a]pyridine (Intermediate 34) for 5-chloro-2,6-bis(trifluoromethyl)-[1,2,4]triazolo[1,5-a]pyridine, employing conventional heating at 90° C. for 17 h. MS (ESI): mass calcd. for $C_{15}H_9ClF_3N_5$, 351.0; m/z found, 352.0 [M+H]$^+$. $^1$H NMR (500 MHz, DMSO-$d_6$) δ 13.93 (s, 1H), 8.35 (s, 1H), 8.01 (d, J=9.4 Hz, 1H), 7.98-7.95 (m, 2H), 7.70 (s, 1H), 2.41 (s, 3H).

Example 22: 2-Methyl-5-(7-methyl-1H-indazol-5-yl)-6-(trifluoromethyl)-[1,2,4]triazolo[1,5-a]pyridine

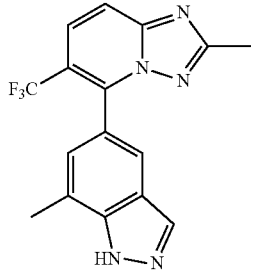 [SMILES: Cc1nc2ccc(C(F)(F)F)c(-c3cc(C)c4[nH]ncc4c3)n2n1]

The title compound was prepared in a manner analogous to Example 1, substituting 5-chloro-2-methyl-6-(trifluoromethyl)-[1,2,4]triazolo[1,5-a]pyridine (Intermediate 34) for 5-chloro-2,6-bis(trifluoromethyl)-[1,2,4]triazolo[1,5-a]pyridine and 7-methyl-5-(4,4,5,5-tetramethyl-1,3,2-dioxaborolan-2-yl)-1H-indazole (Intermediate 2) for 7-chloro-5-(4,4,5,5-tetramethyl-1,3,2-dioxaborolan-2-yl)-1H-indazole, employing conventional heating at 90° C. for 17 h. MS (ESI): mass calcd. for $C_{16}H_{12}F_3N_5$, 331.1; m/z found, 332.1 [M+H]$^+$. $^1$H NMR (600 MHz, DMSO-$d_6$) δ 13.45 (s, 1H), 8.19 (d, J=1.2 Hz, 1H), 8.00 (d, J=9.4 Hz, 1H), 7.93 (d, J=9.4 Hz, 1H), 7.75 (s, 1H), 7.23 (s, 1H), 2.58 (s, 3H), 2.39 (s, 3H).

Example 23: 7-Chloro-5-(2-methyl-6-(trifluoromethyl)-[1,2,4]triazolo[1,5-a]pyridin-5-yl)indolin-2-one

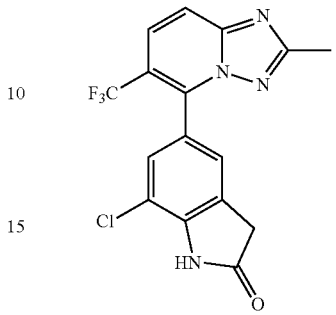

The title compound was prepared in a manner analogous to Example 1, substituting 5-chloro-2-methyl-6-(trifluoromethyl)-[1,2,4]triazolo[1,5-a]pyridine (Intermediate 34) for 5-chloro-2,6-bis(trifluoromethyl)-[1,2,4]triazolo[1,5-a]pyridine and 7-chloro-5-(4,4,5,5-tetramethyl-1,3,2-dioxaborolan-2-yl)-indolin-2-one (Intermediate 5) for 7-chloro-5-(4,4,5,5-tetramethyl-1,3,2-dioxaborolan-2-yl)-1H-indazole, employing conventional heating at 90° C. for 17 h. MS (ESI): mass calcd. for $C_{16}H_{10}ClF_3N_4O$, 366.0; m/z found, 367.0 [M+H]$^+$. $^1$H NMR (600 MHz, DMSO-$d_6$) δ 11.08 (s, 1H), 7.97 (d, J=9.4 Hz, 1H), 7.93 (d, J=9.4 Hz, 1H), 7.49 (s, 1H), 7.34 (s, 1H), 3.73-3.70 (m, 2H), 2.43 (s, 3H).

Example 24: 7-Methyl-5-(2-methyl-6-(trifluoromethyl)-[1,2,4]triazolo[1,5-a]pyridin-5-yl)indolin-2-one

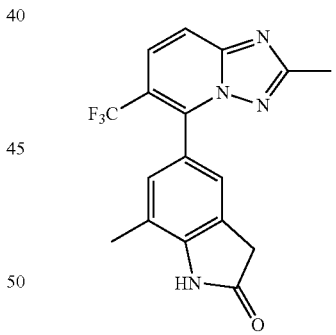

The title compound was prepared in a manner analogous to Example 1, substituting 5-chloro-2-methyl-6-(trifluoromethyl)-[1,2,4]triazolo[1,5-a]pyridine (Intermediate 34) for 5-chloro-2,6-bis(trifluoromethyl)-[1,2,4]triazolo[1,5-a]pyridine and 7-methyl-5-(4,4,5,5-tetramethyl-1,3,2-dioxaborolan-2-yl)-indolin-2-one (Intermediate 3) for 7-methyl-5-(4,4,5,5-tetramethyl-1,3,2-dioxaborolan-2-yl)-1H-indazole, employing conventional heating at 90° C. for 17 h. MS (ESI): mass calcd. for $C_{17}H_{13}F_3N_4O$, 346.1; m/z found, 347.1 [M+H]$^+$. $^1$H NMR (600 MHz, DMSO-$d_6$) δ 10.69 (s, 1H), 7.96 (d, J=9.5 Hz, 1H), 7.89 (d, J=9.5 Hz, 1H), 7.17 (s, 1H), 7.13 (s, 1H), 3.59 (d, J=3.6 Hz, 2H), 2.41 (s, 3H), 2.25 (s, 3H).

Example 25: 5-(7-Chloro-1H-indazol-5-yl)-2-ethyl-6-(trifluoromethyl)-[1,2,4]triazolo[1,5-a]pyridine

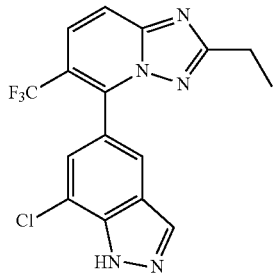 [SMILES: CCc1nc2ccc(C(F)(F)F)c(-c3cc(Cl)c4[nH]ncc4c3)n2n1]

The title compound was prepared in a manner analogous to Example 1, substituting 5-chloro-2-ethyl-6-(trifluoromethyl)-[1,2,4]triazolo[1,5-a]pyridine (Intermediate 23) for 5-chloro-2,6-bis(trifluoromethyl)-[1,2,4]triazolo[1,5-a]pyridine. MS (ESI): mass calcd. for $C_{16}H_{11}ClF_3N_5$, 365.1; m/z found, 366.0 [M+H]$^+$. $^1$H NMR (500 MHz, DMSO-d$_6$) δ 13.93 (s, 1H), 8.35 (s, 1H), 8.04-7.96 (m, 3H), 7.71 (s, 1H), 2.76 (q, J=7.6 Hz, 2H), 1.23 (t, J=7.6 Hz, 3H).

Example 26: 2-Ethyl-5-(7-methyl-1H-indazol-5-yl)-6-(trifluoromethyl)-[1,2,4]triazolo[1,5-a]pyridine

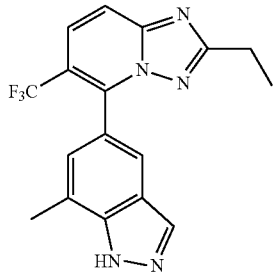 [SMILES: CCc1nc2ccc(C(F)(F)F)c(-c3cc(C)c4[nH]ncc4c3)n2n1]

The title compound was prepared in a manner analogous to Example 1, substituting 5-chloro-2-ethyl-6-(trifluoromethyl)-[1,2,4]triazolo[1,5-a]pyridine (Intermediate 23) for 5-chloro-2,6-bis(trifluoromethyl)-[1,2,4]triazolo[1,5-a]pyridine and 7-methyl-5-(4,4,5,5-tetramethyl-1,3,2-dioxaborolan-2-yl)-1H-indazole (Intermediate 2) for 7-chloro-5-(4,4,5,5-tetramethyl-1,3,2-dioxaborolan-2-yl)-1H-indazole. MS (ESI): mass calcd. for $C_{17}H_{14}F_3N_5$, 345.1; m/z found, 346.0[M+H]$^+$. $^1$H NMR (500 MHz, DMSO-d$_6$) δ 13.45 (s, 1H), 8.19 (s, 1H), 8.00 (d, J=9.5 Hz, 1H), 7.95 (d, J=9.5 Hz, 1H), 7.76 (s, 1H), 7.24 (s, 1H), 2.74 (q, J=7.6 Hz, 2H), 2.58 (s, 3H), 1.22 (t, J=7.6 Hz, 3H).

Example 27: 7-Chloro-5-(2-ethyl-6-(trifluoromethyl)-[1,2,4]triazolo[1,5-a]pyridin-5-yl)indolin-2-one

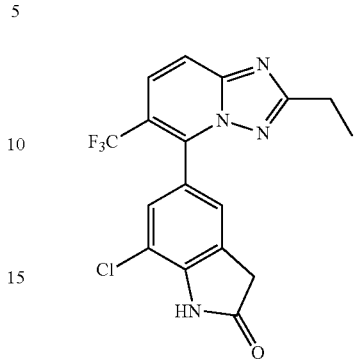

The title compound was prepared in a manner analogous to Example 1, substituting 5-chloro-2-ethyl-6-(trifluoromethyl)-[1,2,4]triazolo[1,5-a]pyridine (Intermediate 23) for 5-chloro-2,6-bis(trifluoromethyl)-[1,2,4]triazolo[1,5-a]pyridine and 7-chloro-5-(4,4,5,5-tetramethyl-1,3,2-dioxaborolan-2-yl)-indolin-2-one (Intermediate 5) for 7-chloro-5-(4,4,5,5-tetramethyl-1,3,2-dioxaborolan-2-yl)-1H-indazole. MS (ESI): mass calcd. for $C_{17}H_{12}ClF_3N_4O$, 380.1; m/z found, 381.0 [M+H]$^+$. $^1$H NMR (500 MHz, DMSO-d$_6$) δ 11.08 (s, 1H), 8.00-7.92 (m, 2H), 7.50 (s, 1H), 7.35 (s, 1H), 3.72 (s, 2H), 2.78 (q, J=7.6 Hz, 2H), 1.25 (t, J=7.6 Hz, 3H).

Example 28: 5-(2-Ethyl-6-(trifluoromethyl)-[1,2,4]triazolo[1,5-a]pyridin-5-yl)-7-methylindolin-2-one

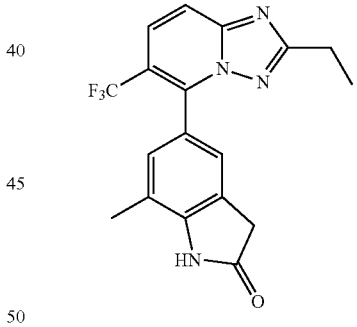

The title compound was prepared in a manner analogous to Example 1, substituting 5-chloro-2-ethyl-6-(trifluoromethyl)-[1,2,4]triazolo[1,5-a]pyridine (Intermediate 23) for 5-chloro-2,6-bis(trifluoromethyl)-[1,2,4]triazolo[1,5-a]pyridine and 7-methyl-5-(4,4,5,5-tetramethyl-1,3,2-dioxaborolan-2-yl)-indolin-2-one (Intermediate 3) for 7-chloro-5-(4,4,5,5-tetramethyl-1,3,2-dioxaborolan-2-yl)-1H-indazole, employing conventional heating at 90° C. for 17 h. MS (ESI): mass calcd. for $C_{18}H_{15}F_3N_4O$, 360.1; m/z found, 361.0 [M+H]$^+$. $^1$H NMR (500 MHz, DMSO-d$_6$) δ 10.69 (s, 1H), 7.96 (d, J=9.5 Hz, 1H), 7.91 (d, J=9.5 Hz, 1H), 7.18 (s, 1H), 7.14 (s, 1H), 3.59 (s, 2H), 2.77 (q, J=7.6 Hz, 2H), 2.26 (s, 3H), 1.25 (t, J=7.6 Hz, 3H).

Example 29: 8-Chloro-5-(7-chloro-1H-indazol-5-yl)-2-ethyl-6-(trifluoromethyl)-[1,2,4]triazolo[1,5-a]pyridine

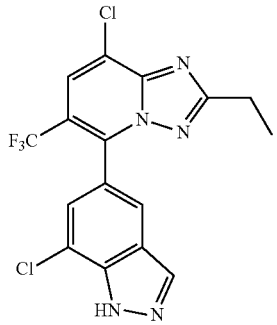 [SMILES: CCc1nc2c(Cl)cc(C(F)(F)F)c(-c3cc(Cl)c4[nH]ncc4c3)n2n1]

The title compound was prepared in a manner analogous to Example 1, substituting 5,8-dichloro-2-ethyl-6-(trifluoromethyl)-[1,2,4]triazolo[1,5-a]pyridine (Intermediate 47) for 5-chloro-2,6-bis(trifluoromethyl)-[1,2,4]triazolo[1,5-a]pyridine, employing conventional heating at 90° C. for 16 h. MS (ESI): mass calcd. for $C_{16}H_{10}Cl_2F_3N_5$, 399.0; m/z found, 400.0 [M+H]$^+$. $^1$H NMR (600 MHz, CD$_3$OD) δ 8.26 (s, 1H), 8.15 (s, 1H), 7.93 (s, 1H), 7.59 (s, 1H), 2.86 (q, J=7.6 Hz, 2H), 1.31 (t, J=7.6 Hz, 3H).

Example 30: 8-Chloro-2-ethyl-5-(7-methyl-1H-indazol-5-yl)-6-(trifluoromethyl)-[1,2,4]triazolo[1,5-a]pyridine

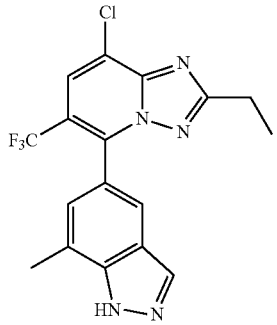

The title compound was prepared in a manner analogous to Example 1, substituting 5,8-dichloro-2-ethyl-6-(trifluoromethyl)-[1,2,4]triazolo[1,5-a]pyridine for 5-chloro-2,6-bis(trifluoromethyl)-[1,2,4]triazolo[1,5-a]pyridine and 7-methyl-5-(4,4,5,5-tetramethyl-1,3,2-dioxaborolan-2-yl)-1H-indazole (Intermediate 2) for 7-chloro-5-(4,4,5,5-tetramethyl-1,3,2-dioxaborolan-2-yl)-1H-indazole, employing conventional heating at 90° C. for 16 h. MS (ESI): mass calcd. for $C_{17}H_{13}ClF_3N_5$, 379.1; m/z found, 380.1 [M+H]$^+$. $^1$H NMR (500 MHz, DMSO-d$_6$) δ 13.43 (s, 1H), 8.25 (s, 1H), 8.20 (s, 1H), 7.76 (s, 1H), 7.24 (s, 1H), 2.77 (q, J=7.6 Hz, 2H), 2.58 (s, 3H), 1.23 (t, J=7.6 Hz, 3H).

Example 31: 5-(7-Chloro-1H-indazol-5-yl)-2-ethyl-8-fluoro-6-(trifluoromethyl)-[1,2,4]triazolo[1,5-a]pyridine

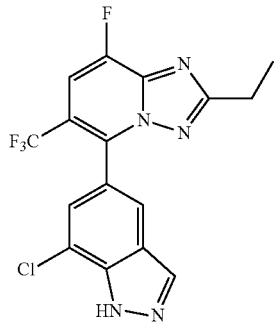 [SMILES: CCc1nc2c(F)cc(C(F)(F)F)c(-c3cc(Cl)c4[nH]ncc4c3)n2n1]

The title compound was prepared in a manner analogous to Example 1, substituting 5-chloro-2-ethyl-8-fluoro-6-(trifluoromethyl)-[1,2,4]triazolo[1,5-a]pyridine (Intermediate 30) for 5-chloro-2,6-bis(trifluoromethyl)-[1,2,4]triazolo[1,5-a]pyridine (Intermediate 16) employing conventional heating at 90° C. for 6 h. MS (ESI): mass calcd. for $C_{16}H_{10}ClF_4N_5$, 383.1; m/z found, 384.0 [M+H]$^+$. $^1$H NMR (400 MHz, CDCl$_3$) δ 11.01 (s, 1H), 8.16 (s, 1H), 7.76 (dd, J=1.2, 0.7 Hz, 1H), 7.60 (d, J=9.7 Hz, 1H), 7.44 (d, J=1.3 Hz, 1H), 2.95 (q, J=7.6 Hz, 2H), 1.38 (t, J=7.6 Hz, 3H).

Example 32: 7-Chloro-5-[2-ethyl-8-fluoro-6-(trifluoromethyl)-[1,2,4]triazolo[1,5-a]pyridin-5-yl]indolin-2-one

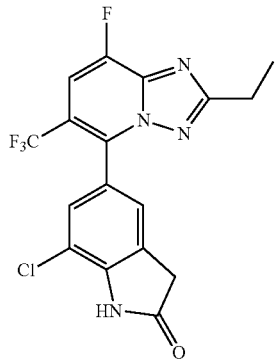 [SMILES: CCc1nc2c(F)cc(C(F)(F)F)c(-c3cc(Cl)c4c(c3)CC(=O)N4)n2n1]

The title compound was prepared in a manner analogous to Example 1, substituting 5-chloro-2-ethyl-8-fluoro-6-(trifluoromethyl)-[1,2,4]triazolo[1,5-a]pyridine (Intermediate 30) for 5-chloro-2,6-bis(trifluoromethyl)-[1,2,4]triazolo[1,5-a]pyridine and 7-chloro-5-(4,4,5,5-tetramethyl-1,3,2-dioxaborolan-2-yl)-indolin-2-one (Intermediate 5) for 7-chloro-5-(4,4,5,5-tetramethyl-1,3,2-dioxaborolan-2-yl)-1H-indazole employing conventional heating at 90° C. for 16 h. MS (ESI): mass calcd. for $C_{17}H_{11}ClF_4N_4O$, 398.1; m/z found, 399.0 [M+H]$^+$. $^1$H NMR (400 MHz, DMSO-d$_6$) δ 11.09 (s, 1H), 8.10 (d, J=10.7 Hz, 1H), 7.47 (d, J=1.5 Hz, 1H), 7.34 (d, J=1.6 Hz, 1H), 3.73 (s, 2H), 2.81 (q, J=7.6 Hz, 2H), 1.27 (t, J=7.6 Hz, 3H).

Example 33: 2-Cyclopropyl-8-fluoro-5-(7-methyl-1H-indazol-5-yl)-6-(trifluoromethyl)-[1,2,4]triazolo[1,5-a]pyridine

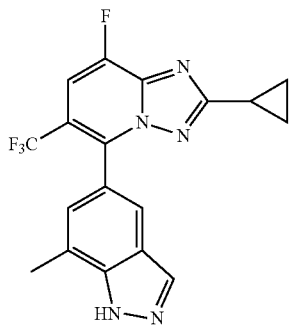 [SMILES: Cc1cc(-c2c(C(F)(F)F)cc(F)c3nc(C4CC4)nn23)cc2cn[nH]c12]

The title compound was prepared in a manner analogous to Example 1, substituting 5-chloro-2-cyclopropyl-8-fluoro-6-(trifluoromethyl)-[1,2,4]triazolo[1,5-a]pyridine for 5-chloro-2,6-bis(trifluoromethyl)-[1,2,4]triazolo[1,5-a]pyridine (Intermediate 48) and 7-methyl-5-(4,4,5,5-tetramethyl-1,3,2-dioxaborolan-2-yl)-1H-indazole (Intermediate 2) for 7-chloro-5-(4,4,5,5-tetramethyl-1,3,2-dioxaborolan-2-yl)-1H-indazole, employing conventional heating at 90° C. for 16 h. MS (ESI): mass calcd. for $C_{18}H_{13}F_4N_5$, 375.3; m/z found, 376.0 [M+H]$^+$. $^1$H NMR (400 MHz, DMSO-d$_6$) δ 13.51 (s, 1H), 8.26 (s, 1H), 8.12 (d, J=10.8 Hz, 1H), 7.80 (s, 1H), 7.28 (t, J=1.3 Hz, 1H), 2.64 (s, 3H), 2.16 (tt, J=8.2, 4.8 Hz, 1H), 1.11-1.05 (m, 2H), 1.03-0.97 (m, 2H).

Example 34: 5-(7-Chloro-1H-indazol-5-yl)-8-fluoro-2-isopropyl-6-(trifluoromethyl)-[1,2,4]triazolo[1,5-a]pyridine

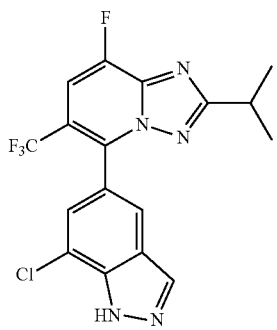 [SMILES: CC(C)c1nc2c(F)cc(C(F)(F)F)c(-c3cc(Cl)c4[nH]ncc4c3)n2n1]

The title compound was prepared in a manner analogous to Example 1, substituting 5-chloro-8-fluoro-2-isopropyl-6-(trifluoromethyl)-[1,2,4]triazolo[1,5-a]pyridine (Intermediate 49) for 5-chloro-2,6-bis(trifluoromethyl)-[1,2,4]triazolo[1,5-a]pyridine (Intermediate 16) employing conventional heating at 90° C. for 16 h. MS (ESI): mass calcd. for $C_{17}H_{12}ClF_4N_5$, 397.7; m/z found, 398.0 [M+H]$^+$. $^1$H NMR (500 MHz, DMSO-d$_6$) δ 13.95 (s, 1H), 8.37 (s, 1H), 8.11 (d, J=10.7 Hz, 1H), 7.97 (d, J=1.2 Hz, 1H), 7.67 (d, J=1.2 Hz, 1H), 3.12 (dt, J=13.8, 6.9 Hz, 1H), 1.26 (t, J=6.4 Hz, 6H).

Example 35: 5-(7-Chloro-1H-indazol-5-yl)-2-ethyl-8-methyl-6-(trifluoromethyl)-[1,2,4]triazolo[1,5-]pyridine

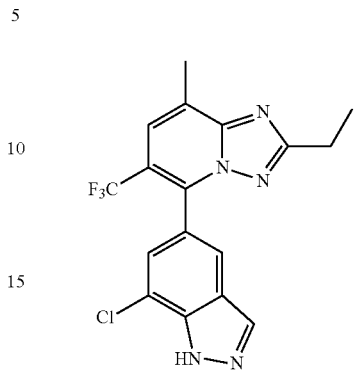

The title compound was prepared in a manner analogous to Example 1, substituting 5-chloro-2-ethyl-8-methyl-6-(trifluoromethyl)-[1,2,4]triazolo[1,5-a]pyridine (Intermediate 50) for 5-chloro-2,6-bis(trifluoromethyl)-[1,2,4]triazolo[1,5-a]pyridine (Intermediate 16) employing conventional heating at 90° C. for 16 h. MS (ESI): mass calcd. for $C_{17}H_{13}ClF_3N_5$, 379.7; m/z found, 380.0 [M+H]$^+$. $^1$H NMR (500 MHz, DMSO-d$_6$) δ 13.92 (s, 1H), 8.35 (s, 1H), 7.93 (d, J=1.2 Hz, 1H), 7.86 (d, J=1.2 Hz, 1H), 7.65 (d, J=1.3 Hz, 1H), 2.76 (q, J=7.6 Hz, 2H), 2.65 (d, J=1.1 Hz, 3H), 1.23 (t, J=7.6 Hz, 3H).

Example 36: 5-(7-Chloro-1H-indazol-5-yl)-2-isopropyl-6-(trifluoromethyl)-[1,2,4]triazolo[1,5-a]pyridine

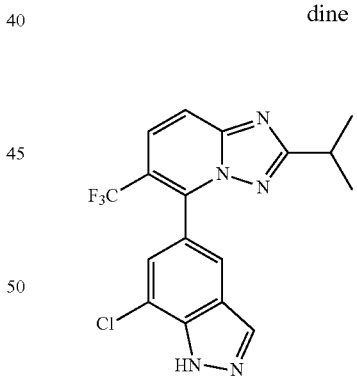

The title compound was prepared in a manner analogous to Example 1, substituting 2-isopropyl-6-(trifluoromethyl)-[1,2,4]triazolo[1,5-a]pyridine (Intermediate 27) for 5-chloro-2,6-bis(trifluoromethyl)-[1,2,4]triazolo[1,5-a]pyridine (Intermediate 16). MS (ESI): mass calcd. for $C_{17}H_{13}ClF_3N_5$, 379.1; m/z found, 380.1 [M+H]$^+$. $^1$H NMR (500 MHz, DMSO-d$_6$) δ 13.94 (s, 1H), 8.36 (s, 1H), 8.04-7.97 (m, 3H), 7.71 (s, 1H), 3.14-3.03 (m, 1H), 1.25 (t, J=6.7 Hz, 6H).

Example 37: 2-Isopropyl-5-(7-methyl-1H-indazol-5-yl)-6-(trifluoromethyl)-[1,2,4]triazolo[1,5-a]pyridine

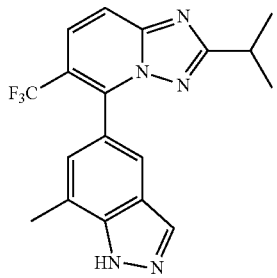 [SMILES: Cc1cc(-c2c(C(F)(F)F)ccc3nc(C(C)C)nn23)cc2cn[nH]c12]

The title compound was prepared in a manner analogous to Example 1, substituting 2-isopropyl-6-(trifluoromethyl)-[1,2,4]triazolo[1,5-a]pyridine (Intermediate 27) for 5-chloro-2,6-bis(trifluoromethyl)-[1,2,4]triazolo[1,5-a]pyridine and 7-methyl-5-(4,4,5,5-tetramethyl-1,3,2-dioxaborolan-2-yl)-1H-indazole (Intermediate 2) for 7-chloro-5-(4,4,5,5-tetramethyl-1,3,2-dioxaborolan-2-yl)-1H-indazole. MS (ESI): mass calcd. for $C_{18}H_{16}F_3N_5$, 359.1; m/z found, 360.1 [M+H]+. $^1$H NMR (600 MHz, DMSO-d$_6$) δ 13.46 (s, 1H), 8.20 (d, J=1.4 Hz, 1H), 8.00 (d, J=9.5 Hz, 1H), 7.96 (d, J=9.5 Hz, 1H), 7.77 (s, 1H), 7.25 (s, 1H), 3.12-3.02 (m, 1H), 2.58 (s, 3H), 1.24 (t, J=7.5 Hz, 6H).

Example 38: 5-(7-Chloro-1H-indazol-5-yl)-2-cyclopropyl-6-(trifluoromethyl)-[1,2,4]triazolo[1,5-a]pyridine

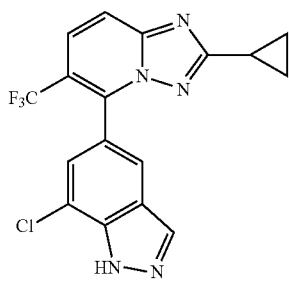 [SMILES: FC(F)(F)c1ccc2nc(C3CC3)nn2c1-c1cc(Cl)c2[nH]ncc2c1]

The title compound was prepared in a manner analogous to Example 1, substituting 5-chloro-2-cyclopropyl-6-(trifluoromethyl)-[1,2,4]triazolo[1,5-a]pyridine (Intermediate 24) for 5-chloro-2,6-bis(trifluoromethyl)-[1,2,4]triazolo[1,5-a]pyridine, employing conventional heating at 90° C. for 17 h. MS (ESI): mass calcd. for $C_{17}H_{11}ClF_3N_5$, 377.1; m/z found, 378.0 [M+H]+. $^1$H NMR (500 MHz, DMSO-d$_6$) δ 13.94 (s, 1H), 8.36 (s, 1H), 8.01-7.96 (m, 2H), 7.90 (d, J=9.5 Hz, 1H), 7.71 (s, 1H), 2.13-2.04 (m, 1H), 1.04-0.97 (m, 2H), 0.95-0.91 (m, 2H).

Example 39: 2-Cyclopropyl-5-(7-methyl-1H-indazol-5-yl)-6-(trifluoromethyl)-[1,2,4]triazolo[1,5-a]pyridine

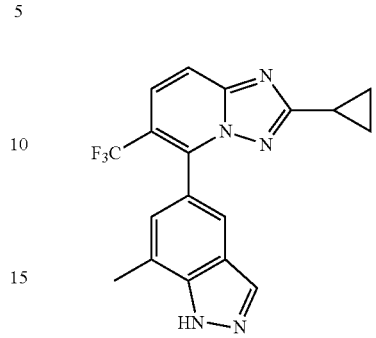

The title compound was prepared in a manner analogous to Example 1, substituting 5-chloro-2-cyclopropyl-6-(trifluoromethyl)-[1,2,4]triazolo[1,5-a]pyridine (Intermediate 24) for 5-chloro-2,6-bis(trifluoromethyl)-[1,2,4]triazolo[1,5-a]pyridine and 7-methyl-5-(4,4,5,5-tetramethyl-1,3,2-dioxaborolan-2-yl)-1H-indazole (Intermediate 2) for 7-chloro-5-(4,4,5,5-tetramethyl-1,3,2-dioxaborolan-2-yl)-1H-indazole, employing conventional heating at 90° C. for 17 h. MS (ESI): mass calcd. for $C_{18}H_{14}F_3N_5$, 357.1; m/z found, 358.0 [M+H]+. $^1$H NMR (600 MHz, DMSO-d$_6$) δ 13.45 (s, 1H), 8.19 (d, J=1.3 Hz, 1H), 7.97 (d, J=9.5 Hz, 1H), 7.87 (d, J=9.4 Hz, 1H), 7.76 (s, 1H), 7.25 (s, 1H), 2.58 (s, 3H), 2.09-2.02 (m, 1H), 1.02-0.98 (m, 2H), 0.95-0.91 (m, 2H).

Example 40: 7-Chloro-5-(2-cyclopropyl-6-(trifluoromethyl)-[1,2,4]triazolo[1,5-a]pyridin-5-yl)indolin-2-one

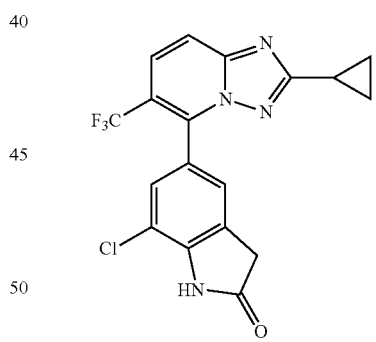

The title compound was prepared in a manner analogous to Example 1, substituting 5-chloro-2-cyclopropyl-6-(trifluoromethyl)-[1,2,4]triazolo[1,5-a]pyridine (Intermediate 24) for 5-chloro-2,6-bis(trifluoromethyl)-[1,2,4]triazolo[1,5-a]pyridine and 7-chloro-5-(4,4,5,5-tetramethyl-1,3,2-dioxaborolan-2-yl)-indolin-2-one (Intermediate 5) for 7-chloro-5-(4,4,5,5-tetramethyl-1,3,2-dioxaborolan-2-yl)-1H-indazole, employing conventional heating at 90° C. for 17 h. MS (ESI): mass calcd. for $C_{18}H_{12}ClF_3N_4O$, 392.1; m/z found, 393.0 [M+H]+. $^1$H NMR (500 MHz, DMSO-d$_6$) δ 11.08 (s, 1H), 7.95 (d, J=9.5 Hz, 1H), 7.87 (d, J=9.5 Hz, 1H), 7.50 (s, 1H), 7.36 (s, 1H), 3.72 (s, 2H), 2.16-2.07 (m, 1H), 1.06-1.00 (m, 2H), 0.99-0.92 (m, 2H).

Example 41: 5-(2-Cyclopropyl-6-(trifluoromethyl)-[1,2,4]triazolo[1,5-a]pyridin-5-yl)-7-methylindolin-2-one

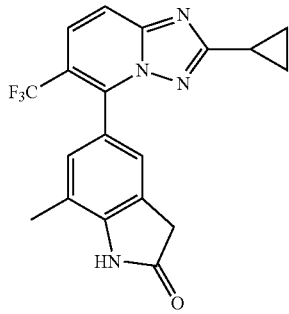 [SMILES: Cc1cc(-c2c(C(F)(F)F)ccc3nc(C4CC4)nn23)cc2c1NC(=O)C2]

The title compound was prepared in a manner analogous to Example 1, substituting 5-chloro-2-cyclopropyl-6-(trifluoromethyl)-[1,2,4]triazolo[1,5-a]pyridine (Intermediate 24) for 5-chloro-2,6-bis(trifluoromethyl)-[1,2,4]triazolo[1,5-a]pyridine and 7-methyl-5-(4,4,5,5-tetramethyl-1,3,2-dioxaborolan-2-yl)-indolin-2-one (Intermediate 3) for 7-chloro-5-(4,4,5,5-tetramethyl-1,3,2-dioxaborolan-2-yl)-1H-indazole. MS (ESI): mass calcd. for $C_{19}H_{15}F_3N_4O$, 372.1; m/z found, 373.0 [M+H]$^+$. $^1$H NMR (500 MHz, DMSO-d$_6$) δ 10.69 (s, 1H), 7.93 (d, J=9.5 Hz, 1H), 7.83 (d, J=9.5 Hz, 1H), 7.19 (s, 1H), 7.14 (s, 1H), 3.59 (d, J=2.2 Hz, 2H), 2.26 (s, 3H), 2.15-2.06 (m, 1H), 1.06-1.00 (m, 2H), 0.96-0.91 (m, 2H).

Example 42: 5-(7-Chloro-1H-indazol-5-yl)-2-(1,1-difluoroethyl)-6-(trifluoromethyl)-[1,2,4]triazolo[1,5-a]pyridine

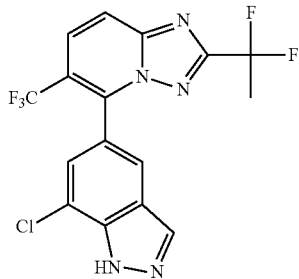 [SMILES: CC(F)(F)c1nc2ccc(C(F)(F)F)c(-c3cc(Cl)c4[nH]ncc4c3)n2n1]

The title compound was prepared in a manner analogous to Example 1, substituting 5-chloro-2-(1,1-difluoroethyl)-6-(trifluoromethyl)-[1,2,4]triazolo[1,5-a]pyridine (Intermediate 51) for 5-chloro-2,6-bis(trifluoromethyl)-[1,2,4]triazolo[1,5-a]pyridine (Intermediate 16) employing conventional heating at 90° C. for 17 h. MS (ESI): mass calcd. for $C_{16}H_9ClF_5N_5$, 401.0; m/z found, 402.0 [M+H]$^+$. $^1$H NMR (600 MHz, DMSO-d$_6$) δ 13.95 (s, 1H), 8.37 (s, 1H), 8.21-8.15 (m, 2H), 8.02 (s, 1H), 7.74 (s, 1H), 2.03 (t, J=19.2 Hz, 3H).

Example 43: 5-(7-Chloro-1H-indazol-5-yl)-2-methoxy-6-(trifluoromethyl)-[1,2,4]triazolo[1,5-a]pyridine

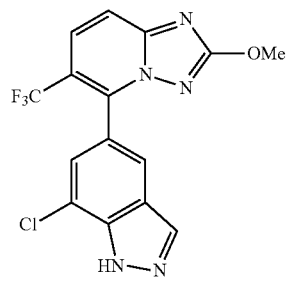 [SMILES: COc1nc2ccc(C(F)(F)F)c(-c3cc(Cl)c4[nH]ncc4c3)n2n1]

The title compound was prepared in a manner analogous to Example 1, substituting 5-chloro-2-methoxy-6-(trifluoromethyl)-[1,2,4]triazolo[1,5-a]pyridine (Intermediate 52) for 5-chloro-2,6-bis(trifluoromethyl)-[1,2,4]triazolo[1,5-a]pyridine. MS (ESI): mass calcd. for $C_{15}H_9ClF_3N_5O$, 367.0; m/z found, 368.0 [M+H]$^+$. $^1$H NMR (600 MHz, DMSO-d$_6$) δ 13.94 (s, 1H), 8.35 (s, 1H), 8.03 (d, J=9.5 Hz, 1H), 7.97 (s, 1H), 7.87 (d, J=9.2 Hz, 1H), 7.70 (s, 1H), 3.92 (s, 3H).

Example 44: 5-(7-Chloro-1H-indazol-5-yl)-6-(difluoromethyl)-2-ethyl-[1,2,4]triazolo[1,5-a]pyridine

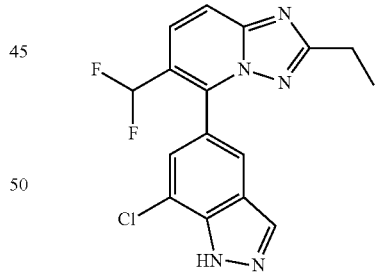

The title compound was prepared in a manner analogous to Example 1, substituting 5-chloro-6-(difluoromethyl)-2-ethyl-[1,2,4]triazolo[1,5-a]pyridine (Intermediate 35) for 5-chloro-2,6-bis(trifluoromethyl)-[1,2,4]triazolo[1,5-a]pyridine. MS (ESI): mass calcd. for $C_{16}H_{12}ClF_2N_5$, 347.1; m/z found, 348.0 [M+H]$^+$. $^1$H NMR (500 MHz, DMSO-d$_6$) δ 13.94 (s, 1H), 8.37 (s, 1H), 7.97-7.92 (m, 3H), 7.72 (d, J=1.4 Hz, 1H), 6.76 (t, J=53.7 Hz, 1H), 2.77 (q, J=7.6 Hz, 2H), 1.24 (t, J=7.6 Hz, 3H).

Example 45: 6-(Difluoromethyl)-2-ethyl-5-(7-methyl-1H-indazol-5-yl)-[1,2,4]triazolo[1,5-a]pyridine

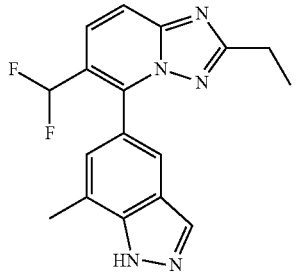 [SMILES: CCc1nc2ccc(C(F)F)c(-c3cc(C)c4[nH]ncc4c3)n2n1]

The title compound was prepared in a manner analogous to Example 1, substituting 5-chloro-6-(difluoromethyl)-2-ethyl-[1,2,4]triazolo[1,5-a]pyridine (Intermediate 35) for 5-chloro-2,6-bis(trifluoromethyl)-[1,2,4]triazolo[1,5-a]pyridine and 7-methyl-5-(4,4,5,5-tetramethyl-1,3,2-dioxaborolan-2-yl)-1H-indazole (Intermediate 2) for 7-chloro-5-(4,4,5,5-tetramethyl-1,3,2-dioxaborolan-2-yl)-1H-indazole. MS (ESI): mass calcd. for $C_{17}H_{15}F_2N_5$, 327.1; m/z found, 328.0 [M+H]$^+$. $^1$H NMR (500 MHz, DMSO-$d_6$) δ 13.48 (s, 1H), 8.23 (s, 1H), 7.91 (d, J=1.4 Hz, 2H), 7.78 (s, 1H), 7.29 (s, 1H), 6.67 (t, J=54.0 Hz, 1H), 2.76 (q, J=7.6 Hz, 2H), 2.60 (s, 3H), 1.24 (t, J=7.6 Hz, 3H).

Example 46: 7-Chloro-5-(6-(difluoromethyl)-2-ethyl-[1,2,4]triazolo[1,5-a]pyridin-5-yl)indolin-2-one

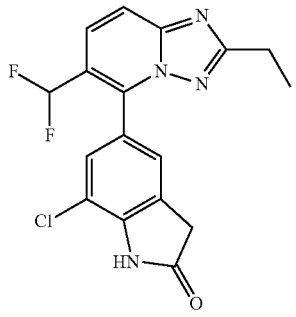 [SMILES: CCc1nc2ccc(C(F)F)c(-c3cc(Cl)c4c(c3)CC(=O)N4)n2n1]

The title compound was prepared in a manner analogous to Example 1, substituting 5-chloro-6-(difluoromethyl)-2-ethyl-[1,2,4]triazolo[1,5-a]pyridine (Intermediate 35) for 5-chloro-2,6-bis(trifluoromethyl)-[1,2,4]triazolo[1,5-a]pyridine and 7-chloro-5-(4,4,5,5-tetramethyl-1,3,2-dioxaborolan-2-yl)-indolin-2-one (Intermediate 5) for 7-chloro-5-(4,4,5,5-tetramethyl-1,3,2-dioxaborolan-2-yl)-1H-indazole. MS (ESI): mass calcd. for $C_{17}H_{13}ClF_2N_4O$, 362.1; m/z found, 363.0 [M+H]$^+$. $^1$H NMR (500 MHz, DMSO-$d_6$) δ 11.11 (s, 1H), 7.90 (d, J=1.1 Hz, 2H), 7.51 (d, J=1.5 Hz, 1H), 7.36 (d, J=1.4 Hz, 1H), 6.75 (t, J=53.8 Hz, 1H), 3.72 (s, 2H), 2.78 (q, J=7.6 Hz, 2H), 1.26 (t, J=7.6 Hz, 3H).

Example 47: 5-(6-(Difluoromethyl)-2-ethyl-[1,2,4]triazolo[1,5-a]pyridin-5-yl)-7-methylindolin-2-one

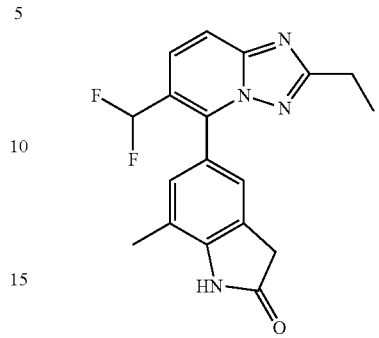

The title compound was prepared in a manner analogous to Example 1, substituting 5-chloro-6-(difluoromethyl)-2-ethyl-[1,2,4]triazolo[1,5-a]pyridine (Intermediate 35) for 5-chloro-2,6-bis(trifluoromethyl)-[1,2,4]triazolo[1,5-a]pyridine and 7-methyl-5-(4,4,5,5-tetramethyl-1,3,2-dioxaborolan-2-yl)-indolin-2-one (Intermediate 3) for 7-chloro-5-(4,4,5,5-tetramethyl-1,3,2-dioxaborolan-2-yl)-1H-indazole, employing conventional heating at 90° C. for 20 h. MS (ESI): mass calcd. for $C_{18}H_{16}F_2N_4O$, 342.1; m/z found, 343.0 [M+H]$^+$. $^1$H NMR (500 MHz, DMSO-$d_6$) δ 10.73 (s, 1H), 7.88 (d, J=1.9 Hz, 2H), 7.23 (s, 1H), 7.18 (s, 1H), 6.68 (t, J=54.0 Hz, 1H), 3.60 (s, 2H), 2.78 (q, J=7.6 Hz, 2H), 2.28 (s, 3H), 1.26 (t, J=7.6 Hz, 3H).

Example 48: 5-(7-Chloro-1H-indazol-5-yl)-2-cyclopropyl-6-(difluoromethyl)-[1,2,4]triazolo[1,5-a]pyridine

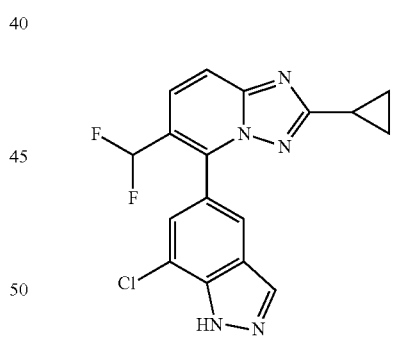

The title compound was prepared in a manner analogous to Example 1, substituting 5-chloro-2-cyclopropyl-6-(difluoromethyl)-[1,2,4]triazolo[1,5-a]pyridine (Intermediate 36) for 5-chloro-2,6-bis(trifluoromethyl)-[1,2,4]triazolo[1,5-a]pyridine. MS (ESI): mass calcd. for $C_{17}H_{12}ClF_2N_5$, 359.1; m/z found, 360.0 [M+H]$^+$. $^1$H NMR (600 MHz, DMSO-$d_6$) δ 13.95 (s, 1H), 8.37 (s, 1H), 7.95 (d, J=1.3 Hz, 1H), 7.90 (d, J=9.3 Hz, 1H), 7.86 (d, J=9.3 Hz, 1H), 7.73 (s, 1H), 6.75 (t, J=53.7 Hz, 1H), 2.14-2.04 (m, 1H), 1.04-0.98 (m, 2H), 0.95-0.91 (m, 2H).

Example 49: 2-Cyclopropyl-6-(difluoromethyl)-5-(7-methyl-1H-indazol-5-yl)-[1,2,4]triazolo[1,5-a]pyridine

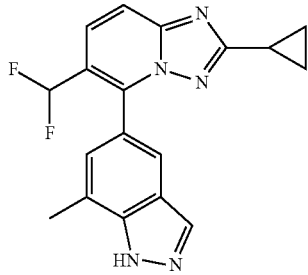 [SMILES: Cc1cc(-c2c(C(F)F)ccc3nc(C4CC4)nn23)cc2cn[nH]c12]

The title compound was prepared in a manner analogous to Example 1, substituting 5-chloro-2-cyclopropyl-6-(difluoromethyl)-[1,2,4]triazolo[1,5-a]pyridine (Intermediate 36) for 5-chloro-2,6-bis(trifluoromethyl)-[1,2,4]triazolo[1,5-a]pyridine and 7-methyl-5-(4,4,5,5-tetramethyl-1,3,2-dioxaborolan-2-yl)-1H-indazole (Intermediate 2) for 7-chloro-5-(4,4,5,5-tetramethyl-1,3,2-dioxaborolan-2-yl)-1H-indazole. MS (ESI): mass calcd. for $C_{18}H_{15}F_2N_5$, 339.1; m/z found, 340.0 [M+H]$^+$. $^1$H NMR (500 MHz, DMSO-d$_6$) δ 13.49 (s, 1H), 8.23 (d, J=1.4 Hz, 1H), 7.89 (d, J=9.4 Hz, 1H), 7.83 (d, J=9.4 Hz, 1H), 7.78 (s, 1H), 7.30 (s, 1H), 6.66 (t, J=54.1 Hz, 1H), 2.60 (s, 3H), 2.12-2.03 (m, 1H), 1.03-0.98 (m, 2H), 0.95-0.91 (m, 2H).

Example 50: 5-(7-Chloro-1H-indazol-5-yl)-6-methoxy-2-(trifluoromethyl)-[1,2,4]triazolo[1,5-a]pyridine

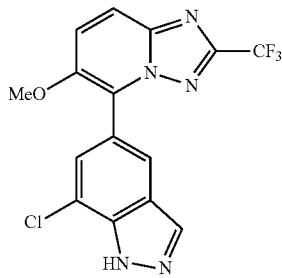 [SMILES: COc1ccc2nc(C(F)(F)F)nn2c1-c1cc(Cl)c2[nH]ncc2c1]

The title compound was prepared in a manner analogous to Example 1, substituting 5-bromo-6-methoxy-2-(trifluoromethyl)-[1,2,4]triazolo[1,5-a]pyridine (Intermediate 18) for 5-chloro-2,6-bis(trifluoromethyl)-[1,2,4]triazolo[1,5-a]pyridine, employing conventional heating at 90° C. for 1 h. MS (ESI): mass calcd. for $C_{15}H_9ClF_3N_5O$, 367.0; m/z found, 368.0 [M+H]$^+$. $^1$H NMR (600 MHz, DMSO-d$_6$) δ 13.84 (s, 1H), 8.35 (s, 1H), 8.12-8.05 (m, 3H), 7.72 (s, 1H), 3.89 (s, 3H).

Example 51: 6-Methoxy-5-(7-methyl-1H-indazol-5-yl)-2-(trifluoromethyl)-[1,2,4]triazolo[1,5-a]pyridine

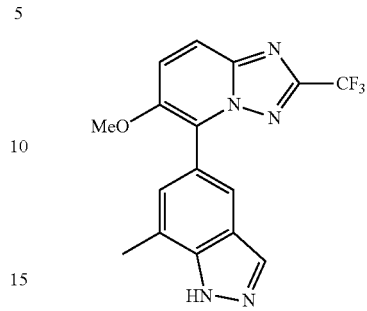

The title compound was prepared in a manner analogous to Example 1, substituting 5-bromo-6-methoxy-2-(trifluoromethyl)-[1,2,4]triazolo[1,5-a]pyridine (Intermediate 18) for 5-chloro-2,6-bis(trifluoromethyl)-[1,2,4]triazolo[1,5-a]pyridine; 7-methyl-5-(4,4,5,5-tetramethyl-1,3,2-dioxaborolan-2-yl)-1H-indazole (Intermediate 2) for 7-chloro-5-(4,4,5,5-tetramethyl-1,3,2-dioxaborolan-2-yl)-1H-indazole; and XPhos-Pd-G2 for Pd(dppf)Cl$_2$—CH$_2$Cl$_2$; employing microwave heating at 150° C. for 1 h. MS (ESI): mass calcd. for $C_{16}H_{12}F_3N_5O$, 347.1; m/z found, 348.1 [M+H]$^+$. $^1$H NMR (600 MHz, DMSO-d$_6$) δ 13.40 (s, 1H), 8.19 (d, J=1.5 Hz, 1H), 8.09 (d, J=8.6 Hz, 1H), 8.06 (d, J=8.6 Hz, 1H), 7.87 (s, 1H), 7.31 (s, 1H), 3.86 (s, 3H), 2.58 (s, 3H).

Example 52: 6-Ethyl-5-(7-methyl-1H-indazol-5-yl)-2-(trifluoromethyl)-[1,2,4]triazolo[1,5-a]pyridine

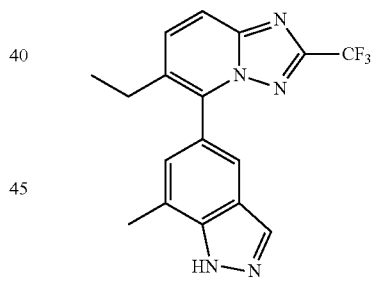

The title compound was prepared in a manner analogous to Example 1, substituting 5-chloro-6-ethyl-2-(trifluoromethyl)-[1,2,4]triazolo[1,5-a]pyridine (Intermediate 53) for 5-chloro-2,6-bis(trifluoromethyl)-[1,2,4]triazolo[1,5-a]pyridine, 7-methyl-5-(4,4,5,5-tetramethyl-1,3,2-dioxaborolan-2-yl)-1H-indazole (Intermediate 2) for 7-chloro-5-(4,4,5,5-tetramethyl-1,3,2-dioxaborolan-2-yl)-1H-indazole, and XPhos-Pd-G2 for Pd(dppf)Cl$_2$—CH$_2$Cl$_2$, employing microwave heating at 190° C. for 1 h. MS (ESI): mass calcd. for $C_{17}H_{14}F_3N_5$, 345.1; m/z found, 346.2 [M+H]$^+$. $^1$H NMR (500 MHz, DMSO-d$_6$) δ 13.44 (s, 1H), 8.19 (s, 1H), 8.01 (d, J=9.2 Hz, 1H), 7.96 (d, J=9.2 Hz, 1H), 7.77 (s, 1H), 7.22 (s, 1H), 2.59 (s, 3H), 2.57-2.51 (m, 2H), 1.11 (t, J=7.5 Hz, 3H).

Example 53: 5-(7-Chloro-1H-indazol-5-yl)-6-(1,1-difluoroethyl)-2-(trifluoromethyl)-[1,2,4]triazolo[1,5-a]pyridine

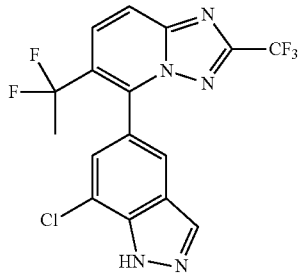 [SMILES: CC(F)(F)c1ccc2nc(C(F)(F)F)nn2c1-c1cc(Cl)c2[nH]ncc2c1]

The title compound was prepared in a manner analogous to Example 1, substituting 6-(1,1-difluoroethyl)-5-iodo-2-(trifluoromethyl)-[1,2,4]triazolo[1,5-a]pyridine (Intermediate 54) for 5-chloro-2,6-bis(trifluoromethyl)-[1,2,4]triazolo[1,5-a]pyridine, employing conventional heating at 90° C. for 1 h. MS (ESI): mass calcd. for $C_{16}H_9ClF_5N_5$, 401.0; m/z found, 402.0 [M+H]$^+$. $^1$H NMR (400 MHz, DMSO-d$_6$) δ 13.95 (s, 1H), 8.36 (s, 1H), 8.23-8.19 (m, 1H), 8.15-8.11 (m, 1H), 8.02-7.97 (m, 1H), 7.71 (d, J=1.3 Hz, 1H), 1.84 (t, J=19.0 Hz, 3H).

Example 54: 6-(2-(Difluoromethyl)-6-(trifluoromethyl)-[1,2,4]triazolo[1,5-a]pyridin-5-yl)benzo[d]thiazol-2(3H)-one

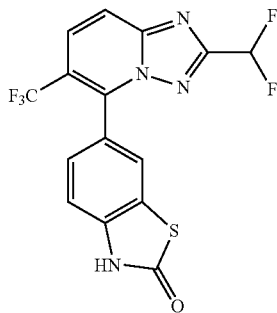 [SMILES: O=c1[nH]c2ccc(-c3c(C(F)(F)F)ccc4nc(C(F)F)nn34)cc2s1]

Step A: 6-(2-(Difluoromethyl)-6-(trifluoromethyl)-[1,2,4]triazolo[1,5-a]pyridin-5-yl)-3-((2-(trimethylsilyl)ethoxy)methyl)benzo[d]thiazol-2(3H)-one The title compound was prepared in a manner analogous to Example 1, substituting 5-chloro-2-(difluoromethyl)-6-(trifluoromethyl)-[1,2,4]triazolo[1,5-a]pyridine (Intermediate 21) for 5-chloro-2,6-bis(trifluoromethyl)-[1,2,4]triazolo[1,5-a]pyridine and 6-(4,4,5,5-tetramethyl-1,3,2-dioxaborolan-2-yl)-3-((2-(trimethylsilyl)ethoxy)methyl)benzo[d]thiazol-2(3H)-one (Intermediate 7) for 7-chloro-5-(4,4,5,5-tetramethyl-1,3,2-dioxaborolan-2-yl)-1H-indazole, employing conventional heating at 90° C. for 17 h. MS (ESI): mass calcd. for $C_{21}H_{21}F_5N_4O_2SSi$, 516.1; m/z found, 517.0 [M+H]$^+$.

Step B: 6-(2-(difluoromethyl)-6-(trifluoromethyl)-[1,2,4]triazolo[1,5-a]pyridin-5-yl)benzo[d]thiazol-2(3H)-one To a solution of 6-(2-(difluoromethyl)-6-(trifluoromethyl)-[1,2,4]triazolo[1,5-a]pyridin-5-yl)-3-((2-(trimethylsilyl)ethoxy)methyl)benzo[d]thiazol-2(3H)-one (38 mg, 0.074 mmol) in DCM (1.2 mL) was added TFA (0.6 mL). The mixture was stirred at rt for 1 h, and then the solvent was removed in vacuo. The residue was dissolved in a 2N solution of NH$_3$ in MeOH (1 mL). After stirring for 1 h, the solvent was removed in vacuo, and the residue was purified by reverse-phase HPLC (XBridge C18 ODB column, 5-99% ACN in 20 mM NH$_4$OH) to yield the title compound (19 mg, 68%). MS (ESI): mass calcd. for $C_5H_7F_5N_4OS$, 386.0; m/z found, 387.0 [M+H]$^+$. $^1$H NMR (500 MHz, CD$_3$OD) δ 8.13 (d, J=9.5 Hz, 1H), 8.03 (d, J=9.5 Hz, 1H), 7.68 (d, J=1.7 Hz, 1H), 7.44 (dd, J=8.2, 1.7 Hz, 1H), 7.32 (d, J=8.3 Hz, 1H), 6.93 (t, J=53.0 Hz, 1H).

Example 55: 6-(4-Fluorophenyl)-5-(7-methyl-1H-indazol-5-yl)-2-(trifluoromethyl)-[1,2,4]triazolo[1,5-a]pyridine

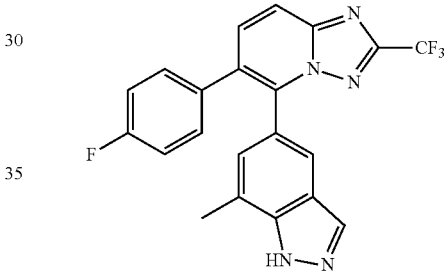

A microwave vial was charged with 5-chloro-6-iodo-2-(trifluoromethyl)-[1,2,4]triazolo[1,5-a]pyridine (Intermediate 17, 30 mg, 86 μmol), 4-fluorophenylboronic acid (12.7 mg, 91 μmol), Pd(PPh$_3$)$_4$ (5.0 mg, 4.3 μmol), sat. aq. Na$_2$CO$_3$ (0.3 mL), and 1,4-dioxane (1.2 mL). The vial was evacuated under vacuum, backfilled with Na (×3), and then capped and sealed. The mixture was heated in a microwave reactor at 110° C. for 1 h. After cooling to rt, the cap of the vial was removed, and 7-methyl-5-(4,4,5,5-tetramethyl-1,3,2-dioxaborolan-2-yl)-1H-indazole (Intermediate 2, 33 mg, 0.13 mmol) and Pd(dppf)Cl$_2$—CH$_2$Cl$_2$ (6.3 mg, 8.6 μmol) were added. The head space was purged with Na and the vial was capped. The reaction mixture was heated in a microwave reactor at 190° C. for 1 h. After cooling to rt, the mixture was diluted with EtOAc and washed with H$_2$O. The aqueous layer was extracted with EtOAc (2×), and the combined organics were washed with brine, dried over Na$_2$SO$_4$ and filtered. After concentrating the filtrate in vacuo, the residue was purified by flash column chromatography (SiO$_2$; 0-100% EtOAc/hexanes) to afford the title compound as a white solid (17 mg, 48%). MS (ESI): mass calcd. for $C_{21}H_{13}F_4N_5$, 411.1; m/z found, 412.0 [M+H]$^+$. $^1$H NMR (600 MHz, CD$_3$OD) δ 8.02 (s, 1H), 7.93 (s, 2H), 7.65 (s, 1H), 7.27-7.21 (m, 2H), 7.18 (t, J=1.2 Hz, 1H), 6.96 (t, J=8.8 Hz, 2H), 2.52 (s, 3H).

Example 56: 6-(4-Fluorophenyl)-5-(1H-indazol-5-yl)-2-(trifluoromethyl)-[1,2,4]triazolo[1,5-a]pyridine

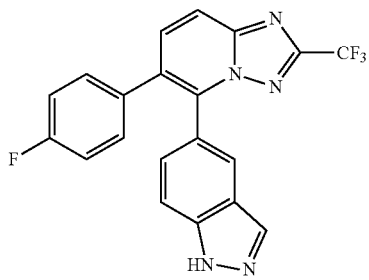 [SMILES: Fc1ccc(-c2ccc3nc(C(F)(F)F)nn3c2-c2ccc3[nH]ncc3c2)cc1]

The title compound was prepared in a manner analogous to, substituting 5-(4,4,5,5-tetramethyl-1,3,2-dioxaborolan-2-yl)-1H-indazole for 7-methyl-5-(4,4,5,5-tetramethyl-1,3,2-dioxaborolan-2-yl)-1H-indazole. MS (ESI): mass calcd. for $C_{20}H_{11}F_4N_5$, 397.1; m/z found, 398.0 [M+H]$^+$. $^1$H NMR (500 MHz, CDCl$_3$) δ 10.77 (s, 1H), 8.02 (d, J=1.1 Hz, 1H), 7.92 (d, J=9.2 Hz, 1H), 7.81-7.76 (m, 2H), 7.49-7.43 (m, 1H), 7.36 (dd, J=8.7, 1.6 Hz, 1H), 7.15-7.09 (m, 2H), 6.93 (t, J=8.7 Hz, 2H).

Example 57: 5-(6-(4-Fluorophenyl)-2-(trifluoromethyl)-[1,2,4]triazolo[1,5-a]pyridin-5-yl)-7-methylindolin-2-one

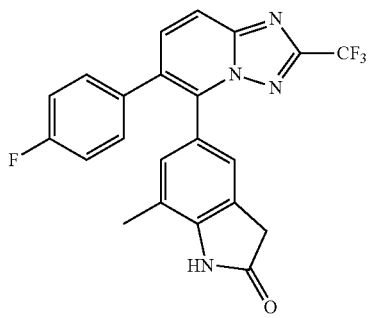 [SMILES: Cc1cc(-c2c(-c3ccc(F)cc3)ccc3nc(C(F)(F)F)nn23)cc2c1NC(=O)C2]

The title compound was prepared in a manner analogous to Example 55, substituting 7-methyl-5-(4,4,5,5-tetramethyl-1,3,2-dioxaborolan-2-yl)-indolin-2-one (Intermediate 3) for 7-methyl-5-(4,4,5,5-tetramethyl-1,3,2-dioxaborolan-2-yl)-1H-indazole. MS (ESI): mass calcd. for $C_{22}H_{14}F_4N_4O$, 426.1; m/z found, 427.0 [M+H]$^+$. $^1$H NMR (600 MHz, DMSO-d$_6$) δ 10.59 (s, 1H), 8.06 (d, J=9.2 Hz, 1H), 7.94 (d, J=9.2 Hz, 1H), 7.30-7.25 (m, 2H), 7.19-7.12 (m, 3H), 7.00 (s, 1H), 3.47 (s, 2H), 2.11 (s, 3H).

Example 58: 5-(7-Methyl-1H-indazol-5-yl)-6-(pyridin-3-yl)-2-(trifluoromethyl)-[1,2,4]triazolo[1,5-a]pyridine

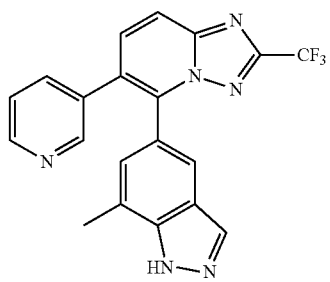 [SMILES: Cc1cc(-c2c(-c3cccnc3)ccc3nc(C(F)(F)F)nn23)cc2cn[nH]c12]

The title compound was prepared in a manner analogous to Example 55, substituting pyridine-3-boronic acid for 4-fluorophenylboronic acid. MS (ESI): mass calcd. for $C_{20}H_{13}F_3N_6$, 394.1; m/z found, 395.0 [M+H]$^+$. $^1$H NMR (500 MHz, CD$_3$OD) δ 8.40-8.35 (m, 2H), 8.04-7.98 (m, 3H), 7.77 (dt, J=7.9, 1.9 Hz, 1H), 7.66 (s, 1H), 7.34 (dd, J=7.9, 5.0 Hz, 1H), 7.24 (s, 1H), 2.53 (s, 3H).

Example 59: 5-(7-Methyl-1H-indazol-5-yl)-6-(pyridin-4-yl)-2-(trifluoromethyl)-[1,2,4]triazolo[1,5-a]pyridine

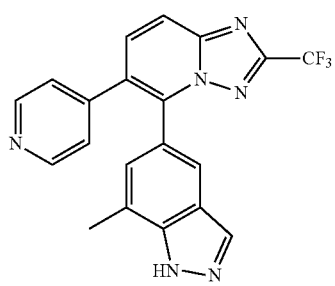 [SMILES: Cc1cc(-c2c(-c3ccncc3)ccc3nc(C(F)(F)F)nn23)cc2cn[nH]c12]

The title compound was prepared in a manner analogous to Example 55, substituting pyridine-4-boronic acid for 4-fluorophenylboronic acid. MS (ESI): mass calcd. for $C_{20}H_{13}F_3N_6$, 394.1; m/z found, 395.1 [M+H]$^+$. $^1$H NMR (500 MHz, CD$_3$OD) δ 8.40 (d, J=6.1 Hz, 2H), 8.05-7.97 (m, 3H), 7.67 (s, 1H), 7.33-7.28 (m, 2H), 7.25 (s, 1H), 2.54 (s, 3H).

Example 60: 6-(4-Fluorophenyl)-2-methyl-5-(7-methyl-1H-indazol-5-yl)-[1,2,4]triazolo[1,5-a]pyridine

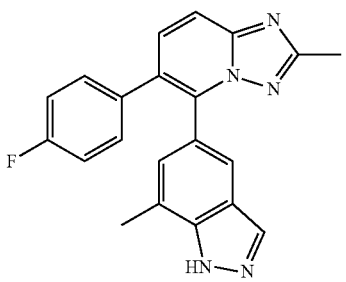 [SMILES: Cc1nc2ccc(-c3ccc(F)cc3)c(-c3cc(C)c4[nH]ncc4c3)n2n1]

The title compound was prepared in a manner analogous to Example 55, substituting 5-chloro-6-iodo-2-methyl-[1,2,4]triazolo[1,5-a]pyridine (Intermediate 55) for 5-chloro-6-iodo-2-(trifluoromethyl)-[1,2,4]triazolo[1,5-a]pyridine, and substituting XPhos-Pd-G2 for Pd(dppf)Cl$_2$—CH$_2$Cl$_2$. MS (ESI): mass calcd. for C$_{21}$H$_{16}$FN$_5$, 357.1; m/z found, 358.2 [M+H]$^+$. $^1$H NMR (500 MHz, CD$_3$OD) δ 8.00 (s, 1H), 7.77 (d, J=9.1 Hz, 1H), 7.72 (d, J=9.1 Hz, 1H), 7.59 (s, 1H), 7.23-7.16 (m, 3H), 6.93 (t, J=8.8 Hz, 2H), 2.52 (s, 3H), 2.48 (s, 3H).

Example 61: 2-Ethyl-6-(4-fluorophenyl)-5-(7-methyl-1H-indazol-5-yl)-[1,2,4]triazolo[1,5-a]pyridine

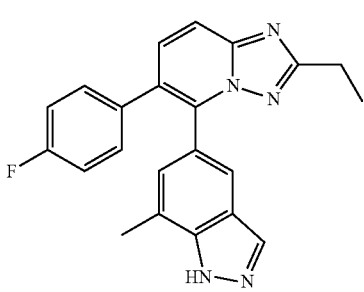 [SMILES: CCc1nc2ccc(-c3ccc(F)cc3)c(-c3cc(C)c4[nH]ncc4c3)n2n1]

The title compound was prepared in a manner analogous to Example 55, substituting 5-chloro-2-ethyl-6-iodo-[1,2,4]triazolo[1,5-a]pyridine (Intermediate 25) for 5-chloro-6-iodo-2-(trifluoromethyl)-[1,2,4]triazolo[1,5-a]pyridine, and substituting XPhos-Pd-G2 for Pd(dppf)Cl$_2$—CH$_2$Cl$_2$. MS (ESI): mass calcd. for C$_{22}$H$_{18}$FN$_5$, 371.2; m/z found, 372.1 [M+H]$^+$. $^1$H NMR (500 MHz, CD$_3$OD) δ 8.00 (s, 1H), 7.77 (d, J=9.2 Hz, 1H), 7.73 (d, J=9.2 Hz, 1H), 7.60 (s, 1H), 7.22-7.17 (m, 3H), 6.93 (t, J=8.8 Hz, 2H), 2.84 (q, J=7.6 Hz, 2H), 2.51 (s, 3H), 1.33 (t, J=7.6 Hz, 3H).

Example 62: 2-Cyclopropyl-6-(4-fluorophenyl)-5-(7-methyl-1H-indazol-5-yl)-[1,2,4]triazolo[1,5-a]pyridine

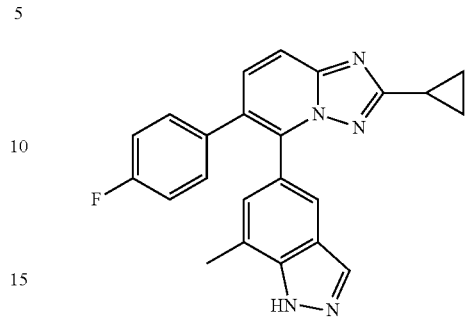

The title compound was prepared in a manner analogous to Example 55, substituting 5-chloro-2-cyclopropyl-6-iodo-[1,2,4]triazolo[1,5-a]pyridine (Intermediate 26) for 5-chloro-6-iodo-2-(trifluoromethyl)-[1,2,4]triazolo[1,5-a]pyridine. MS (ESI): mass calcd. for C$_{23}$H$_{18}$FN$_5$, 383.2; m/z found, 384.0 [M+H]$^+$. $^1$H NMR (500 MHz, DMSO-d$_6$) δ 13.30 (s, 1H), 8.05 (s, 1H), 7.74 (d, J=9.1 Hz, 1H), 7.68 (d, J=9.1 Hz, 1H), 7.56 (s, 1H), 7.25-7.19 (m, 2H), 7.15 (s, 1H), 7.06 (t, J=8.9 Hz, 2H), 2.47 (s, 3H), 2.12-2.02 (m, 1H), 1.02-0.90 (m, 4H).

Example 63: 5-(2,6-Bis(trifluoromethyl)pyrazolo[1,5-a]pyridin-7-yl)-7-chloro-1H-indazole

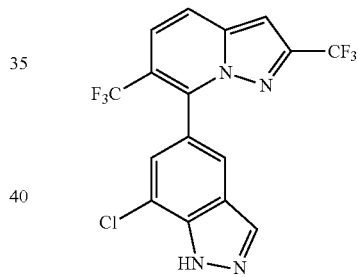

Step A: Ethyl 7-(7-chloro-1H-indazol-5-yl)-2,6-bis(trifluoromethyl)pyrazolo[1,5-c]pyridine-3-carboxylate A solution of ethyl 7-chloro-2,6-bis(trifluoromethyl)pyrazolo[1,5-c]pyridine-3-carboxylate (Intermediate 41, 300 mg, 0.832 mmol), 7-chloro-5-(4,4,5,5-tetramethyl-1,3,2-dioxaborolan-2-yl)-1H-indazole (Intermediate 1, 300 mg, 1.08 mmol), K$_2$CO$_3$ (287 mg, 2.08 mmol), Pd(dppf)Cl$_2$ (61 mg, 0.0834 mmol) and water (360 µL) in 1,4-dioxane (3.6 mL) was stirred at 110° C. for 18 h under argon. The reaction mixture was evaporated under reduced pressure. Purification (FCC, SiO$_2$; 0-10% EtOAc/hexanes) afforded the title compound (95 mg, 24%) as a yellow solid. MS (ESI): mass calcd. for C$_{19}$H$_{11}$ClF$_6$N$_4$O$_2$, 476.1; m/z found, 477.1 [M+H]$^+$.

Step B: 7-(7-Chloro-1H-indazol-5-yl)-2,6-bis(trifluoromethyl)pyrazolo[1,5-a]pyridine-3-carboxylic acid A solution of ethyl 7-(7-chloro-1H-indazol-5-yl)-2,6-bis(trifluoromethyl)pyrazolo[1,5-c]pyridine-3-carboxylate (120 mg, 0.252 mmol), lithium hydroxide monohydrate (32 mg, 0.763 mmol) and water (650 μL) in 1,4-dioxane (3.2 mL) was stirred at 60° C. for 3 h. The reaction mixture was cooled to rt and stirred for 18 h, followed by heating at 60° C. for 1 h. After cooling to rt, the reaction mixture was acidified to pH 3 by addition of 0.5 M HCl. The mixture was concentrated to remove 1,4-dioxane and the residue was diluted with water (20 mL). The aqueous layer was extracted with EtOAc (3×20 mL). The combined organic layers were dried over $Na_2SO_4$, filtered and evaporated to give the title compound (55 mg, 48%) as a yellow solid. MS (ESI): mass calcd. for $C_{17}H_7ClF_6N_4O_2$, 476.1; m/z found, 448.7 $[M+H]^+$.

Step C: 7-(7-Chloro-1H-indazol-5-yl)-2,6-bis(trifluoromethyl)pyrazolo[1,5-a]pyridine To a solution of 7-(7-chloro-1H-indazol-5-yl)-2,6-bis(trifluoromethyl)pyrazolo[1,5-a]pyridine-3-carboxylic acid (54 mg, 0.12 mmol) and AcOH (1 μL, 0.0175 mmol) in DMSO (2 mL) was added silver carbonate (10 mg, 0.0363 mmol), and the reaction mixture was stirred at 120° C. for 1.5 h. After cooling to rt, the mixture was diluted with EtOAc (50 mL) and the layers were separated. The organic layer was washed with brine (5×15 mL). The combined aqueous layers were extracted with EtOAc (2×15 mL). The combined organic layers were dried over $Na_2SO_4$, filtered and evaporated. The residue was purified by flash column chromatography ($SiO_2$; 0-1% $MeOH/CHCl_3$). The crude product was taken up in EtOH and evaporated (3×5 mL). The residue was triturated with $Et_2O$ (2 mL) to give the title compound (25 mg, 51%) as a white solid. MS (ESI): mass calcd. for $C_{16}H_8ClF_6N_4$, 404.0; m/z found, 405.0 $[M+H]^+$. $^1H$ NMR (300 MHz, DMSO-$d_6$) δ 13.94 (s, 1H), 8.35 (s, 1H), 8.18-8.08 (m, 1H), 7.98 (s, 1H), 7.79 (d, J=9.5 Hz, 1H), 7.71 (s, 1H), 7.39 (s, 1H).

Example 64: 5-(2,6-Bis(trifluoromethyl)pyrazolo[1,5-a]pyridin-7-yl)-7-methyl-1H-indazole

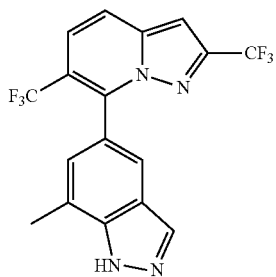 [SMILES: Cc1cc(-c2c(C(F)(F)F)ccc3cc(C(F)(F)F)nn23)cc2cn[nH]c12]

The title compound was prepared in a manner analogous to Example 63, substituting 7-methyl-5-(4,4,5,5-tetramethyl-1,3,2-dioxaborolan-2-yl)-1H-indazole (Intermediate 2) for 7-chloro-5-(4,4,5,5-tetramethyl-1,3,2-dioxaborolan-2-yl)-1H-indazole in Step A. MS (ESI): mass calcd. for $C_{17}H_{11}F_6N_4$, 384.1; m/z found, 385.1 $[M+H]^+$. $^1H$ NMR (300 MHz, DMSO-$d_6$) δ 13.46 (s, 1H), 8.19 (d, J=1.4 Hz, 1H), 8.10 (d, J=9.4 Hz, 1H), 7.79 (d, J=9.3 Hz, 1H), 7.78-7.74 (m, 1H), 7.37 (s, 1H), 7.23 (s, 1H), 2.58 (s, 3H).

Example 65: 5-(2,6-Bis(trifluoromethyl)pyrazolo[1,5-a]pyridin-7-yl)-7-methylindolin-2-one

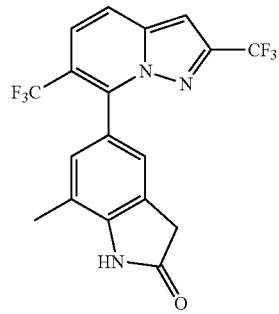 [SMILES: Cc1cc(-c2c(C(F)(F)F)ccc3cc(C(F)(F)F)nn23)cc2c1NC(=O)C2]

A mixture of 7-chloro-2,6-bis(trifluoromethyl)pyrazolo[1,5-a]pyridine (Intermediate 42, 180 mg, 0.624 mmol), 7-methyl-5-(4,4,5,5-tetramethyl-1,3,2-dioxaborolan-2-yl)indolin-2-one (Intermediate 3, 221 mg, 0.809 mmol), $K_2CO_3$ (216 mg, 1.56 mmol), and $Pd(dppf)Cl_2$ (46 mg, 0.063 mmol) in a mixture of 1,4-dioxane and water (10:1, 2.2 mL) was stirred at 110° C. for 18 h under argon. After cooling to rt, additional $Pd(dppf)Cl_2$ (46 mg, 0.063 mmol) was added and the reaction mixture was stirred at 110° C. for 2 h. The mixture was loaded directly onto a silica gel column and eluted with diisopropyl ether. The crude product was purified by preparative HPLC eluting with acetonitrile:water (80:20→5:95→80:20) over 14 min. The product was taken up in water (30 mL) and extracted with ethyl acetate (2×30 mL). The combined organic layers were dried over $MgSO_4$, filtered and evaporated. The residue was taken up in EtOH and evaporated (3×5 mL). The crude product was triturated with $Et_2O$ to give the title compound (36 mg, 14%) as a white solid. MS (ESI): mass calcd. for $C_{18}H_{11}F_6N_3O$, 399.1; m/z found, 400.1 $[M+H]^+$. $^1H$ NMR (500 MHz, DMSO-$d_6$) δ 10.68 (s, 1H), 8.06 (d, J=9.4 Hz, 1H), 7.74 (d, J=9.5 Hz, 1H), 7.35 (s, 1H), 7.21-7.15 (m, 1H), 7.15-7.09 (m, 1H), 3.61 (d, J=22.6 Hz, 1H), 3.56 (d, J=22.8 Hz, 1H), 2.26 (s, 3H).

Example 66: 5-(2,6-Bis(trifluoromethyl)pyrazolo[1,5-a]pyridin-7-yl)-7-chloroindolin-2-one

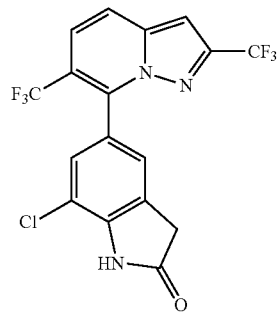 [SMILES: O=C1Cc2cc(-c3c(C(F)(F)F)ccc4cc(C(F)(F)F)nn34)cc(Cl)c2N1]

The title compound was prepared in a manner analogous to Example 65, substituting 7-chloro-5-(4,4,5,5-tetramethyl-1,3,2-dioxaborolan-2-yl)indolin-2-one (Intermediate 5) for 7-methyl-5-(4,4,5,5-tetramethyl-1,3,2-dioxaborolan-2-yl)indolin-2-one. MS (ESI): mass calcd. for $C_{17}H_8ClF_6N_3O$, 419.0; m/z found, 420.0 [M+H]+. 1H NMR (300 MHz, DMSO-d6) δ 11.09 (s, 1H), 8.09 (d, J=9.4 Hz, 1H), 7.75 (d, J=9.5 Hz, 1H), 7.54-7.47 (m, 1H), 7.38 (s, 1H), 7.38-7.33 (m, 1H), 3.76-3.72 (m, 2H).

Example 67: 5-(2-Cyclopropyl-6-(trifluoromethyl) pyrazolo[1,5-a]pyridin-7-yl)-7-methylindolin-2-one

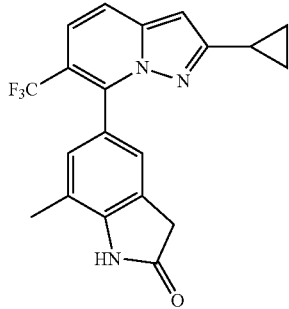

A mixture of 7-bromo-2-cyclopropyl-6-(trifluoromethyl) pyrazolo[1,5-a]pyridine (Intermediate 43, 137 mg, 0.449 mmol), 7-methyl-5-(4,4,5,5-tetramethyl-1,3,2-dioxaborolan-2-yl)indolin-2-one (Intermediate 3, 122 mg, 0.447 mmol), K2CO3 (155 mg, 1.12 mmol) and Pd(dppf)Cl2 (33 mg, 0.0451 mmol) in a mixture of 1,4-dioxane and water (10:1, 2.2 mL) was stirred at 110° C. for 18 h under argon. After cooling to rt, the solvent was removed in vacuo. The residue was taken up in EtOAc (40 mL) and washed with water (2×10 mL). The organic layer was dried over MgSO4, filtered and evaporated. The residue was purified by flash column chromatography (SiO2; 5% MeOH/Et2O). The crude product was taken up in EtOH and evaporated (3×5 mL). The residue was triturated with diethyl ether to give the title compound (74 mg, 44%) as a tan solid. MS (ESI): mass calcd. for C20H16F3N3O, 371.1; m/z found, 372.1 [M+H]+, 1H NMR (500 MHz, DMSO-d6) δ 10.66 (s, 1H), 7.70 (d, J=9.4 Hz, 1H), 7.44 (d, J=9.4 Hz, 1H), 7.12-7.09 (m, 1H), 7.07-7.04 (m, 1H), 6.42 (s, 1H), 3.62 (d, J=22.9 Hz, 1H), 3.57 (d, J=22.9 Hz, 1H), 2.25 (s, 3H), 2.02-1.92 (m, 1H), 1.00-0.91 (m, 2H), 0.74-0.65 (m, 2H).

Example 68: 5-(2-Cyclopropyl-6-(trifluoromethyl) pyrazolo[1,5-a]pyridin-7-yl)-7-chloroindolin-2-one

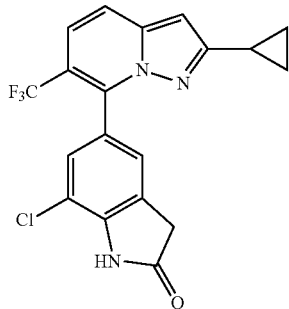

The title compound was prepared in a manner analogous to Example 67, substituting 7-chloro-5-(4,4,5,5-tetramethyl-1,3,2-dioxaborolan-2-yl)indolin-2-one (Intermediate 5) for 7-methyl-5-(4,4,5,5-tetramethyl-1,3,2-dioxaborolan-2-yl) indolin-2-one. MS (ESI): mass calcd. for C19H13ClF3N3O, 391.1; m/z found, 392.0 [M+H]+. 1H NMR (500 MHz, DMSO-d6) δ 11.05 (s, 1H), 7.74 (d, J=9.4 Hz, 1H), 7.45 (d, J=9.4 Hz, 1H), 7.41-7.38 (m, 1H), 7.29-7.25 (m, 1H), 6.45 (s, 1H), 3.71 (d, J=22.7 Hz, 1H), 3.70 (d, J=22.8 Hz, 1H), 2.03-1.93 (m, 1H), 1.01-0.91 (m, 2H), 0.77-0.65 (m, 2H).

Example 69: 5-(2-Cyclopropyl-6-(trifluoromethyl) pyrazolo[1,5-a]pyridin-7-yl)-7-methyl-1H-indazole

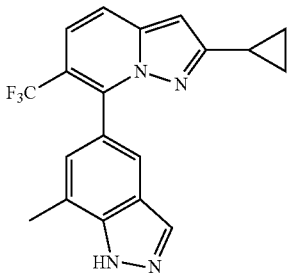 [SMILES: Cc1cc(-c2c(C(F)(F)F)ccc3cc(C4CC4)nn23)cc2cn[nH]c12]

The title compound was prepared in a manner analogous to Example 67, substituting 7-methyl-5-(4,4,5,5-tetramethyl-1,3,2-dioxaborolan-2-yl)-1H-indazole (Intermediate 2) for 7-methyl-5-(4,4,5,5-tetramethyl-1,3,2-dioxaborolan-2-yl)indolin-2-one. MS (ESI): mass calcd. for C19H15F3N4, 356.1; m/z found, 357.2 [M+H]+. 1H NMR (500 MHz, CDCl3) δ 10.93 (br s, 1H), 8.02 (s, 1H), 7.66-7.63 (m, 1H), 7.52 (d, J=9.4 Hz, 1H), 7.40 (d, J=9.4 Hz, 1H), 7.19-7.16 (m, 1H), 6.24 (s, 1H), 2.68-2.41 (m, 3H), 2.20-2.12 (m, 1H), 1.06-0.98 (m, 2H), 0.85-0.77 (m, 2H).

Example 70: 7-Chloro-5-(2-cyclopropyl-6-(trifluoromethyl)pyrazolo[1,5-a]pyridin-7-yl)-1H-indazole

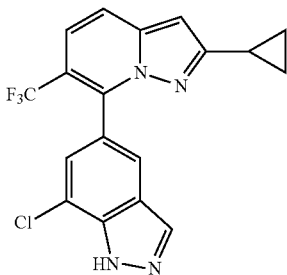

The title compound was prepared in a manner analogous to Example 67, substituting 7-chloro-5-(4,4,5,5-tetramethyl-1,3,2-dioxaborolan-2-yl)-1H-indazole (Intermediate 1) for 7-methyl-5-(4,4,5,5-tetramethyl-1,3,2-dioxaborolan-2-yl) indolin-2-one. MS (ESI): mass calcd. for C18H12ClF3N4, 376.1; m/z found, 377.1 [M+H]+. 1HNMR (300 MHz, DMSO-d6) δ 13.90 (br s, 1H), 8.33 (s, 1H), 7.92-7.83 (m, 1H), 7.78 (d, J=9.3 Hz, 1H), 7.63-7.56 (m, 1H), 7.49 (d, J=9.4 Hz, 1H), 6.48 (s, 1H), 2.01-1.90 (m, 1H), 1.00-0.88 (m, 2H), 0.73-0.64 (m, 2H).

Example 71: 5-(2-Isopropyl-6-(trifluoromethyl)pyrazolo[1,5-a]pyridin-7-yl)-7-methylindolin-2-one

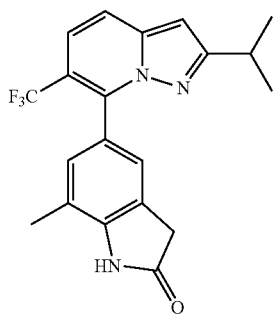 [SMILES: Cc1cc(-c2c(C(F)(F)F)ccc3cc(C(C)C)nn23)cc2c1NC(=O)C2]

The title compound was prepared in a manner analogous to Example 67, substituting 7-bromo-2-isopropyl-6-(trifluoromethyl)pyrazolo[1,5-a]pyridine (Intermediate 44) for 7-bromo-2-cyclopropyl-6-(trifluoromethyl)pyrazolo[1,5-c]pyridine. MS (ESI): mass calcd. for $C_{20}H_{18}F_3N_3O$, 373.1; m/z found, 374.2 [M+H]$^+$. $^1$H NMR (300 MHz, DMSO-d$_6$) δ 10.65 (s, 1H), 7.77 (d, J=9.3 Hz, 1H), 7.46 (d, J=9.4 Hz, 1H), 7.15-7.09 (m, 1H), 7.09-7.05 (m, 1H), 6.68 (s, 1H), 3.57 (s, 2H), 3.07-2.90 (m, 1H), 2.25 (s, 3H), 1.20 (d, J=6.9 Hz, 6H).

Example 72: 5-(2-Isopropyl-6-(trifluoromethyl)pyrazolo[1,5-a]pyridin-7-yl)-7-chloroindolin-2-one

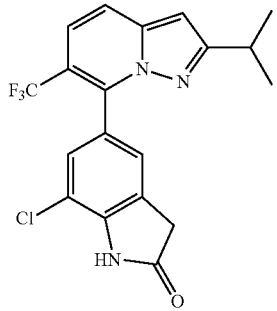 [SMILES: CC(C)c1cc2ccc(C(F)(F)F)c(-c3cc(Cl)c4c(c3)CC(=O)N4)n2n1]

The title compound was prepared in a manner analogous to Example 67, substituting 7-bromo-2-isopropyl-6-(trifluoromethyl)pyrazolo[1,5-c]pyridine (Intermediate 44) for 7-bromo-2-cyclopropyl-6-(trifluoromethyl)pyrazolo[1,5-c]pyridine and 7-chloro-5-(4,4,5,5-tetramethyl-1,3,2-dioxaborolan-2-yl)indolin-2-one (Intermediate 5) for 7-methyl-5-(4,4,5,5-tetramethyl-1,3,2-dioxaborolan-2-yl)indolin-2-one. MS (ESI): mass calcd. for $C_{19}H_{15}ClF_3N_3O$, 393.1; m/z found, 394.1 [M+H]$^+$. $^1$H NMR (300 MHz, DMSO-d$_6$) δ 11.04 (s, 1H), 7.81 (d, J=9.3 Hz, 1H), 7.47 (d, J=9.4 Hz, 1H), 7.44-7.37 (m, 1H), 7.31-7.25 (m, 1H), 6.70 (s, 1H), 3.70 (s, 2H), 3.10-2.91 (m, 1H), 1.21 (d, J=6.9 Hz, 6H).

Example 73: 7-Chloro-5-(2-isopropyl-6-(trifluoromethyl)pyrazolo[1,5-a]pyridin-7-yl)-1H-indazole

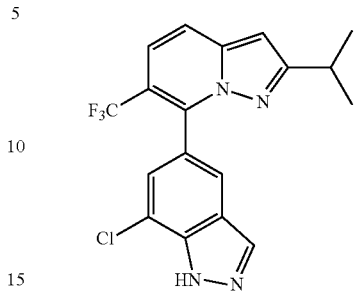

The title compound was prepared in a manner analogous to Example 67, substituting 7-bromo-2-isopropyl-6-(trifluoromethyl)pyrazolo[1,5-a]pyridine (Intermediate 44) for 7-bromo-2-cyclopropyl-6-(trifluoromethyl)pyrazolo[1,5-a]pyridine and 7-chloro-5-(4,4,5,5-tetramethyl-1,3,2-dioxaborolan-2-yl)-1H-indazole (Intermediate 1) for 7-methyl-5-(4,4,5,5-tetramethyl-1,3,2-dioxaborolan-2-yl)indolin-2-one. MS (ESI): mass calcd. for $C_{18}H_{14}ClF_3N_4$, 378.1; m/z found, 379.1 [M+H]$^+$. $^1$H NMR (500 MHz, DMSO-d$_6$) δ 13.87 (br s, 1H), 8.38-8.29 (m, 1H), 7.92-7.87 (m, 1H), 7.84 (d, J=9.4 Hz, 1H), 7.63-7.56 (m, 1H), 7.51 (d, J=9.4 Hz, 1H), 6.72 (s, 1H), 3.05-2.89 (m, 1H), 1.26-1.13 (m, 6H).

Example 74: 5-(2-Isopropyl-6-(trifluoromethyl)pyrazolo[1,5-a]pyridin-7-yl)-7-methyl-1H-indazole

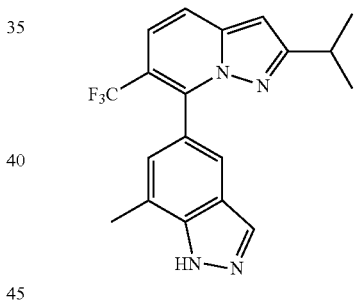

Step A: 7-methyl-5-[3-(trifluoromethyl)-2-pyridyl]-1H-indazole

A mixture of 2-bromo-3-(trifluoromethyl)pyridine (1 g, 4.42 mmol), tert-butyl 7-methyl-5-(4,4,5,5-tetramethyl-1,3,2-dioxaborolan-2-yl)indazole-1-carboxylate (Intermediate 45, 2.06 g, 5.75 mmol), $K_2CO_3$ (1.55 g, 11.2 mmol), and Pd(dppf)Cl$_2$ (330 mg, 0.451 mmol) in a mixture of 1,4-dioxane and water (10:1, 33 mL) was stirred at 110° C. for 18 h under argon. After cooling to rt, the solvents were removed in vacuo. The residue was purified by flash column column chromatography (SiO$_2$; 20-50% EtOAc/hexanes) to give the title compound (560 mg, 45% yield) as a pale yellow solid. MS (ESI): mass calcd. for $C_{14}H_{10}F_3N_3$, 277.1; m/z found, 278.1 [M+H]$^+$.

Step B: 7-Methyl-1-tetrahydropyran-2-yl-5-[3-(trifluoromethyl)-2-pyridyl]indazole To a solution of 7-methyl-5-[3-(trifluoromethyl)-2-pyridyl]-1H-indazole (1.24 g, 4.47 mmol) in DCM (20 mL)

was added 3,4-dihydro-2H-pyran (1.8 mL, 19.7 mmol) and pyridinium p-toluenesulfonate (250 mg, 0.995 mmol). The reaction mixture was stirred at rt for 18 h. The mixture was diluted with DCM (150 mL) and washed with water (3×30 mL). The organic layer was dried over MgSO$_4$, filtered and evaporated to give the title compound (1.72 g, crude) as a yellow oil. MS (ESI): mass calcd. for $C_{19}H_{18}F_3N_3O$, 361.1; m/z found, 362.2 [M+H]$^+$.

Step C: 2-(7-Methyl-1-tetrahydropyran-2-yl-indazol-5-yl)-3-(trifluoromethyl)pyridin-1-ium-1-amine 2,4,6-trimethylbenzenesulfonate To a cooled (−5° C.) solution of TFA (6.9 mL, 90.1 mmol) and water (0.8 mL) was added ethyl (1E)-N-(2,4,6-trimethylphenyl)sulfonyloxyethanimidate (1.27 g, 4.45 mmol), and the reaction mixture was stirred for 1.5 h. To the reaction mixture was added ice water (30 mL). The precipitate was collected and washed with water (10×10 mL). The solid was dissolved in DCM (15 mL), dried over MgSO$_4$, and filtered. The filtrate was cooled to 0° C. and 7-methyl-1-tetrahydropyran-2-yl-5-[3-(trifluoromethyl)-2-pyridyl]indazole (1.72 g, 4.76 mmol) in DCM (3 mL) was added. The reaction mixture was allowed to warm to rt and stirred for 1 h. The solvents were removed in vacuo and the residue was triturated with Et$_2$O (4×10 mL) to give the title compound (1.77 g, crude) as a yellow foam. MS (ESI): mass calcd. for $C_{19}H_{20}F_3N_4O$, 377.2; m/z found, 378.2 [M+H]$^+$.

Step D: Ethyl 2-isopropyl-7-(7-methyl-1-tetrahydropyran-2-yl-indazol-5-yl)-6-(trifluoromethyl)pyrazolo[1,5-c]pyridine-3-carboxylate To a solution of 2-(7-methyl-1-tetrahydropyran-2-yl-indazol-5-yl)-3-(trifluoromethyl)pyridin-1-ium-1-amine 2,4,6-trimethylbenzenesulfonate (1.7 g, 2.95 mmol) in DMF (25 mL) was added ethyl 4-methylpent-2-ynoate (500 mg, 3.57 mmol) and K$_2$CO$_3$ (490 mg, 3.55 mmol). The reaction mixture was stirred at rt for 18 h. The reaction mixture was diluted with EtOAc (300 mL) and washed with water (4×50 mL). The organic layer was dried over MgSO$_4$, filtered and evaporated. The residue was purified by flash column chromatography (SiO$_2$; 0-10% diisopropyl ether/hexanes) to give the title compound (459 mg, 30% yield) as a yellow foam. MS (ESI): mass calcd. for $C_{27}H_{29}F_3N_4O_3$, 514.2; m/z found, 515.2 [M+H]$^+$.

Step E: 2-Isopropyl-7-(7-methyl-1H-indazol-5-yl)-6-(trifluoromethyl)pyrazolo[1,5-c]pyridine-3-carboxylic acid To a suspension of ethyl 2-isopropyl-7-(7-methyl-1-tetrahydropyran-2-yl-indazol-5-yl)-6-(trifluoromethyl)pyrazolo[1,5-c]pyridine-3-carboxylate (450 mg, 0.875 mmol) in a mixture of 1,4-dioxane and water (5:1, 20.4 mL) was added lithium hydroxide monohydrate (55 mg, 1.31 mmol). The reaction mixture was stirred at 60° C. for 3 h and then at 90° C. for 21 h. Additional lithium hydroxide monohydrate (7 mg, 0.17 mmol) was added and the stirring continued at 90° C. for 6 h. After cooling to rt, the mixture was acidified to pH 3 by addition of 1 M HCl. The mixture was stirred at room temperature for 3 h and concentrated in vacuo. The residue was taken up in water (40 mL) and extracted with EtOAc (2×100 mL). The combined organic layers were washed with water (30 mL), dried over MgSO$_4$, filtered and evaporated to give the title compound (380 mg, crude) as a white solid. MS (ESI): mass calcd. for $C_{20}H_{17}F_3N_4O_2$, 402.1; m/z found, 403.2 [M+H]$^+$.

Step F: 2-Isopropyl-7-(7-methyl-1H-indazol-5-yl)-6-(trifluoromethyl)pyrazolo[1,5-a]pyridine To a solution of 2-isopropyl-7-(7-methyl-1H-indazol-5-yl)-6-(trifluoromethyl)pyrazolo[1,5-a]pyridine-3-carboxylic acid (380 mg, 0.944 mmol) in DMSO (16 mL) was added AcOH (8 µL, 0.14 mmol) and silver carbonate (78 mg, 0.283 mmol). The reaction mixture was heated at 120° C. for 2 h. The mixture was diluted with EtOAc (50 mL) and the layers were separated. The organic layer was washed with brine (5×20 mL), dried over MgSO$_4$, filtered, and evaporated. The residue was purified by flash column chromatography (SiO$_2$; 100% diisopropyl ether). The crude product was triturated with diethyl ether (3 mL) and dried in vacuo to give the title compound (31 mg, 9%) as a white solid. MS (ESI): mass calcd. for $C_{19}H_{17}F_3N_4$, 358.1; m/z found, 359.2 [M+H]$^+$. $^1$H NMR (500 MHz, DMSO-d$_6$) δ 13.38 (s, 1H), 8.21-8.12 (m, 1H), 7.81 (d, J=9.3 Hz, 1H), 7.72-7.64 (m, 1H), 7.49 (d, J=9.3 Hz, 1H), 7.22-7.13 (m, 1H), 6.73-6.65 (m, 1H), 3.00-2.90 (m, 1H), 2.57 (s, 3H), 1.24-1.13 (m, 6H).

Example 75: 7-Chloro-5-(2-cyclopropyl-8-methyl-6-(trifluoromethyl)-[1,2,4]triazolo[1,5-a]pyridin-5-yl)indolin-2-one

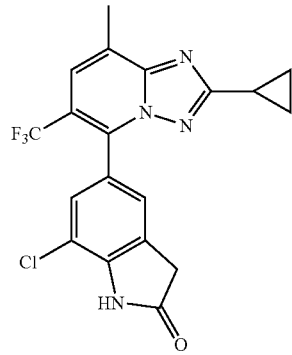 [SMILES: Cc1cc(C(F)(F)F)c(-c2cc(Cl)c3c(c2)CC(=O)N3)n2nc(C3CC3)nc12]

The title compound was prepared in a manner analogous to Example 1, using 7-chloro-5-(4,4,5,5-tetramethyl-1,3,2-dioxaborolan-2-yl)indolin-2-one (Intermediate 5) and 5-chloro-2-cyclopropyl-8-methyl-6-(trifluoromethyl)-[1,2,4]triazolo[1,5-a]pyridine (Intermediate 74). MS (ESI): mass calcd. for $C_{19}H_{14}F_3N_4O$, 406.8; m/z found, 407.3 [M+H]$^+$. $^1$H NMR (400 MHz, DMSO-d$_6$) δ 11.10 (s, 1H), 7.82 (d, J=1.3 Hz, 1H), 7.47 (d, J=1.5 Hz, 1H), 7.33 (d, J=1.6 Hz, 1H), 3.73 (s, 2H), 2.58 (d, J=1.1 Hz, 3H), 2.12 (tt, J=6.3, 4.9 Hz, 1H), 1.06-1.00 (m, 2H), 0.96 (dd, J=4.6, 2.7 Hz, 2H).

Example 76: 2-Cyclopropyl-8-methyl-5-(7-methyl-1H-indazol-5-yl)-6-(trifluoromethyl)-[1,2,4]triazolo[1,5-a]pyridine

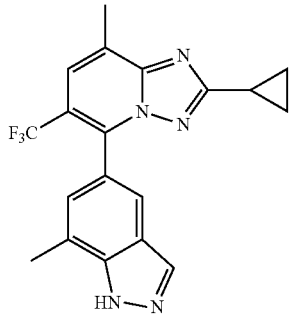 [SMILES: Cc1cc(-c2c(C(F)(F)F)cc(C)c3nc(C4CC4)nn23)cc2cn[nH]c12]

The title compound was prepared in a manner analogous to Example 1, using 7-methyl-5-(4,4,5,5-tetramethyl-1,3,2-dioxaborolan-2-yl)-1H-indazole (Intermediate 2) and 5-chloro-2-cyclopropyl-8-methyl-6-(trifluoromethyl)-[1,2,4]triazolo[1,5-a]pyridine (Intermediate 74). MS (ESI): mass calcd. for $C_{19}H_{16}F_3N_5$, 371.4; m/z found, 372.3 [M+H]$^+$. $^1$H NMR (400 MHz, DMSO-d$_6$) δ 13.46 (s, 1H), 8.20 (d, J=2.0 Hz, 1H), 7.84 (dd, J=2.7, 1.4 Hz, 1H), 7.73 (s, 1H), 7.23 (s, 1H), 2.62-2.58 (m, 6H), 2.12-2.03 (m, 1H), 1.00 (dd, J=10.3, 3.8 Hz, 2H), 0.97-0.92 (m, 2H).

Example 77: 5-(7-Chloro-1H-indazol-5-yl)-6-(difluoromethyl)-8-methyl-2-(trifluoromethyl)-[1,2,4]triazolo[1,5-a]pyridine

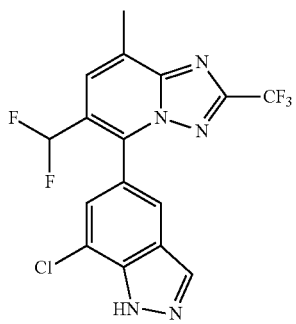 [SMILES: Cc1cc(C(F)F)c(-c2cc(Cl)c3[nH]ncc3c2)n2nc(C(F)(F)F)nc12]

The title compound was prepared in a manner analogous to Example 1, 7-chloro-5-(4,4,5,5-tetramethyl-1,3,2-dioxaborolan-2-yl)-1H-indazole (Intermediate 1) and 5-chloro-6-(difluoromethyl)-8-methyl-2-(trifluoromethyl)-[1,2,4]triazolo[1,5-a]pyridine (Intermediate 75). MS (ESI): mass calcd. for $C_{16}H_9ClF_5N_5$, 401.7; m/z found, 402.7 [M+H]$^+$. $^1$H NMR (500 MHz, DMSO-d$_6$) δ 13.98 (s, 1H), 8.40 (s, 1H), 8.02 (d, J=1.4 Hz, 1H), 7.98 (d, J=1.3 Hz, 1H), 7.72 (d, J=1.3 Hz, 1H), 6.82 (t, J=53.5 Hz, 1H), 2.71 (d, J=1.2 Hz, 3H).

Example 78: 5-(7-Chloro-1H-indazol-5-yl)-2-(difluoromethyl)-8-methyl-6-(trifluoromethyl)-[1,2,4]triazolo[1,5-a]pyridine

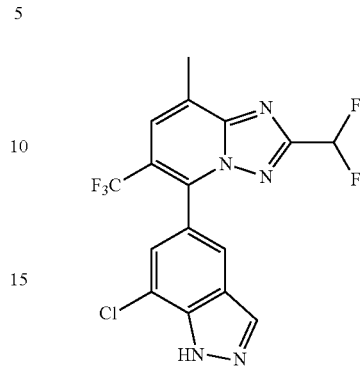

The title compound was prepared in a manner analogous to Example 1, using 5-chloro-2-(difluoromethyl)-8-methyl-6-(trifluoromethyl)-[1,2,4]triazolo[1,5-a]pyridine (Intermediate 68) and 7-chloro-5-(4,4,5,5-tetramethyl-1,3,2-dioxaborolan-2-yl)-1H-indazole (Intermediate 1), employing conventional heating at 90° C. for 16 h. MS (ESI): mass calcd. for $C_{16}H_9ClF_5N_5$, 401.0; m/z found, 401.7 [M+H]$^+$. $^1$H NMR (600 MHz, DMSO-d$_6$) δ 13.97 (s, 1H), 8.37 (s, 1H), 8.07 (d, J=1.1 Hz, 1H), 7.99 (d, J=0.7 Hz, 1H), 7.71 (s, 1H), 7.27 (d, J=52.6 Hz, 1H), 2.71 (d, J=0.8 Hz, 3H).

Example 79: 2-(Difluoromethyl)-8-methyl-5-(7-methyl-1H-indazol-5-yl)-6-(trifluoromethyl)-[1,2,4]triazolo[1,5-a]pyridine

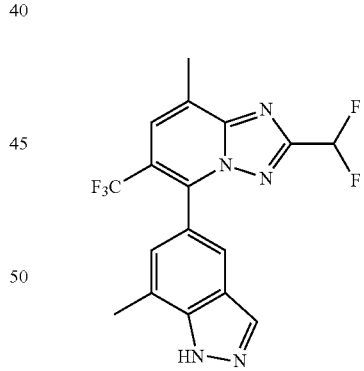

The title compound was prepared in a manner analogous to Example 1, using 5-chloro-2-(difluoromethyl)-8-methyl-6-(trifluoromethyl)-[1,2,4]triazolo[1,5-a]pyridine (Intermediate 68) and 7-methyl-5-(4,4,5,5-tetramethyl-1,3,2-dioxaborolan-2-yl)-1H-indazole (Intermediate 2). MS (ESI): mass calcd. for $C_{17}H_{12}F_5N_5$, 381.1; m/z found, 382.1 [M+H]$^+$. $^1$H NMR (600 MHz, DMSO-d$_6$) δ 13.47 (s, 1H), 8.20 (s, 1H), 8.05 (d, J=1.1 Hz, 1H), 7.78 (s, 1H), 7.36-7.13 (m, 2H), 2.70 (d, J=0.8 Hz, 3H), 2.58 (s, 3H).

Example 80: 5-(7-Chloro-1H-indazol-5-yl)-2-cyclopropyl-8-ethyl-6-(trifluoromethyl)-[1,2,4]triazolo[1,5-a]pyridine

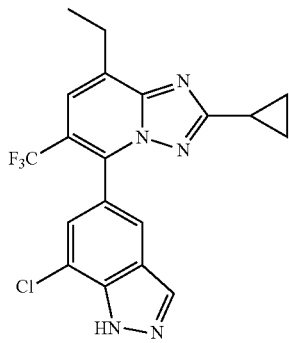 [SMILES: CCc1cc(C(F)(F)F)c(-c2cc(Cl)c3[nH]ncc3c2)n2nc(C3CC3)nc12]

The title compound was prepared in a manner analogous to Example 1, using 5-chloro-2-cyclopropyl-8-ethyl-6-(trifluoromethyl)-[1,2,4]triazolo[1,5-a]pyridine (Intermediate 65) and 7-chloro-5-(4,4,5,5-tetramethyl-1,3,2-dioxaborolan-2-yl)-1H-indazole (Intermediate 1). MS (ESI): mass calcd. for $C_{19}H_{15}ClF_3N_5$, 405.1; m/z found, 406.1 [M+H]$^+$. $^1$H NMR (600 MHz, DMSO-d$_6$) δ 13.91 (s, 1H), 8.34 (s, 1H), 7.93 (s, 1H), 7.78 (s, 1H), 7.66 (s, 1H), 3.00 (q, J=7.4 Hz, 2H), 2.11-2.05 (m, 1H), 1.35 (t, J=7.5 Hz, 3H), 1.03-0.98 (m, 2H), 0.94-0.91 (m, 2H).

Example 81: 2-Cyclopropyl-8-ethyl-5-(7-methyl-1H-indazol-5-yl)-6-(trifluoromethyl)-[1,2,4]triazolo[1,5-a]pyridine

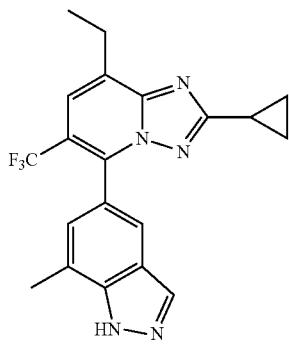 [SMILES: CCc1cc(C(F)(F)F)c(-c2cc(C)c3[nH]ncc3c2)n2nc(C3CC3)nc12]

The title compound was prepared in a manner analogous to Example 1, using 5-chloro-2-cyclopropyl-8-ethyl-6-(trifluoromethyl)-[1,2,4]triazolo[1,5-a]pyridine (Intermediate 65) and 7-methyl-5-(4,4,5,5-tetramethyl-1,3,2-dioxaborolan-2-yl)-1H-indazole (Intermediate 2). MS (ESI): mass calcd. for $C_{20}H_{18}F_3N_5$, 385.2; m/z found, 386.1 [M+H]$^+$. $^1$H NMR (600 MHz, DMSO-d$_6$) δ 13.41 (s, 1H), 8.18 (s, 1H), 7.76 (s, 1H), 7.72 (s, 1H), 7.21 (s, 1H), 2.99 (q, J=7.5 Hz, 2H), 2.58 (s, 3H), 2.10-2.02 (m, 1H), 1.35 (t, J=7.5 Hz, 3H), 1.01-0.97 (m, 2H), 0.94-0.90 (m, 2H).

Example 82: 5-(2-Cyclopropyl-8-ethyl-6-(trifluoromethyl)-[1,2,4]triazolo[1,5-a]pyridin-5-yl)-7-methylindolin-2-one

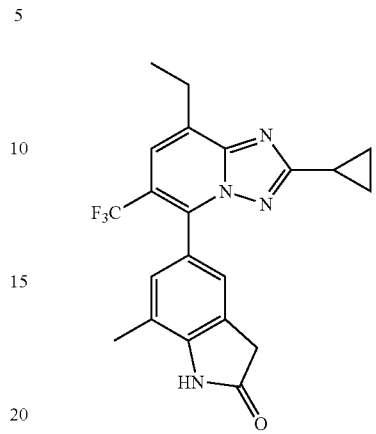

The title compound was prepared in a manner analogous to Example 1, using 5-chloro-2-cyclopropyl-8-ethyl-6-(trifluoromethyl)-[1,2,4]triazolo[1,5-a]pyridine (Intermediate 65) and 7-methyl-5-(4,4,5,5-tetramethyl-1,3,2-dioxaborolan-2-yl)indolin-2-one (Intermediate 3). MS (ESI): mass calcd. for $C_{21}H_{19}F_3N_4O$, 400.2; m/z found, 401.3 [M+H]$^+$. $^1$H NMR (600 MHz, DMSO-d$_6$) δ 10.66 (s, 1H), 7.72 (s, 1H), 7.15 (s, 1H), 7.10 (s, 1H), 3.58 (d, J=3.7 Hz, 2H), 3.00-2.93 (m, 2H), 2.25 (s, 3H), 2.12-2.06 (m, 1H), 1.33 (t, J=7.5 Hz, 3H), 1.04-0.98 (m, 2H), 0.95-0.92 (m, 2H).

Example 83: 5-(7-Chloro-1H-indazol-5-yl)-8-methyl-2-propyl-6-(trifluoromethyl)-[1,2,4]triazolo[1,5-a]pyridine

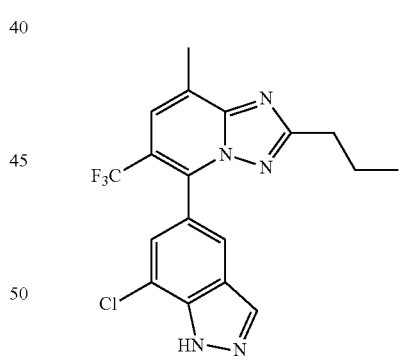

The title compound was prepared in a manner analogous to Example 1, using 5-chloro-8-methyl-2-propyl-6-(trifluoromethyl)-[1,2,4]triazolo[1,5-a]pyridine (Intermediate 67) and 7-chloro-5-(4,4,5,5-tetramethyl-1,3,2-dioxaborolan-2-yl)-1H-indazole (Intermediate 1). MS (ESI): mass calcd. for $C_{18}H_{15}ClF_3N_5$, 393.1; m/z found, 394.0 [M+H]$^+$. $^1$H NMR (600 MHz, DMSO-d$_6$) δ 13.91 (s, 1H), 8.34 (s, 1H), 7.93 (s, 1H), 7.85 (d, J=1.1 Hz, 1H), 7.64 (d, J=0.6 Hz, 1H), 2.70 (t, J=7.5 Hz, 2H), 2.64 (d, J=0.9 Hz, 3H), 1.69 (h, J=7.4 Hz, 2H), 0.89 (t, J=7.4 Hz, 3H).

Example 84: 8-Methyl-5-(7-methyl-1H-indazol-5-yl)-2-propyl-6-(trifluoromethyl)-[1,2,4]triazolo[1,5-a]pyridine

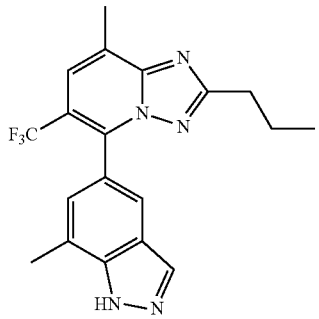 [SMILES: CCCc1nc2c(C)cc(C(F)(F)F)c(-c3cc(C)c4[nH]ncc4c3)n2n1]

The title compound was prepared in a manner analogous to Example 1, using 5-chloro-8-methyl-2-propyl-6-(trifluoromethyl)-[1,2,4]triazolo[1,5-a]pyridine (Intermediate 67) and 7-methyl-5-(4,4,5,5-tetramethyl-1,3,2-dioxaborolan-2-yl)-1H-indazole (Intermediate 2). MS (ESI): mass calcd. for $C_{19}H_{18}F_3N_5$, 373.2; m/z found, 374.1 [M+H]$^+$. $^1$H NMR (600 MHz, DMSO-d$_6$) δ 13.41 (s, 1H), 8.18 (s, 1H), 7.83 (d, J=1.1 Hz, 1H), 7.72 (s, 1H), 7.20 (s, 1H), 2.69 (t, J=7.5 Hz, 2H), 2.65-2.63 (m, 3H), 2.57 (s, 3H), 1.73-1.64 (m, 2H), 0.89 (t, J=7.4 Hz, 3H).

Example 85: 7-Methyl-5-(8-methyl-2-propyl-6-(trifluoromethyl)-[1,2,4]triazolo[1,5-a]pyridin-5-yl)indolin-2-one

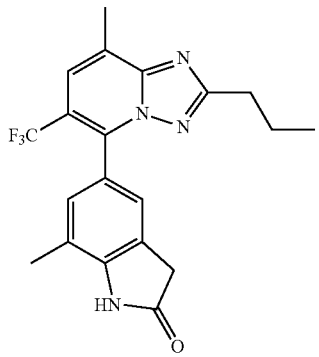 [SMILES: CCCc1nc2c(C)cc(C(F)(F)F)c(-c3cc(C)c4c(c3)CC(=O)N4)n2n1]

The title compound was prepared in a manner analogous to Example 1, using 5-chloro-8-methyl-2-propyl-6-(trifluoromethyl)-[1,2,4]triazolo[1,5-a]pyridine (Intermediate 67) and 7-methyl-5-(4,4,5,5-tetramethyl-1,3,2-dioxaborolan-2-yl)indolin-2-one (Intermediate 3). MS (ESI): mass calcd. for $C_{20}H_{19}F_3N_4O$, 388.2; m/z found, 389.1 [M+H]$^+$. $^1$H NMR (600 MHz, DMSO-d$_6$) δ 10.68 (s, 1H), 7.81 (d, J=1.1 Hz, 1H), 7.15 (s, 1H), 7.10 (s, 1H), 3.58 (d, J=2.4 Hz, 2H), 2.71 (t, J=7.6 Hz, 2H), 2.61 (d, J=0.9 Hz, 3H), 2.25 (s, 3H), 1.74-1.66 (m, 2H), 0.91 (t, J=7.4 Hz, 3H).

Example 86: 2-(Difluoromethyl)-8-methyl-5-(7-methyl-1H-indazol-5-yl)-6-(trifluoromethyl)-[1,2,4]triazolo[1,5-a]pyridine

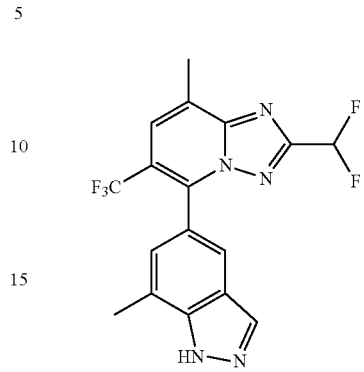

The title compound was prepared in a manner analogous to Example 1, using 5-chloro-2-(difluoromethyl)-8-methyl-6-(trifluoromethyl)-[1,2,4]triazolo[1,5-a]pyridine (Intermediate 68) and 7-methyl-5-(4,4,5,5-tetramethyl-1,3,2-dioxaborolan-2-yl)-1H-indazole (Intermediate 2). MS (ESI): mass calcd. for $C_{17}H_{12}F_5N_5$, 381.1; m/z found, 382.1 [M+H]$^+$. $^1$H NMR (600 MHz, DMSO-d$_6$) δ 13.47 (s, 1H), 8.20 (s, 1H), 8.05 (d, J=1.1 Hz, 1H), 7.78 (s, 1H), 7.36-7.13 (m, 2H), 2.70 (d, J=0.8 Hz, 3H), 2.58 (s, 3H).

Example 87: 5-(7-Chloro-1H-indazol-5-yl)-2-(difluoromethyl)-8-ethyl-6-(trifluoromethyl)-[1,2,4]triazolo[1,5-a]pyridine

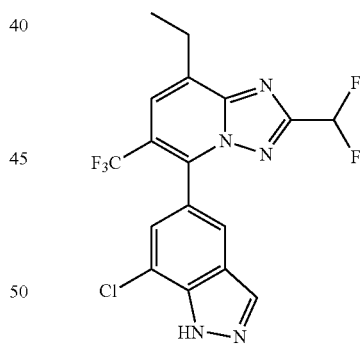

The title compound was prepared in a manner analogous to Example 1, using 5-chloro-2-(difluoromethyl)-8-ethyl-6-(trifluoromethyl)-[1,2,4]triazolo[1,5-a]pyridine (Intermediate 69) and 7-chloro-5-(4,4,5,5-tetramethyl-1,3,2-dioxaborolan-2-yl)-1H-indazole (Intermediate 1), employing conventional heating at 90° C. for 16 h. MS (ESI): mass calcd. for $C_{17}H_{11}ClF_5N_5$, 415.1; m/z found, 416.0 [M+H]$^+$. $^1$H NMR (600 MHz, DMSO-d$_6$) δ 13.94 (s, 1H), 8.36 (s, 1H), 8.00 (s, 2H), 7.72 (s, 1H), 7.26 (t, J=52.7 Hz, 1H), 3.12 (q, J=7.4 Hz, 2H), 1.41 (t, J=7.5 Hz, 3H).

Example 88: 2-(Difluoromethyl)-8-ethyl-5-(7-methyl-1H-indazol-5-yl)-6-(trifluoromethyl)-[1,2,4]triazolo[1,5-a]pyridine

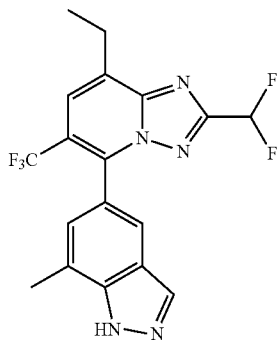 [SMILES: CCc1cc(C(F)(F)F)c(-c2cc(C)c3[nH]ncc3c2)n2nc(C(F)F)nc12]

The title compound was prepared in a manner analogous to Example 1, using 5-chloro-2-(difluoromethyl)-8-ethyl-6-(trifluoromethyl)-[1,2,4]triazolo[1,5-a]pyridine (Intermediate 69) and 7-methyl-5-(4,4,5,5-tetramethyl-1,3,2-dioxaborolan-2-yl)-1H-indazole (Intermediate 2). MS (ESI): mass calcd. for $C_{18}H_{14}F_5N_5$, 395.1; m/z found, 396.0 [M+H]$^+$. $^1$H NMR (600 MHz, DMSO-$d_6$) δ 13.44 (s, 1H), 8.20 (s, 1H), 7.98 (s, 1H), 7.79 (s, 1H), 7.34-7.13 (m, 2H), 3.11 (q, J=7.6 Hz, 2H), 2.58 (s, 3H), 1.40 (t, J=7.5 Hz, 3H).

Example 89: 5-(7-Chloro-1H-indazol-5-yl)-2,8-diethyl-6-(trifluoromethyl)-[1,2,4]triazolo[1,5-a]pyridine

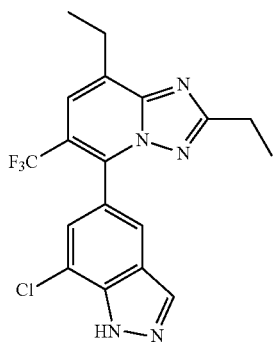 [SMILES: CCc1nc2c(CC)cc(C(F)(F)F)c(-c3cc(Cl)c4[nH]ncc4c3)n2n1]

The title compound was prepared in a manner analogous to Example 1, using 5-chloro-2,8-diethyl-6-(trifluoromethyl)-[1,2,4]triazolo[1,5-a]pyridine (Intermediate 70) and 7-chloro-5-(4,4,5,5-tetramethyl-1,3,2-dioxaborolan-2-yl)-1H-indazole (Intermediate 1). MS (ESI): mass calcd. for $C_{18}H_{15}ClF_3N_5$, 393.1; m/z found, 394.1 [M+H]$^+$. $^1$H NMR (600 MHz, DMSO-$d_6$) δ 13.91 (s, 1H), 8.34 (s, 1H), 7.94 (s, 1H), 7.80 (s, 1H), 7.66 (s, 1H), 3.06 (q, J=7.5 Hz, 2H), 2.76 (q, J=7.6 Hz, 2H), 1.39 (t, J=7.5 Hz, 3H), 1.23 (t, J=7.6 Hz, 3H).

Example 90: 2,8-Diethyl-5-(7-methyl-1H-indazol-5-yl)-6-(trifluoromethyl)-[1,2,4]triazolo[1,5-a]pyridine

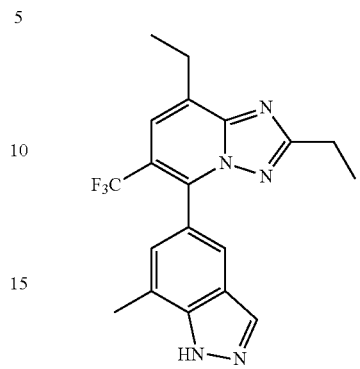

The title compound was prepared in a manner analogous to Example 1, using 5-chloro-2,8-diethyl-6-(trifluoromethyl)-[1,2,4]triazolo[1,5-a]pyridine (Intermediate 70) and 7-methyl-5-(4,4,5,5-tetramethyl-1,3,2-dioxaborolan-2-yl)-1H-indazole (Intermediate 2). MS (ESI): mass calcd. for $C_{19}H_{18}F_3N_5$, 373.2; m/z found, 374.1 [M+H]$^+$. $^1$H NMR (600 MHz, DMSO-$d_6$) δ 13.41 (s, 1H), 8.18 (s, 1H), 7.79 (s, 1H), 7.73 (s, 1H), 7.21 (s, 1H), 3.05 (q, J=7.4 Hz, 2H), 2.75 (q, J=7.6 Hz, 2H), 2.57 (s, 3H), 1.38 (t, J=7.5 Hz, 3H), 1.22 (t, J=7.6 Hz, 3H).

Example 91: 5-(7-Chloro-1H-indazol-5-yl)-6-(difluoromethyl)-8-ethyl-2-(trifluoromethyl)-[1,2,4]triazolo[1,5-a]pyridine

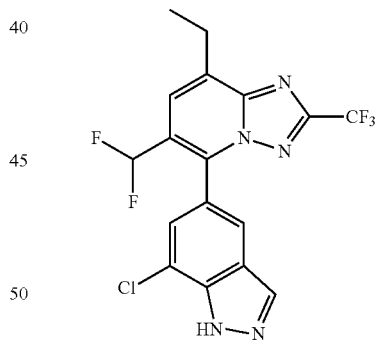

The title compound was prepared in a manner analogous to Example 1, using 5-chloro-6-(difluoromethyl)-8-ethyl-2-(trifluoromethyl)-[1,2,4]triazolo[1,5-a]pyridine (Intermediate 64) and 7-chloro-5-(4,4,5,5-tetramethyl-1,3,2-dioxaborolan-2-yl)-1H-indazole (Intermediate 1), employing conventional heating at 90° C. for 16 h. MS (ESI): mass calcd. for $C_{17}H_{11}ClF_5N_5$, 415.1; m/z found, 416.0 [M+H]$^+$. $^1$H NMR (600 MHz, DMSO-$d_6$) δ 13.98 (s, 1H), 8.39 (s, 1H), 8.02-7.96 (m, 2H), 7.75 (s, 1H), 6.84 (t, J=53.5 Hz, 1H), 3.16-3.05 (m, 2H), 1.40 (t, J=7.5 Hz, 3H).

Example 92: 6-(Difluoromethyl)-8-ethyl-5-(7-methyl-1H-indazol-5-yl)-2-(trifluoromethyl)-[1,2,4]triazolo[1,5-a]pyridine

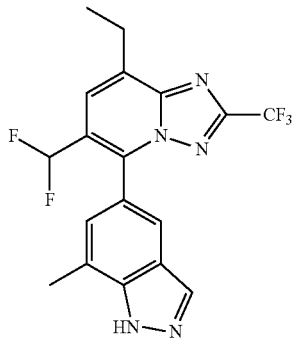 [SMILES: CCc1cc(C(F)F)c(-c2cc(C)c3[nH]ncc3c2)n2nc(C(F)(F)F)nc12]

The title compound was prepared in a manner analogous to Example 1, using 5-chloro-6-(difluoromethyl)-8-ethyl-2-(trifluoromethyl)-[1,2,4]triazolo[1,5-a]pyridine (Intermediate 64) and 7-methyl-5-(4,4,5,5-tetramethyl-1,3,2-dioxaborolan-2-yl)-1H-indazole (Intermediate 2), employing conventional heating at 90° C. for 16 h. MS (ESI): mass calcd. for $C_{18}H_{14}F_5N_5$, 395.1; m/z found, 396.0 [M+H]$^+$. $^1$H NMR (600 MHz, DMSO-d$_6$) δ 13.52 (s, 1H), 8.25 (s, 1H), 7.97 (s, 1H), 7.82 (s, 1H), 7.32 (s, 1H), 6.74 (t, J=53.7 Hz, 1H), 3.11 (q, J=7.5 Hz, 2H), 2.60 (s, 3H), 1.40 (t, J=7.5 Hz, 3H).

Example 93: 5-(7-Chloro-1H-indazol-5-yl)-2-cyclopropyl-6-(difluoromethyl)-8-ethyl-[1,2,4]triazolo[1,5-a]pyridine

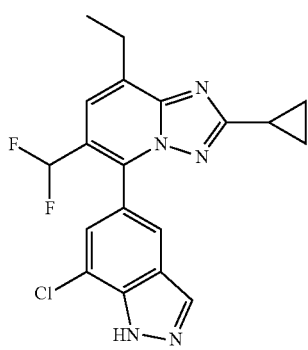 [SMILES: CCc1cc(C(F)F)c(-c2cc(Cl)c3[nH]ncc3c2)n2nc(C3CC3)nc12]

The title compound was prepared in a manner analogous to Example 1, using 5-chloro-2-cyclopropyl-6-(difluoromethyl)-8-ethyl-[1,2,4]triazolo[1,5-a]pyridine (Intermediate 71) and 7-chloro-5-(4,4,5,5-tetramethyl-1,3,2-dioxaborolan-2-yl)-1H-indazole (Intermediate 1). MS (ESI): mass calcd. for $C_{19}H_{16}ClF_2N_5$, 387.1; m/z found, 388.1 [M+H]$^+$. $^1$H NMR (600 MHz, DMSO-d$_6$) δ 13.94 (s, 1H), 8.37 (s, 1H), 7.92 (d, J=1.3 Hz, 1H), 7.71-7.67 (m, 2H), 6.73 (t, J=53.8 Hz, 1H), 2.99 (qd, J=7.6, 1.0 Hz, 2H), 2.12-2.07 (m, 1H), 1.35 (t, J=7.5 Hz, 3H), 1.02-0.97 (m, 2H), 0.95-0.91 (m, 2H).

Example 94: 2-Cyclopropyl-6-(difluoromethyl)-8-ethyl-5-(7-methyl-1H-indazol-5-yl)-[1,2,4]triazolo[1,5-a]pyridine

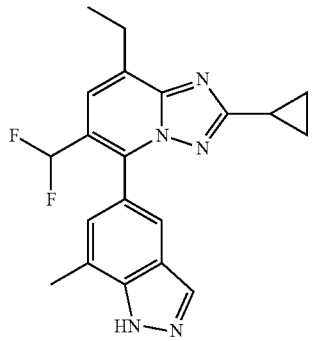 [SMILES: CCc1cc(C(F)F)c(-c2cc(C)c3[nH]ncc3c2)n2nc(C3CC3)nc12]

The title compound was prepared in a manner analogous to Example 1, using 5-chloro-2-cyclopropyl-6-(difluoromethyl)-8-ethyl-[1,2,4]triazolo[1,5-a]pyridine (Intermediate 71) and 7-methyl-5-(4,4,5,5-tetramethyl-1,3,2-dioxaborolan-2-yl)-1H-indazole (Intermediate 2). MS (ESI): mass calcd. for $C_{20}H_{19}F_2N_5$, 367.2; m/z found, 368.1 [M+H]$^+$. $^1$H NMR (600 MHz, DMSO-d$_6$) δ 13.47 (s, 1H), 8.22 (s, 1H), 7.75 (s, 1H), 7.68 (s, 1H), 7.27 (s, 1H), 6.64 (t, J=54.1 Hz, 1H), 2.98 (q, J=7.4 Hz, 2H), 2.59 (s, 3H), 2.11-2.05 (m, 1H), 1.34 (t, J=7.5 Hz, 3H), 1.02-0.97 (m, 2H), 0.95-0.89 (m, 2H).

Example 95: 6-(Difluoromethyl)-8-methyl-5-(7-methyl-1H-indazol-5-yl)-2-propyl-[1,2,4]triazolo[1,5-a]pyridine

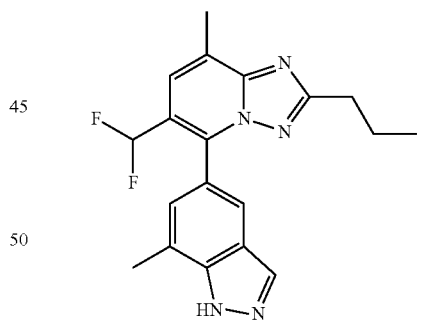

The title compound was prepared in a manner analogous to Example 1, using 5-chloro-6-(difluoromethyl)-8-methyl-2-propyl-[1,2,4]triazolo[1,5-a]pyridine (Intermediate 72) and 7-methyl-5-(4,4,5,5-tetramethyl-1,3,2-dioxaborolan-2-yl)-1H-indazole (Intermediate 2), employing conventional heating at 90° C. for 16 h. MS (ESI): mass calcd. for $C_{19}H_{19}F_2N_5$, 355.2; m/z found, 356.1 [M+H]$^+$. $^1$H NMR (500 MHz, DMSO-d$_6$) δ 13.48 (s, 1H), 8.22 (s, 1H), 7.75 (s, 2H), 7.26 (s, 1H), 6.64 (t, J=54.1 Hz, 1H), 2.71 (t, J=7.5 Hz, 2H), 2.62 (s, 3H), 2.59 (s, 3H), 1.70 (h, J=7.4 Hz, 2H), 0.90 (t, J=7.4 Hz, 3H).

Example 96: 8-Chloro-5-(7-chloro-1H-indazol-5-yl)-2-propyl-6-(trifluoromethyl)-[1,2,4]triazolo[1,5-a]pyridine

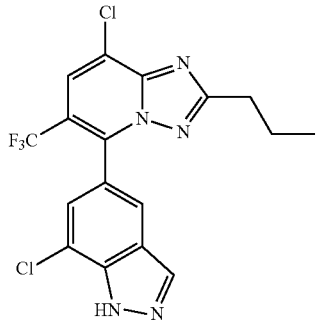 [SMILES: CCCc1nc2c(Cl)cc(C(F)(F)F)c(-c3cc(Cl)c4[nH]ncc4c3)n2n1]

The title compound was prepared in a manner analogous to Example 1, using 5,8-dichloro-2-propyl-6-(trifluoromethyl)-[1,2,4]triazolo[1,5-a]pyridine (Intermediate 73) and 7-chloro-5-(4,4,5,5-tetramethyl-1,3,2-dioxaborolan-2-yl)-1H-indazole (Intermediate 1); and substituting Pd(PPh$_3$)$_4$ for Pd(dppf)Cl$_2$—CH$_2$Cl$_2$, employing conventional heating at 90° C. for 16 h. MS (ESI): mass calcd. for C$_{17}$H$_{12}$Cl$_2$F$_3$N$_5$, 413.0; m/z found, 413.7 [M+H]$^+$. $^1$H NMR (500 MHz, MeOD) δ 8.28 (s, 1H), 8.16 (s, 1H), 7.94 (d, J=0.5 Hz, 1H), 7.59 (d, J=0.9 Hz, 1H), 2.83 (t, J=7.5 Hz, 2H), 1.87-1.76 (m, 2H), 0.97 (t, J=7.4 Hz, 3H).

Example 97: 7-Chloro-5-(8-chloro-2-propyl-6-(trifluoromethyl)-[1,2,4]triazolo[1,5-a]pyridin-5-yl)indolin-2-one

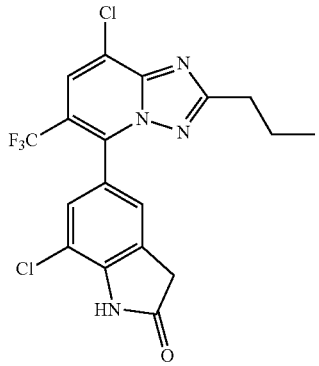 [SMILES: CCCc1nc2c(Cl)cc(C(F)(F)F)c(-c3cc(Cl)c4c(c3)CC(=O)N4)n2n1]

The title compound was prepared in a manner analogous to Example 1, using 5,8-dichloro-2-propyl-6-(trifluoromethyl)-[1,2,4]triazolo[1,5-a]pyridine (Intermediate 73) and 7-chloro-5-(4,4,5,5-tetramethyl-1,3,2-dioxaborolan-2-yl)-indolin-2-one (Intermediate 5), and substituting Pd(PPh$_3$)$_4$ for Pd(dppf)Cl$_2$—CH$_2$Cl$_2$. MS (ESI): mass calcd. for C$_{18}$H$_{13}$Cl$_2$F$_3$N$_4$O, 428.0; m/z found, 428.7 [M+H]$^+$. $^1$H NMR (500 MHz, MeOD) δ 8.11 (s, 1H), 7.43 (s, 1H), 7.34 (s, 1H), 3.73 (s, 2H), 2.82 (t, J=7.5 Hz, 2H), 1.86-1.75 (m, 2H), 0.97 (t, J=7.4 Hz, 3H).

Example 98: 5-(8-Chloro-2-propyl-6-(trifluoromethyl)-[1,2,4]triazolo[1,5-a]pyridin-5-yl)-7-methylindolin-2-one

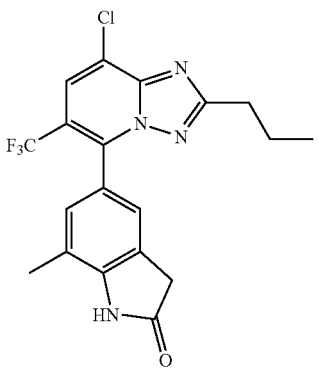 [SMILES: CCCc1nc2c(Cl)cc(C(F)(F)F)c(-c3cc(C)c4c(c3)CC(=O)N4)n2n1]

The title compound was prepared in a manner analogous to Example 1, using 5,8-dichloro-2-propyl-6-(trifluoromethyl)-[1,2,4]triazolo[1,5-a]pyridine (Intermediate 73) and 7-methyl-5-(4,4,5,5-tetramethyl-1,3,2-dioxaborolan-2-yl) indolin-2-one (Intermediate 3), and substituting Pd(PPh$_3$)$_4$ for Pd(dppf)Cl$_2$—CH$_2$Cl$_2$, employing conventional heating at 90° C. for 18 h. MS (ESI): mass calcd. for C$_{19}$H$_{16}$ClF$_3$N$_4$O, 408.1; m/z found, 409.1 [M+H]$^+$. $^1$H NMR (500 MHz, MeOD) δ 8.11 (s, 1H), 7.22 (s, 1H), 7.18 (s, 1H), 3.63 (s, 2H), 2.81 (t, J=7.6 Hz, 2H), 2.34 (s, 3H), 1.85-1.75 (m, 2H), 0.96 (t, J=7.4 Hz, 3H).

Example 99: 5-(2-Cyclopropyl-8-methyl-6-(trifluoromethyl)-[1,2,4]triazolo[1,5-a]pyridin-5-yl)-7-methylindolin-2-one

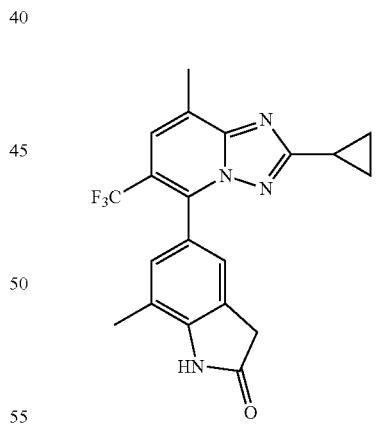

The title compound was prepared in a manner analogous to Example 1, using 5-chloro-2-cyclopropyl-8-methyl-6-(trifluoromethyl)-[1,2,4]triazolo[1,5-a]pyridine (Intermediate 74) and 7-methyl-5-(4,4,5,5-tetramethyl-1,3,2-dioxaborolan-2-yl)-indolin-2-one (Intermediate 3). MS (ESI): mass calcd. for C$_{20}$H$_{17}$F$_3$N$_4$O, 386.4; m/z found, 387.1 [M+H]$^+$. $^1$H NMR (400 MHz, DMSO-d$_6$) δ 10.68 (s, 1H), 7.78 (d, J=1.3 Hz, 1H), 7.12 (d, J=18.7 Hz, 2H), 3.59 (s, 2H), 2.56 (d, J=1.1 Hz, 3H), 2.26 (s, 3H), 2.13-2.05 (m, 1H), 1.03-0.98 (m, 2H), 0.97-0.91 (m, 2H).

Example 100: 7-Chloro-5-(2-ethyl-8-methyl-6-(trifluoromethyl)-[1,2,4]triazolo[1,5-a]pyridin-5-yl)indolin-2-one

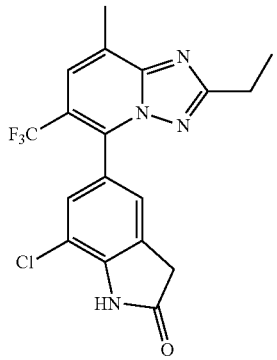 [SMILES: CCc1nc2c(C)cc(C(F)(F)F)c(-c3cc(Cl)c4c(c3)CC(=O)N4)n2n1]

The title compound was prepared in a manner analogous to Example 1, using 5-chloro-2-ethyl-8-methyl-6-(trifluoromethyl)-[1,2,4]triazolo[1,5-a]pyridine (Intermediate 50) and 7-chloro-5-(4,4,5,5-tetramethyl-1,3,2-dioxaborolan-2-yl)-indolin-2-one (Intermediate 5). MS (ESI): mass calcd. for $C_{18}H_{14}ClF_3N_4O$, 394.8; m/z found, 395.8 [M+H]$^+$. $^1$H NMR (500 MHz, DMSO-d$_6$) δ 11.05 (s, 1H), 7.82 (q, J=1.0 Hz, 1H), 7.45 (d, J=1.4 Hz, 1H), 7.31 (d, J=1.4 Hz, 1H), 3.71 (d, J=2.3 Hz, 2H), 2.78 (q, J=7.6 Hz, 2H), 2.62 (d, J=1.1 Hz, 3H), 1.25 (t, J=7.6 Hz, 3H).

Example 101: 2-Ethyl-8-methyl-6-(trifluoromethyl)-5-(7-(trifluoromethyl)-1H-indazol-5-yl)-[1,2,4]triazolo[1,5-a]pyridine

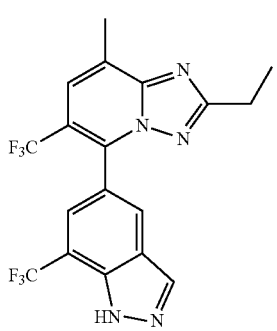 [SMILES: CCc1nc2c(C)cc(C(F)(F)F)c(-c3cc(C(F)(F)F)c4[nH]ncc4c3)n2n1]

The title compound was prepared in a manner analogous to Example 1, using 5-chloro-2-ethyl-8-methyl-6-(trifluoromethyl)-[1,2,4]triazolo[1,5-a]pyridine (Intermediate 50) and 5-(4,4,5,5-tetramethyl-1,3,2-dioxaborolan-2-yl)-7-(trifluoromethyl)-1H-indazole (Intermediate 4). MS (ESI): mass calcd. for $C_{18}H_{13}F_6N_5$, 413.3; m/z found, 414.0 [M+H]$^+$. $^1$H NMR (400 MHz, DMSO-d$_6$) δ 14.03 (s, 1H), 8.46 (s, 1H), 8.31 (s, 1H), 8.01-7.82 (m, 2H), 2.76 (q, J=7.6 Hz, 2H), 2.66 (d, J=1.1 Hz, 3H), 1.22 (t, J=7.6 Hz, 3H).

Example 102: 5-(2-Ethyl-8-methyl-6-(trifluoromethyl)-[1,2,4]triazolo[1,5-a]pyridin-5-yl)-7-(trifluoromethyl)indolin-2-one

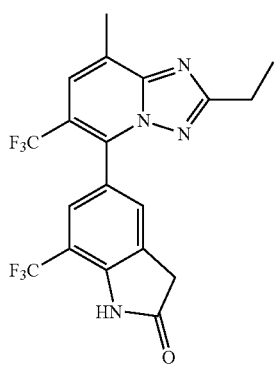 [SMILES: CCc1nc2c(C)cc(C(F)(F)F)c(-c3cc4c(c(C(F)(F)F)c3)NC(=O)C4)n2n1]

The title compound was prepared in a manner analogous to Example 1, using 5-chloro-2-ethyl-8-methyl-6-(trifluoromethyl)-[1,2,4]triazolo[1,5-a]pyridine (Intermediate 50) and 5-(4,4,5,5-tetramethyl-1,3,2-dioxaborolan-2-yl)-7-(trifluoromethyl)indolin-2-one (Intermediate 56). MS (ESI): mass calcd. for $C_{19}H_{14}F_6N_4O$, 428.34; m/z found, 429.0 [M+H]$^+$. $^1$H NMR (400 MHz, DMSO-d$_6$) δ 11.17 (s, 1H), 7.87-7.83 (m, 1H), 7.66 (q, J=7.2, 4.7 Hz, 2H), 3.76-3.68 (m, 2H), 2.83-2.73 (m, 2H), 2.63 (s, 3H), 1.30-1.22 (m, 3H).

Example 103: 7-Chloro-5-(2-ethyl-8-methyl-6-(trifluoromethyl)-[1,2,4]triazolo[1,5-a]pyridin-5-yl)indolin-2-one

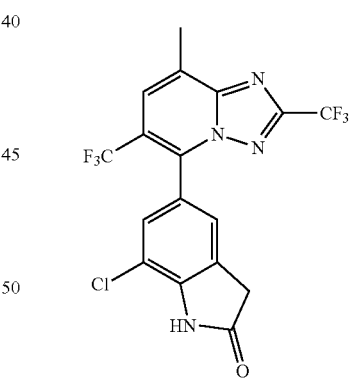

The title compound was prepared in a manner analogous to Example 1, using 5-chloro-8-methyl-2,6-bis(trifluoromethyl)-[1,2,4]triazolo[1,5-a]pyridine (Intermediate 76) and 7-chloro-5-(4,4,5,5-tetramethyl-1,3,2-dioxaborolan-2-yl)indolin-2-one (Intermediate 5). MS (ESI): mass calcd. for $C_{17}H_9ClF_6N_4O$, 434.7; m/z found, 435.0 [M+H]$^+$. $^1$H NMR (500 MHz, DMSO-d$_6$) δ 11.13 (s, 1H), 8.12 (d, J=1.3 Hz, 1H), 7.52 (d, J=1.5 Hz, 1H), 7.37 (d, J=1.5 Hz, 1H), 3.73 (d, J=5.0 Hz, 2H), 2.70 (d, J=1.1 Hz, 3H).

Example 104: 7-Ethyl-5-(8-methyl-2,6-bis(trifluoromethyl)-[1,2,4]triazolo[1,5-a]pyridin-5-yl)indolin-2-one

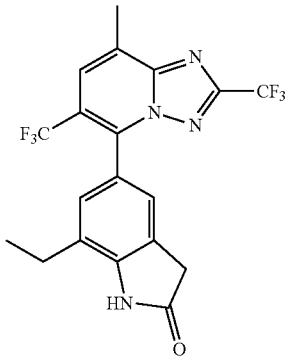 [SMILES: CCc1cc(-c2c(C(F)(F)F)cc(C)c3nc(C(F)(F)F)nn23)cc2c1NC(=O)C2]

The title compound was prepared in a manner analogous to Example 1, using 5-chloro-8-methyl-2,6-bis(trifluoromethyl)-[1,2,4]triazolo[1,5-a]pyridine (Intermediate 76) and 7-ethyl-5-(4,4,5,5-tetramethyl-1,3,2-dioxaborolan-2-yl)indolin-2-one (Intermediate 57). MS (ESI): mass calcd. for $C_{19}H_{14}F_6N_4O$, 428.3; m/z found, 429.0 [M+H]$^+$. $^1$H NMR (500 MHz, DMSO-d$_6$) δ 10.76 (s, 1H), 8.09 (d, J=1.2 Hz, 1H), 7.29-7.14 (m, 2H), 3.60 (d, J=5.5 Hz, 2H), 2.69 (d, J=1.1 Hz, 3H), 2.65-2.59 (m, 2H), 1.13 (t, J=7.5 Hz, 3H).

Example 105: 7-Methyl-5-(8-methyl-2,6-bis(trifluoromethyl)-[1,2,4]triazolo[1,5-a]pyridin-5-yl)indolin-2-one

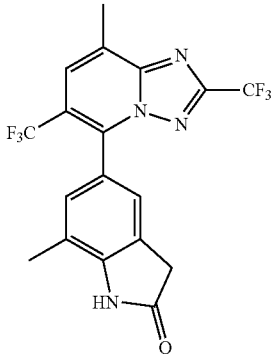 [SMILES: Cc1cc(-c2c(C(F)(F)F)cc(C)c3nc(C(F)(F)F)nn23)cc2c1NC(=O)C2]

The title compound was prepared in a manner analogous to Example 1, using 5-chloro-8-methyl-2,6-bis(trifluoromethyl)-[1,2,4]triazolo[1,5-a]pyridine (Intermediate 76) and 7-methyl-5-(4,4,5,5-tetramethyl-1,3,2-dioxaborolan-2-yl)indolin-2-one (Intermediate 3). MS (ESI): mass calcd. for $C_{18}H_{12}F_6N_4O$, 414.3; m/z found, 415.0 [M+H]$^+$. $^1$H NMR (500 MHz, DMSO-d$_6$) δ 10.74 (s, 1H), 8.09 (d, J=1.2 Hz, 1H), 7.24-7.12 (m, 2H), 3.68-3.53 (m, 2H), 2.69 (d, J=1.2 Hz, 3H), 2.26 (s, 3H).

Example 106: 7-Methoxy-5-(8-methyl-2,6-bis(trifluoromethyl)-[1,2,4]triazolo[1,5-a]pyridin-5-yl)indolin-2-one

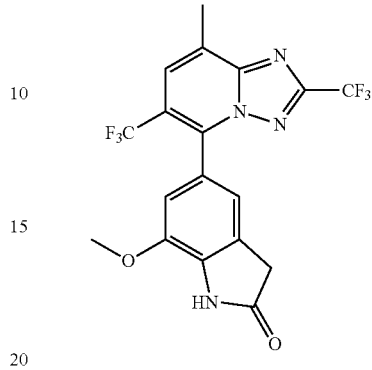

The title compound was prepared in a manner analogous to Example 1, using 5-chloro-8-methyl-2,6-bis(trifluoromethyl)-[1,2,4]triazolo[1,5-a]pyridine (Intermediate 76) and 7-methoxy-5-(4,4,5,5-tetramethyl-1,3,2-dioxaborolan-2-yl)indolin-2-one (Intermediate 6). MS (ESI): mass calcd. for $C_{18}H_{12}F_6N_4O_2$, 430.3; m/z found, 431.1 [M+H]$^+$. $^1$H NMR (500 MHz, DMSO-d$_6$) δ 10.74 (s, 1H), 8.11 (q, J=1.0 Hz, 1H), 7.15 (d, J=1.4 Hz, 1H), 7.04 (d, J=1.4 Hz, 1H), 3.77 (s, 3H), 3.61 (d, J=4.6 Hz, 2H), 2.70 (d, J=1.1 Hz, 3H).

Example 107: 8-Methyl-5-(7-methyl-1H-indazol-5-yl)-2,6-bis(trifluoromethyl)-[1,2,4]triazolo[1,5-a]pyridine

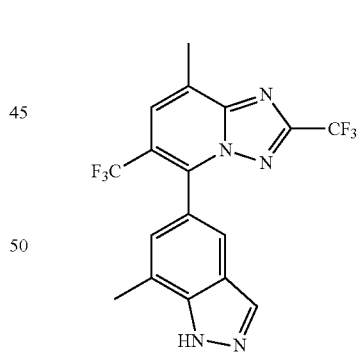

The title compound was prepared in a manner analogous to Example 1, using 5-chloro-8-methyl-2,6-bis(trifluoromethyl)-[1,2,4]triazolo[1,5-a]pyridine (Intermediate 76) and 7-methyl-5-(4,4,5,5-tetramethyl-1,3,2-dioxaborolan-2-yl)-1H-indazole (Intermediate 2). MS (ESI): mass calcd. for $C_{17}H_{11}F_6N_5$, 399.3; m/z found, 400.0 [M+H]$^+$. $^1$H NMR (500 MHz, DMSO-d$_6$) δ 13.50 (s, 1H), 8.22 (s, 1H), 8.13 (d, J=1.4 Hz, 1H), 7.87-7.72 (m, 1H), 7.27 (t, J=1.2 Hz, 1H), 2.71 (d, J=1.2 Hz, 3H), 2.58 (s, 3H).

Example 108: 5-(8-Methyl-2,6-bis(trifluoromethyl)-[1,2,4]triazolo[1,5-a]pyridin-5-yl)-2-oxoindoline-7-carbonitrile

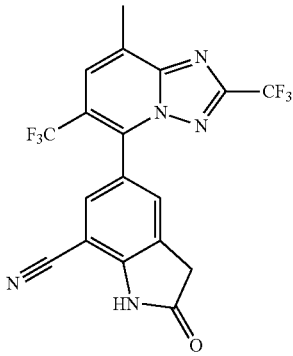 [SMILES: Cc1cc(C(F)(F)F)c(-c2cc(C#N)c3c(c2)CC(=O)N3)n2nc(C(F)(F)F)nc12]

The title compound was prepared in a manner analogous to Example 1, using 5-chloro-8-methyl-2,6-bis(trifluoromethyl)-[1,2,4]triazolo[1,5-a]pyridine (Intermediate 76) and 2-oxo-5-(4,4,5,5-tetramethyl-1,3,2-dioxaborolan-2-yl)indoline-7-carbonitrile (Intermediate 58). MS (ESI): mass calcd. for $C_{18}H_9F_6N_5O$, 425.3; m/z found, 426.0 [M+H]$^+$. $^1$H NMR (400 MHz, DMSO-d$_6$) δ 11.70 (s, 1H), 8.14 (d, J=1.6 Hz, 1H), 7.80 (d, J=1.5 Hz, 1H), 7.68 (d, J=1.4 Hz, 1H), 3.71 (d, J=3.7 Hz, 2H), 2.72 (s, 3H).

Example 109: 5-(7-Chloro-1H-indazol-5-yl)-6-(difluoromethyl)-8-methyl-2-(trifluoromethyl)-[1,2,4]triazolo[1,5-a]pyridine

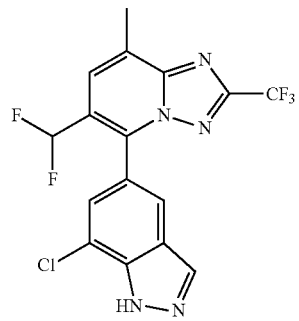 [SMILES: Cc1cc(C(F)F)c(-c2cc(Cl)c3[nH]ncc3c2)n2nc(C(F)(F)F)nc12]

The title compound was prepared in a manner analogous to Example 1, using 5-chloro-6-(difluoromethyl)-8-methyl-2-(trifluoromethyl)-[1,2,4]triazolo[1,5-a]pyridine (Intermediate 75) and 7-chloro-5-(4,4,5,5-tetramethyl-1,3,2-dioxaborolan-2-yl)-1H-indazole (Intermediate 1). MS (ESI): mass calcd. for $C_{16}H_9ClF_5N_5$, 401.7; m/z found, 401.7 [M+H]$^+$. $^1$H NMR (500 MHz, DMSO-d$_6$) δ 13.98 (s, 1H), 8.40 (s, 1H), 8.02 (d, J=1.4 Hz, 1H), 7.98 (d, J=1.3 Hz, 1H), 7.72 (d, J=1.3 Hz, 1H), 6.82 (t, J=53.5 Hz, 1H), 2.71 (d, J=1.2 Hz, 3H).

Example 110: 7-Chloro-5-(6-(difluoromethyl)-8-methyl-2-(trifluoromethyl)-[1,2,4]triazolo[1,5-a]pyridin-5-yl)indolin-2-one

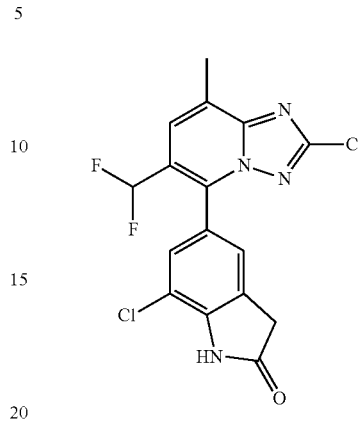

The title compound was prepared in a manner analogous to Example 1, using 5-chloro-6-(difluoromethyl)-8-methyl-2-(trifluoromethyl)-[1,2,4]triazolo[1,5-a]pyridine (Intermediate 75) and 7-chloro-5-(4,4,5,5-tetramethyl-1,3,2-dioxaborolan-2-yl)indolin-2-one (Intermediate 5). MS (ESI): mass calcd. for $C_{17}H_{10}ClF_5N_4O$, 416.7 m/z found, 416.7 [M+H]$^+$. $^1$H NMR (500 MHz, DMSO-d$_6$) δ 11.14 (s, 1H), 7.99 (d, J=1.3 Hz, 1H), 7.53 (dt, J=1.5, 0.8 Hz, 1H), 7.38 (q, J=1.3 Hz, 1H), 6.81 (t, J=53.6 Hz, 1H), 3.73 (s, 2H), 2.69 (d, J=1.2 Hz, 3H).

Example 111: 6-(Difluoromethyl)-8-methyl-5-(7-methyl-1H-indazol-5-yl)-2-(trifluoromethyl)-[1,2,4]triazolo[1,5-a]pyridine

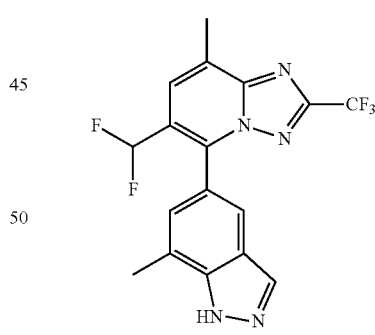

The title compound was prepared in a manner analogous to Example 1, using 5-chloro-6-(difluoromethyl)-8-methyl-2-(trifluoromethyl)-[1,2,4]triazolo[1,5-a]pyridine (Intermediate 75) and 7-methyl-5-(4,4,5,5-tetramethyl-1,3,2-dioxaborolan-2-yl)-1H-indazole (Intermediate 2). MS (ESI): mass calcd. for $C_{17}H_{12}F_5N_5$, 381.3 m/z found, 381.8 [M+H]$^+$. $^1$H NMR (500 MHz, DMSO-d$_6$) δ 13.51 (s, 1H), 8.24 (s, 1H), 8.01 (d, J=1.4 Hz, 1H), 7.81 (d, J=1.4 Hz, 1H), 7.30 (s, 1H), 6.72 (t, J=53.7 Hz, 1H), 2.70 (s, 3H), 2.60 (s, 3H).

Example 112: 5-(7-Chloro-1H-indazol-5-yl)-2-cyclopropyl-6-(difluoromethyl)-8-methyl-[1,2,4]triazolo[1,5-a]pyridine

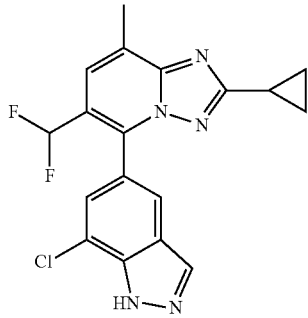 [SMILES: Cc1cc(C(F)F)c(-c2cc(Cl)c3[nH]ncc3c2)n2nc(C3CC3)nc12]

The title compound was prepared in a manner analogous to Example 1, using 5-chloro-2-cyclopropyl-6-(difluoromethyl)-8-methyl-[1,2,4]triazolo[1,5-a]pyridine (Intermediate 77) and 7-chloro-5-(4,4,5,5-tetramethyl-1,3,2-dioxaborolan-2-yl)-1H-indazole (Intermediate 1). MS (ESI): mass calcd. for $C_{18}H_{14}ClF_2N_5$, 373.8 m/z found, 373.8 [M+H]$^+$. $^1$H NMR (500 MHz, DMSO-d$_6$) δ 13.93 (s, 1H), 8.37 (s, 1H), 7.91 (d, J=1.3 Hz, 1H), 7.70 (dd, J=29.7, 1.3 Hz, 2H), 6.72 (t, J=53.9 Hz, 1H), 2.58 (d, J=1.1 Hz, 3H), 2.09 (tt, J=8.2, 4.9 Hz, 1H), 1.01-0.97 (m, 2H), 0.96-0.92 (m, 2H).

Example 113: 7-Chloro-5-(2-cyclopropyl-6-(difluoromethyl)-8-methyl-[1,2,4]triazolo[1,5-a]pyridin-5-yl)indolin-2-one

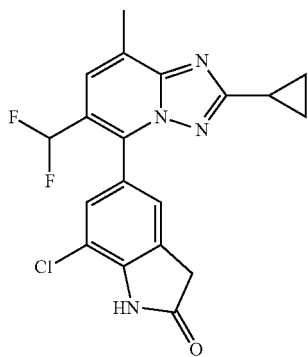 [SMILES: Cc1cc(C(F)F)c(-c2cc(Cl)c3c(c2)CC(=O)N3)n2nc(C3CC3)nc12]

The title compound was prepared in a manner analogous to Example 1, using 5-chloro-2-cyclopropyl-6-(difluoromethyl)-8-methyl-[1,2,4]triazolo[1,5-a]pyridine (Intermediate 77) and 7-chloro-5-(4,4,5,5-tetramethyl-1,3,2-dioxaborolan-2-yl)indolin-2-one (Intermediate 5). MS (ESI): mass calcd. for $C_{19}H_{15}ClF_2N_4O$, 388.8 m/z found, 388.8 [M+H]$^+$. $^1$H NMR (400 MHz, DMSO-d$_6$) δ 11.13 (s, 1H), 7.71 (dd, J=2.6, 1.3 Hz, 1H), 7.48 (dd, J=2.5, 1.3 Hz, 1H), 7.34 (dd, J=2.7, 1.4 Hz, 1H), 6.88-6.58 (m, 1H), 3.74 (s, 2H), 2.57 (d, J=1.6 Hz, 3H), 2.16-2.08 (m, 1H), 1.05-0.99 (m, 2H), 0.99-0.93 (m, 2H).

Example 114: 2-Cyclopropyl-6-(difluoromethyl)-8-methyl-5-(7-methyl-1H-indazol-5-yl)-[1,2,4]triazolo[1,5-a]pyridine

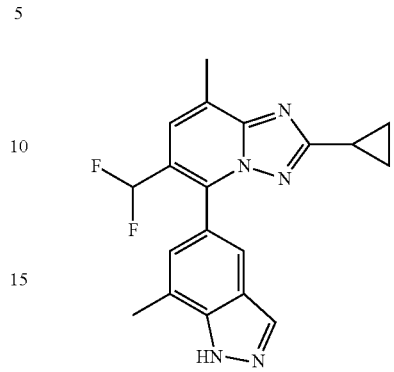

The title compound was prepared in a manner analogous to Example 1, using 5-chloro-2-cyclopropyl-6-(difluoromethyl)-8-methyl-[1,2,4]triazolo[1,5-a]pyridine (Intermediate 77) and 7-methyl-5-(4,4,5,5-tetramethyl-1,3,2-dioxaborolan-2-yl)-1H-indazole (Intermediate 2). MS (ESI): mass calcd. for $C_{19}H_{17}F_2N_5$, 353.4 m/z found, 353.9 [M+H]$^+$. $^1$H NMR (400 MHz, DMSO-d$_6$) δ 13.50 (s, 1H), 8.34-8.13 (m, 1H), 7.84-7.64 (m, 2H), 7.35-7.21 (m, 1H), 6.64 (t, J=54.2 Hz, 1H), 2.61 (d, J=0.8 Hz, 3H), 2.59 (d, J=1.4 Hz, 3H), 2.08 (ddd, J=12.8, 7.4, 4.0 Hz, 1H), 1.04-0.98 (m, 2H), 0.95 (dt, J=4.7, 2.4 Hz, 2H).

Example 115: 5-(7-Chloro-1H-indazol-5-yl)-6-(difluoromethyl)-2-ethyl-8-methyl-[1,2,4]triazolo[1,5-a]pyridine

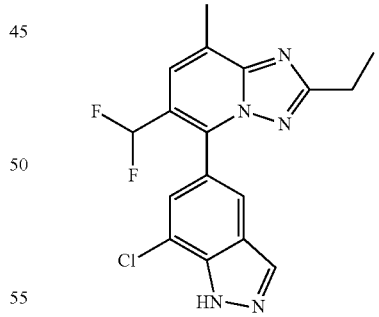

The title compound was prepared in a manner analogous to Example 1, using 5-chloro-6-(difluoromethyl)-2-ethyl-8-methyl-[1,2,4]triazolo[1,5-a]pyridine (Intermediate 78) and 7-chloro-5-(4,4,5,5-tetramethyl-1,3,2-dioxaborolan-2-yl)-1H-indazole (Intermediate 1). MS (ESI): mass calcd. for $C_{17}H_{14}ClF_2N_5$, 361.8 m/z found, 363.0 [M+H]$^+$. $^1$H NMR (400 MHz, DMSO-d$_6$) δ 13.94 (s, 1H), 8.37 (s, 1H), 7.91 (d, J=1.3 Hz, 1H), 7.85-7.62 (m, 2H), 6.73 (t, J=53.8 Hz, 1H), 2.77 (q, J=7.6 Hz, 2H), 2.63 (d, J=1.2 Hz, 3H), 1.24 (t, J=7.6 Hz, 3H).

Example 116: 5-(7-Chloro-1H-indazol-5-yl)-2,8-dimethyl-6-(trifluoromethyl)-[1,2,4]triazolo[1,5-a]pyridine

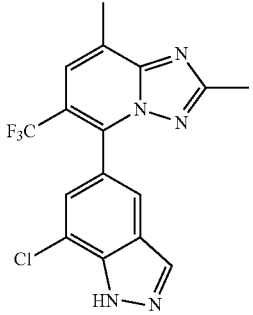 [SMILES: Cc1nc2c(C)cc(C(F)(F)F)c(-c3cc(Cl)c4[nH]ncc4c3)n2n1]

The title compound was prepared in a manner analogous to Example 1, using 5-chloro-2,8-dimethyl-6-(trifluoromethyl)-[1,2,4]triazolo[1,5-a]pyridine (Intermediate 79) and 7-chloro-5-(4,4,5,5-tetramethyl-1,3,2-dioxaborolan-2-yl)-1H-indazole (Intermediate 1). MS (ESI): mass calcd. for $C_{16}H_{11}ClF_3N_5$, 365.7 m/z found, 366.7 [M+H]$^+$. $^1$H NMR (400 MHz, DMSO-d$_6$) δ 13.95 (s, 1H), 8.36 (s, 1H), 7.94 (s, 1H), 7.88 (s, 1H), 7.67 (t, J=2.5 Hz, 1H), 2.65 (s, 3H), 2.42 (s, 3H).

Example 117: 5-(7-Chloro-1H-indazol-5-yl)-2-ethoxy-8-methyl-6-(trifluoromethyl)-[1,2,4]triazolo[1,5-a]pyridine

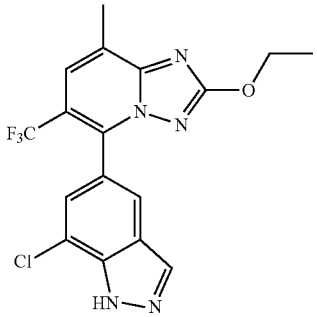 [SMILES: CCOc1nc2c(C)cc(C(F)(F)F)c(-c3cc(Cl)c4[nH]ncc4c3)n2n1]

The title compound was prepared in a manner analogous to Example 1, using 5-chloro-2,8-dimethyl-6-(trifluoromethyl)-[1,2,4]triazolo[1,5-a]pyridine (Intermediate 80) and 7-chloro-5-(4,4,5,5-tetramethyl-1,3,2-dioxaborolan-2-yl)-1H-indazole (Intermediate 1). MS (ESI): mass calcd. for $C_{17}H_{13}ClF_3N_5O$, 395.7 m/z found, 396.7 [M+H]$^+$. $^1$H NMR (400 MHz, DMSO-d$_6$) δ 13.95 (s, 1H), 8.36 (s, 1H), 7.96-7.89 (m, 2H), 7.66 (d, J=1.4 Hz, 1H), 4.41-4.26 (m, 2H), 2.60 (d, J=1.3 Hz, 3H), 1.30 (t, J=6.9 Hz, 3H).

Example 118: 7-Chloro-5-(2-cyclopropyl-6-(trifluoromethyl)pyrazolo[1,5-a]pyridin-7-yl)-1H-indazole

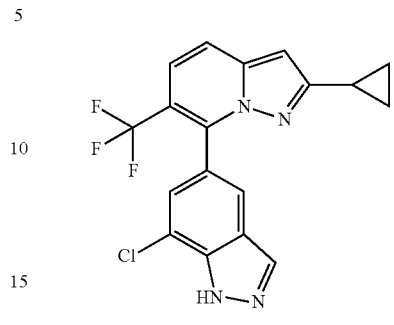

The title compound was prepared in a manner analogous to Example 65, using 7-bromo-2-cyclopropyl-6-(trifluoromethyl)pyrazolo[1,5-a]pyridine (Intermediate 43) and 7-chloro-5-(4,4,5,5-tetramethyl-1,3,2-dioxaborolan-2-yl)-1H-indazole (Intermediate 1). $^1$H NMR (300 MHz, DMSO-d$_6$) δ 13.90 (br s, 1H), 8.33 (s, 1H), 7.92-7.83 (m, 1H), 7.78 (d, J=9.3 Hz, 1H), 7.63-7.56 (m, 1H), 7.49 (d, J=9.4 Hz, 1H), 6.48 (s, 1H), 2.01-1.90 (m, 1H), 1.00-0.88 (m, 2H), 0.73-0.64 (m, 2H).

Example 119: 5-[6-(Difluoromethyl)-2-(trifluoromethyl)pyrazolo[1,5-a]pyridin-7-yl]-7-methyl-indolin-2-one

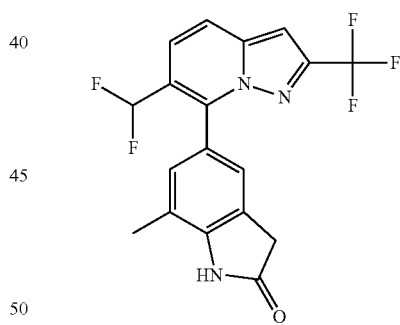

The title compound was prepared in a manner analogous to Example 65, using 7-chloro-6-(difluoromethyl)-2-(trifluoromethyl)pyrazolo[1,5-a]pyridine (Intermediate 62) and 7-methyl-5-(4,4,5,5-tetramethyl-1,3,2-dioxaborolan-2-yl)indolin-2-one (Intermediate 3). $^1$H NMR (500 MHz, DMSO-d$_6$) δ 10.73 (s, 1H), 8.01 (d, J=9.3 Hz, 1H), 7.67 (d, J=9.3 Hz, 1H), 7.30 (s, 1H), 7.25-7.19 (m, 1H), 7.19-7.13 (m, 1H), 6.63 (t, J=54.0 Hz, 1H), 3.68-3.59 (m, 1H), 3.56 (d, J=23.9 Hz, 1H), 2.28 (s, 3H).

Example 120: 7-(7-Chloro-1H-indazol-5-yl)-6-(difluoromethyl)-2-(trifluoromethyl)pyrazolo[1,5-a]pyridine

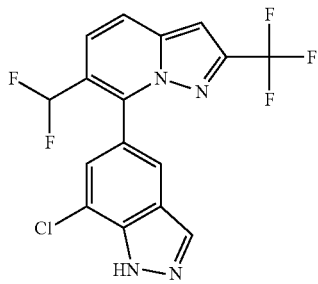 [SMILES: FC(F)c1ccc2cc(C(F)(F)F)nn2c1-c1cc(Cl)c2[nH]ncc2c1]

The title compound was prepared in a manner analogous to Example 65, using 7-chloro-6-(difluoromethyl)-2-(trifluoromethyl)pyrazolo[1,5-a]pyridine (Intermediate 62) and 7-chloro-5-(4,4,5,5-tetramethyl-1,3,2-dioxaborolan-2-yl)-1H-indazole (Intermediate 1). $^1$H NMR (500 MHz, DMSO-d$_6$) δ 13.96 (s, 1H), 8.39-8.34 (m, 1H), 8.07 (d, J=9.3 Hz, 1H), 7.98-7.92 (m, 1H), 7.72 (d, J=9.4 Hz, 1H), 7.72-7.69 (m, 1H), 7.34 (s, 1H), 6.71 (t, J=53.7 Hz, 1H).

Example 121: 6-(Difluoromethyl)-7-(7-methyl-1H-indazol-5-yl)-2-(trifluoromethyl)pyrazolo[1,5-a]pyridine

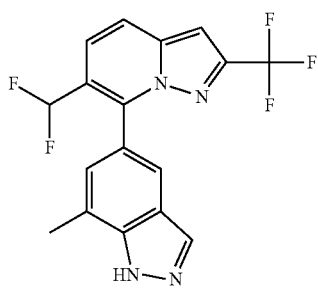 [SMILES: Cc1cc(-c2c(C(F)F)ccc3cc(C(F)(F)F)nn23)cc2cn[nH]c12]

The title compound was prepared in a manner analogous to Example 65, using 7-chloro-6-(difluoromethyl)-2-(trifluoromethyl)pyrazolo[1,5-a]pyridine (Intermediate 62) and 7-methyl-5-(4,4,5,5-tetramethyl-1,3,2-dioxaborolan-2-yl)-1H-indazole (Intermediate 2). $^1$H NMR (300 MHz, DMSO-d$_6$) δ 13.49 (s, 1H), 8.22 (s, 1H), 8.05 (d, J=9.3 Hz, 1H), 7.82-7.75 (m, 1H), 7.71 (d, J=9.4 Hz, 1H), 7.33 (s, 1H), 7.30-7.23 (m, 1H), 6.61 (t, J=54.0 Hz, 1H), 2.60 (s, 3H).

Example 122: 5-[6-(Difluoromethyl)-4-methyl-2-(trifluoromethyl)pyrazolo[1,5-a]pyridin-7-yl]-7-methyl-indolin-2-one

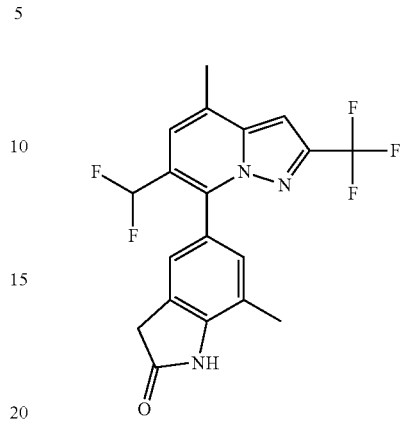

The title compound was prepared in a manner analogous to Example 65, using 7-chloro-6-(difluoromethyl)-4-methyl-2-(trifluoromethyl)pyrazolo[1,5-a]pyridine (Intermediate 63) and 7-methyl-5-(4,4,5,5-tetramethyl-1,3,2-dioxaborolan-2-yl)indolin-2-one (Intermediate 3). $^1$H NMR (500 MHz, DMSO-d$_6$) δ 10.74 (s, 1H), 7.48 (s, 1H), 7.38 (s, 1H), 7.20-7.16 (m, 1H), 7.14-7.11 (m, 1H), 6.60 (t, J=54.1 Hz, 1H), 3.61 (d, J=21.8 Hz, 1H), 3.58 (d, J=20.8 Hz, 1H), 2.59 (s, 3H), 2.27 (s, 3H).

Example 123: 6-(Difluoromethyl)-4-methyl-7-(7-methyl-1H-indazol-5-yl)-2-(trifluoromethyl)pyrazolo[1,5-a]pyridine

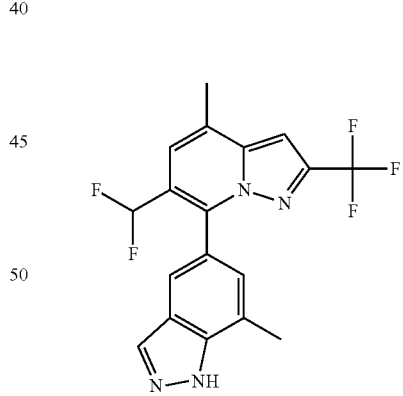

The title compound was prepared in a manner analogous to Example 65, using 7-chloro-6-(difluoromethyl)-4-methyl-2-(trifluoromethyl)pyrazolo[1,5-a]pyridine (Intermediate 63) and 7-methyl-5-(4,4,5,5-tetramethyl-1,3,2-dioxaborolan-2-yl)-1H-indazole (Intermediate 2). $^1$H NMR (300 MHz, DMSO-d$_6$) δ 13.48 (s, 1H), 8.22 (s, 1H), 7.78-7.71 (m, 1H), 7.52 (s, 1H), 7.40 (s, 1H), 7.28-7.20 (m, 1H), 6.59 (t, J=54.1 Hz, 1H), 2.62 (s, 3H), 2.59 (s, 3H).

Example 124: 7-Chloro-5-[6-(difluoromethyl)-4-methyl-2-(trifluoromethyl)pyrazolo[1,5-a]pyridin-7-yl]indolin-2-one

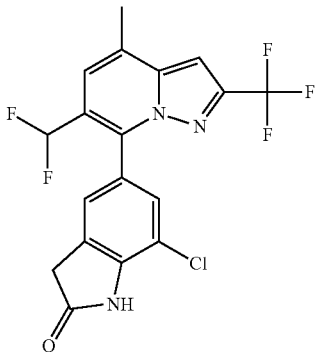

The title compound was prepared in a manner analogous to Example 65, using 7-chloro-6-(difluoromethyl)-4-methyl-2-(trifluoromethyl)pyrazolo[1,5-a]pyridine (Intermediate 63) and 7-chloro-5-(4,4,5,5-tetramethyl-1,3,2-dioxaborolan-2-yl)indolin-2-one (Intermediate 5). $^1$H NMR (500 MHz, DMSO-$d_6$) δ 11.11 (s, 1H), 7.50 (s, 1H), 7.48-7.43 (m, 1H), 7.40 (s, 1H), 7.34-7.29 (m, 1H), 6.68 (t, J=53.8 Hz, 1H), 3.83-3.60 (m, 2H), 2.60 (s, 3H).

Example 125: 7-(7-Chloro-1H-indazol-5-yl)-6-(difluoromethyl)-4-methyl-2-(trifluoromethyl)pyrazolo[1,5-a]pyridine

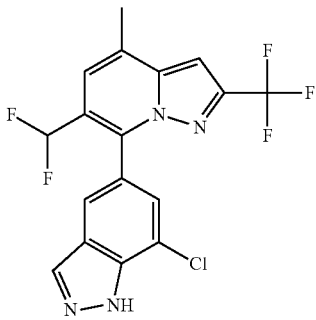 [SMILES: Cc1cc(-c2c(C(F)F)cc(C)c3cc(C(F)(F)F)nn23)cc2cn[nH]c12]

The title compound was prepared in a manner analogous to Example 65, using 7-chloro-6-(difluoromethyl)-4-methyl-2-(trifluoromethyl)pyrazolo[1,5-a]pyridine (Intermediate 63) and 7-chloro-5-(4,4,5,5-tetramethyl-1,3,2-dioxaborolan-2-yl)-1H-indazole (Intermediate 1). $^1$H NMR (500 MHz, DMSO-$d_6$) δ 13.94 (s, 1H), 8.36 (s, 1H), 7.96-7.87 (m, 1H), 7.70-7.62 (m, 1H), 7.54 (s, 1H), 7.42 (s, 1H), 6.69 (t, J=53.7 Hz, 1H), 2.62 (s, 3H).

Biological Assays

Calcium Flux Assay

This assay was used to test compounds for their ability to inhibit TARP γ8 dependent AMPA receptor activity. The AMPA receptor is a non-selective cation channel activated by glutamate. Ionotropic glutamate receptors normally desensitize too rapidly to allow detectable calcium influx in a FLIPR assay (Strange et al. (2006). "Functional characterisation of homomeric ionotropic glutamate receptors GluR1-GluR6 in a fluorescence-based high throughput screening assay." *Comb Chem High Throughput Screen* 9(2): 147-158). But, this desensitization is incomplete, and a substantial steady-state current remains in the sustained presence of glutamate (Cho et al. (2007). "Two families of TARP isoforms that have distinct effects on the kinetic properties of AMPA receptors and synaptic currents." *Neuron* 55(6): 890-904).

An in vitro assay was used to determine the potency of test compounds as inhibitors of the glutamate response of the channel formed by GluA1o-γ8. To ensure a 1:1 stoichiometry of GluA1o and γ8 subunits in the expressed channel, a fusion of the cDNAs for GRIA1o and CACNG8 was used. Following Shi et al (2009) "The stoichiometry of AMPA receptors and TARPs varies by neuronal cell type." *Neuron* 62(5): 633-640), the C-terminus of the cDNA for GRIA1o was fused to the N-terminus of the cDNA for γ8. The linker sequence was QQQQQQQQQQEFAT. Channels expressed with this construct appear to have similar properties to channels formed by co-expression of GRIA1o with an excess of CACNG8 (Shi et al. 2009). A clonal cell line in HEK293 cells stably expressing this construct, with a geneticin selection marker, was generated for use in this assay.

Cell expressing the GRIA1o-CACNG8 fusion construct were grown in a monolayer in 96- or 384-well microtiter plates. They were washed with assay buffer (135 mM NaCl, 4 mM KCl, 3 mM $CaCl_2$, 1 mM $MgCl_2$, 5 mM glucose, 10 mM HEPES, pH 7.4, 300 mOs) using a Biotek EL405 plate washer. The cells were then loaded with a calcium-sensitive dye (Calcium-5 or Calcium-6, Molecular Devices) and the test compounds at a range of concentrations. Calcium flux following the addition of 15 μM glutamate was monitored using a Molecular Devices FLIPR Tetra.

The fluorescence in each well was normalized to the fluorescence of negative and positive control wells. The negative control wells had no added compounds, and the positive control wells had been incubated with 10 μM CP465022 (a non-subtype-selective AMPA receptor antagonist) (Lazzaro et al. (2002). "Functional characterization of CP-465,022, a selective, noncompetitive AMPA receptor antagonist." *Neuropharmacology* 42(2): 143-153). The responses to glutamate as functions of the test compound concentrations were fitted to a four-parameter logistic function. The fitted parameter corresponding to the midpoint was taken to be the potency of inhibition of the compound. The data in Table 4 below illustrates the observed potency for the compounds described herein. $pIC_{50}$ refers to the negative log of the $IC_{50}$ in molar.

Using a similar protocol, compounds were also tested for their ability to inhibit TARP γ2 dependent AMPA receptor activity. The compounds that were tested for TARP γ2 AMPA receptor activity had $pIC_{50}$ values less than 6.

TABLE 4

| Ex # | Compound Name | $pIC_{50}$ |
|---|---|---|
| 1 | 5-(7-Chloro-1H-indazol-5-yl)-2,6-bis(trifluoromethyl)-[1,2,4]triazolo[1,5-a]pyridine; | 10.1 |
| 2 | 5-(7-Methyl-1H-indazol-5-yl)-2,6-bis(trifluoromethyl)-[1,2,4]triazolo[1,5-a]pyridine; | 9.7 |
| 3 | 5-(2,6-Bis(trifluoromethyl)-[1,2,4]triazolo[1,5-a]pyridin-5-yl)-7-chloroindolin-2-one; | 9.6 |
| 4 | 5-(2,6-Bis(trifluoromethyl)-[1,2,4]triazolo[1,5-a]pyridin-5-yl)-7-methylindolin-2-one; | 9.3 |
| 5 | 8-Chloro-5-(7-chloro-1H-indazol-5-yl)-2,6-bis(trifluoromethyl)-[1,2,4]triazolo[1,5-a]pyridine; | 9.5 |
| 6 | 5-(7-Chloro-1H-indazol-5-yl)-8-methyl-2,6-bis(trifluoromethyl)-[1,2,4]triazolo[1,5-a]pyridine; | 9.7 |

TABLE 4-continued

| Ex # | Compound Name | pIC$_{50}$ |
|---|---|---|
| 7 | 5-(7-Chloro-1H-indazol-5-yl)-2-(difluoromethyl)-6-(trifluoromethyl)-[1,2,4]triazolo[1,5-a]pyridine; | 10.2 |
| 8 | 5-(7-Methyl-1H-indazol-5-yl)-2-(difluoromethyl)-6-(trifluoromethyl)-[1,2,4]triazolo[1,5-a]pyridine; | 9.4 |
| 9 | 7-Chloro-5-(2-(difluoromethyl)-6-(trifluoromethyl)-[1,2,4]triazolo[1,5-a]pyridin-5-yl)indolin-2-one; | 9.4 |
| 10 | 7-Methyl-5-(2-(difluoromethyl)-6-(trifluoromethyl)-[1,2,4]triazolo[1,5-a]pyridin-5-yl)indolin-2-one; | 9.1 |
| 11 | 2-(Difluoromethyl)-6-(trifluoromethyl)-5-(7-(trifluoromethyl)-1H-indazol-5-yl)-[1,2,4]triazolo[1,5-a]pyridine; | 9.8 |
| 12 | 5-(2-(Difluoromethyl)-6-(trifluoromethyl)-[1,2,4]triazolo[1,5-a]pyridin-5-yl)-7-methoxyindolin-2-one; | 8.3 |
| 13 | 5-(7-Chloro-1H-indazol-5-yl)-2-(difluoromethyl)-6-methoxy-[1,2,4]triazolo[1,5-a]pyridine; | 8.3 |
| 14 | 2-(Difluoromethyl)-6-methoxy-5-(7-methyl-1H-indazol-5-yl)-[1,2,4]triazolo[1,5-a]pyridine; | 8.3 |
| 15 | 2-(Difluoromethyl)-6-methoxy-5-(7-(trifluoromethyl)-1H-indazol-5-yl)-[1,2,4]triazolo[1,5-a]pyridine; | 8.7 |
| 16 | 5-(7-Chloro-1H-indazol-5-yl)-6-(difluoromethyl)-2-(trifluoromethyl)-[1,2,4]triazolo[1,5-a]pyridine; | 10.0 |
| 17 | 6-(Difluoromethyl)-5-(7-methyl-1H-indazol-5-yl)-2-(trifluoromethyl)-[1,2,4]triazolo[1,5-a]pyridine; | 9.8 |
| 18 | 7-Chloro-5-(6-(difluoromethyl)-2-(trifluoromethyl)-[1,2,4]triazolo[1,5-a]pyridin-5-yl)indolin-2-one; | 9.6 |
| 19 | 5-[6-(Difluoromethyl)-2-(trifluoromethyl)-[1,2,4]triazolo[1,5-a]pyridin-5-yl]-7-methyl-indolin-2-one; | 9.2 |
| 20 | 5-[6-(Difluoromethyl)-2-(trifluoromethyl)-[1,2,4]triazolo[1,5-a]pyridin-5-yl]-7-methoxy-indolin-2-one; | 8.6 |
| 21 | 5-(7-Chloro-1H-indazol-5-yl)-2-methyl-6-(trifluoromethyl)-[1,2,4]triazolo[1,5-a]pyridine; | 9.2 |
| 22 | 2-Methyl-5-(7-methyl-1H-indazol-5-yl)-6-(trifluoromethyl)-[1,2,4]triazolo[1,5-a]pyridine; | 7.9 |
| 23 | 7-Chloro-5-(2-methyl-6-(trifluoromethyl)-[1,2,4]triazolo[1,5-a]pyridin-5-yl)indolin-2-one; | 8.0 |
| 24 | 7-Methyl-5-(2-methyl-6-(trifluoromethyl)-[1,2,4]triazolo[1,5-a]pyridin-5-yl)indolin-2-one; | 7.7 |
| 25 | 5-(7-Chloro-1H-indazol-5-yl)-2-ethyl-6-(trifluoromethyl)-[1,2,4]triazolo[1,5-a]pyridine; | 9.4 |
| 26 | 2-Ethyl-5-(7-methyl-1H-indazol-5-yl)-6-(trifluoromethyl)-[1,2,4]triazolo[1,5-a]pyridine; | 9.0 |
| 27 | 7-Chloro-5-(2-ethyl-6-(trifluoromethyl)-[1,2,4]triazolo[1,5-a]pyridin-5-yl)indolin-2-one; | 8.9 |
| 28 | 5-(2-Ethyl-6-(trifluoromethyl)-[1,2,4]triazolo[1,5-a]pyridin-5-yl)-7-methylindolin-2-one; | 8.4 |
| 29 | 8-Chloro-5-(7-chloro-1H-indazol-5-yl)-2-ethyl-6-(trifluoromethyl)-[1,2,4]triazolo[1,5-a]pyridine; | 9.4 |
| 30 | 8-Chloro-2-ethyl-5-(7-methyl-1H-indazol-5-yl)-6-(trifluoromethyl)-[1,2,4]triazolo[1,5-a]pyridine; | 8.4 |
| 31 | 5-(7-Chloro-1H-indazol-5-yl)-2-ethyl-8-fluoro-6-(trifluoromethyl)-[1,2,4]triazolo[1,5-a]pyridine; | 8.9 |
| 32 | 7-Chloro-5-[2-ethyl-8-fluoro-6-(trifluoromethyl)-[1,2,4]triazolo[1,5-a]pyridin-5-yl]indolin-2-one; | 8.7 |
| 33 | 2-Cyclopropyl-8-fluoro-5-(7-methyl-1H-indazol-5-yl)-6-(trifluoromethyl)-[1,2,4]triazolo[1,5-a]pyridine; | 9.7 |
| 34 | 5-(7-Chloro-1H-indazol-5-yl)-8-fluoro-2-isopropyl-6-(trifluoromethyl)-[1,2,4]triazolo[1,5-a]pyridine; | 9.5 |
| 35 | 5-(7-Chloro-1H-indazol-5-yl)-2-ethyl-8-methyl-6-(trifluoromethyl)-[1,2,4]triazolo[1,5-]pyridine; | 9.4 |
| 36 | 5-(7-Chloro-1H-indazol-5-yl)-2-isopropyl-6-(trifluoromethyl)-[1,2,4]triazolo[1,5-a]pyridine; | 10.1 |
| 37 | 2-Isopropyl-5-(7-methyl-1H-indazol-5-yl)-6-(trifluoromethyl)-[1,2,4]triazolo[1,5-a]pyridine; | 9.5 |
| 38 | 5-(7-Chloro-1H-indazol-5-yl)-2-cyclopropyl-6-(trifluoromethyl)-[1,2,4]triazolo[1,5-a]pyridine; | 9.9 |
| 39 | 2-Cyclopropyl-5-(7-methyl-1H-indazol-5-yl)-6-(trifluoromethyl)-[1,2,4]triazolo[1,5-a]pyridine; | 9.5 |
| 40 | 7-Chloro-5-(2-cyclopropyl-6-(trifluoromethyl)-[1,2,4]triazolo[1,5-a]pyridin-5-yl)indolin-2-one; | 9.4 |
| 41 | 5-(2-Cyclopropyl-6-(trifluoromethyl)-[1,2,4]triazolo[1,5-a]pyridin-5-yl)-7-methylindolin-2-one; | 9.2 |
| 42 | 5-(7-Chloro-1H-indazol-5-yl)-2-(1,1-difluoroethyl)-6-(trifluoromethyl)-[1,2,4]triazolo[1,5-a]pyridine; | 10.0 |
| 43 | 5-(7-Chloro-1H-indazol-5-yl)-2-methoxy-6-(trifluoromethyl)-[1,2,4]triazolo[1,5-a]pyridine; | 8.5 |
| 44 | 5-(7-Chloro-1H-indazol-5-yl)-6-(difluoromethyl)-2-ethyl-[1,2,4]triazolo[1,5-a]pyridine; | 9.4 |
| 45 | 6-(Difluoromethyl)-2-ethyl-5-(7-methyl-1H-indazol-5-yl)-[1,2,4]triazolo[1,5-a]pyridine; | 8.9 |
| 46 | 7-Chloro-5-(6-(difluoromethyl)-2-ethyl-[1,2,4]triazolo[1,5-a]pyridin-5-yl)indolin-2-one; | 8.4 |
| 47 | 5-(6-(Difluoromethyl)-2-ethyl-[1,2,4]triazolo[1,5-a]pyridin-5-yl)-7-methylindolin-2-one; | 8.4 |
| 48 | 5-(7-Chloro-1H-indazol-5-yl)-2-cyclopropyl-6-(difluoromethyl)-[1,2,4]triazolo[1,5-a]pyridine; | 9.7 |
| 49 | 2-Cyclopropyl-6-(difluoromethyl)-5-(7-methyl-1H-indazol-5-yl)-[1,2,4]triazolo[1,5-a]pyridine; | 9.1 |
| 50 | 5-(7-Chloro-1H-indazol-5-yl)-6-methoxy-2-(trifluoromethyl)-[1,2,4]triazolo[1,5-a]pyridine; | 9.0 |
| 51 | 6-Methoxy-5-(7-methyl-1H-indazol-5-yl)-2-(trifluoromethyl)-[1,2,4]triazolo[1,5-a]pyridine; | 8.3 |
| 52 | 6-Ethyl-5-(7-methyl-1H-indazol-5-yl)-2-(trifluoromethyl)-[1,2,4]triazolo[1,5-a]pyridine; | 9.3 |
| 53 | 5-(7-Chloro-1H-indazol-5-yl)-6-(1,1-difluoroethyl)-2-(trifluoromethyl)-[1,2,4]triazolo[1,5-a]pyridine; | 10.3 |
| 54 | 6-(2-(Difluoromethyl)-6-(trifluoromethyl)-[1,2,4]triazolo[1,5-a]pyridin-5-yl)benzo[d]thiazol-2(3H)-one; | 9.1 |
| 55 | 6-(4-Fluorophenyl)-5-(7-methyl-1H-indazol-5-yl)-2-(trifluoromethyl)-[1,2,4]triazolo[1,5-a]pyridine; | 10.4 |
| 56 | 6-(4-Fluorophenyl)-5-(1H-indazol-5-yl)-2-(trifluoromethyl)-[1,2,4]triazolo[1,5-a]pyridine; | 8.9 |
| 57 | 5-(6-(4-Fluorophenyl)-2-(trifluoromethyl)-[1,2,4]triazolo[1,5-a]pyridin-5-yl)-7-methylindolin-2-one; | 10.2 |
| 58 | 5-(7-Methyl-1H-indazol-5-yl)-6-(pyridin-3-yl)-2-(trifluoromethyl)-[1,2,4]triazolo[1,5-a]pyridine; | 9.1 |
| 59 | 5-(7-Methyl-1H-indazol-5-yl)-6-(pyridin-4-yl)-2-(trifluoromethyl)-[1,2,4]triazolo[1,5-a]pyridine; | 8.2 |
| 60 | 6-(4-Fluorophenyl)-2-methyl-5-(7-methyl-1H-indazol-5-yl)-[1,2,4]triazolo[1,5-a]pyridine; | 8.9 |
| 61 | 2-Ethyl-6-(4-fluorophenyl)-5-(7-methyl-1H-indazol-5-yl)-[1,2,4]triazolo[1,5-a]pyridine; | 9.7 |
| 62 | 2-Cyclopropyl-6-(4-fluorophenyl)-5-(7-methyl-1H-indazol-5-yl)-[1,2,4]triazolo[1,5-a]pyridine; | 9.9 |
| 63 | 5-(2,6-Bis(trifluoromethyl)pyrazolo[1,5-a]pyridin-7-yl)-7-chloro-1H-indazole; | 10.8 |
| 64 | 5-(2,6-Bis(trifluoromethyl)pyrazolo[1,5-a]pyridin-7-yl)-7-methyl-1H-indazole; | 10.8 |
| 65 | 5-(2,6-Bis(trifluoromethyl)pyrazolo[1,5-a]pyridin-7-yl)-7-methylindolin-2-one; | 10.8 |
| 66 | 5-(2,6-Bis(trifluoromethyl)pyrazolo[1,5-a]pyridin-7-yl)-7-chloroindolin-2-one; | 10.9 |
| 67 | 5-(2-Cyclopropyl-6-(trifluoromethyl)pyrazolo[1,5-a]pyridin-7-yl)-7-methylindolin-2-one; | 10.3 |
| 68 | 5-(2-Cyclopropyl-6-(trifluoromethyl)pyrazolo[1,5-a]pyridin-7-yl)-7-chloroindolin-2-one; | 10.7 |
| 69 | 5-(2-Cyclopropyl-6-(trifluoromethyl)pyrazolo[1,5-a]pyridin-7-yl)-7-methyl-1H-indazole; | 10.3 |
| 70 | 7-Chloro-5-(2-cyclopropyl-6-(trifluoromethyl)pyrazolo[1,5-a]pyridin-7-yl)-1H-indazole; | 10.2 |
| 71 | 5-(2-Isopropyl-6-(trifluoromethyl)pyrazolo[1,5-a]pyridin-7-yl)-7-methylindolin-2-one; | 10.8 |
| 72 | 5-(2-Isopropyl-6-(trifluoromethyl)pyrazolo[1,5-a]pyridin-7-yl)-7-chloroindolin-2-one; | 10.9 |
| 73 | 7-Chloro-5-(2-isopropyl-6-(trifluoromethyl)pyrazolo[1,5-a]pyridin-7-yl)-1H-indazole; | 11.0 |
| 74 | 5-(2-Isopropyl-6-(trifluoromethyl)pyrazolo[1,5-a]pyridin-7-yl)-7-methyl-1H-indazole; | 10.1 |
| 75 | 7-Chloro-5-(2-cyclopropyl-8-methyl-6-(trifluoromethyl)-[1,2,4]triazolo[1,5-a]pyridin-5-yl)indolin-2-one; | 9.9 |
| 76 | 2-Cyclopropyl-8-methyl-5-(7-methyl-1H-indazol-5-yl)-6-(trifluoromethyl)-[1,2,4]triazolo[1,5-a]pyridine; | 9.8 |
| 77 | 5-(7-Chloro-1H-indazol-5-yl)-6-(difluoromethyl)-8-methyl-2-(trifluoromethyl)-[1,2,4]triazolo[1,5-a]pyridine; | 9.6 |
| 78 | 5-(7-Chloro-1H-indazol-5-yl)-2-(difluoromethyl)-8-methyl-6-(trifluoromethyl)-[1,2,4]triazolo[1,5-a]pyridine; | 9.9 |
| 79 | 2-(Difluoromethyl)-8-methyl-5-(7-methyl-1H-indazol-5-yl)-6-(trifluoromethyl)-[1,2,4]triazolo[1,5-a]pyridine; | 9.4 |
| 80 | 5-(7-Chloro-1H-indazol-5-yl)-2-cyclopropyl-8-ethyl-6-(trifluoromethyl)-[1,2,4]triazolo[1,5-a]pyridine; | 9.8 |
| 81 | 2-Cyclopropyl-8-ethyl-5-(7-methyl-1H-indazol-5-yl)-6-(trifluoromethyl)-[1,2,4]triazolo[1,5-a]pyridine; | 9.3 |
| 82 | 5-(2-Cyclopropyl-8-ethyl-6-(trifluoromethyl)-[1,2,4]triazolo[1,5-a]pyridin-5-yl)-7-methylindolin-2-one; | 9.5 |

TABLE 4-continued

| Ex # | Compound Name | pIC$_{50}$ |
|---|---|---|
| 83 | 5-(7-Chloro-1H-indazol-5-yl)-8-methyl-2-propyl-6-(trifluoromethyl)-[1,2,4]triazolo[1,5-a]pyridine; | 9.7 |
| 84 | 8-Methyl-5-(7-methyl-1H-indazol-5-yl)-2-propyl-6-(trifluoromethyl)-[1,2,4]triazolo[1,5-a]pyridine; | 9.0 |
| 85 | 7-Methyl-5-(8-methyl-2-propyl-6-(trifluoromethyl)-[1,2,4]triazolo[1,5-a]pyridin-5-yl)indolin-2-one; | 9.5 |
| 86 | 2-(Difluoromethyl)-8-methyl-5-(7-methyl-1H-indazol-5-yl)-6-(trifluoromethyl)-[1,2,4]triazolo[1,5-a]pyridine; | 9.4 |
| 87 | 5-(7-Chloro-1H-indazol-5-yl)-2-(difluoromethyl)-8-ethyl-6-(trifluoromethyl)-[1,2,4]triazolo[1,5-a]pyridine; | 9.4 |
| 88 | 2-(Difluoromethyl)-8-ethyl-5-(7-methyl-1H-indazol-5-yl)-6-(trifluoromethyl)-[1,2,4]triazolo[1,5-a]pyridine; | 8.8 |
| 89 | 5-(7-Chloro-1H-indazol-5-yl)-2,8-diethyl-6-(trifluoromethyl)-[1,2,4]triazolo[1,5-a]pyridine; | 9.1 |
| 90 | 2,8-Diethyl-5-(7-methyl-1H-indazol-5-yl)-6-(trifluoromethyl)-[1,2,4]triazolo[1,5-a]pyridine; | 8.5 |
| 91 | 5-(7-Chloro-1H-indazol-5-yl)-6-(difluoromethyl)-8-ethyl-2-(trifluoromethyl)-[1,2,4]triazolo[1,5-a]pyridine; | 9.3 |
| 92 | 6-(Difluoromethyl)-8-ethyl-5-(7-methyl-1H-indazol-5-yl)-2-(trifluoromethyl)-[1,2,4]triazolo[1,5-a]pyridine; | 9.0 |
| 93 | 5-(7-Chloro-1H-indazol-5-yl)-2-cyclopropyl-6-(difluoromethyl)-8-ethyl-[1,2,4]triazolo[1,5-a]pyridine; | 9.8 |
| 94 | 2-Cyclopropyl-6-(difluoromethyl)-8-ethyl-5-(7-methyl-1H-indazol-5-yl)-[1,2,4]triazolo[1,5-a]pyridine; | 9.4 |
| 95 | 6-(Difluoromethyl)-8-methyl-5-(7-methyl-1H-indazol-5-yl)-2-propyl[1,2,4]triazolo[1,5-a]pyridine; | 8.5 |
| 96 | 8-Chloro-5-(7-chloro-1H-indazol-5-yl)-2-propyl-6-(trifluoromethyl)-[1,2,4]triazolo[1,5-a]pyridine; | 9.4 |
| 97 | 7-Chloro-5-(8-chloro-2-propyl-6-(trifluoromethyl)-[1,2,4]triazolo[1,5-a]pyridin-5-yl)indolin-2-one; | 9.3 |
| 98 | 5-(8-Chloro-2-propyl-6-(trifluoromethyl)-[1,2,4]triazolo[1,5-a]pyridin-5-yl)-7-methylindolin-2-one; | 9.1 |
| 99 | 5-(2-Cyclopropyl-8-methyl-6-(trifluoromethyl)-[1,2,4]triazolo[1,5-a]pyridin-5-yl)-7-methylindolin-2-one; | 9.6 |
| 100 | 7-Chloro-5-(2-ethyl-8-methyl-6-(trifluoromethyl)-[1,2,4]triazolo[1,5-a]pyridin-5-yl)indolin-2-one; | 9.2 |
| 101 | 2-Ethyl-8-methyl-6-(trifluoromethyl)-5-(7-(trifluoromethyl)-1H-indazol-5-yl)-[1,2,4]triazolo[1,5-a]pyridine; | 9.5 |
| 102 | 5-(2-Ethyl-8-methyl-6-(trifluoromethyl)-[1,2,4]triazolo[1,5-a]pyridin-5-yl)-7-(trifluoromethyl)indolin-2-one; | 8.8 |
| 103 | 7-Chloro-5-(2-ethyl-8-methyl-6-(trifluoromethyl)-[1,2,4]triazolo[1,5-a]pyridin-5-yl)indolin-2-one; | 9.8 |
| 104 | 7-Ethyl-5-(8-methyl-2,6-bis(trifluoromethyl)-[1,2,4]triazolo[1,5-a]pyridin-5-yl)indolin-2-one; | 9.8 |
| 105 | 7-Methyl-5-(8-methyl-2,6-bis(trifluoromethyl)-[1,2,4]triazolo[1,5-a]pyridin-5-yl)indolin-2-one; | 9.5 |
| 106 | 7-Methoxy-5-(8-methyl-2,6-bis(trifluoromethyl)-[1,2,4]triazolo[1,5-a]pyridin-5-yl)indolin-2-one; | 8.9 |
| 107 | 8-Methyl-5-(7-methyl-1H-indazol-5-yl)-2,6-bis(trifluoromethyl)-[1,2,4]triazolo[1,5-a]pyridine; | 9.3 |
| 108 | 5-(8-Methyl-2,6-bis(trifluoromethyl)-[1,2,4]triazolo[1,5-a]pyridin-5-yl)-2-oxoindoline-7-carbonitrile; | 8.4 |
| 109 | 5-(7-Chloro-1H-indazol-5-yl)-6-(difluoromethyl)-8-methyl-2-(trifluoromethyl)-[1,2,4]triazolo[1,5-a]pyridine; | 9.6 |
| 110 | 7-Chloro-5-(6-(difluoromethyl)-8-methyl-2-(trifluoromethyl)-[1,2,4]triazolo[1,5-a]pyridin-5-yl)indolin-2-one; | 9.1 |
| 111 | 6-(Difluoromethyl)-8-methyl-5-(7-methyl-1H-indazol-5-yl)-2-(trifluoromethyl)-[1,2,4]triazolo[1,5-a]pyridine; | 9.1 |
| 112 | 5-(7-Chloro-1H-indazol-5-yl)-2-cyclopropyl-6-(difluoromethyl)-8-methyl-[1,2,4]triazolo[1,5-a]pyridine; | 10.0 |
| 113 | 7-Chloro-5-(2-cyclopropyl-6-(difluoromethyl)-8-methyl-[1,2,4]triazolo[1,5-a]pyridin-5-yl)indolin-2-one; | 9.5 |
| 114 | 2-Cyclopropyl-6-(difluoromethyl)-8-methyl-5-(7-methyl-1H-indazol-5-yl)-[1,2,4]triazolo[1,5-a]pyridine; | 9.4 |
| 115 | 5-(7-Chloro-1H-indazol-5-yl)-6-(difluoromethyl)-2-ethyl-8-methyl-[1,2,4]triazolo[1,5-a]pyridine; | 8.7 |
| 116 | 5-(7-Chloro-1H-indazol-5-yl)-2,8-dimethyl-6-(trifluoromethyl)-[1,2,4]triazolo[1,5-a]pyridine; | 8.6 |
| 117 | 5-(7-Chloro-1H-indazol-5-yl)-2-ethoxy-8-methyl-6-(trifluoromethyl)-[1,2,4]triazolo[1,5-a]pyridine; | 8.6 |
| 118 | 7-Chloro-5-(2-cyclopropyl-6-(trifluoromethyl)pyrazolo[1,5-a]pyridin-7-yl)-1H-indazole; | 10.2 |
| 119 | 5-[6-(Difluoromethyl)-2-(trifluoromethyl)pyrazolo[1,5-a]pyridin-7-yl]-7-methyl-indolin-2-one; | 10.3 |
| 120 | 7-(7-Chloro-1H-indazol-5-yl)-6-(difluoromethyl)-2-(trifluoromethyl)pyrazolo[1,5-a]pyridine; | 10.8 |
| 121 | 6-(Difluoromethyl)-7-(7-methyl-1H-indazol-5-yl)-2-(trifluoromethyl)pyrazolo[1,5-a]pyridine; | 10.6 |
| 122 | 5-[6-(Difluoromethyl)-4-methyl-2-(trifluoromethyl)pyrazolo[1,5-a]pyridin-7-yl]-7-methyl-indolin-2-one; | 10.3 |
| 123 | 6-(Difluoromethyl)-4-methyl-7-(7-methyl-1H-indazol-5-yl)-2-(trifluoromethyl)pyrazolo[1,5-a]pyridine; | 9.9 |
| 124 | 7-Chloro-5-[6-(difluoromethyl)-4-methyl-2-(trifluoromethyl)pyrazolo[1,5-a]pyridin-7-yl]indolin-2-one; and | 9.6 |
| 125 | 7-(7-Chloro-1H-indazol-5-yl)-6-(difluoromethyl)-4-methyl-2-(trifluoromethyl)pyrazolo[1,5-a]pyridine. | 10.0 |

What is claimed:
1. A compound of Formula (I):

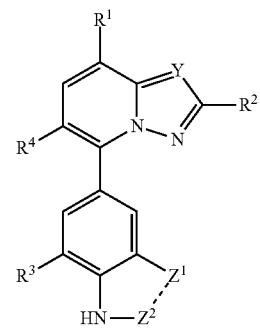

(I)

wherein
Y is N or CH;
R$^1$ is selected from the group consisting of: H, halo, and C$_{1-6}$alkyl;
R$^2$ is selected from the group consisting of: C$_{1-6}$alkyl, C$_{1-6}$haloalkyl, C$_{1-6}$alkoxy, and C$_{3-8}$cycloalkyl;
R$^3$ is selected from the group consisting of: H, halo, C$_{1-6}$alkyl, C$_{1-6}$alkoxy, CN, and CF$_3$;
R$^4$ is selected from the group consisting of: C$_{1-6}$alkyl, C$_{1-6}$haloalkyl, C$_{1-6}$alkoxy, phenyl substituted with F, and pyridyl; and

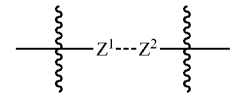

is selected from the group consisting of: —CH=N—, —CH$_2$—C(=O)—, and —S—C(=O)—; and
pharmaceutically acceptable salts, N-oxides, or solvates thereof.
2. The compound of claim 1, wherein Y is N.
3. The compound of claim 1, wherein Y is CH.
4. The compound of claim 1, wherein R$^1$ is H.
5. The compound of claim 1, wherein R$^1$ is Cl or F.
6. The compound of claim 1, wherein R$^1$ is CH$_3$ or CH$_2$CH$_3$.
7. The compound of claim 1, wherein R$^2$ is CF$_3$, CHF$_2$, or CF$_2$(CH$_3$).
8. The compound of claim 1, wherein R$^2$ is CH$_3$, CH$_2$CH$_3$, CH$_2$CH$_2$CH$_3$, or CH(CH$_3$)$_2$.
9. The compound of claim 1, wherein R$^2$ is cyclopropyl.

10. The compound of claim 1, wherein R² is OCH₃ or OCH₂CH₃.

11. The compound of claim 1, wherein R³ is H, Cl, CH₃, or CH₂CH₃.

12. The compound of claim 1, wherein R³ is OCH₃ or CN.

13. The compound of claim 1, wherein R³ is CF₃.

14. The compound of claim 1, wherein R⁴ is CF₃, CF₂(CH₃), or CHF₂.

15. The compound of claim 1, wherein R⁴ is OCH₃.

16. The compound of claim 1, wherein R⁴ is CH₂CH₃.

17. The compound of claim 1, wherein R⁴ is 4-fluorophenyl, pyridin-3-yl, or pyridin-4-yl.

18. The compound of claim 1, wherein

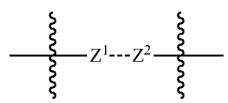

is —CH=N—.

19. The compound of claim 1, wherein

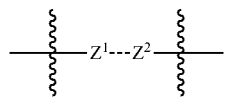

is —CH₂—C(=O)—.

20. The compound of claim 1, wherein

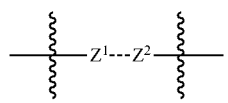

is —S—C(=O)—.

21. The compound of claim 1, and pharmaceutically acceptable salts, solvates, or N-oxides thereof, having the structure of Formula (1A):

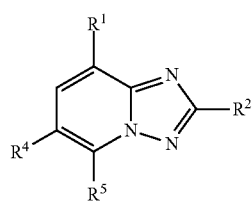

wherein
R¹ is selected from the group consisting of: H, halo, CH₃, and CH₂CH₃;
R² is selected from the group consisting of: C₁₋₆alkyl, C₁₋₆haloalkyl, C₁₋₆alkoxy, and C₃₋₈cycloalkyl;
R⁴ is selected from the group consisting of: C₁₋₆alkyl, C₁₋₆haloalkyl, C₁₋₆alkoxy, phenyl substituted with F, and pyridyl; and R⁵ is selected from the group consisting of:

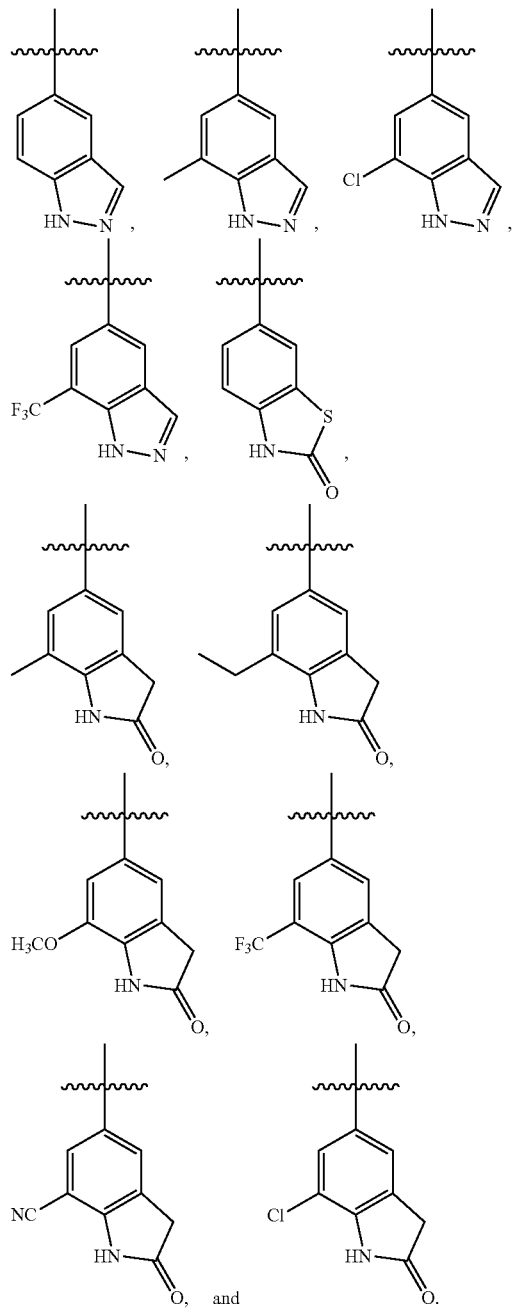

22. The compound of claim 1, and pharmaceutically acceptable salts, solvates, or N-oxides thereof, having the structure of Formula (1B):

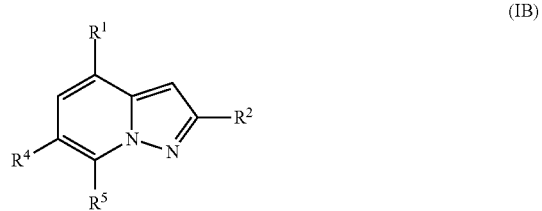

wherein
R¹ is H, or $C_{1-6}$alkyl;
R² is selected from the group consisting of: $C_{1-6}$alkyl, $C_{1-6}$haloalkyl, and $C_{3-8}$cycloalkyl;
R⁴ is $CF_2H$ or $CF_3$; and
R⁵ is selected from the group consisting of:

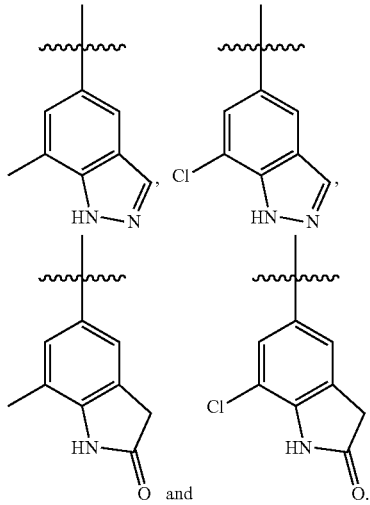

23. A compound selected from the group consisting of:
5-(7-Chloro-1H-indazol-5-yl)-2,6-bis(trifluoromethyl)-[1,2,4]triazolo[1,5-a]pyridine;
5-(7-Methyl-1H-indazol-5-yl)-2,6-bis(trifluoromethyl)-[1,2,4]triazolo[1,5-a]pyridine;
5-(2,6-Bis(trifluoromethyl)-[1,2,4]triazolo[1,5-a]pyridin-5-yl)-7-chloroindolin-2-one;
5-(2,6-Bis(trifluoromethyl)-[1,2,4]triazolo[1,5-a]pyridin-5-yl)-7-methylindolin-2-one;
8-Chloro-5-(7-chloro-1H-indazol-5-yl)-2,6-bis(trifluoromethyl)-[1,2,4]triazolo[1,5-a]pyridine;
5-(7-Chloro-1H-indazol-5-yl)-8-methyl-2,6-bis(trifluoromethyl)-[1,2,4]triazolo[1,5-a]pyridine;
5-(7-Chloro-1H-indazol-5-yl)-2-(difluoromethyl)-6-(trifluoromethyl)-[1,2,4]triazolo[1,5-a]pyridine;
5-(7-Methyl-1H-indazol-5-yl)-2-(difluoromethyl)-6-(trifluoromethyl)-[1,2,4]triazolo[1,5-a]pyridine;
7-Chloro-5-(2-(difluoromethyl)-6-(trifluoromethyl)-[1,2,4]triazolo[1,5-a]pyridin-5-yl)indolin-2-one;
7-Methyl-5-(2-(difluoromethyl)-6-(trifluoromethyl)-[1,2,4]triazolo[1,5-a]pyridin-5-yl)indolin-2-one;
2-(Difluoromethyl)-6-(trifluoromethyl)-5-(7-(trifluoromethyl)-1H-indazol-5-yl)-[1,2,4]triazolo[1,5-a]pyridine;
5-(2-(Difluoromethyl)-6-(trifluoromethyl)-[1,2,4]triazolo[1,5-a]pyridin-5-yl)-7-methoxyindolin-2-one;
5-(7-Chloro-1H-indazol-5-yl)-2-(difluoromethyl)-6-methoxy-[1,2,4]triazolo[1,5-a]pyridine;
2-(Difluoromethyl)-6-methoxy-5-(7-methyl-1H-indazol-5-yl)-[1,2,4]triazolo[1,5-a]pyridine;
2-(Difluoromethyl)-6-methoxy-5-(7-(trifluoromethyl)-1H-indazol-5-yl)-[1,2,4]triazolo[1,5-a]pyridine;
5-(7-Chloro-1H-indazol-5-yl)-6-(difluoromethyl)-2-(trifluoromethyl)-[1,2,4]triazolo[1,5-a]pyridine;
6-(Difluoromethyl)-5-(7-methyl-1H-indazol-5-yl)-2-(trifluoromethyl)-[1,2,4]triazolo[1,5-a]pyridine;
7-Chloro-5-(6-(difluoromethyl)-2-(trifluoromethyl)-[1,2,4]triazolo[1,5-a]pyridin-5-yl)indolin-2-one;
5-[6-(Difluoromethyl)-2-(trifluoromethyl)-[1,2,4]triazolo[1,5-a]pyridin-5-yl]-7-methyl-indolin-2-one;
5-[6-(Difluoromethyl)-2-(trifluoromethyl)-[1,2,4]triazolo[1,5-a]pyridin-5-yl]-7-methoxy-indolin-2-one;
5-(7-Chloro-1H-indazol-5-yl)-2-methyl-6-(trifluoromethyl)-[1,2,4]triazolo[1,5-a]pyridine;
2-Methyl-5-(7-methyl-1H-indazol-5-yl)-6-(trifluoromethyl)-[1,2,4]triazolo[1,5-a]pyridine;
7-Chloro-5-(2-methyl-6-(trifluoromethyl)-[1,2,4]triazolo[1,5-a]pyridin-5-yl)indolin-2-one;
7-Methyl-5-(2-methyl-6-(trifluoromethyl)-[1,2,4]triazolo[1,5-a]pyridin-5-yl)indolin-2-one;
5-(7-Chloro-1H-indazol-5-yl)-2-ethyl-6-(trifluoromethyl)-[1,2,4]triazolo[1,5-a]pyridine;
2-Ethyl-5-(7-methyl-1H-indazol-5-yl)-6-(trifluoromethyl)-[1,2,4]triazolo[1,5-a]pyridine;
7-Chloro-5-(2-ethyl-6-(trifluoromethyl)-[1,2,4]triazolo[1,5-a]pyridin-5-yl)indolin-2-one;
5-(2-Ethyl-6-(trifluoromethyl)-[1,2,4]triazolo[1,5-a]pyridin-5-yl)-7-methylindolin-2-one;
8-Chloro-5-(7-chloro-1H-indazol-5-yl)-2-ethyl-6-(trifluoromethyl)-[1,2,4]triazolo[1,5-a]pyridine;
8-Chloro-2-ethyl-5-(7-methyl-1H-indazol-5-yl)-6-(trifluoromethyl)-[1,2,4]triazolo[1,5-a]pyridine;
5-(7-Chloro-1H-indazol-5-yl)-2-ethyl-8-fluoro-6-(trifluoromethyl)-[1,2,4]triazolo[1,5-a]pyridine;
7-Chloro-5-[2-ethyl-8-fluoro-6-(trifluoromethyl)-[1,2,4]triazolo[1,5-a]pyridin-5-yl]indolin-2-one;
2-Cyclopropyl-8-fluoro-5-(7-methyl-1H-indazol-5-yl)-6-(trifluoromethyl)-[1,2,4]triazolo[1,5-a]pyridine;
5-(7-Chloro-1H-indazol-5-yl)-8-fluoro-2-isopropyl-6-(trifluoromethyl)-[1,2,4]triazolo[1,5-a]pyridine;
5-(7-Chloro-1H-indazol-5-yl)-2-ethyl-8-methyl-6-(trifluoromethyl)-[1,2,4]triazolo[1,5-]pyridine;
5-(7-Chloro-1H-indazol-5-yl)-2-isopropyl-6-(trifluoromethyl)-[1,2,4]triazolo[1,5-a]pyridine;
2-Isopropyl-5-(7-methyl-1H-indazol-5-yl)-6-(trifluoromethyl)-[1,2,4]triazolo[1,5-a]pyridine;
5-(7-Chloro-1H-indazol-5-yl)-2-cyclopropyl-6-(trifluoromethyl)-[1,2,4]triazolo[1,5-a]pyridine;
2-Cyclopropyl-5-(7-methyl-1H-indazol-5-yl)-6-(trifluoromethyl)-[1,2,4]triazolo[1,5-a]pyridine;
7-Chloro-5-(2-cyclopropyl-6-(trifluoromethyl)-[1,2,4]triazolo[1,5-a]pyridin-5-yl)indolin-2-one;
5-(2-Cyclopropyl-6-(trifluoromethyl)-[1,2,4]triazolo[1,5-a]pyridin-5-yl)-7-methylindolin-2-one;
5-(7-Chloro-1H-indazol-5-yl)-2-(1,1-difluoroethyl)-6-(trifluoromethyl)-[1,2,4]triazolo[1,5-a]pyridine;
5-(7-Chloro-1H-indazol-5-yl)-2-methoxy-6-(trifluoromethyl)-[1,2,4]triazolo[1,5-a]pyridine;
5-(7-Chloro-1H-indazol-5-yl)-6-(difluoromethyl)-2-ethyl-[1,2,4]triazolo[1,5-a]pyridine;
6-(Difluoromethyl)-2-ethyl-5-(7-methyl-1H-indazol-5-yl)-[1,2,4]triazolo[1,5-a]pyridine;
7-Chloro-5-(6-(difluoromethyl)-2-ethyl-[1,2,4]triazolo[1,5-a]pyridin-5-yl)indolin-2-one;
5-(6-(Difluoromethyl)-2-ethyl-[1,2,4]triazolo[1,5-a]pyridin-5-yl)-7-methylindolin-2-one;
5-(7-Chloro-1H-indazol-5-yl)-2-cyclopropyl-6-(difluoromethyl)-[1,2,4]triazolo[1,5-a]pyridine;
2-Cyclopropyl-6-(difluoromethyl)-5-(7-methyl-1H-indazol-5-yl)-[1,2,4]triazolo[1,5-a]pyridine;
5-(7-Chloro-1H-indazol-5-yl)-6-methoxy-2-(trifluoromethyl)-[1,2,4]triazolo[1,5-a]pyridine;
6-Methoxy-5-(7-methyl-1H-indazol-5-yl)-2-(trifluoromethyl)-[1,2,4]triazolo[1,5-a]pyridine;

6-Ethyl-5-(7-methyl-1H-indazol-5-yl)-2-(trifluoromethyl)-[1,2,4]triazolo[1,5-a]pyridine;
5-(7-Chloro-1H-indazol-5-yl)-6-(1,1-difluoroethyl)-2-(trifluoromethyl)-[1,2,4]triazolo[1,5-a]pyridine;
6-(2-(Difluoromethyl)-6-(trifluoromethyl)-[1,2,4]triazolo[1,5-a]pyridin-5-yl)benzo[d]thiazol-2(3H)-one;
6-(4-Fluorophenyl)-5-(7-methyl-1H-indazol-5-yl)-2-(trifluoromethyl)-[1,2,4]triazolo[1,5-a]pyridine;
6-(4-Fluorophenyl)-5-(1H-indazol-5-yl)-2-(trifluoromethyl)-[1,2,4]triazolo[1,5-a]pyridine;
5-(6-(4-Fluorophenyl)-2-(trifluoromethyl)-[1,2,4]triazolo[1,5-a]pyridin-5-yl)-7-methylindolin-2-one;
5-(7-Methyl-1H-indazol-5-yl)-6-(pyridin-3-yl)-2-(trifluoromethyl)-[1,2,4]triazolo[1,5-a]pyridine;
5-(7-Methyl-1H-indazol-5-yl)-6-(pyridin-4-yl)-2-(trifluoromethyl)-[1,2,4]triazolo[1,5-a]pyridine;
6-(4-Fluorophenyl)-2-methyl-5-(7-methyl-1H-indazol-5-yl)-[1,2,4]triazolo[1,5-a]pyridine;
2-Ethyl-6-(4-fluorophenyl)-5-(7-methyl-1H-indazol-5-yl)-[1,2,4]triazolo[1,5-a]pyridine;
2-Cyclopropyl-6-(4-fluorophenyl)-5-(7-methyl-1H-indazol-5-yl)-[1,2,4]triazolo[1,5-a]pyridine;
5-(2,6-Bis(trifluoromethyl)pyrazolo[1,5-a]pyridin-7-yl)-7-chloro-1H-indazole;
5-(2,6-Bis(trifluoromethyl)pyrazolo[1,5-a]pyridin-7-yl)-7-methyl-1H-indazole;
5-(2,6-Bis(trifluoromethyl)pyrazolo[1,5-a]pyridin-7-yl)-7-methylindolin-2-one;
5-(2,6-Bis(trifluoromethyl)pyrazolo[1,5-a]pyridin-7-yl)-7-chloroindolin-2-one;
5-(2-Cyclopropyl-6-(trifluoromethyl)pyrazolo[1,5-a]pyridin-7-yl)-7-methylindolin-2-one;
5-(2-Cyclopropyl-6-(trifluoromethyl)pyrazolo[1,5-a]pyridin-7-yl)-7-chloroindolin-2-one;
5-(2-Cyclopropyl-6-(trifluoromethyl)pyrazolo[1,5-a]pyridin-7-yl)-7-methyl-1H-indazole;
7-Chloro-5-(2-cyclopropyl-6-(trifluoromethyl)pyrazolo[1,5-a]pyridin-7-yl)-1H-indazole;
5-(2-Isopropyl-6-(trifluoromethyl)pyrazolo[1,5-a]pyridin-7-yl)-7-methylindolin-2-one;
5-(2-Isopropyl-6-(trifluoromethyl)pyrazolo[1,5-a]pyridin-7-yl)-7-chloroindolin-2-one;
7-Chloro-5-(2-isopropyl-6-(trifluoromethyl)pyrazolo[1,5-a]pyridin-7-yl)-1H-indazole; and
5-(2-Isopropyl-6-(trifluoromethyl)pyrazolo[1,5-a]pyridin-7-yl)-7-methyl-1H-indazole; and
pharmaceutically acceptable salts, N-oxides or solvates thereof.

24. A compound selected from the group consisting of:
7-Chloro-5-(2-cyclopropyl-8-methyl-6-(trifluoromethyl)-[1,2,4]triazolo[1,5-a]pyridin-5-yl)indolin-2-one;
2-Cyclopropyl-8-methyl-5-(7-methyl-1H-indazol-5-yl)-6-(trifluoromethyl)-[1,2,4]triazolo[1,5-a]pyridine;
5-(7-Chloro-1H-indazol-5-yl)-6-(difluoromethyl)-8-methyl-2-(trifluoromethyl)-[1,2,4]triazolo[1,5-a]pyridine;
5-(7-Chloro-1H-indazol-5-yl)-2-(difluoromethyl)-8-methyl-6-(trifluoromethyl)-[1,2,4]triazolo[1,5-a]pyridine;
2-(Difluoromethyl)-8-methyl-5-(7-methyl-1H-indazol-5-yl)-6-(trifluoromethyl)-[1,2,4]triazolo[1,5-a]pyridine;
2-(Difluoromethyl)-8-methyl-5-(7-methyl-1H-indazol-5-yl)-6-(trifluoromethyl)-[1,2,4]triazolo[1,5-a]pyridine;
5-(7-Chloro-1H-indazol-5-yl)-2-cyclopropyl-8-ethyl-6-(trifluoromethyl)-[1,2,4]triazolo[1,5-a]pyridine;
2-Cyclopropyl-8-ethyl-5-(7-methyl-1H-indazol-5-yl)-6-(trifluoromethyl)-[1,2,4]triazolo[1,5-a]pyridine;
5-(2-Cyclopropyl-8-ethyl-6-(trifluoromethyl)-[1,2,4]triazolo[1,5-a]pyridin-5-yl)-7-methylindolin-2-one;
5-(7-Chloro-1H-indazol-5-yl)-8-methyl-2-propyl-6-(trifluoromethyl)-[1,2,4]triazolo[1,5-a]pyridine;
8-Methyl-5-(7-methyl-1H-indazol-5-yl)-2-propyl-6-(trifluoromethyl)-[1,2,4]triazolo[1,5-a]pyridine;
7-Methyl-5-(8-methyl-2-propyl-6-(trifluoromethyl)-[1,2,4]triazolo[1,5-a]pyridin-5-yl)indolin-2-one;
2-(Difluoromethyl)-8-methyl-5-(7-methyl-1H-indazol-5-yl)-6-(trifluoromethyl)-[1,2,4]triazolo[1,5-a]pyridine;
5-(7-Chloro-1H-indazol-5-yl)-2-(difluoromethyl)-8-ethyl-6-(trifluoromethyl)-[1,2,4]triazolo[1,5-a]pyridine;
2-(Difluoromethyl)-8-ethyl-5-(7-methyl-1H-indazol-5-yl)-6-(trifluoromethyl)-[1,2,4]triazolo[1,5-a]pyridine;
5-(7-Chloro-1H-indazol-5-yl)-2,8-diethyl-6-(trifluoromethyl)-[1,2,4]triazolo[1,5-a]pyridine;
2,8-Diethyl-5-(7-methyl-1H-indazol-5-yl)-6-(trifluoromethyl)-[1,2,4]triazolo[1,5-a]pyridine;
5-(7-Chloro-1H-indazol-5-yl)-6-(difluoromethyl)-8-ethyl-2-(trifluoromethyl)-[1,2,4]triazolo[1,5-a]pyridine;
6-(Difluoromethyl)-8-ethyl-5-(7-methyl-1H-indazol-5-yl)-2-(trifluoromethyl)-[1,2,4]triazolo[1,5-a]pyridine;
5-(7-Chloro-1H-indazol-5-yl)-2-cyclopropyl-6-(difluoromethyl)-8-ethyl-[1,2,4]triazolo[1,5-a]pyridine;
2-Cyclopropyl-6-(difluoromethyl)-8-ethyl-5-(7-methyl-1H-indazol-5-yl)-[1,2,4]triazolo[1,5-a]pyridine;
6-(Difluoromethyl)-8-methyl-5-(7-methyl-1H-indazol-5-yl)-2-propyl-[1,2,4]triazolo[1,5-a]pyridine;
8-Chloro-5-(7-chloro-1H-indazol-5-yl)-2-propyl-6-(trifluoromethyl)-[1,2,4]triazolo[1,5-a]pyridine;
7-Chloro-5-(8-chloro-2-propyl-6-(trifluoromethyl)-[1,2,4]triazolo[1,5-a]pyridin-5-yl)indolin-2-one;
5-(8-Chloro-2-propyl-6-(trifluoromethyl)-[1,2,4]triazolo[1,5-a]pyridin-5-yl)-7-methylindolin-2-one;
5-(2-Cyclopropyl-8-methyl-6-(trifluoromethyl)-[1,2,4]triazolo[1,5-a]pyridin-5-yl)-7-methylindolin-2-one;
7-Chloro-5-(2-ethyl-8-methyl-6-(trifluoromethyl)-[1,2,4]triazolo[1,5-a]pyridin-5-yl)indolin-2-one;
2-Ethyl-8-methyl-6-(trifluoromethyl)-5-(7-(trifluoromethyl)-1H-indazol-5-yl)-[1,2,4]triazolo[1,5-a]pyridine;
5-(2-Ethyl-8-methyl-6-(trifluoromethyl)-[1,2,4]triazolo[1,5-a]pyridin-5-yl)-7-(trifluoromethyl)indolin-2-one;
7-Chloro-5-(2-ethyl-8-methyl-6-(trifluoromethyl)-[1,2,4]triazolo[1,5-a]pyridin-5-yl)indolin-2-one;
7-Ethyl-5-(8-methyl-2,6-bis(trifluoromethyl)-[1,2,4]triazolo[1,5-a]pyridin-5-yl)indolin-2-one;
7-Methyl-5-(8-methyl-2,6-bis(trifluoromethyl)-[1,2,4]triazolo[1,5-a]pyridin-5-yl)indolin-2-one;
7-Methoxy-5-(8-methyl-2,6-bis(trifluoromethyl)-[1,2,4]triazolo[1,5-a]pyridin-5-yl)indolin-2-one;
8-Methyl-5-(7-methyl-1H-indazol-5-yl)-2,6-bis(trifluoromethyl)-[1,2,4]triazolo[1,5-a]pyridine;
5-(8-Methyl-2,6-bis(trifluoromethyl)-[1,2,4]triazolo[1,5-a]pyridin-5-yl)-2-oxoindoline-7-carbonitrile;
5-(7-Chloro-1H-indazol-5-yl)-6-(difluoromethyl)-8-methyl-2-(trifluoromethyl)-[1,2,4]triazolo[1,5-a]pyridine;
7-Chloro-5-(6-(difluoromethyl)-8-methyl-2-(trifluoromethyl)-[1,2,4]triazolo[1,5-a]pyridin-5-yl)indolin-2-one;
6-(Difluoromethyl)-8-methyl-5-(7-methyl-1H-indazol-5-yl)-2-(trifluoromethyl)-[1,2,4]triazolo[1,5-a]pyridine;
5-(7-Chloro-1H-indazol-5-yl)-2-cyclopropyl-6-(difluoromethyl)-8-methyl-[1,2,4]triazolo[1,5-a]pyridine;
7-Chloro-5-(2-cyclopropyl-6-(difluoromethyl)-8-methyl-[1,2,4]triazolo[1,5-a]pyridin-5-yl)indolin-2-one;

2-Cyclopropyl-6-(difluoromethyl)-8-methyl-5-(7-methyl-1H-indazol-5-yl)-[1,2,4]triazolo[1,5-a]pyridine;
5-(7-Chloro-1H-indazol-5-yl)-6-(difluoromethyl)-2-ethyl-8-methyl-[1,2,4]triazolo[1,5-a]pyridine;
5-(7-Chloro-1H-indazol-5-yl)-2,8-dimethyl-6-(trifluoromethyl)-[1,2,4]triazolo[1,5-a]pyridine;
5-(7-Chloro-1H-indazol-5-yl)-2-ethoxy-8-methyl-6-(trifluoromethyl)-[1,2,4]triazolo[1,5-a]pyridine;
7-Chloro-5-(2-cyclopropyl-6-(trifluoromethyl)pyrazolo[1,5-a]pyridin-7-yl)-1H-indazole;
5-[6-(Difluoromethyl)-2-(trifluoromethyl)pyrazolo[1,5-a]pyridin-7-yl]-7-methyl-indolin-2-one;
7-(7-Chloro-1H-indazol-5-yl)-6-(difluoromethyl)-2-(trifluoromethyl)pyrazolo[1,5-a]pyridine;
6-(Difluoromethyl)-7-(7-methyl-1H-indazol-5-yl)-2-(trifluoromethyl)pyrazolo[1,5-a]pyridine;
5-[6-(Difluoromethyl)-4-methyl-2-(trifluoromethyl)pyrazolo[1,5-a]pyridin-7-yl]-7-methyl-indolin-2-one;
6-(Difluoromethyl)-4-methyl-7-(7-methyl-1H-indazol-5-yl)-2-(trifluoromethyl)pyrazolo[1,5-a]pyridine;
7-Chloro-5-[6-(difluoromethyl)-4-methyl-2-(trifluoromethyl)pyrazolo[1,5-a]pyridin-7-yl]indolin-2-one; and
7-(7-Chloro-1H-indazol-5-yl)-6-(difluoromethyl)-4-methyl-2-(trifluoromethyl)pyrazolo[1,5-a]pyridine; and pharmaceutically acceptable salts, N-oxides or solvates thereof.

25. A pharmaceutical composition comprising:
(A) an effective amount of at least one compound of Formula (I):

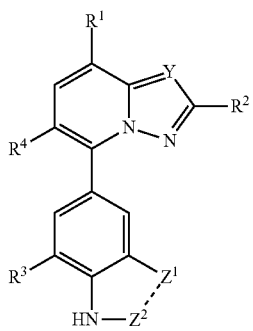

(I)

wherein

Y is N or CH;

$R^1$ is selected from the group consisting of: H, halo, $C_{1-6}$alkyl;

$R^2$ is selected from the group consisting of: $C_{1-6}$alkyl, $C_{1-6}$haloalkyl, $C_{1-6}$alkoxy, and $C_{3-8}$cycloalkyl;

$R^3$ is selected from the group consisting of: H, halo, $C_{1-6}$alkyl, $C_{1-6}$alkoxy, CN, and $CF_3$;

$R^4$ is selected from the group consisting of: $C_{1-6}$alkyl, $C_{1-6}$haloalkyl, $C_{1-6}$alkoxy, phenyl substituted with F, and pyridyl; and

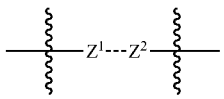

is selected from the group consisting of: —CH=N—, —CH$_2$—C(=O)—, and —S—C(=O)—; and pharmaceutically acceptable salts, N-oxides or solvates of compounds of Formula (I); and (B) at least one pharmaceutically acceptable excipient.

26. A pharmaceutical composition comprising an effective amount of at least one compound of claim 22 and at least one pharmaceutically acceptable excipient.

* * * * *